(12) United States Patent
Bradner et al.

(10) Patent No.: US 10,633,371 B2
(45) Date of Patent: Apr. 28, 2020

(54) EZH2 INHIBITORS AND USES THEREOF

(71) Applicant: Dana-Farber Cancer Institute, Inc., Boston, MA (US)

(72) Inventors: James E. Bradner, Weston, MA (US); Joshiawa Paulk, Cambridge, MA (US); Jun Qi, Sharon, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/095,188

(22) PCT Filed: Apr. 21, 2017

(86) PCT No.: PCT/US2017/028885
§ 371 (c)(1),
(2) Date: Oct. 19, 2018

(87) PCT Pub. No.: WO2017/184999
PCT Pub. Date: Oct. 26, 2017

(65) Prior Publication Data
US 2019/0135796 A1 May 9, 2019
US 2020/0039968 A9 Feb. 6, 2020

Related U.S. Application Data
(60) Provisional application No. 62/326,036, filed on Apr. 22, 2016.

(51) Int. Cl.
*C07D 405/14* (2006.01)
*A61K 45/06* (2006.01)
(Continued)

(52) U.S. Cl.
CPC ............ *C07D 405/14* (2013.01); *A61K 45/06* (2013.01); *C07D 401/12* (2013.01); *C07D 405/12* (2013.01); *C07D 413/14* (2013.01)

(58) Field of Classification Search
CPC .................................................. C07D 405/14
(Continued)

(56) References Cited

U.S. PATENT DOCUMENTS 8,338,464 B2   12/2012   Melnick et al.
8,410,088 B2 *  4/2013   Kuntz ................. C07D 213/64
                                                   514/211.15
(Continued)

FOREIGN PATENT DOCUMENTS

WO   WO 2008/066887 A2   6/2008
WO   WO 2010/008436 A1   1/2010
(Continued)

OTHER PUBLICATIONS

Haedke, U. et al., Bioorg. Med. Chem., 2012, vol. 20, pp. 633-640.*
(Continued)

*Primary Examiner* — Niloofar Rahmani
(74) *Attorney, Agent, or Firm* — Wolf, Greenfield & Sacks, P.C.

(57) ABSTRACT

The present disclosure provides compounds of any one of Formulae (I), (II), and (III). The compounds described herein are inhibitors of histone methyltransferases (e.g., enhancer of zeste homolog 1 (EZH1) and enhancer of zeste homolog 2 (EZH2)) and are useful in treating and/or preventing a broad range of diseases (e.g., proliferative diseases). Also provided in the present disclosure are pharmaceutical compositions, kits, methods, and uses including or using a compound described herein.

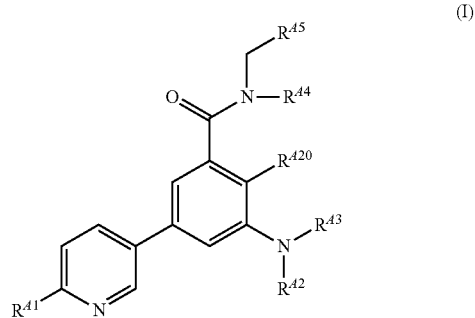

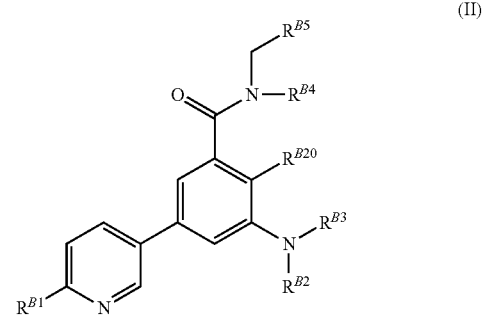

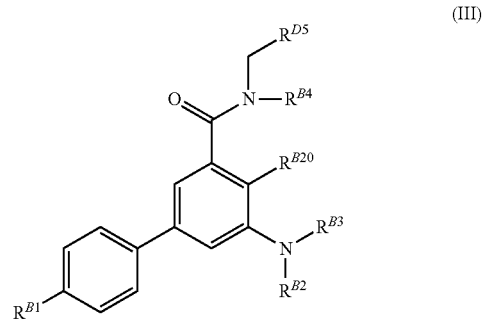

17 Claims, 3 Drawing Sheets

(51) Int. Cl.
  *C07D 405/12* (2006.01)
  *C07D 401/12* (2006.01)
  *C07D 413/14* (2006.01)

(58) Field of Classification Search
  USPC .......................................................... 546/255
  See application file for complete search history.

(56) References Cited

U.S. PATENT DOCUMENTS

| | | | |
|---|---|---|---|
| 8,895,245 B2* | 11/2014 | Copelandˌ........... | A61K 31/7076 435/6.11 |
| 9,175,331 B2 | 11/2015 | Kuntz et al. | |
| 9,562,041 B2* | 2/2017 | Burgess ............... | C07D 213/64 |
| 2008/0305113 A1 | 12/2008 | Kwon et al. | |
| 2012/0014979 A1 | 1/2012 | Dent et al. | |
| 2013/0040906 A1 | 2/2013 | Kuntz et al. | |
| 2013/0059849 A1 | 3/2013 | Burgess et al. | |
| 2013/0184264 A1 | 7/2013 | Bradner et al. | |
| 2013/0280332 A1 | 10/2013 | Moss et al. | |
| 2013/0317026 A1 | 11/2013 | Kuntz et al. | |
| 2015/0126522 A1 | 5/2015 | Burgess et al. | |
| 2016/0022693 A1 | 1/2016 | Kuntz et al. | |
| 2018/0297993 A1 | 10/2018 | Bradner et al. | |
| 2019/0000860 A1 | 1/2019 | Bradner et al. | |

FOREIGN PATENT DOCUMENTS

| | | |
|---|---|---|
| WO | WO 2011/14032 A1 | 11/2011 |
| WO | WO 2011/140324 A1 | 11/2011 |
| WO | WO 2012/005805 A1 | 1/2012 |
| WO | WO 2012/118812 A2 | 9/2012 |
| WO | WO 2013/039988 A1 | 3/2013 |
| WO | WO 2013/049770 A2 | 4/2013 |
| WO | WO 2013/067296 A1 | 5/2013 |
| WO | WO 2013/067300 A1 | 5/2013 |
| WO | WO 2013/067302 A1 | 5/2013 |
| WO | 2013138361 * | 9/2013 |
| WO | WO 2013/155464 A1 | 10/2013 |
| WO | 2013173441 * | 11/2013 |
| WO | WO 2013/173441 A2 | 11/2013 |
| WO | WO 2014/100080 A1 | 6/2014 |
| WO | WO 2014/100646 A1 | 6/2014 |
| WO | WO 2014/100665 A1 | 6/2014 |
| WO | WO 2014/155301 A1 | 10/2014 |
| WO | WO 2015/010049 A1 | 1/2015 |
| WO | WO 2015/077193 A1 | 5/2015 |
| WO | 2015110999 * | 7/2015 |

OTHER PUBLICATIONS

International Search Report and Written Opinion for PCT/US15/59622, dated Mar. 30, 2016.
International Preliminary Report on Patentability for PCT/US15/59622, dated May 18, 2017.
International Search Report and Written Opinion for PCT/US2015/059551, dated Jan. 13, 2016.
International Preliminary Report on Patentability for PCT/US2015/059551, dated May 18, 2017.
Invitation to Pay Additional Fees for PCT/US17/28885, dated Jul. 10, 2017.
International Search Report and Written Opinion for PCT/US17/28885, dated Sep. 8, 2017.
International Preliminary Report on Patentability for PCT/US17/28885, dated Nov. 1, 2018.
Partial Supplementary European Search Report for EP 15 856 340.3, dated Mar. 27, 2018.
Partial Supplementary European Search Report for EP 15 857 195.0, dated Apr. 16, 2018.
Extended European Search Report for EP 15856340.3, dated Jul. 6, 2018.
Extended European Search Report for EP 15857195.0, dated Jul. 26, 2018.
[No Author Listed] "Methanesulfonyl chloride: Difference between revisions." Wikipedia Entry, Mar. 28, 2014. https://en.wikipedia.org/w/index.php?title=Methanesulfonyl_chloride&d.
[No Author Listed] PubChem CID 55504609. Create date: Jan. 25, 2012.
[No Author Listed] PubChem CID 56267130. Create date: Jan. 25, 2012.
Beguelin et al., EZH2 is required for germinal center formation and somatic EZH2 mutations promote lymphoid transformation. Cancer Cell. May 13, 2013;23(5):677-92. doi: 10.1016/j.ccr.2013.04.011.
Campbell et al., EPZ011989, A Potent, Orally-Available EZH2 Inhibitor with Robust in Vivo Activity. ACS Med Chem Lett. Mar. 4, 2015;6(5):491-5. doi: 10.1021/acsmedchemlett.5b00037. eCollection May 14, 2015.
Czermin et al., *Drosophila* enhancer of Zeste/ESC complexes have a histone H3 methyltransferase activity that marks chromosomal Polycomb sites. Cell. Oct. 18, 2002;111(2):185-96.
Flynn et al., Increased T follicular helper cells and germinal center B cells are required for cGVHD and bronchiolitis obliterans. Blood. Jun. 19, 2014;123(25):3988-98. doi: 10.1182/blood-2014-03-562231. Epub May 12, 2014.
He et al., The histone methyltransferase Ezh2 is a crucial epigenetic regulator of allogeneic T-cell responses mediating graft-versus-host disease. Blood. Dec. 12, 2013;122(25):4119-28. doi: 10.1182/blood-2013-05-505180. Epub Oct. 18, 2013.
Knutson et al., A selective inhibitor of EZH2 blocks H3K27 methylation and kills mutant lymphoma cells. Nat Chem Biol. Nov. 2012;8(11):890-6. doi: 10.1038/nchembio.1084. Epub Sep. 30, 2012.
Konze et al., An orally bioavailable chemical probe of the Lysine Methyltransferases EZH2 and EZH1. ACS Chem Biol. 2013;8(6):1324-34. doi: 10.1021/cb400133j. Epub Apr. 24, 2013.
Verma et al., Identification of Potent, Selective, Cell-Active Inhibitors of the Histone Lysine Methyltransferase EZH2. ACS Med Chem Lett. Oct. 19, 2012;3(12):1091-6. doi: 10.1021/ml3003346. eCollection Dec. 13, 2012.
[No Author Listed], FCH Group, "Products". Online http://web.archive.org/web/20120317091129/http://www.fchgroup.net/. Dated Mar. 17, 2012, accessed Oct. 12, 2016.
STN Chemical Database entry for 1-(2-furanylmethyl)-N-[(2-methoxyphenyl)methyl]-6-(3-pyridinyl)-1H-Pyrazolo[3,4-b]pyridine-4-carboxamide RN 1296983-00-0 Entered STN: May 19, 2011, LC STN Files: CHEMCATS.
Wermuth, Molecular Variation Based on Isosteric Replacements. Chapter 13, The Practice of Medicinal Chemistry, Academic: 1996, pp. 203-237.
Wislicenus, Adolph Strecker's Short Textbook of Organic Chemistry. 1881, Spottiswoode: London, pp. 38-39.
Supplementary European Search Report on Patentability for EP17786731, dated Sep. 16, 2019.
[No Author Listed], CAS Registry and CAS registry No. FAQs. 2018. Last accessed at haps://www.cas.org/support/documentation/chemical-substances/faqs on Sep. 14, 2018.
[No Author Listed], Chemcats Supplier Data Submission. 2018. Last accessed at https://www.cas.org/products/chemcats/chemical-suppliers/data-submission on Sep. 14, 2018.
[No Author Listed], Chemist Consultation Substance Identification. 2018. Last accessed at https://www.cas.org/services/knowledge/chemist-consultation on Sep. 14, 2018.
[No Author Listed], ClientServices Chemist Consultation Order Form Substance Identification. 2018. Last accessed at https://www.cas.org/sites/default/files/documents/chemconsultform_v0.pdf on Sep. 14, 2018.
Eikel et al., Liquid extraction surface analysis mass spectrometry (LESA-MS) as a novel profiling tool for drug distribution and metabolism analysis: the terfenadine example. Rapid Commun Mass Spectrom. Dec. 15, 2011;25(23):3587-96. doi: 10.1002/rcm.5274.
Nguyen et al., Chiral drugs: an overview.Int J Biomed Sci. Jun. 2006;2(2):85-100.

(56) References Cited

OTHER PUBLICATIONS

Shaikh, The changing face of antihistamines and cardiac adverse drug reactions: a clinical perspective. J. Indian Med Assoc. 2000;98(7):397-99.
Stefan-Van Staden, Enantioanalysis of S-Ibuprofen using [5-6] fullerene-C70 and diethyl (1,2-methanofullerene C70)-71-71-dicarboxy ate. R. Anal. Methods 2010;2:37-40.
STN Chemical Database entry for N-[ (2, 5-dimethoxyphenyl)methyl]-1-(2-furanyl methyl)-6-(3-pyridi nyl)-1 H-Pyrazolo[3 ,4-b ]pyridine-4-carboxamide, RN 1296380-48-7 Entered STN: May 18, 2011, LC STN Files: CHEMCATS.
EP17786731, Sep. 16, 2019, Supplementary European Search Report.

\* cited by examiner

| | Y641C | | Y641N | | Y641S | | WT | |
|---|---|---|---|---|---|---|---|---|
| Pre-incubation time | 10 min | 60 min | 10 min | 60 min | 10 min | 60 min | 10 min | 60 min |
| UNC1999 | 162.10 | 126.40 | 51.78 | 33.72 | 26.43 | 24.18 | 27.10 | 31.20 |
| EZ-40 | 19220.00 | 8725.00 | 9043.00 | 1135.00 | 6500.00 | 1845.00 | 415.60 | 116.00 |

Figure 1B. $IC_{50}$ (nM)

| | EZH1-15min | EZH1-60 min | Time dependence | | EZH2-15min | EZH2-60 min | Time dependence | EZH2/EZH1 (60 min) |
|---|---|---|---|---|---|---|---|---|
| EZ-40 | 2.61E-06 | 4.87E-06 | 0.54 | EZ-40 | 3.85E-07 | 1.59E-07 | 2.43 | 30.69 |
| EZ-49 | 3.42E-06 | 3.19E-06 | 1.07 | EZ-49 | 2.64E-07 | 2.98E-07 | 0.89 | 10.70 |
| EZ-51 | 4.46E-07 | 5.38E-07 | 0.83 | EZ-51 | 2.75E-08 | 2.47E-08 | 1.12 | 21.84 |
| EZ-52 | 7.21E-06 | 6.41E-06 | 1.12 | EZ-52 | 4.45E-07 | 5.27E-07 | 0.84 | 12.15 |
| JQ-80 | 2.63E-05 | 1.51E-05 | 1.74 | JQ-80 | 1.09E-06 | 1.06E-06 | 1.02 | 14.20 |
| EZ-53 | 7.82E-07 | 5.67E-07 | 1.38 | EZ-53 | 3.03E-08 | 1.87E-08 | 1.63 | 30.39 |

Figure 2A

| | EZH1 | EZH2 | EZH2 selectivity | | EZH2-15min | EZH2-60 min | Time dependence |
|---|---|---|---|---|---|---|---|
| UNC1999 | 1.27E-07 | 5.43E-09 | 23.40 | EZ-40 | 8.35E-07 | 3.75E-07 | 2.23 |
| EZ-48 | 3.39E-06 | 1.48E-07 | 22.95 | EZ-49 | 8.49E-07 | 5.11E-07 | 1.66 |
| EZ-50 | 4.62E-06 | 4.76E-07 | 9.70 | EZ-51 | 6.54E-08 | 7.18E-08 | 0.91 |
| | | | | EZ-52 | 1.26E-06 | 9.43E-07 | 1.33 |
| | | | | JQ-80 | 3.57E-06 | 3.44E-06 | 1.04 |
| | | | | EZ-53 | 1.17E-07 | 1.48E-07 | 0.79 |

Figure 2B

EZH2 INHIBITORS AND USES THEREOF

RELATED APPLICATIONS

This application is a national stage filing under 35 U.S.C. § 371 of international PCT application, PCT/US2017/028885, filed Apr. 21, 2017, which claims priority under 35 U.S.C. § 119(e) to U.S. Provisional Application, U.S. Ser. No. 62/326,036, filed Apr. 22, 2016, each of which is incorporated herein by reference.

BACKGROUND OF THE INVENTION

Chromatin structure contains important regulatory information for all DNA-based processes, such as transcription, repair, and replication. The polycomb group (PcG) and trithorax group (TrxG) protein complexes regulate chromatin structure through evolutionarily conserved mechanisms in eukaryotes for gene silencing or activation, respectively (Schuettengruber et al., 2007). Polycomb proteins assemble into at least two distinct complexes, the polycomb repressive complexes 1 and 2 (PRC1 and PRC2, respectively). Several lines of evidence suggest that PCR2 is involved in recruiting the PRC1 complex to promoters of their common target genes. A delicate balance of PcG protein levels ensures proper cell proliferation and normal tissue homeostasis while abnormal expression patterns or genomic alterations in PcG proteins can result in transcriptional dysregulation and cause various diseases including cancer (Laugesen and Helin, 2014).

Histone tails extruding from the nucleosome core are subject to multiple modifications including phosphorylation, acetylation, methylation, ubiquitination, and sumoylation. Histone modifications exert substantial influence on transcriptional regulation by modulating higher-order chromatin structures. There are two functional states of chromatin: euchromatin and heterochromatin, which are transcriptionally active and inactive, respectively. Some histone modifications, such as tri-methylation at histone 4 lysine 20 (H4K20me3), histone 3 lysine 9 (H3K9me3) or lysine 79 (H3K79me3), predominantly occur in constitutive heterochromatin domains; whereas others, such as tri-methylation at histone 3 lysine 4 (H3K4me3) and acetylation at histone 3 lysine 27 (H3K27ac), are regarded as hallmarks of actively transcribed regions in euchromatin. Tri-methylation at histone 3 lysine 27 (H3K27me3) is generally associated with transcriptional repression in higher eukaryotes (Cao et al., 2002; Czermin et al., 2002; Muller et al., 2002). Bivalent domains, termed by the paradoxical coexistence of repressive mark H3K27me3 and activating mark H3K4me3, keep developmental genes in a silent but poised state for activation upon differentiation (Chen and Dent, 2014).

Enhancer of zeste homolog 2 (EZH2) is core component of PRC2 that catalyzes the di- and tri-methylation at histone H3 lysine 27 (H3K27me2/3). EZH2 plays a critical role in normal development, and EZH2-deficient mice died at early stage of embryo due to the failure of implantation and gastrulation (O'Carroll et al., 2001). Somatic mutations in the SET domain of EZH2 (e.g., Y641N) resulting hyperactivity of the enzyme have been identified in a large portion of follicular and diffuse large B-cell lymphomas, implicating a driver function of EZH2 in cancer formation (Beguelin et al., 2013; Morin et al., 2010). A GEM model with conditional expression of mutant EZH2 (Y641N) was recently developed, which induced germinal center (GC) hyperplasia and accelerates lymphomagenesis in cooperation with BCL2 (Beguelin et al., 2013).

SUMMARY OF THE INVENTION

In one aspect, described herein are compounds of the Formulae (I), (II), and (III), and pharmaceutically acceptable salts, solvates, hydrates, polymorphs, co-crystals, tautomers, stereoisomers, isotopically labeled derivatives, and prodrugs thereof. The compounds described herein are inhibitors of histone methyltransferases (HMTs, e.g., enhancer of zeste homolog 1 (EZH1), enhancer of zeste homolog 2 (EZH2)). The compounds described herein are inhibitors of EZH1. The compounds described herein are inhibitors of EZH2. The compounds are useful in treating and/or preventing diseases associated with aberrant or increased activity of an HMT, e.g., proliferative disease, inflammatory disease, autoimmune disease, genetic disease, hematological disease, neurological disease, painful condition, psychiatric disorder, or metabolic disorder, in a subject in need thereof. The compounds are also useful in inducing apoptosis in a cell. Also provided are pharmaceutical compositions, kits, methods, and uses including a compound described herein.

In one aspect, the present disclosure provides compounds of Formula (I):

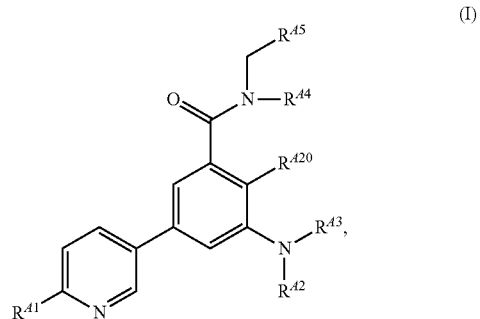

and pharmaceutically acceptable salts, solvates, hydrates, polymorphs, co-crystals, tautomers, stereoisomers, isotopically labeled derivatives, and prodrugs thereof, wherein $R^{A1}$, $R^{A2}$, $R^{A3}$, $R^{A4}$, $R^{A5}$, and $R^{A20}$ are defined herein. Formula (I) requires that at least one of $R^{A2}$, $R^{A10}$, $R^{A12}$, and $R^{A17}$ is a warhead; and/or at least one of $R^{A1}$ and $R^{A2}$ is a tag; and/or when $R^{A2}$ is of the formula,

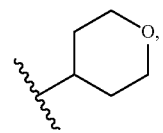

$R^{A3}$ is not substituted or unsubstituted $C_{1-3}$ alkyl. In Formula (I), $R^{A5}$ is of the formula:

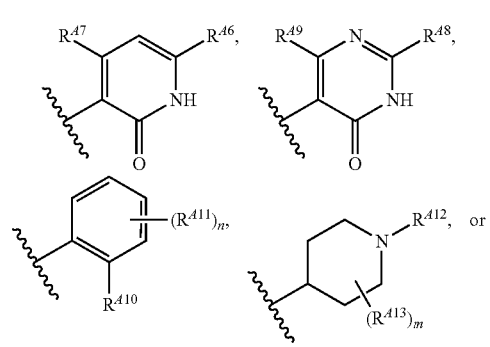
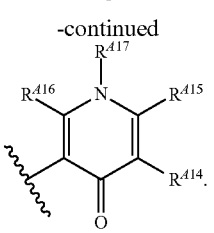
Exemplary compounds of Formula (I) include, but are not limited to:
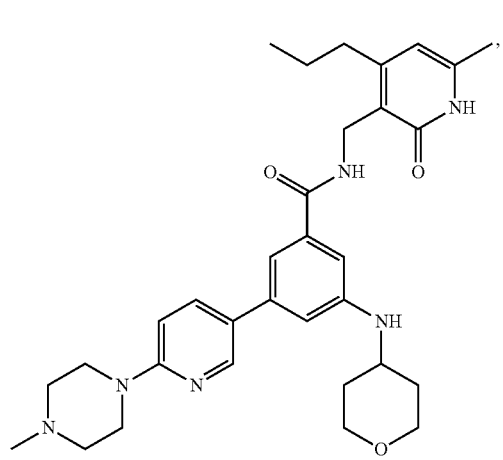
(EZ-46)
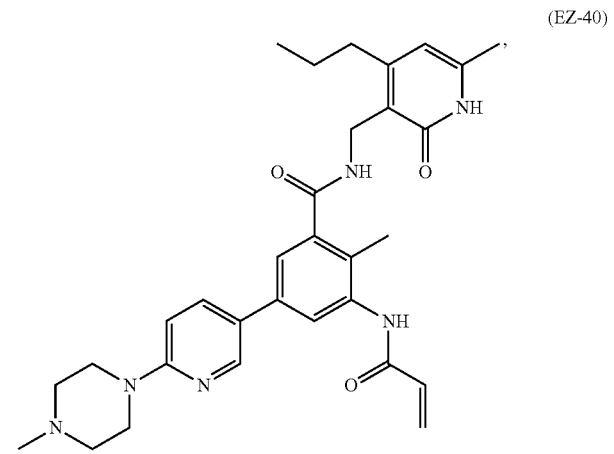
(EZ-40)
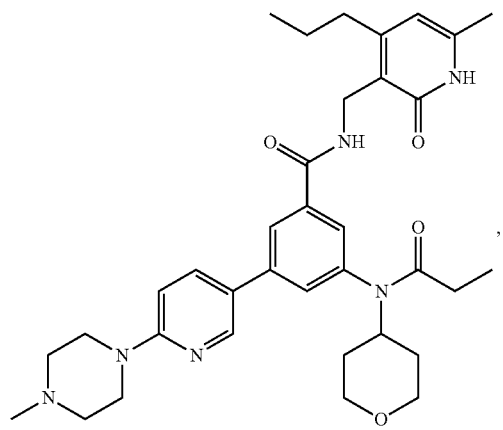
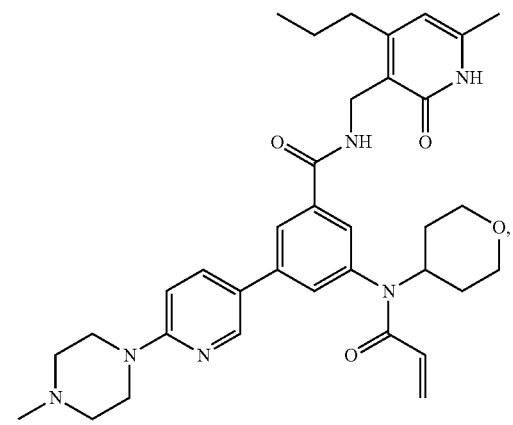

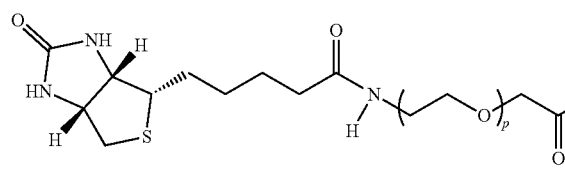
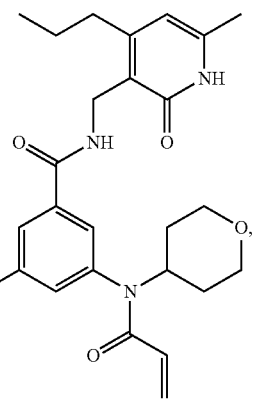
wherein p is an integer between 2 and 20, inclusive; and q is an integer between 2 and 10, inclusive;
(EZ-48)
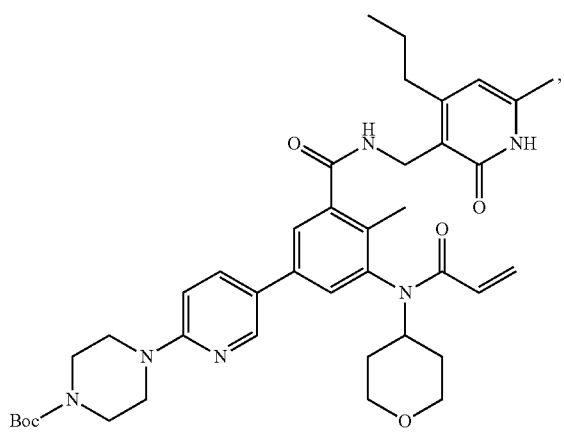
-continued
(EZ-23)
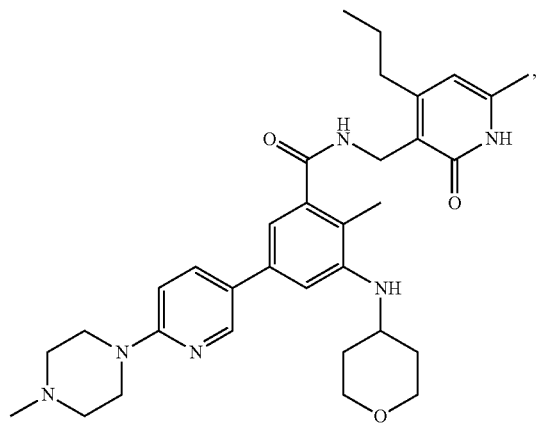
(EZ-49)
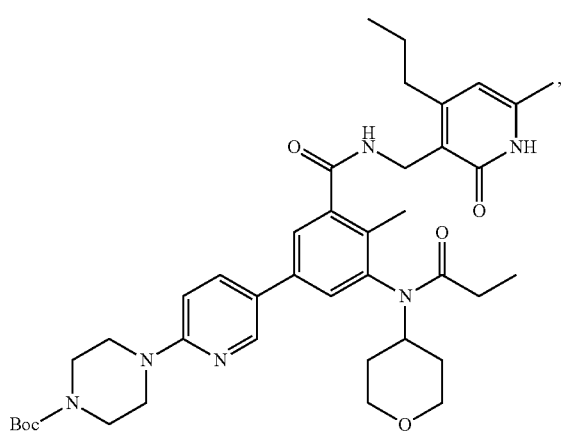
(EZ-53)
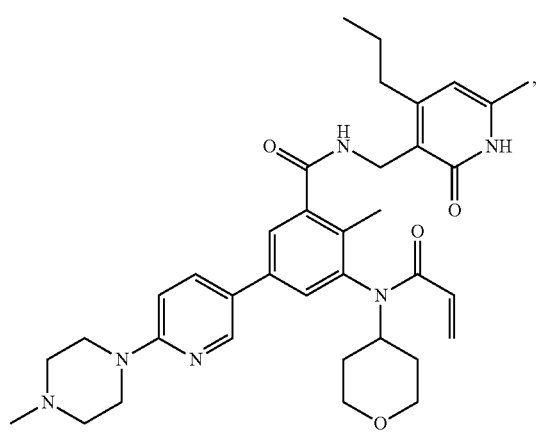

(JQ-80)

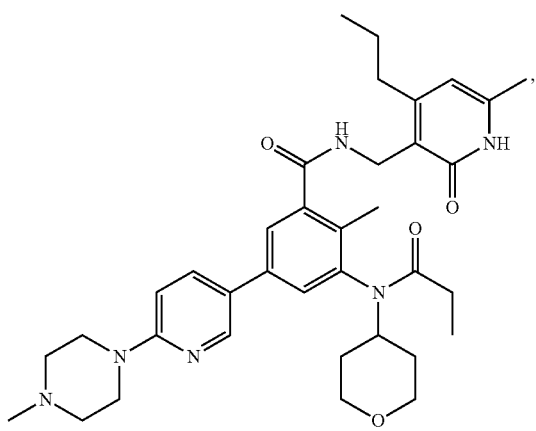

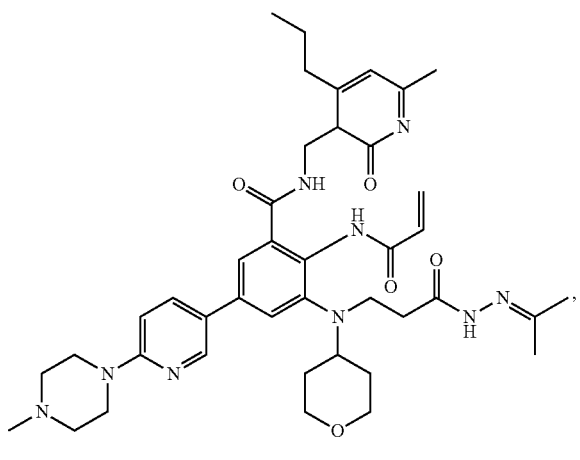

and pharmaceutically acceptable salts, solvates, hydrates, polymorphs, co-crystals, tautomers, stereoisomers, isotopically labeled derivatives, and prodrugs thereof.

In another aspect, the present disclosure provides compounds of Formula (II):

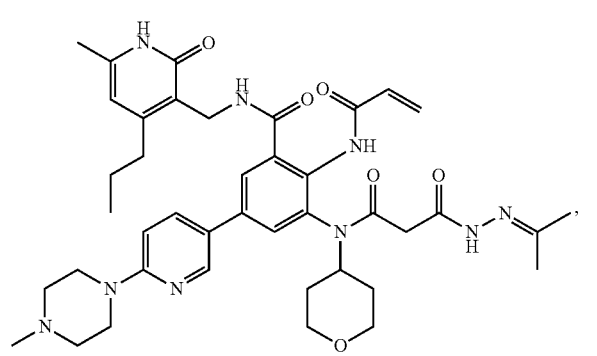

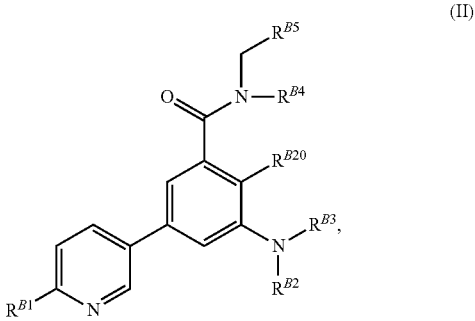

and pharmaceutically acceptable salts, solvates, hydrates, polymorphs, co-crystals, tautomers, stereoisomers, isotopically labeled derivatives, and prodrugs thereof, wherein $R^{B1}$, $R^{B2}$, $R^{B3}$, $R^{B4}$, $R^{B5}$, and $R^{B20}$ are defined herein. Formula (II) does not have the Formula (I) requirement that at least one of $R^{A2}$, $R^{A10}$, $R^{A12}$, and $R^{A17}$ is a warhead; and/or at least one of $R^{A1}$ and $R^{A2}$ is a tag; and/or when $R^{A2}$ is of the formula.

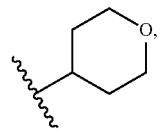

$R^{A3}$ is not substituted or unsubstituted $C_{1-3}$ alkyl. In Formula (II), $R^{B5}$ is of the formula:

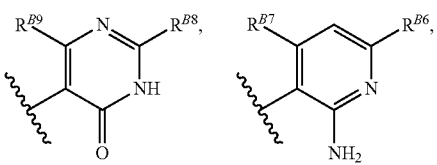

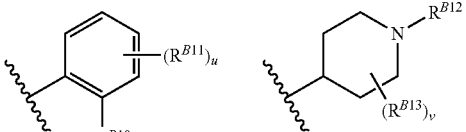

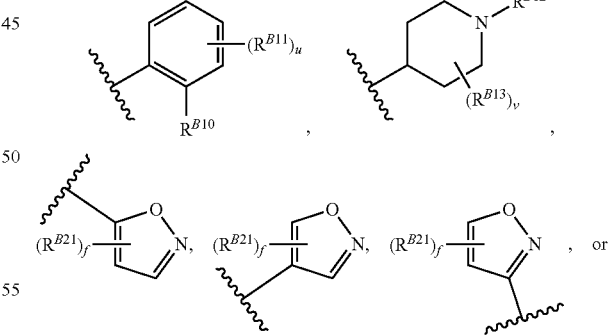

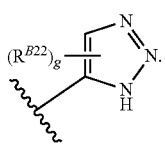

Exemplary compounds of Formula (II) include, but are not limited to:

9
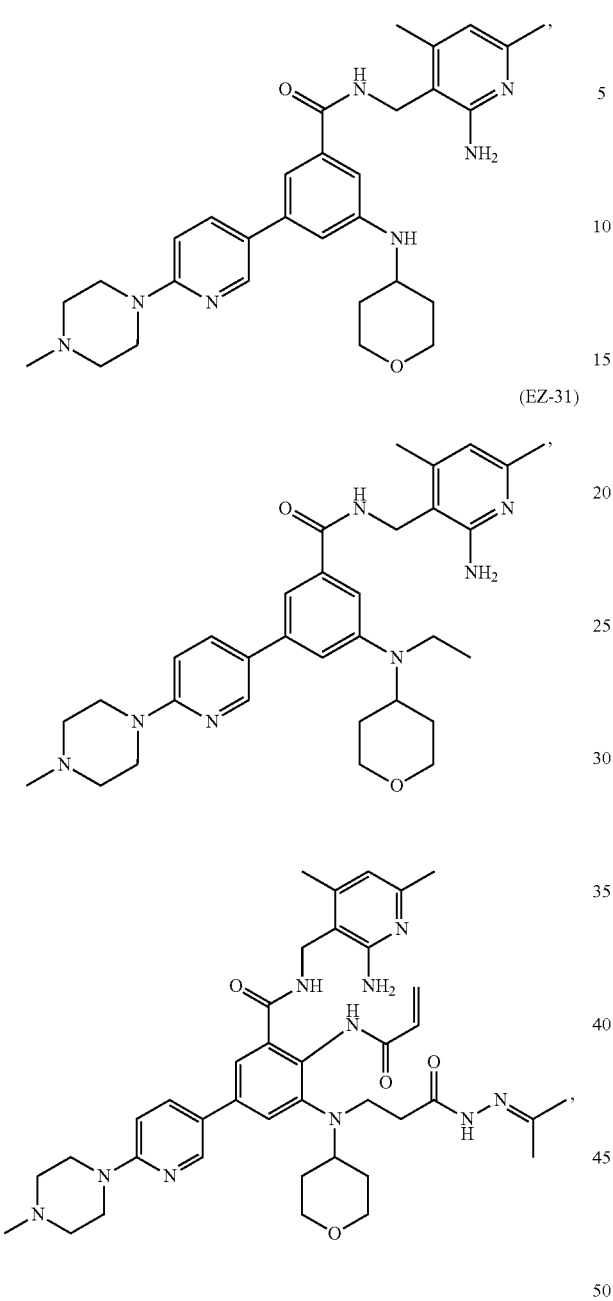
(EZ-31)
10
-continued
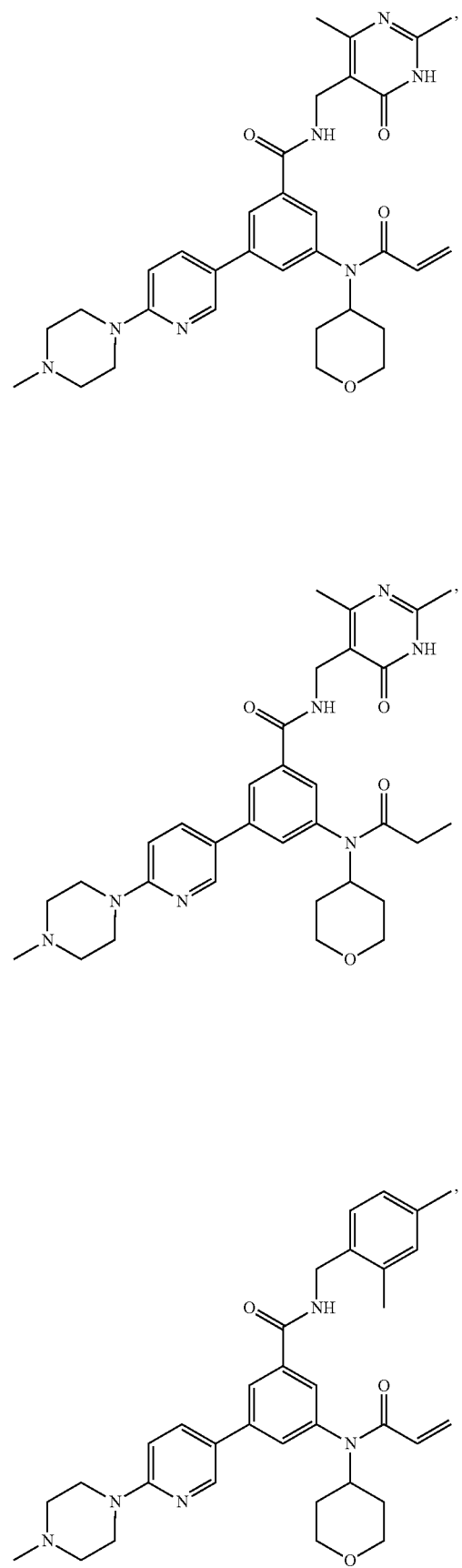

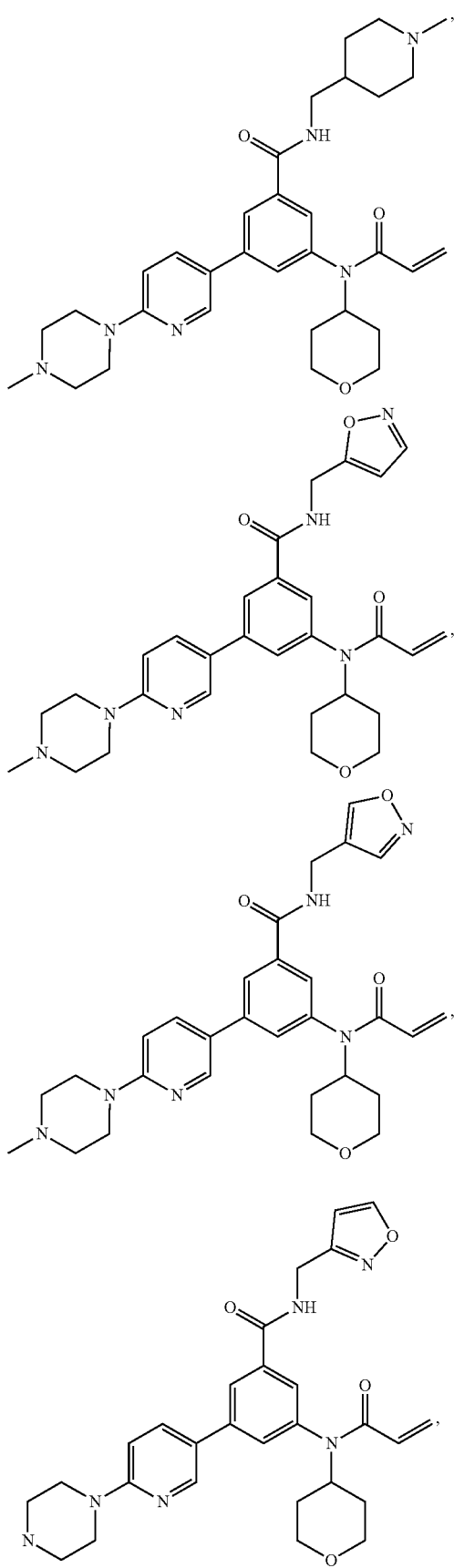

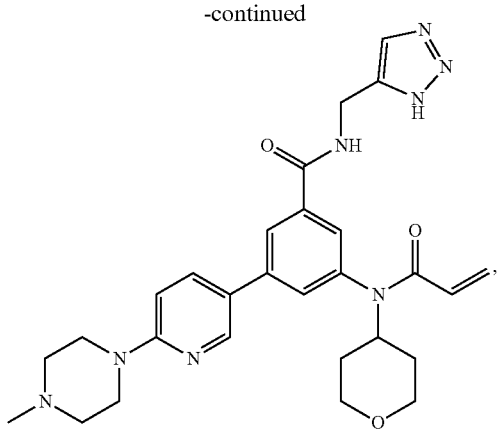

and pharmaceutically acceptable salts, solvates, hydrates, polymorphs, co-crystals, tautomers, stereoisomers, isotopically labeled derivatives, and prodrugs thereof.

In another aspect, the present disclosure provides compounds of Formula (III):

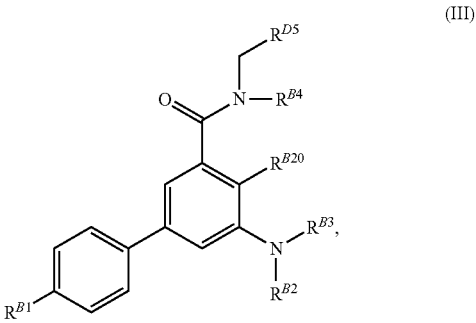

and pharmaceutically acceptable salts, solvates, hydrates, polymorphs, co-crystals, tautomers, stereoisomers, isotopically labeled derivatives, and prodrugs thereof, wherein $R^{B1}$, $R^{B2}$, $R^{B3}$, $R^{B4}$, $R^{D5}$, and $R^{B20}$ are defined herein. In Formula (III), $R^{D5}$ is of the formula:

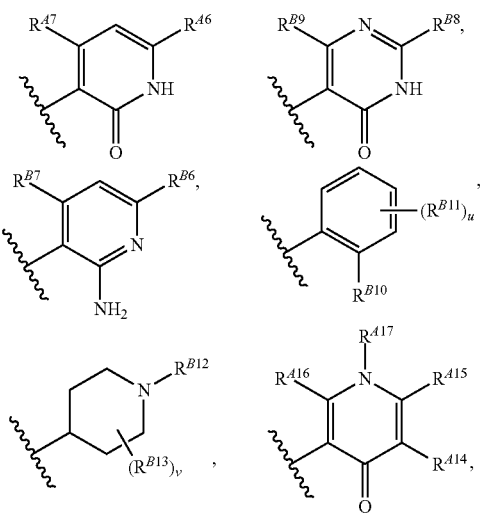

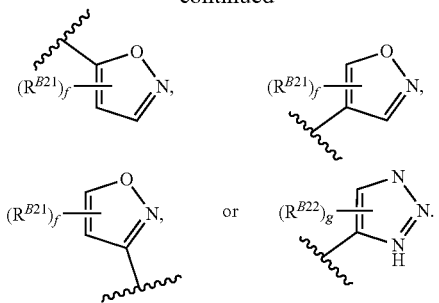

Exemplary compounds of Formula (III) include, but are not limited to:

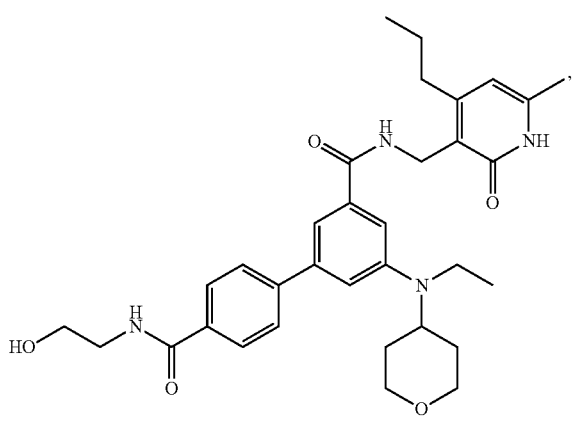

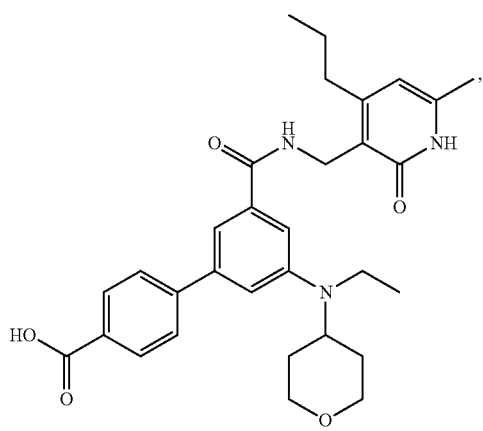

and pharmaceutically acceptable salts, solvates, hydrates, polymorphs, co-crystals, tautomers, stereoisomers, isotopically labeled derivatives, and prodrugs thereof.

In another aspect, described herein are pharmaceutical compositions including a compound described herein, and optionally a pharmaceutically acceptable excipient. In certain embodiments, a pharmaceutical composition described herein includes a therapeutically or prophylactically effective amount of a compound described herein. In certain embodiments, a pharmaceutical composition described herein further comprises an additional pharmaceutical agent. The pharmaceutical compositions may be useful in modulating (e.g., inhibiting) the activity of an HMT (e.g., EZH1, EZH2, DOT1) in a subject, biological sample, tissue, or cell; in treating a disease (e.g., a proliferative disease) in a subject in need thereof; or in preventing a disease in a subject in need thereof.

In certain embodiments, the disease is a disease associated with aberrant activity of an HMT. In certain embodiments, the aberrant activity of an HMT (e.g., EZH1, EZH2, DOT1) is increased activity of the HMT. In certain embodiments, the disease is a disease associated with increased activity of an HMT (e.g., EZH1, EZH2, DOT1) compared with a normal cell. In certain embodiments, the disease is a proliferative disease (e.g., cancer, benign neoplasm, pathological angiogenesis), inflammatory disease, autoimmune disease, genetic disease, hematological disease, neurological disease, painful condition, psychiatric disorder, or metabolic disorder.

In certain embodiments, the subject is a human. In certain embodiments, the subject is a non-human animal. In certain embodiments, the cell is in vitro. In certain embodiments, the cell is in vivo.

In still another aspect, described herein are kits including a container with a compound or pharmaceutical composition described herein. A kit described herein may include a single dose or multiple doses of the compound or pharmaceutical composition. The described kits may be useful in inhibiting the activity of an HMT (e.g., EZH1, EZH2, DOT1) in a subject, biological sample, tissue, or cell, in treating a disease associated with aberrant activity of an HMT (e.g., EZH1, EZH2, DOT1) in a subject in need thereof, in preventing a disease associated with aberrant activity of an HMT (e.g., EZH1, EZH2, DOT1) in a subject in need thereof, in treating a disease (e.g., proliferative disease, inflammatory disease, autoimmune disease, genetic disease, hematological disease, neurological disease, painful condition, psychiatric disorder, or metabolic disorder) in a subject in need thereof, and/or in preventing a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, a kit described herein further includes instructions for using the compound or pharmaceutical composition included in the kit.

In another aspect, the present disclosure provides methods of modulating (e.g., inhibiting) the aberrant activity of an HMT (e.g., EZH1, EZH2, DOT1) in a subject in need thereof, the methods comprising administering to the subject a therapeutically effective amount of a compound or pharmaceutical composition described herein.

In another aspect, the present disclosure provides methods of modulating (e.g., inhibiting) the activity of an HMT (e.g., EZH1, EZH2, DOT1) in a biological sample, tissue, or cell, the methods comprising contacting the biological sample, tissue, or cell with an effective amount of a compound or pharmaceutical composition described herein.

In certain embodiments, the compound being administered or used selectively inhibits the activity of a particular HMT (e.g., EZH1, EZH2, DOT1). When a compound, pharmaceutical composition, method, use, or kit is referred to as "selectively," "specifically," or "competitively" inhibiting an HMT, the compound, pharmaceutical composition, method, use, or kit inhibits the HMT to a greater extent (e.g., not less than 2-fold, not less than 5-fold, not less than 10-fold, not less than 30-fold, not less than 100-fold, not less than 1,000-fold, or not less than 10,000-fold; and/or: not more than 2-fold, not more than 5-fold, not more than 10-fold, not more than 30-fold, not more than 100-fold, not more than 1,000-fold, or not more than 10,000-fold) than inhibiting a different HMT.

In another aspect, the present disclosure provides methods of inducing apoptosis in a cell, the methods comprising contacting the cell with an effective amount of a compound or pharmaceutical composition described herein.

Another aspect of the present disclosure relates to methods of treating a disease in a subject in need thereof, the methods comprising administering to the subject a therapeutically effective amount of a compound or pharmaceutical composition described herein.

In another aspect, the present disclosure provides methods of preventing a disease in a subject in need thereof, the methods comprising administering to the subject a prophylactically effective amount of a compound or pharmaceutical composition described herein.

Another aspect of the present disclosure relates to methods of decreasing the methylation of a histone in a subject in need thereof, the methods comprising administering to the subject an effective amount of a compound or pharmaceutical composition described herein.

Another aspect of the present disclosure relates to methods of decreasing the methylation of a histone in a biological sample, tissue, or cell, the methods comprising contacting the biological sample, tissue, or cell with an effective amount of a compound or pharmaceutical composition described herein.

Another aspect of the present disclosure relates to methods of modulating (e.g., down-regulating or up-regulating) the expression of a gene in a subject in need thereof, the methods comprising administering to the subject an effective amount of a compound or pharmaceutical composition described herein.

Another aspect of the present disclosure relates to methods of modulating (e.g., down-regulating or up-regulating) the expression of a gene in a biological sample, tissue, or cell, the methods comprising contacting the biological sample, tissue, or cell with an effective amount of a compound or pharmaceutical composition described herein.

Another aspect of the disclosure relates to methods of screening a library of compounds to identify a compound that is useful in a method described herein.

In yet another aspect, the present disclosure provides compounds and pharmaceutical compositions described herein for use in a method of the disclosure (e.g., a method of inhibiting the aberrant activity of an HMT, a method of inducing apoptosis, a method of treating a disease (e.g., a proliferative disease), or a method of preventing a disease (e.g., a proliferative disease)).

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=$CHCH_3$ or 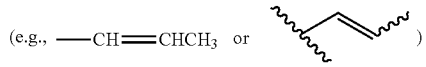)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like.

As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —C, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, hydrogen, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$+X$^-$, —NH(C$_{1-6}$ alkyl)$_2$+X$^-$, —NH$_2$(C$_{1-6}$ alkyl)+X$^-$, —NH$_3$+X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3rd edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1- methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $-S(=O)_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, o-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —C(=O)$SR^{aa}$, —C(=O)$R^{aa}$, —$CO_2R^{aa}$, —C(=O)$N(R^{bb})_2$, —C(=$NR^{bb}$)$R^{aa}$, —C(=$NR^{bb}$)$OR^{aa}$, —C(=$NR^{bb}$)$N(R^{bb})_2$, —S(=O)$R^{aa}$, —$SO_2R^{aa}$, —Si$(R^{aa})_3$, —P$(R^{cc})_2$, —P$(R^{cc})_3^+X^-$, —P$(OR^{cc})_2$, —P$(OR^{cc})_3^+X^-$, —P(=O)$(R^{aa})_2$, —P(=O)$(OR^{cc})_2$, and —P(=O)$(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March Advanced Organic Chemistry 6th ed. (501-502). Exemplary leaving groups include, but are not limited to, halo (e.g., chloro, bromo, iodo) and activated substituted hydroxyl groups (e.g., —OC(=O)$SR^{aa}$, —OC(=O)$R^{aa}$, —$OCO_2R^{aa}$, —OC(=O)$N(R^{bb})_2$, —OC(=$NR^{bb}$)$R^{aa}$, —OC(=$NR^{bb}$)$OR^{aa}$, —OC(=$NR^{bb}$)$N(R^{bb})_2$, —OS(=O)$R^{aa}$, —$OSO_2R^{aa}$, —OP$(R^{cc})_2$, —OP$(R^{cc})_3$, —OP(=O)$_2R^{aa}$, —OP(=O)$(R^{aa})_2$, —OP(=O)$(OR^{cc})_2$, —OP(=O)$_2N(R^{bb})_2$, and —OP(=O)$(NR^{bb})_2$, wherein $R^{aa}$, $R^{bb}$, and $R^{cc}$ are as defined herein).

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —CH($C_2H_5$)— is a $C_1$ hydrocarbon chain, and

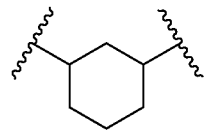 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C≡C—$CH_2$—, and —C≡C—CH=CH— are all examples of a unsubstituted and unsaturated hydrocarbon chain. In certain embodiments, the hydrocarbon chain is unsubstituted (e.g., —C≡C— or —$(CH_2)_4$—). In certain embodiments, the hydrocarbon chain is substituted (e.g., —CH($C_2H_5$)— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

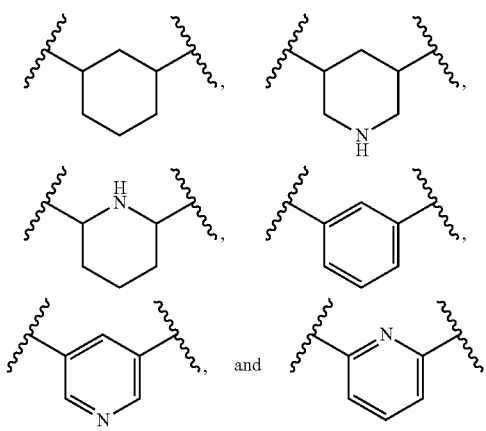

are all examples of a hydrocarbon chain. In contrast, in certain embodiments,

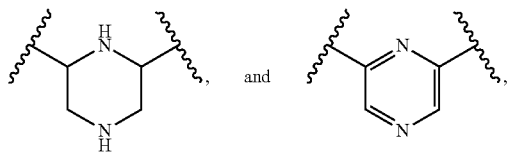 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

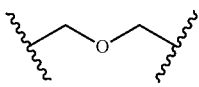 [SMILES: *COC*]

is a $C_3$ hydrocarbon chain wherein one chain atom is replaced with an oxygen atom.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R\cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R\cdot 0.5\ H_2O$)), and polyhydrates (x is a number greater than 1, e.g., dihydrates ($R\cdot 2\ H_2O$) and hexahydrates ($R\cdot 6\ H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "small molecule drug" refers to a small molecule that has been approved by a governmental agency (e.g., FDA) for administering to a subject (e.g., human or non-human aminal), or a radical of such a small molecule.

The term "small molecule label" refers to a small molecule that is capable of being detected, or a radical of such a small molecule. Exemplary small molecule labels include, but are not limited to, biotin, radioactive isotopes, enzymes, luminescent agents, precipitating agents, fluorophores, and dyes.

The term "small molecule fluorophore" refers to a small molecule that is fluorescent, e.g., being able to re-emit light upon light excitation. Exemplary small molecule fluorophores include, but are not limited to, fluorescein, rhodamine, coumarin, cyanine, and derivatives thereof.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonucleotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

Polynucleotides described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., *Nucl. Acids Res.*, 16, 3209, (1988), methylphosphonate oligonucleotides can be prepared by use of controlled pore glass polymer supports (Sarin et al., *Proc. Natl. Acad. Sci. U.S.A.* 85, 7448-7451, (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Any type of plasmid, cosmid, yeast artificial chromosome, or viral vector can be used to prepare the recombinant DNA construct that can be introduced directly into the tissue site.

The polynucleotides may be flanked by natural regulatory (expression control) sequences or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications, such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, isotopes (e.g., radioactive isotopes), biotin, and the like.

As used herein the term "inhibit" or "inhibition" in the context of enzymes, for example, in the context of a histone methyltransferase, refers to a reduction in the activity of the enzyme. In some embodiments, the term refers to a reduction of the level of enzyme activity, e.g., an histone methyltransferase activity, to a level that is statistically significantly lower than an initial level, which may, for example, be a baseline level of enzyme activity. In some embodiments, the term refers to a reduction of the level of enzyme activity, e.g., (TARGET) activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

When a compound, pharmaceutical composition, method, use, or kit is referred to as "selectively," "specifically," or "competitively" inhibiting an HMT, the compound, pharmaceutical composition, method, use, or kit inhibits the HMT to a greater extent (e.g., not less than 2-fold, not less than 5-fold, not less than 10-fold, not less than 30-fold, not less than 100-fold, not less than 1,000-fold, or not less than 10,000-fold; and/or: not more than 2-fold, not more than 5-fold, not more than 10-fold, not more than 30-fold, not more than 100-fold, not more than 1,000-fold, or not more than 10,000-fold) than inhibiting a different HMT.

The term "aberrant activity" refers to activity deviating from normal activity. In certain embodiments, the aberrant activity is increased activity. In certain embodiments, the aberrant activity is decreased activity. The term "increased activity" refers to activity higher than normal activity. The term "decreased activity" refers to activity lower than normal activity.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount effective to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "histone" refers to highly alkaline proteins found in eukaryotic cell nuclei that package and order DNA into structural units called nucleosomes. They are the chief protein components of chromatin, acting as spools around which DNA winds, and play a role in gene regulation. In certain embodiments, the histone is histone H1 (e.g., histone H1F, histone H1H1). In certain embodiments, the histone is histone H2A (e.g., histone H2AF, histone H2A1, histone H2A2). In certain embodiments, the histone is histone H2B (e.g., histone H2BF, histone H2B1, histone H2B2). In certain embodiments, the histone is histone H3 (e.g., histone H3A1, histone H3A2, histone H3A3). In certain embodiments, the histone is histone H4 (e.g., histone H41, histone H44).

"Histone methyltransferases" or "HMTs" are histone-modifying enzymes that catalyze the transfer of one, two, or three methyl groups to lysine and/or arginine residues of histone proteins. HMTs modify histones at certain sites through methylation. Methylation of histones is of biological significance because such methylation is a principal epigenetic modification of chromatin that determines gene expression, genomic stability, stem cell maturation, cell lineage development, genetic imprinting, DNA methylation, and/or cell mitosis. In certain embodiments, an HMT described herein is a histone-lysine N-methyltransferase. In certain embodiments, an HMT described herein is a histone-arginine N-methyltransferase. In certain embodiments, an HMT described herein is EZH1. In certain embodiments, an HMT described herein is EZH2. In certain embodiments, an HMT described herein is DOT1. In certain embodiments, an HMT described herein is G9a, GLP, MLL1, MLL2, MLL3, MLL4, NSD2, PRMT1, PRMT3, PRMT4, PRMT5, PRMT6, SET1b, SET7/9, SET8, SETMAR, SMYD2, SUV39H1, or SUV39H2.

The term "enhancer of zeste homolog 1," "enhancer of zeste 2 polycomb repressive complex 1 subunit," "EZH1," "EZH1 enzyme," "histone-lysine N-methyltransferase EZH1" refers to an enzyme that is encoded by the EZH1 gene. ENSEMBL of human EZH1 gene: ENSG00000108799.

The term "enhancer of zeste homolog 2," "enhancer of zeste 2 polycomb repressive complex 2 subunit," "EZH2," "EZH2 enzyme," "histone-lysine N-methyltransferase EZH2" refers to an enzyme that is encoded by the EZH2 gene. EZH2 is a core catalytic component of the Polycomb-group (PcG) protein complex family. EZH2 is a histone methyltransferase that that catalyzes the di- and tri-methylation at histone H3 lysine 27 (H3K27me2/3), thereby silencing gene expression. The catalytic site of EZH2 is present within a SET domain, a highly conserved sequence motif that is found in several chromatin-associated proteins. EZH2 plays a critical role in normal development and EZH2 deficient mice die at early stage of embryo due to the failure of implantation and gastrulation. EZH2 is known to associate with the embryonic ectoderm development protein, the VAV1 oncoprotein, and the X-linked nuclear protein (XNP). EZH2 may also play a role in the hematopoietic and central nervous systems. ENSEMBL of human EZH2 gene: ENSG00000106462.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, dexpression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, malignant melanoma, manic dexpression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism. In certain embodiments, a hematological disease is a hematological malignancy. The term "hematological malignancy" refers to tumors that affect blood, bone marrow, and/or lymph nodes. Exemplary hematological malignancies include, but are not limited to, leukemia, such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt lymphoma, Waldenström's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphomalleukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemiallymphoma as described above; myelodysplasia; and multiple myeloma (MM).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, antiphospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina *bifida*; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the Diagnostic and Statistical Manual of Mental Disorders—Fourth Edition (DSM-IV), published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., dexpression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

BRIEF DESCRIPTION OF THE DRAWINGS

FIG. 1B shows exemplary $IC_{50}$ values (in nM) of select compounds against wild type (WT) EZH2, or EZH2 with a Y641C mutation, Y641N mutation, or Y641S mutation.

FIG. 2A shows the time dependence and activity of select compounds against EZH2 and EZH1. FIG. 2B shows the time dependence and activity of select compounds against EZH2 and EZH1, in presence of dithiothreitol (DTT).

DETAILED DESCRIPTION OF CERTAIN EMBODIMENTS OF THE INVENTION

Figure 1A:
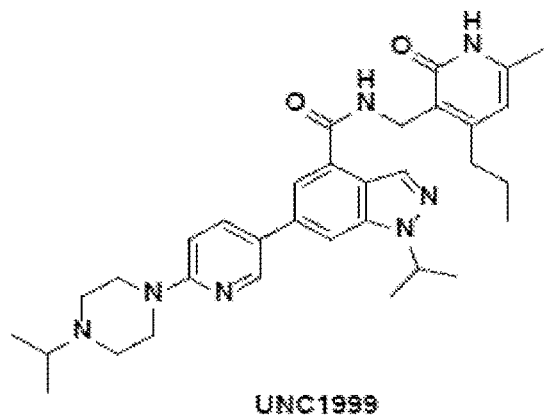
FIG. 1A shows the chemical structures of select compounds.
Figure 1C:
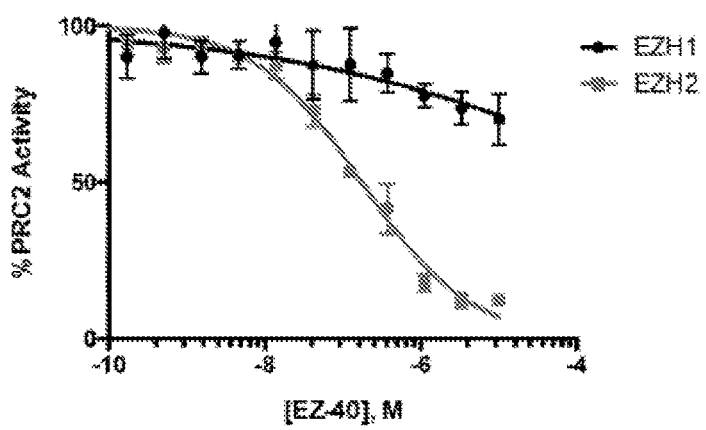
FIG. 1C shows exemplary % PRC2 activity of compound EZ-40 at different concentrations (in M) for EZH2 and EZH1.
Figure 3A:
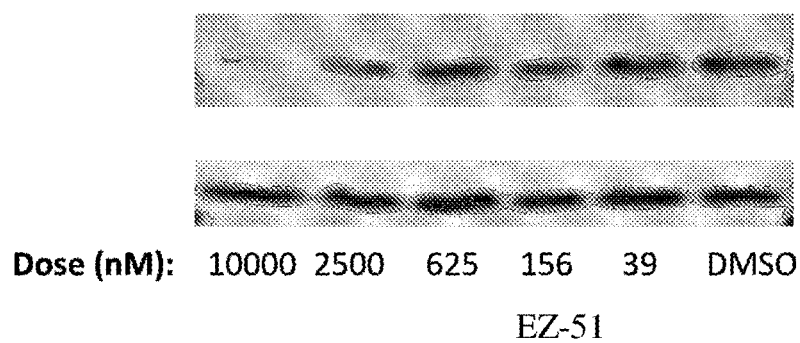
FIG. 3A shows exemplary Western blotting results of H3K27me3 treated for 72 hours with DMSO and different concentrations (in nM) of compound EZ-51.
Figure 3B:
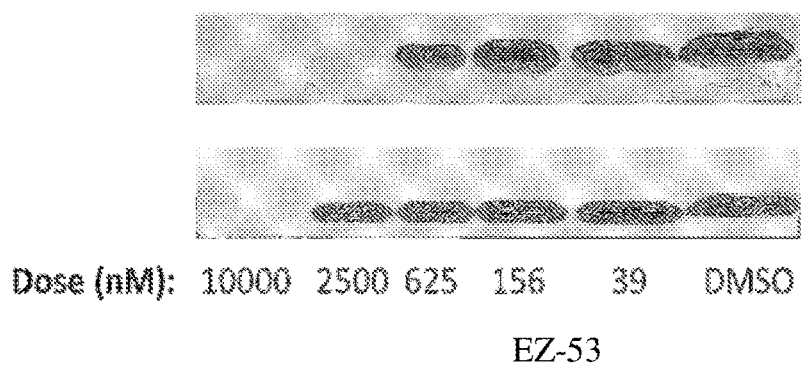
FIG. 3B shows exemplary Western blotting results of H3K27me3 treated for 72 hours with DMSO and different concentrations (in nM) of compound EZ-53.
Figure 3C:
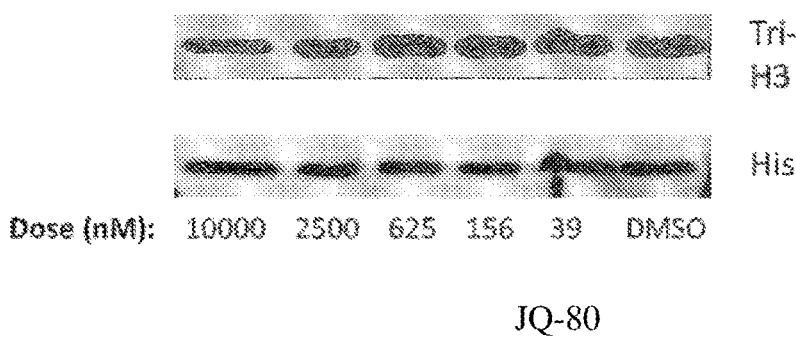
FIG. 3C shows exemplary Western blotting results of H3K27me3 treated for 72 hours with DMSO and different concentrations (in nM) of compound JQ-80.

Described herein are compounds of Formulae (I), (II), and (III), and pharmaceutically acceptable salts, solvates, hydrates, polymorphs, co-crystals, tautomers, stereoisomers, isotopically labeled derivatives, and prodrugs thereof. The compounds described herein bind histone methyltransferases (HMTs, such as EZH1 and EZH2) and are useful in modulating (e.g., inhibiting) the activity (e.g., aberrant activity) of HMTs in a subject, biological sample, tissue, or cell. The compounds may be useful in treating or preventing a disease (e.g., proliferative disease, inflammatory disease, autoimmune disease, genetic disease, hematological disease, neurological disease, painful condition, psychiatric disorder, or metabolic disorder) in a subject in need thereof, and/or in treating or preventing a disease associated with aberrant or increased activity of an HMT in a subject. Also provided are pharmaceutical compositions, kits, and uses including a compound described herein.

Compounds

One aspect of the present disclosure relates to the compounds described herein. The compounds described herein are inhibitors of HMTs (e.g., EZH1, EZH2, DOT1). In certain embodiments, a compound described herein is a compound of Formula (I), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I), or a pharmaceutically acceptable salt thereof. In certain embodiments, a compound described herein is a compound of Formula (II), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (II), or a pharmaceutically acceptable salt thereof. In certain embodiments, a compound described herein is a compound of Formula (III), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (III), or a pharmaceutically acceptable salt thereof. Formula (I) requires that at least one of $R^{A2}$, $R^{A10}$, $R^{A12}$, and $R^{A17}$ is a warhead; and/or at least one of $R^{A1}$ and $R^{A2}$ is a tag; and/or when $R^{A2}$ is of the formula:

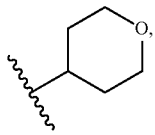 [SMILES: *C1CCOCC1]

$R^{A3}$ is not substituted or unsubstituted $C_{1-3}$ alkyl; Formula (II) and Formula (III) do not have this requirement. In Formula (I), $R^{A5}$ is of the formula:

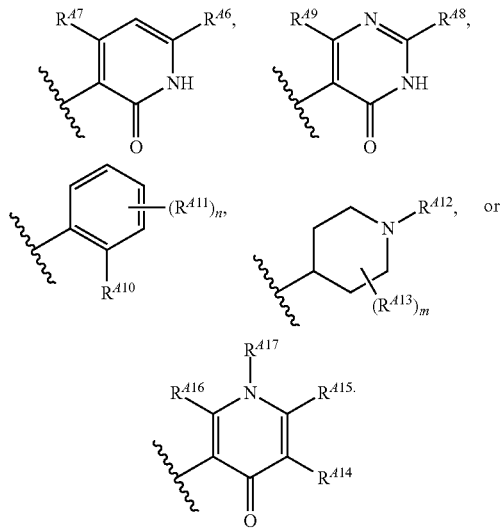

In Formula (II), $R^{B5}$ is of the formula:

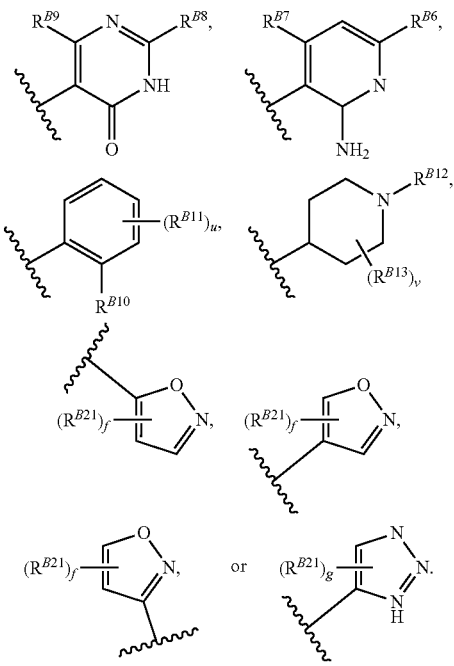

In Formula (III), $R^{D5}$ is of the formula:

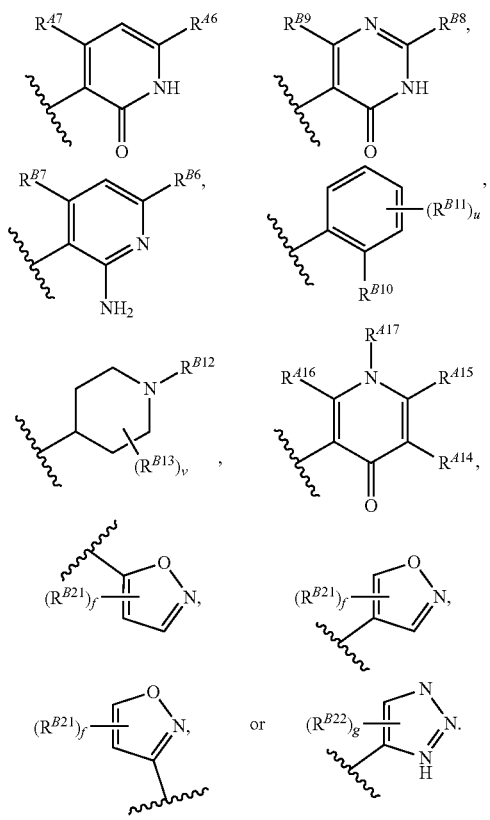

In one aspect, the present disclosure provides compounds of Formula (I):

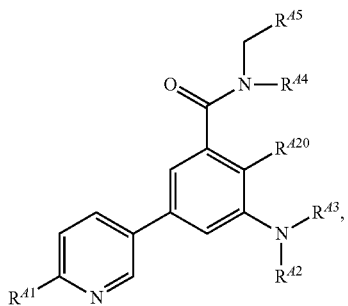

(I)

and pharmaceutically acceptable salts, solvates, hydrates, polymorphs, co-crystals, tautomers, stereoisomers, isotopically labeled derivatives, and prodrugs thereof, wherein:

$R^{A1}$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^{a1})_2$, —$SR^a$, —CN, —SCN, —$C(=NR^a)R^a$, —$C(=NR^a)OR^a$, —$C(=NR^a)N(R^{a1})_2$, —$C(=O)R^a$, —$C(=O)OR^a$, —$C(=O)N(R^{a1})_2$, —$NO_2$, —$NR^aC(=O)R^a$, —$NR^aC(=O)OR^a$, —$NR^aC(=O)N(R^{a1})_2$, —$OC(=O)R^a$, —$OC(=O)OR^a$, —$OC(=O)N(R^{a1})_2$, a tag, or

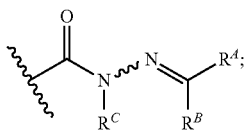

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom;

each instance of $R^{a1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or two instances of $R^{a1}$ are joined to form a substituted or unsubstituted, heterocyclic ring, or substituted or unsubstituted, heteroaryl ring;

$R^A$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

or $R^A$ and $R^B$ are joined to form a substituted or unsubstituted, carbocyclic ring, or a substituted or unsubstituted, heterocyclic ring;

$R^C$ is hydrogen, substituted or unsubstituted $C_{1-6}$ alkyl, or a nitrogen protecting group;

$R^{A2}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, a nitrogen protecting group, a tag, or a warhead;

$R^{A3}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or a nitrogen protecting group;

$R^{A20}$ is hydrogen, halogen, substituted or unsubstituted $C_{1-6}$ alkyl, —$OR^a$, or —$N(R^{a1})_2$;

$R^{A4}$ is hydrogen, substituted or unsubstituted $C_{1-6}$ alkyl, or a nitrogen protecting group;

$R^{A5}$ is of the formula:

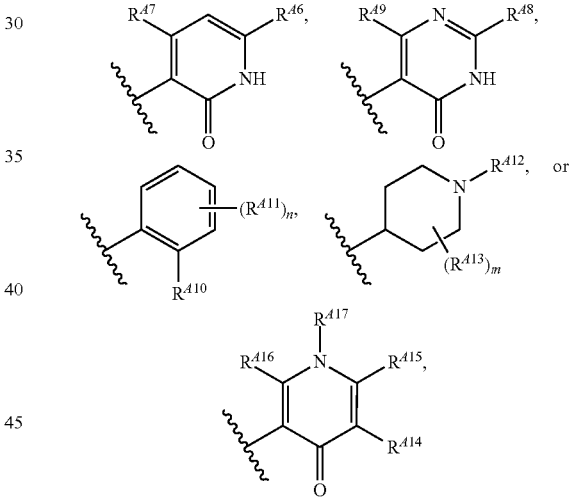

wherein:
$R^{A6}$ is hydrogen, halogen, substituted or unsubstituted $C_{1-6}$ alkyl, —$OR^a$, or —$N(R^{a1})_2$;
$R^{A7}$ is hydrogen, halogen, substituted or unsubstituted $C_{2-6}$ alkyl, substituted or unsubstituted, 3- to 7-membered, monocyclic carbocyclyl comprising 0, 1, or 2 double bonds in the carbocyclic ring system, —$OR^a$, or —$N(R^{a1})_2$;
$R^{A8}$ is hydrogen, halogen, substituted or unsubstituted $C_{1-6}$ alkyl, —$OR^a$, or —$N(R^{a1})_2$;
$R^{A9}$ is hydrogen, halogen, substituted or unsubstituted $C_{1-6}$ alkyl, substituted or unsubstituted, 3- to 7-membered, monocyclic carbocyclyl comprising 0, 1, or 2 double bonds in the carbocyclic ring system, —$OR^a$, or —$N(R^{a1})_2$;
$R^{A10}$ is —$OR^a$, —$N(R^{a1})_2$, or a warhead;
each instance of $R^{A11}$ is independently halogen, substituted or unsubstituted $C_{1-6}$ alkyl, substituted or unsubstituted, 3- to 7-membered, monocyclic carbocyclyl comprising 0, 1, or 2 double bonds in the carbocyclic ring system, —OR$^a$, or —N(R$^{a1}$)$_2$;

n is 0, 1, 2, 3, or 4;

R$^{A12}$ is hydrogen, substituted or unsubstituted C$_{1-6}$ alkyl, a nitrogen protecting group, or a warhead;

each instance of R$^{A13}$ is independently halogen, substituted or unsubstituted C$_{1-6}$ alkyl, substituted or unsubstituted, 3- to 7-membered, monocyclic carbocyclyl comprising 0, 1, or 2 double bonds in the carbocyclic ring system, —OR$^a$, or —N(R$^{a1}$)$_2$;

m is 0, 1, 2, 3, 4, 5, 6, 7, 8, or 9;

R$^{A14}$ is hydrogen, halogen, substituted or unsubstituted C$_{1-6}$ alkyl, —OR$^a$, or —N(R$^{a1}$)$_2$;

R$^{A15}$ is hydrogen, halogen, substituted or unsubstituted C$_{1-6}$ alkyl, —OR$^a$, or —N(R$^{a1}$)$_2$;

R$^{A16}$ is hydrogen, halogen, substituted or unsubstituted C$_{2-6}$ alkyl, substituted or unsubstituted, 3- to 7-membered, monocyclic carbocyclyl comprising 0, 1, or 2 double bonds in the carbocyclic ring system, —OR$^a$, or —N(R$^{a1}$)$_2$; and R$^{A17}$ is hydrogen, substituted or unsubstituted acyl, substituted or unsubstituted C$_{1-6}$ alkyl, a nitrogen protecting group, or a warhead; and each instance of the warhead is independently:

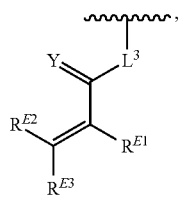
(i-1)

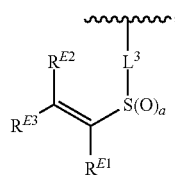
(i-2)

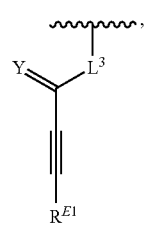
(i-3)

(i-4)

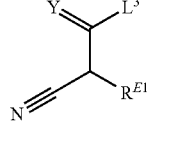
(i-5)

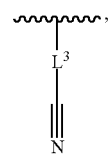

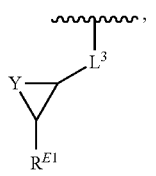
(i-6)

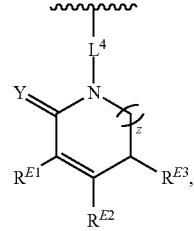
(i-7)

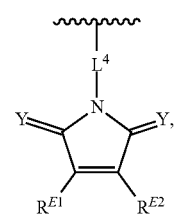
(i-8)

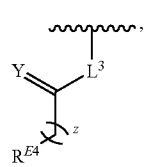
(i-9)

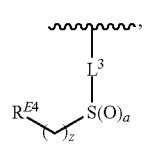
(i-10)

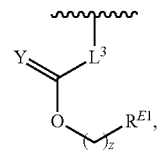
(i-11)

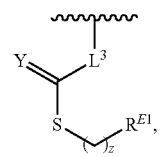
(i-12)

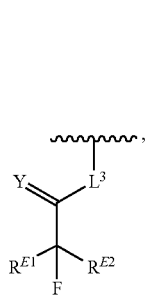
(i-13)

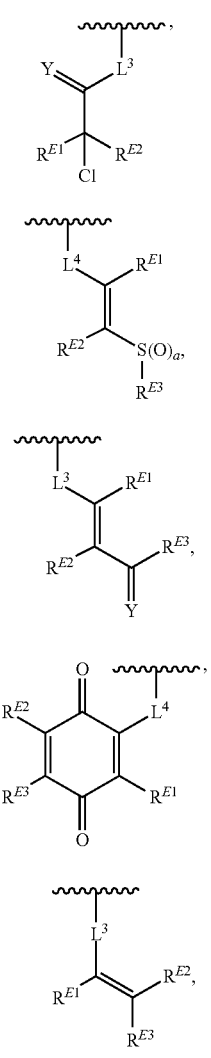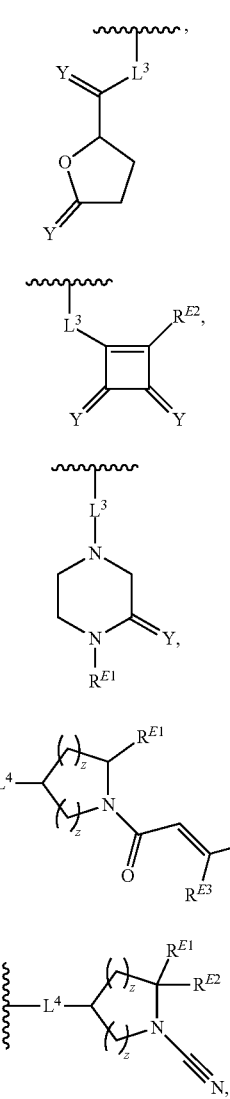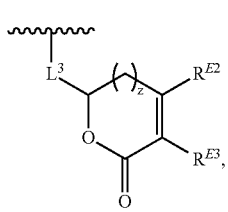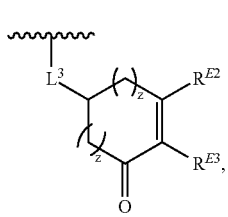

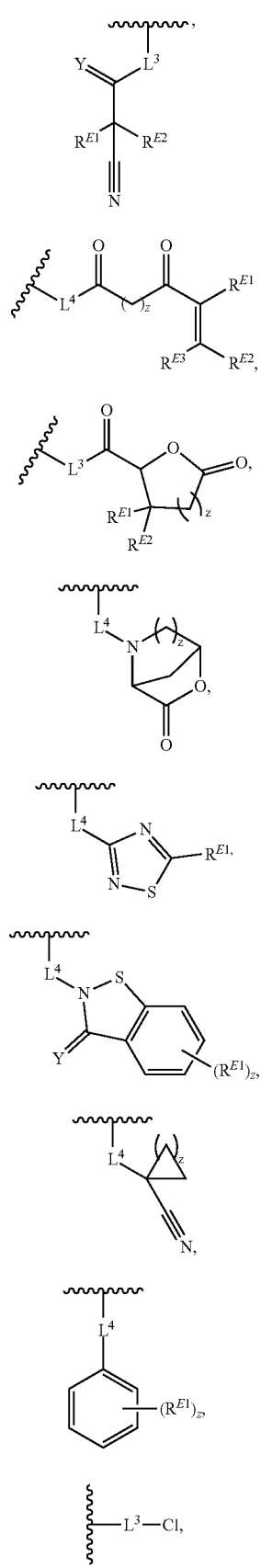
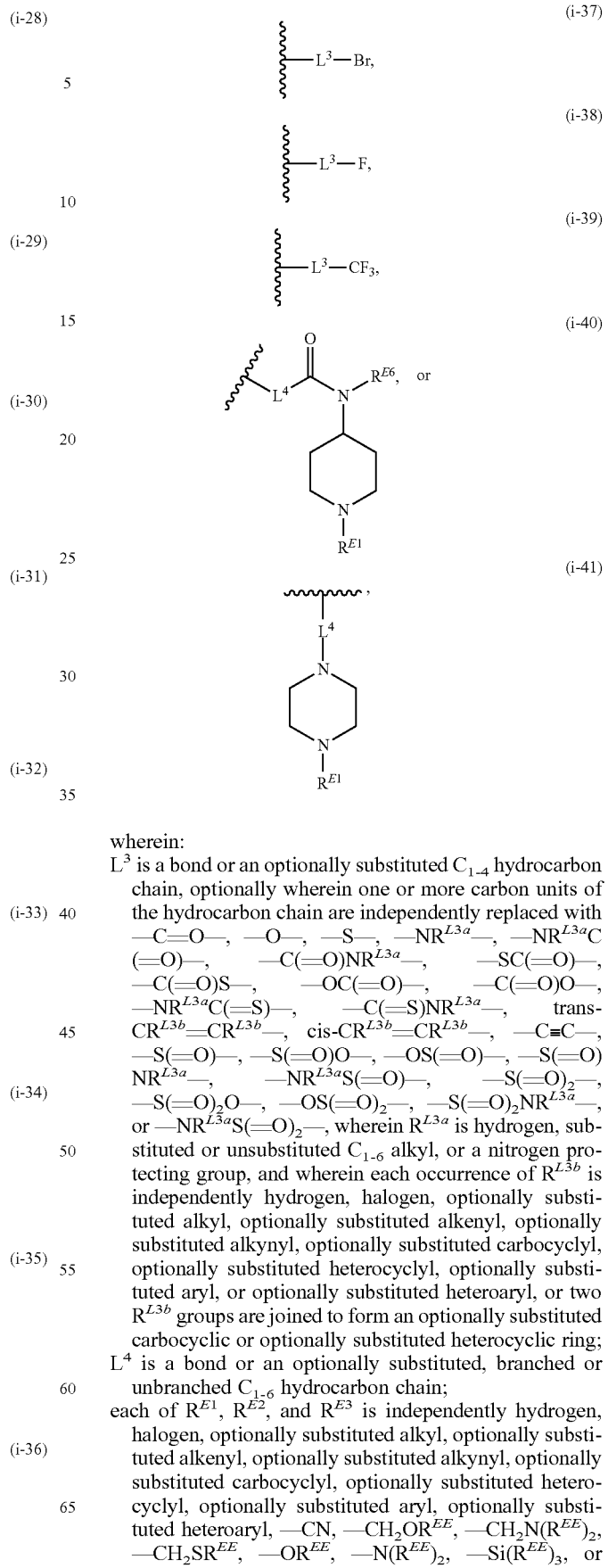

wherein:

L³ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

L⁴ is a bond or an optionally substituted, branched or unbranched $C_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, substituted or unsubstituted C$_{1-6}$ alkyl, or a nitrogen protecting group;

each instance of Y is independently O, S, or NR$^{E7}$, wherein R$^{E7}$ is hydrogen, substituted or unsubstituted C$_{1-6}$ alkyl, or a nitrogen protecting group;

a is 1 or 2; and each instance of z is independently 0, 1, 2, 3, 4, 5, or 6, as valency permits;

provided that:

at least one of R$^{A2}$, R$^{A10}$, R$^{A12}$, and R$^{A17}$ is a warhead; and/or at least one of R$^{A1}$ and R$^{A2}$ is a tag; and/or when R$^{A2}$ is of the formula.

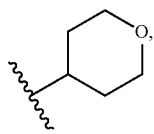 [SMILES: *C1CCOCC1]

R$^{A3}$ is not substituted or unsubstituted C$_{1-3}$ alkyl.

Formula (I) includes substituent R$^{A1}$ on the pyridinyl ring. In certain embodiments, R$^{A1}$ is halogen (e.g., F, Cl, Br, or I). In certain embodiments, R$^{A1}$ is substituted or unsubstituted acyl. In certain embodiments, R$^{A1}$ is of the formula:

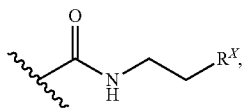

wherein R$^X$ is substituted or unsubstituted, 5- to 10-membered monocyclic or bicyclic heterocyclic ring, wherein one or two atoms in the heterocyclic ring are independently nitrogen, oxygen, or sulfur. In certain embodiments, R$^X$ is substituted or unsubstituted phenyl. In certain embodiments, R$^X$ is substituted or unsubstituted tetrahydrofuran. In certain embodiments, R$^X$ is substituted or unsubstituted pyrrolidine. In certain embodiments, R$^X$ is substituted or unsubstituted piperazine. In certain embodiments, R$^{A1}$ is of the formula:

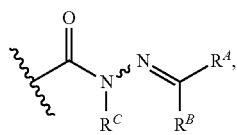

wherein R$^A$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; R$^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; or R$^A$ and R$^B$ are joined to form a substituted or unsubstituted, carbocyclic ring, or a substituted or unsubstituted, heterocyclic ring; and R$^C$ is hydrogen, substituted or unsubstituted C$_{1-6}$ alkyl, or a nitrogen protecting group.

The moiety

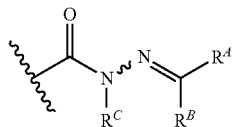

of any one of Formulae (I), (II), and (III) includes substituents R$^A$, R$^B$, and R$^C$. In certain embodiments, R$^A$ and R$^B$ are the same. In certain embodiments, R$^A$ and R$^B$ are different from each other. In certain embodiments, R$^A$ is H. In certain embodiments, R$^A$ is substituted or unsubstituted acyl. In certain embodiments, R$^A$ is substituted or unsubstituted alkyl (e.g., substituted or unsubstituted C$_{1-6}$ alkyl). In certain embodiments, R$^A$ is substituted or unsubstituted alkenyl (e.g., substituted or unsubstituted C$_{2-6}$ alkenyl). In certain embodiments, R$^A$ is substituted or unsubstituted alkynyl (e.g., substituted or unsubstituted C$_{2-6}$ alkynyl). In certain embodiments, R$^A$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, R$^A$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R$^A$ is substituted or unsubstituted aryl (e.g., substituted or unsubstituted, 6- to 10-membered aryl). In certain embodiments, R$^A$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, R$^B$ is H. In certain embodiments, R$^B$ is substituted or unsubstituted acyl. In certain embodiments, R$^B$ is substituted or unsubstituted alkyl (e.g., substituted or unsubstituted C$_{1-6}$ alkyl). In certain embodiments, R$^B$ is substituted or unsubstituted alkenyl (e.g., substituted or unsubstituted C$_{2-6}$ alkenyl). In certain embodiments, R$^B$ is substituted or unsubstituted alkynyl (e.g., substituted or unsubstituted C$_{2-6}$ alkynyl). In certain embodiments, R$^B$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, R$^B$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R$^B$ is substituted or unsubstituted aryl (e.g., substituted or unsubstituted, 6- to 10-membered aryl). In certain embodiments, R$^B$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, R$^A$ and R$^B$ are joined to form a substituted or unsubstituted, carbocyclic ring (e.g., substituted or unsubstituted, 3- to 7-membered, monocyclic carbocyclyl comprising zero, one, or two double bonds in the carbocyclic ring system). In certain embodiments, R$^A$ and R$^B$ are joined to form a substituted or unsubstituted, heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R$^C$ is H. In certain embodiments, R$^C$ is substituted or unsubstituted C$_{1-6}$ alkyl (e.g., substituted or unsubstituted Et or substituted or unsubstituted Me). In certain embodiments, R$^C$ is a nitrogen protecting group (e.g., Bn, Boc, Cbz, Fmoc, trifluoroacetyl, triphenylmethyl, acetyl, or Ts).

In certain embodiments, R$^{41}$ is substituted or unsubstituted alkyl (e.g., substituted or unsubstituted C$_{1-6}$ alkyl). In certain embodiments, R$^{41}$ is methyl. In certain embodiments, R$^{41}$ is —CF$_3$, Bn, Et, perfluoroethyl, Pr, perfluoropropyl, Bu, or perfluorobutyl. In certain embodiments, R$^{41}$ is substituted or unsubstituted alkenyl (e.g., substituted or unsubstituted C$_{2-6}$ alkenyl). In certain embodiments, R$^{41}$ is substituted or unsubstituted alkynyl (e.g., substituted or unsubstituted C$_{1-6}$ alkynyl). In certain embodiments, R$^{41}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, R$^{41}$ is substituted or unsubstituted, 3- to 7-membered, monocyclic heterocyclyl comprising 0, 1, or 2 double bonds in the heterocyclic ring system, wherein 1, 2, or 3 atoms in the heterocyclic ring system are independently nitrogen, oxygen, or sulfur. In certain embodiments, R$^{41}$ is substituted or unsubstituted piperazinyl. In certain embodiments, R$^{41}$ is of the formula:

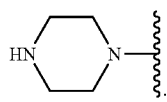

In certain embodiments, R$^{41}$ is of the formula:

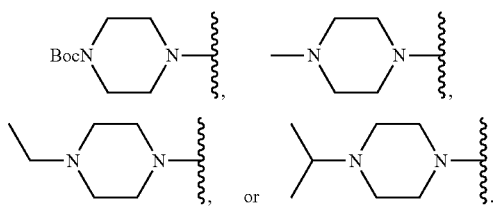

In certain embodiments, R$^{41}$ is of the formula:

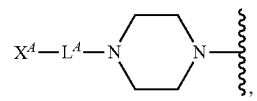

wherein L$^A$ is a bond or substituted or unsubstituted C$_{1-100}$ hydrocarbon chain, optionally wherein one or more chain atoms of the hydrocarbon chain are independently replaced with —O—, —S—, or —NR$^a$—; and X$^A$ is a small molecule, peptide, protein, or polynucleotide. In certain embodiments, R$^{41}$ is of the formula:

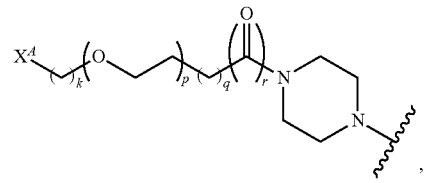

wherein r is 0 or 1; k is an integer between 0 and 10, inclusive; p is an integer between 2 and 20, inclusive; and q is an integer between 2 and 10, inclusive. In certain embodiments, p is an integer between 3 and 11, inclusive, q is 0, and k is 0, 1, 2, 3, 4, 5, or 6. In certain embodiments, X$^A$ is a small molecule. In certain embodiments, X$^A$ is a small molecule tag (e.g., a biotin moiety

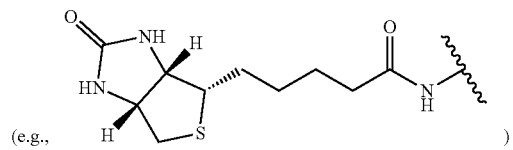

(e.g., or a small molecule fluorophore). In certain embodiments, at least one of R$^{41}$ and R$^{42}$ is a small molecule tag. In certain embodiments, R$^{41}$ is

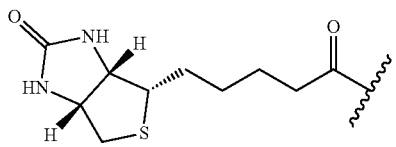

In certain embodiments, R$^{41}$ is substituted or unsubstituted aryl (e.g., substituted or unsubstituted, 6- to 10-membered aryl). In certain embodiments, R$^{41}$ is substituted or unsubstituted phenyl. In certain embodiments, R$^{41}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, R$^{41}$ is —OR$^a$ (e.g., —OH, —O(substituted or unsubstituted C$_{1-6}$ alkyl) (e.g., —OMe, —OEt, —OPr, —OBu, or —OBn), or —O(substituted or unsubstituted phenyl) (e.g., —OPh)). In certain embodiments, R$^{41}$ is —SR$^a$ (e.g., —SH, —S(substituted or unsubstituted C$_{1-6}$ alkyl) (e.g., —SMe, —SEt, —SPr, —SBu, or —SBn), or —S(substituted or unsubstituted phenyl) (e.g., —SPh)). In certain embodiments, R$^{41}$ is —N(R$^{a1}$)$_2$ (e.g., —NH$_2$, —NH (substituted or unsubstituted C$_{1-6}$ alkyl) (e.g., —NHMe), or —N(substituted or unsubstituted $C_{1-6}$ alkyl)-(substituted or unsubstituted $C_{1-6}$ alkyl) (e.g., —NMe$_2$)). In certain embodiments, $R^{41}$ is —CN. In certain embodiments, $R^{41}$ is —SCN or —NO$_2$. In certain embodiments, $R^{41}$ is —C(=NR$^a$)R$^a$, —C(=NR$^a$)OR$^a$, or —C(=NR$^a$)N(R$^{a1}$)$_2$. In certain embodiments, $R^{41}$ is —C(=O)R$^a$ (e.g., —C(=O)(substituted or unsubstituted alkyl) or —C(=O)(substituted or unsubstituted phenyl)). In certain embodiments, $R^{41}$ is —C(=O)OR$^a$ (e.g., —C(=O)OH, —C(=O)O (substituted or unsubstituted alkyl) (e.g., —C(=O)OMe), or —C(=O)O (substituted or unsubstituted phenyl)). In certain embodiments, $R^{41}$ is —C(=O)N(R$^{a1}$)$_2$ (e.g., —C(=O)NH$_2$, —C(=O)NH (substituted or unsubstituted alkyl), —C(=O)NH (substituted or unsubstituted phenyl), —C(=O)N (substituted or unsubstituted alkyl)-(substituted or unsubstituted alkyl), or —C(=O)N (substituted or unsubstituted phenyl)-(substituted or unsubstituted alkyl)). In certain embodiments, $R^{41}$ is —NR$^a$C(=O)R$^a$ (e.g., —NHC(=O)Me). In certain embodiments, $R^{41}$ is —NR$^a$C(=O)OR$^a$ or —NR$^a$C(=O)N(R$^{a1}$)$_2$. In certain embodiments, $R^{41}$ is —OC(=O)R$^a$, —OC(=O)OR$^a$, or —OC(=O)N(R$^{a1}$)$_2$. In certain embodiments, $R^{41}$ is substituted or unsubstituted alkyl, —OR$^a$, —N(R$^{a1}$)$_2$, —C(=O)OR$^a$, or —NR$^a$C(=O)R$^a$. In certain embodiments, $R^{41}$ is unsubstituted $C_{1-6}$ alkyl, —OMe, —NH$_2$, —N(Me)$_2$, —C(=O)OH, —C(=O)OMe, or —NHC(=O)Me.

Formula (I) may include one or more instances of substituent R$^a$. When Formula (I) includes two or more instances of R$^a$, any two instances of R$^a$ may be the same or different from each other. In certain embodiments, at least one instance of R$^a$ is H. In certain embodiments, each instance of R$^a$ is H. In certain embodiments, at least one instance of R$^a$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridinesulfenyl, or triphenylmethyl) when attached to a sulfur atom. Formula (I) may include one or more instances of substituent R$^{a1}$. When Formula (I) includes two or more instances of R$^{a1}$, any two instances of R$^{a1}$ may be the same or different from each other. In certain embodiments, at least one instance of R$^{a1}$ is H. In certain embodiments, each instance of R$^{a1}$ is H. In certain embodiments, at least one instance of R$^{a1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group (e.g., Bn, Boc, Cbz, Fmoc, trifluoroacetyl, triphenylmethyl, acetyl, or Ts) when attached to a nitrogen atom. In certain embodiments, two instances of R$^{a1}$ are joined to form a substituted or unsubstituted, heterocyclic ring, or substituted or unsubstituted, heteroaryl ring.

In certain embodiments, $R^{41}$ is a tag (e.g., a biotin derivative, radiometric label, or fluorophore)

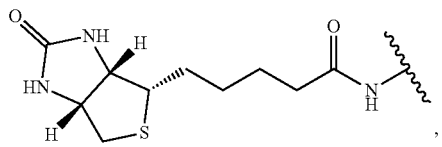 [SMILES: *NC(=O)CCCC[C@@H]1SC[C@@H]2NC(=O)N[C@@H]21 ; ","]

or a small molecule fluorophore). A tag is a label. The term "label" includes any moiety that allows the compound to which it is attached to be captured, detected, or visualized. A label may be directly detectable (i.e., it does not require any further reaction or manipulation to be detectable, e.g., a fluorophore or chromophore is directly detectable) or it may be indirectly detectable (i.e., it is made detectable through reaction with or binding to another entity that is detectable, e.g., a hapten is detectable by immunostaining after reaction with an appropriate antibody comprising a reporter such as a fluorophore). Labels suitable for use in the present invention may be detectable by any of a variety of means including, but not limited to, spectroscopic, photochemical, biochemical, immunochemical, electrical, optical, or chemical means. Suitable labels include, but are not limited to, affinity tags, radiometric labels (e.g., radionuclides (such as, for example, $^{32}$P, $^{35}$S, $^{3}$H, $^{14}$C, $^{125}$I, $^{131}$I, and the like)), fluorescent dyes, phosphorescent dyes, chemiluminescent agents (such as, for example, acridinium esters, stabilized dioxetanes, and the like), spectrally resolvable inorganic fluorescent semiconductor nanocrystals (i.e., quantum dots), metal nanoparticles (e.g., gold, silver, copper, and platinum) or nanoclusters, enzymes (such as, for example, those used in an ELISA, i.e., horseradish peroxidase, beta-galactosidase, luciferase, alkaline phosphatase), colorimetric labels (such as, for example, dyes, colloidal gold, and the like), magnetic labels (such as, for example, Dynabeads™), and haptens.

In certain embodiments, the label comprises a fluorescent moiety. Numerous known fluorescent labeling moieties of a wide variety of chemical structures and physical characteristics are suitable for use in the practice of the present invention. Suitable fluorescent dyes include, but are not limited to, fluorescein and fluorescein dyes (e.g., fluorescein isothiocyanine (FITC), naphthofluorescein, 4',5'-dichloro-2',7'-dimethoxy-fluorescein, 6-carboxyfluorescein or FAM), carbocyanine, merocyanine, styryl dyes, oxonol dyes, phycoerythrin, erythrosin, eosin, rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine or TMR), coumarin and coumarin dyes (e.g., methoxycoumarin, dialkylaminocoumarin, hydroxycoumarin and aminomethylcoumarin or AMCA), Oregon Green Dyes (e.g., Oregon Green 488, Oregon Green 500, Oregon Green 514), Texas Red, Texas Red-X, Spectrum Red™, Spectrum Green™, cyanine dyes (e.g. Cy-3™, Cy-5™, Cy-3.5™, Cy-5.5™), Alexa Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), IRDyes (e.g., IRD40, IRD 700, IRD 800), and the like. For more examples of suitable fluorescent dyes and methods for coupling fluorescent dyes to other chemical entities see, for example, *The Handbook of Fluorescent Probes and Research Products*, 9th Ed., Molecular Probes, Inc., Eugene, Oreg.

The term "luminescence" or "luminescent" means any process of light emission including fluorescence, phosphorescence, scintillation, chemiluminescence, and bioluminescence. The term "chemiluminescence," "chemiluminescent," or "chemiluminescent substrate" refers to a chemical that produces light as a result of a chemical reaction. Commonly used chemiluminescent substrates include, but are not limited to, luminol (5-amino-2,3-dihydro-1,4-phthalazinedione), lophine (2, 4, 5-triphenylimidazole), lucigenin (bis-N-methylacridinium), other acridinium esters, luciferin-luciferase, and thioxene derivatives. For example, in the art-recognized ECL™ detection system of Amersham, an acridinium substrate is oxidized by horse radish peroxidase to produce acridinium esters, which react with excess peroxide at an alkaline pH to produce visible chemiluminescence at 430 nm.

In certain embodiments, the label comprises an affinity tag. The term "affinity tag" includes any moiety that takes part in an interaction (e.g., antigen and antibody, enzyme and substrate, receptor and ligand) that facilitates capture and/or purification of the molecule. Examples of such affinity moieties include small chemical compounds (such as biotin and derivatives thereof), short amino acid sequences (e.g., 2 to 20 amino acids in length, 4 to 12 amino acids in length), such as the $(His)_6$ tag, $(Leu)_3$ tag, or FLAG tag. The affinity moiety may also be a fluorous tag, which is a fluorinated alkyl group (e.g., perfluoroalkyl) that allows for recovery of the molecule via its interaction with a fluorous phase (e.g., a fluorous liquid phase, a fluorous solid phase). Other affinity moieties are well known in the art.

In certain embodiments, the affinity moiety is selected from the group consisting of $(His)_6$ tag, $(His)_4$ tag, $(His)_3$ tag, $(His)_2$ tag, $(Leu)_4$ tag, $(Leu)_3$ tag, $(Leu)_2$ tag, HA tag, FLAG tag, VSV-G tag, HSV tag, V5 tag, biotin and derivatives thereof, carbohydrates, and glycans. In certain embodiments, the affinity moiety is $C_4$-$C_{20}$ perfluoroalkyl (e.g., $C_6$-$C_{12}$ perfluoroalkyl, $C_6$-$C_8$ perfluoroalkyl, $C_4$ perfluoroalkyl, $C_5$ perfluoroalkyl, $C_6$ perfluoroalkyl, $C_7$ perfluoroalkyl, $C_8$ perfluoroalkyl, $C_9$ perfluoroalkyl, $C_{10}$ perfluoroalkyl, $C_{11}$ perfluoroalkyl, $C_{12}$ perfluoroalkyl, $C_{13}$ perfluoroalkyl, $C_{14}$ perfluoroalkyl, $C_{15}$ perfluoroalkyl, $C_{16}$ perfluoroalkyl, $C_{17}$ perfluoroalkyl, $C_{18}$ perfluoroalkyl, $C_{19}$ perfluoroalkyl, or $C_{20}$ perfluoroalkyl). In certain embodiments, the affinity moiety is biotin. In certain embodiments, the affinity moiety is $C_8$ perfluoroalkyl.

A tag may include a divalent linker. In certain embodiments, the divalent linker is an optionally substituted $C_{1-60}$ hydrocarbon chain, optionally wherein one or more carbon units of the hydrocarbon chain are independently replaced with —C=O—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—. In certain embodiments, the divalent linker is a PEG moiety (e.g., -(PEG)$_{1-20}$-, -(PEG)$_{1-12}$-, -(PEG)$_{1-6}$-, -(PEG)$_{6-12}$-). In certain embodiments, the divalent linker is —(CH$_2$)$_{1-40}$— (e.g., —(CH$_2$)$_{1-20}$—, —(CH$_2$)$_{1-10}$—). In certain embodiments, the divalent linker is a combination of one or more PEG moieties (e.g., independently, -(PEG)$_{1-20}$-, -(PEG)$_{1-12}$-, -(PEG)$_{1-6}$-, -(PEG)$_{6-12}$-) and one or more —(CH$_2$)$_{1-40}$— moieties (e.g., independently, —(CH$_2$)$_{1-20}$—, —(CH$_2$)$_{1-10}$—), optionally wherein one or more methylene units of the PEG moieties and/or of the —(CH$_2$)$_{1-40}$— moieties are independently replaced with —C(=O)NH— or —NHC(=O)—.

Formula (I) includes substituent $R^{A2}$. In certain embodiments, $R^{A2}$ is substituted or unsubstituted acyl. In certain embodiments, $R^{A2}$ is —C(=O)R$^a$, optionally wherein R$^a$ is substituted or unsubstituted $C_{1-6}$ alkyl (e.g., Me) or substituted or unsubstituted $C_{2-6}$ alkenyl. In certain embodiments, $R^{A2}$ is —C(=O)R$^a$, wherein R$^a$ is substituted or unsubstituted vinyl. In certain embodiments, $R^{A2}$ is —C(=O)CH=CH$_2$. In certain embodiments, $R^{A2}$ is —C(=O)OR$^a$, optionally wherein R$^a$ is H, substituted or unsubstituted $C_{1-6}$ alkyl (e.g., Me), or an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, $R^{A2}$ is —C(=O)N(R$^{a1}$)$_2$, optionally wherein each instance of R$^{a1}$ is independently H, substituted or unsubstituted $C_{1-6}$ alkyl (e.g., Me), or a nitrogen protecting group (e.g., Bn, Boc, Cbz, Fmoc, trifluoroacetyl, triphenylmethyl, acetyl, or Ts). In certain embodiments, $R^{A2}$ is substituted or unsubstituted alkyl (e.g., substituted or unsubstituted $C_{1-6}$ alkyl). In certain embodiments, $R^{A2}$ is Me. In certain embodiments, $R^{A2}$ is Et. In certain embodiments, $R^{A2}$ is n-Pr. In certain embodiments, $R^{A2}$ is i-Pr. In certain embodiments, $R^{A2}$ is Bu (e.g., n-Bu, i-Bu, sec-Bu, or t-Bu). In certain embodiments, $R^{A2}$ is unsubstituted pentyl (e.g., unsubstituted n-pentyl, unsubstituted t-pentyl, unsubstituted neopentyl, unsubstituted isopentyl, unsubstituted sec-pentyl, or unsubstituted 3-pentyl). In certain embodiments, $R^{A2}$ is sec-Bu, t-Bu, or unsubstituted 3-pentyl. In certain embodiments, $R^{A2}$ is —CF$_3$, Bn, perfluoroethyl, perfluoropropyl, perfluorobutyl, or perfluoropentyl. In certain embodiments, $R^{A2}$ is —CH$_2$C(=O)—NH—N=C(R$^{a1}$)$_2$. In certain embodiments, $R^{A2}$ is substituted or unsubstituted alkenyl (e.g., substituted or unsubstituted $C_{2-6}$ alkenyl). In certain embodiments, $R^{A2}$ is substituted or unsubstituted alkynyl (e.g., substituted or unsubstituted $C_{1-6}$ alkynyl). In certain embodiments, $R^{A2}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{A2}$ is substituted or unsubstituted cyclopropyl. In certain embodiments, $R^{A2}$ is unsubstituted cyclopropyl. In certain embodiments, $R^{A2}$ is substituted or unsubstituted cyclobutyl. In certain embodiments, $R^{A2}$ is substituted or unsubstituted cyclopentyl. In certain embodiments, $R^{A2}$ is unsubstituted cyclopropyl, unsubstituted cyclobutyl, or unsubstituted cyclopentyl. In certain embodiments, $R^{A2}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{A2}$ is substituted or unsubstituted tetrahydropyranyl. In certain embodiments, $R^{A2}$ is of the formula:

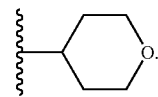

In certain embodiments, $R^{A2}$ is of the formula:

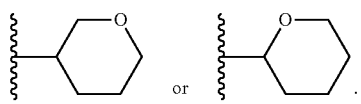

In certain embodiments, $R^{A2}$ is substituted or unsubstituted oxetanyl, substituted or unsubstituted tetrahydrofuranyl, substituted or unsubstituted pyrrolidinyl, substituted or unsubstituted piperidinyl, substituted or unsubstituted morpholinyl, or substituted or unsubstituted piperazinyl. In certain embodiments, $R^{A2}$ is of the formula:

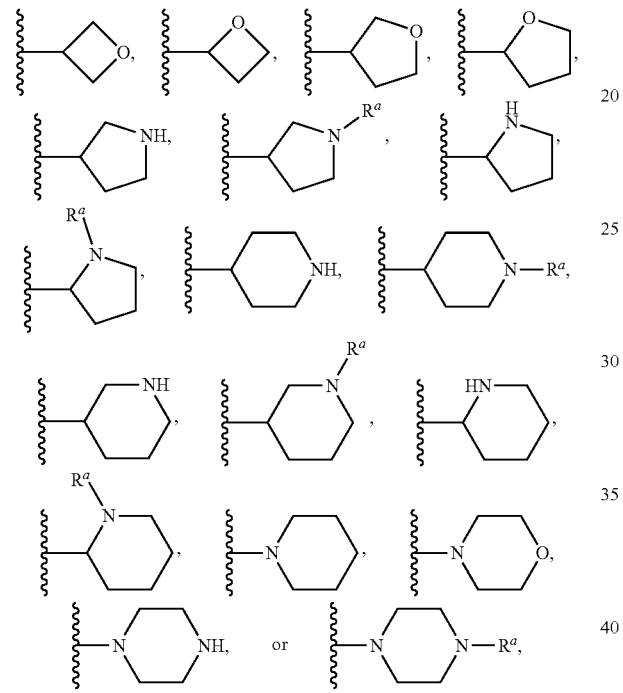

wherein each instance of $R^a$ is independently H or unsubstituted alkyl (e.g., Me)). In certain embodiments, $R^{A2}$ is substituted or unsubstituted aryl (e.g., substituted or unsubstituted, 6- to 10-membered aryl). In certain embodiments, $R^{A2}$ is substituted or unsubstituted phenyl. In certain embodiments, $R^{A2}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, $R^{A2}$ is a nitrogen protecting group (e.g., Bn, Boc, Cbz, Fmoc, trifluoroacetyl, triphenylmethyl, acetyl, or Ts). In certain embodiments, $R^{A2}$ is Boc. In certain embodiments, $R^{A2}$ is a tag (e.g., a biotin moiety (e.g., 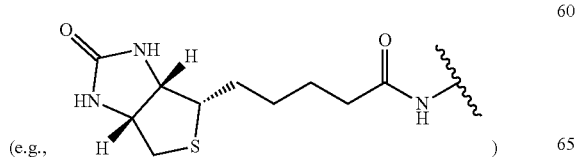)

or a small molecule fluorophore). In certain embodiments, $R^{A2}$ is a warhead.

Formulae (I), (II), and (III) may include one or more warheads, which are independently selected from the group consisting of:

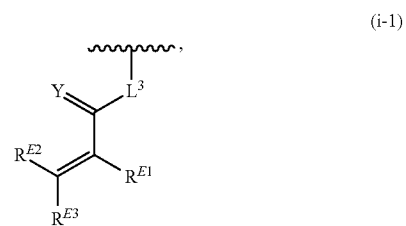 (i-1)

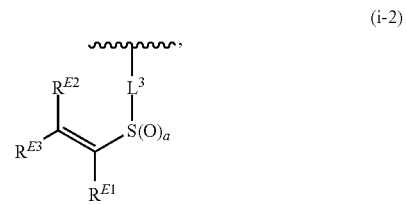 (i-2)

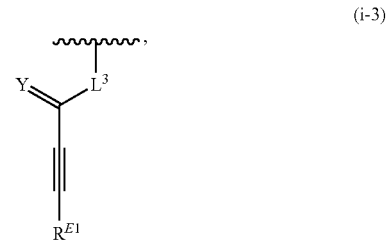 (i-3)

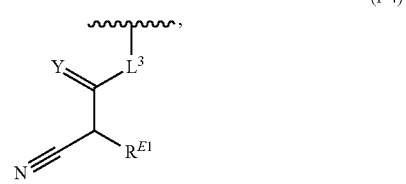 (i-4)

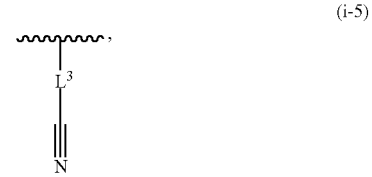 (i-5)

 (i-6)

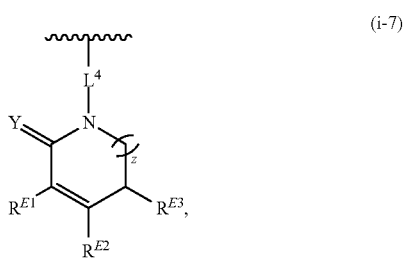 (i-7)

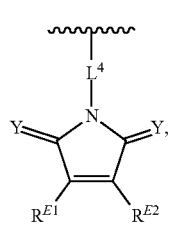 (i-8)
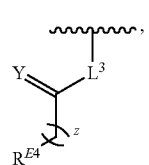 (i-9)
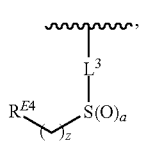 (i-10)
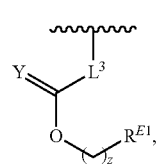 (i-11)
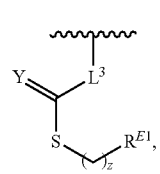 (i-12)
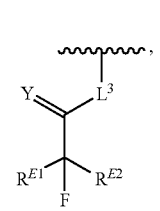 (i-13)
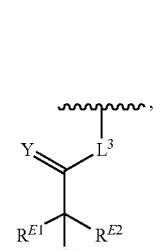 (i-14)
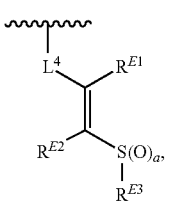 (i-15)
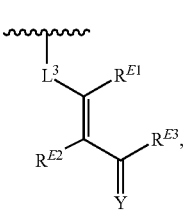 (i-16)
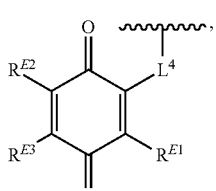 (i-17)
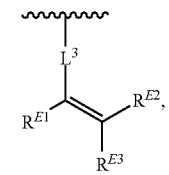 (i-18)
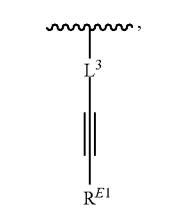 (i-19)
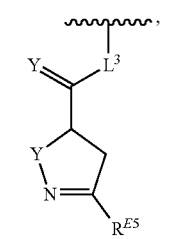 (i-20)
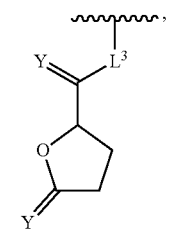 (i-21)
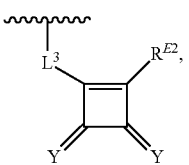 (i-22)

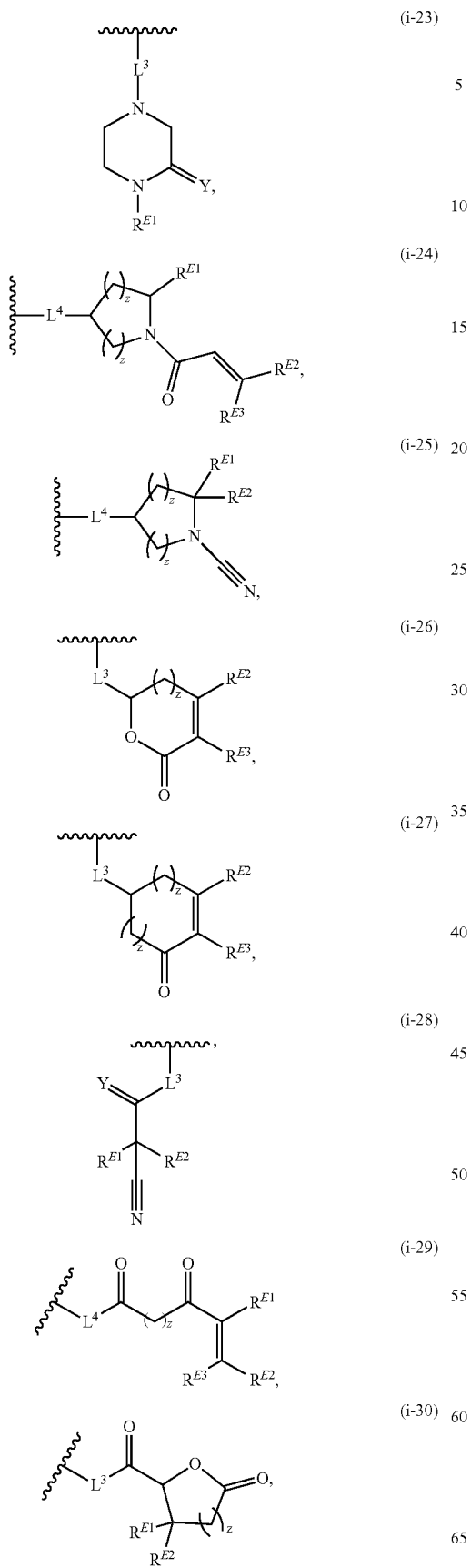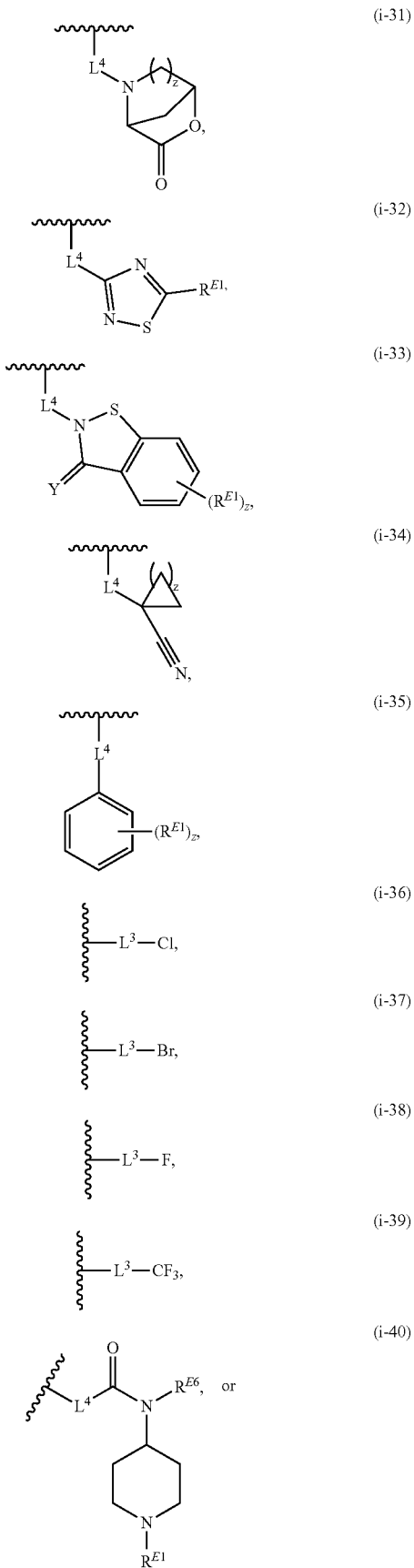

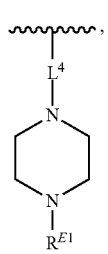
(i-41)

wherein: $L^3$ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$ CR$^{L3b}$C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring; $L^4$ is a bond or an optionally substituted, branched or unbranched $C_{1-6}$ hydrocarbon chain; each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring; R$^{E4}$ is a leaving group; R$^{E5}$ is halogen; R$^{E6}$ is hydrogen, substituted or unsubstituted $C_{1-6}$ alkyl, or a nitrogen protecting group; each instance of Y is independently O, S, or NR$^{E7}$, wherein R$^{E7}$ is hydrogen, substituted or unsubstituted $C_{1-6}$ alkyl, or a nitrogen protecting group; a is 1 or 2; and each instance of z is independently 0, 1, 2, 3, 4, 5, or 6, as valency permits.

In certain embodiments, any one of Formulae (I), (II), and (III) includes one warhead. In certain embodiments, any one of Formulae (I), (II), and (III) includes two or more warheads. When Formula (I), (II), or (III) include two or more warheads, any two of the warheads may be the same or different from each other. In certain embodiments, in Formula (I), at least one of at least one of R$^{42}$, R$^{410}$, R$^{412}$, and R$^{417}$ is a warhead.

In certain embodiments, at least one instance of the warhead is of the formula

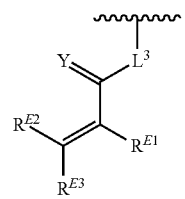
(i-1)

In certain embodiments, at least one instance of the warhead is of the formula

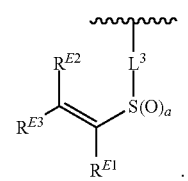
(i-2)

In certain embodiments, at least one instance of the warhead is of the formula

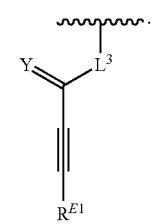
(i-3)

In certain embodiments, at least one instance of the warhead is of the formula

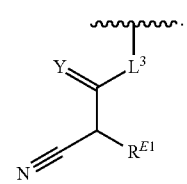
(i-4)

In certain embodiments, at least one instance of the warhead is of the formula

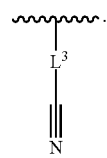
(i-5)

In certain embodiments, at least one instance of the warhead is of the formula

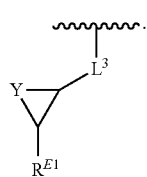
(i-6)

In certain embodiments, at least one instance of the warhead is of the formula

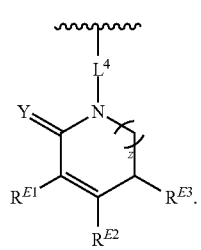
(i-7)

In certain embodiments, at least one instance of the warhead is of the formula

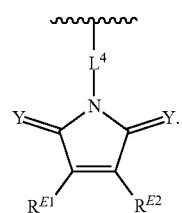
(i-8)

In certain embodiments, at least one instance of the warhead is of the formula

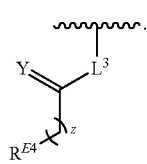
(i-9)

In certain embodiments, at least one instance of the warhead is of the formula

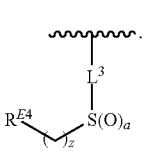
(i-10)

In certain embodiments, at least one instance of the warhead is

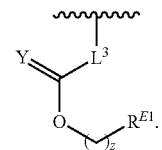
(i-11)

In certain embodiments, at least one instance of the warhead is of the formula

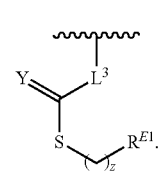
(i-12)

In certain embodiments, at least one instance of the warhead is of the formula

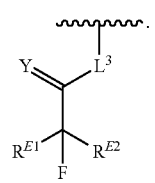
(i-13)

In certain embodiments, at least one instance of the warhead is of the formula

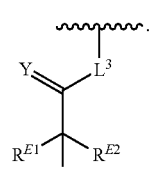
(i-14)

In certain embodiments, at least one instance of the warhead is of the formula

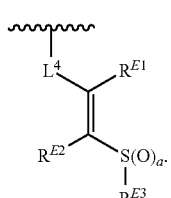
(i-15)

In certain embodiments, at least one instance of the warhead is of the formula

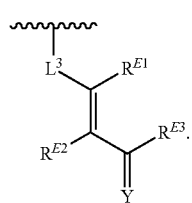
(i-16)

In certain embodiments, at least one instance of the warhead is of the formula

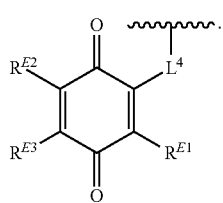
(i-17)

In certain embodiments, at least one instance of the warhead is of the formula

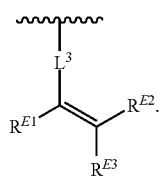
(i-18)

In certain embodiments, at least one instance of the warhead is of the formula

(i-19)

In certain embodiments, at least one instance of the warhead is of the formula

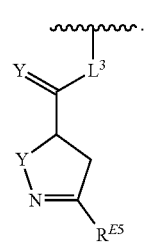
(i-20)

In certain embodiments, at least one instance of the warhead is

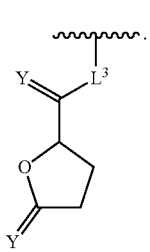
(i-21)

In certain embodiments, at least one instance of the warhead is of the formula

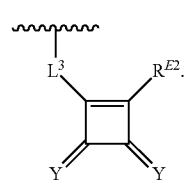
(i-22)

In certain embodiments, at least one instance of the warhead is of the formula

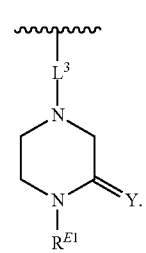
(i-23)

In certain embodiments, at least one instance of the warhead is of the formula

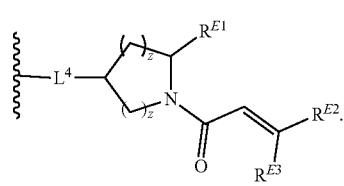
(i-24)

In certain embodiments, at least one instance of the warhead is of the formula

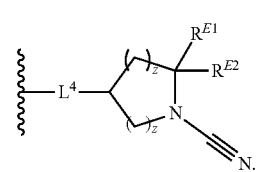
(i-25)

In certain embodiments, at least one instance of the warhead is of the formula

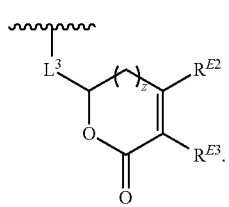
(i-26)

In certain embodiments, at least one instance of the warhead is of the formula

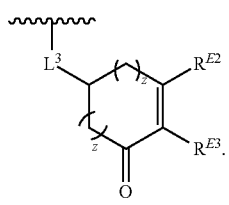
(i-27)

In certain embodiments, at least one instance of the warhead is of the formula

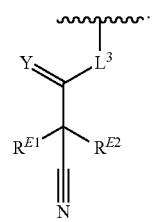
(i-28)

In certain embodiments, at least one instance of the warhead is of the formula

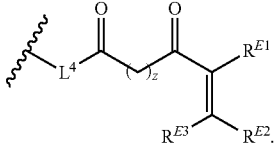
(i-29)

In certain embodiments, at least one instance of the warhead is of the formula

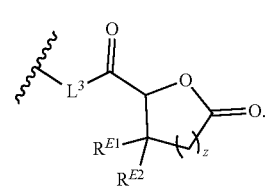
(i-30)

In certain embodiments, at least one instance of the warhead is of the formula

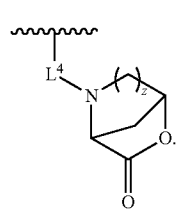
(i-31)

In certain embodiments, at least one instance of the warhead is of the formula

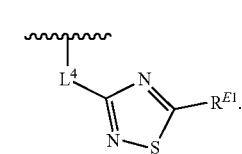
(i-32)

In certain embodiments, at least one instance of the warhead is of the formula

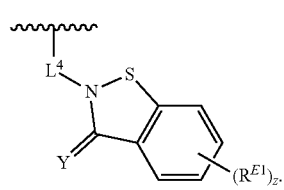
(i-33)

In certain embodiments, at least one instance of the warhead is of the formula

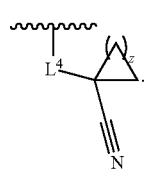
(i-34)

In certain embodiments, at least one instance of the warhead is of the formula

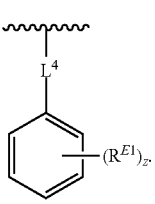
(i-35)

In certain embodiments, at least one instance of the warhead is of the formula

In certain embodiments, at least one instance of the warhead is of the formula

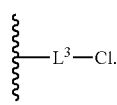
(i-36)

In certain embodiments, at least one instance of the warhead is of the formula

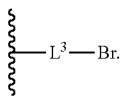
(i-37)

In certain embodiments, at least one instance of the warhead is of the formula

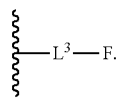
(i-38)

In certain embodiments, at least one instance of the warhead is of the formula

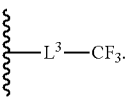
(i-39)

In certain embodiments, at least one instance of the warhead is of the formula

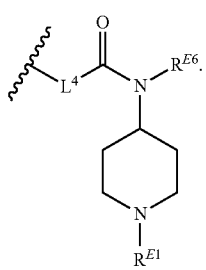
(i-40)

In certain embodiments, at least one instance of the warhead is of the formula

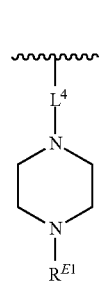
(i-41)

In certain embodiments, $L^3$ is a bond (e.g., a single bond, a double bond, or a triple bond). In certain embodiments, $L^3$ is an optionally substituted $C_{1-4}$ hydrocarbon chain, optionally wherein one or more carbon units of the hydrocarbon chain are independently replaced with —C=O—, —O—, —S—, —$NR^{L3a}$—, —$NR^{L3a}$C(=O)—, —C(=O)$NR^{L3a}$—, —SC(=O)—, —C(=O)S—, —OC(=O)—, —C(=O)O—, —$NR^{L3a}$C(=S)—, —C(=S)$NR^{L3a}$—, trans-$CR^{L3b}$=$CR^{L3b}$—, cis-$CR^{L3b}$=$CR^{L3b}$—, —C≡C—, —S(=O)—, —S(=O)O—, —OS(=O)—, —S(=O)$NR^{L3a}$—, —$NR^{L3a}$S(=O)—, —S(=O)$_2$—, —S(=O)$_2$O—, —OS(=O)$_2$—, —S(=O)$_2NR^{L3a}$—, or —$NR^{L3a}$S(=O)$_2$—, wherein $R^{L3a}$ is hydrogen, substituted or unsubstituted $C_{1-6}$ alkyl, or a nitrogen protecting group, and wherein each occurrence of $R^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{L3b}$ groups are joined to form an optionally substituted carbocyclic or optionally substituted heterocyclic ring. In certain embodiments, $L^4$ is a bond (e.g., a single bond, a double bond, or a triple bond). In certain embodiments, $L^4$ is an optionally substituted branched $C_{1-6}$ hydrocarbon chain (e.g., i-Pr). In certain embodiments, $L^4$ is an optionally substituted unbranched $C_{1-6}$ hydrocarbon chain (e.g., n-Pr, or n-Bu). In certain embodiments, at least one instance of $R^{E1}$ is H. In certain embodiments, at least one instance of $R^{E1}$ is halogen (e.g., F, Cl, Br, or I). In certain embodiments, at least one instance of $R^{E1}$ is optionally substituted alkyl (e.g., Me, or Et). In certain embodiments, at least one instance of $R^{E1}$ is optionally substituted alkenyl (e.g., optionally substituted vinyl). In certain embodiments, at least one instance of $R^{E1}$ is optionally substituted alkynyl. In certain embodiments, at least one instance of $R^{E1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{E1}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{E1}$ is substituted or unsubstituted aryl (e.g., substituted or unsubstituted, 6- to 10-membered aryl). In certain embodiments, at least one instance of $R^{E1}$ is substituted or unsubstituted phenyl. In certain embodiments, at least one instance of $R^{E1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{E1}$ is —CN. In certain embodiments, at least one instance of $R^{E1}$ is —CH$_2$OR$^{EE}$, wherein each instance of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of $R^{E1}$ is —CH$_2$N(R$^{EF}$)$_2$ or N(R$^{EF}$)$_2$, wherein each instance of $R^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two $R^{EF}$ groups are joined to form an optionally substituted heterocyclic ring. In certain embodiments, at least one instance of $R^{E1}$ is —CH$_2$SR$^{EE}$ or —SR$^{EE}$ (e.g., —CH$_2$SMe or —SMe). In certain embodiments, at least one instance of $R^{E1}$ is —OR$^{EE}$ (e.g., —OMe). In certain embodiments, at least one instance of $R^{E1}$ is —Si(R$^{EG}$)$_3$, wherein each instance of $R^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —Si(Me)$_3$).

In certain embodiments, at least one instance of $R^{E2}$ is H. In certain embodiments, at least one instance of $R^{E2}$ is halogen (e.g., F, Cl, Br, or I). In certain embodiments, at least one instance of $R^{E2}$ is optionally substituted alkyl (e.g., Me, or Et). In certain embodiments, at least one instance of $R^{E2}$ is optionally substituted alkenyl (e.g., optionally substituted vinyl). In certain embodiments, at least one instance of $R^{E2}$ is optionally substituted alkynyl. In certain embodiments, at least one instance of $R^{E2}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{E2}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{E2}$ is substituted or unsubstituted aryl (e.g., substituted or unsubstituted, 6- to 10-membered aryl). In certain embodiments, at least one instance of $R^{E2}$ is substituted or unsubstituted phenyl. In certain embodiments, at least one instance of $R^{E2}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{E2}$ is —CN. In certain embodiments, at least one instance of $R^{E2}$ is —CH$_2$OR$^{EE}$, wherein each instance of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of $R^{E2}$ is —CH$_2$N(R$^{EF}$)$_2$ or N(R$^{EF}$)$_2$, wherein each instance of $R^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two $R^{EF}$ groups are joined to form an optionally substituted heterocyclic ring. In certain embodiments, at least one instance of $R^{E2}$ is —CH$_2$SR$^{EE}$ or —SR$^{EE}$ (e.g., CH$_2$SMe or —SMe). In certain embodiments, at least one instance of $R^{E2}$ is —OR$^{EE}$ (e.g., —OMe). In certain embodiments, at least one instance of $R^{E2}$ is —Si(R$^{EG}$)$_3$, wherein each instance of $R^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —Si(Me)$_3$). In certain embodiments, at least one instance of $R^{E3}$ is H. In certain embodiments, at least one instance of $R^{E3}$ is halogen (e.g., F, Cl, Br, or I). In certain embodiments, at least one instance of $R^{E3}$ is optionally substituted alkyl (e.g., Me, or Et). In certain embodiments, at least one instance of $R^{E3}$ is optionally substituted alkenyl (e.g., optionally substituted vinyl). In certain embodiments, at least one instance of $R^{E3}$ is optionally substituted alkynyl. In certain embodiments, at least one instance of $R^{E3}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{E3}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{E3}$ is substituted or unsubstituted aryl (e.g., substituted or unsubstituted, 6- to 10-membered aryl). In certain embodiments, at least one instance of $R^{E3}$ is substituted or unsubstituted phenyl. In certain embodiments, at least one instance of $R^{E3}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{E3}$ is —CN. In certain embodiments, at least one instance of $R^{E3}$ is —CH$_2$OR$^{EE}$, wherein each instance of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of $R^{E3}$ is —CH$_2$N(R$^{EF}$)$_2$ or N(R$^{EF}$)$_2$, wherein each instance of $R^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two $R^{EF}$ groups are joined to form an optionally substituted heterocyclic ring. In certain embodiments, at least one instance of $R^{E3}$ is —CH$_2$SR$^{EE}$ or —SR$^{EE}$ (e.g., —CH$_2$SMe or —SMe). In certain embodiments, at least one instance of $R^{E3}$ is —OR$^{EE}$ (e.g., —OMe). In certain embodiments, at least one instance of $R^{E3}$ is —Si(R$^{EG}$)$_3$, wherein each instance of $R^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —Si(Me)$_3$). In certain embodiments, $R^{E1}$ and $R^{E3}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, $R^{E1}$ and $R^{E3}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{E2}$ and $R^{E3}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, $R^{E2}$ and $R^{E3}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{E1}$ and $R^{E2}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, $R^{E1}$ and $R^{E2}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{E4}$ is a leaving group (e.g., halogen, or a sulfonic acid ester, e.g., —O(tosylate) or —O(mesylate)). In certain embodiments, $R^{E5}$ is halogen (e.g., F, Cl, Br, or I). In certain embodiments, $R^{E6}$ is H. In certain embodiments, $R^{E6}$ is substituted or unsubstituted $C_{1-6}$ alkyl (e.g., Me, is —$CF_3$, Bn, Et, perfluoroethyl, Pr, perfluoropropyl, Bu, or perfluorobutyl). In certain embodiments, $R^{E6}$ is a nitrogen protecting group (e.g., Bn, Boc, Cbz, Fmoc, trifluoroacetyl, triphenylmethyl, acetyl, or Ts). In certain embodiments, at least one instance of Y is O. In certain embodiments, at least one instance of Y is S. In certain embodiments, at least one instance of Y is $NR^{E7}$, wherein $R^{E7}$ is hydrogen, substituted or unsubstituted $C_1$ alkyl, or a nitrogen protecting group (e.g., NMe). In certain embodiments, a is 1. In certain embodiments, a is 2. In certain embodiments, at least one instance of z is 0. In certain embodiments, at least one instance of z is 1. In certain embodiments, at least one instance of z is 2. In certain embodiments, at least one instance of z is 3. In certain embodiments, at least one instance of z is 4. In certain embodiments, at least one instance of z is 5. In certain embodiments, at least one instance of z is 6.

Formula (I) includes substituent $R^{A3}$. Formula (I) includes substituent $R^{A3}$. In certain embodiments, $R^{A3}$ is H. In certain embodiments, $R^{A3}$ is substituted or unsubstituted acyl (e.g., acetyl). In certain embodiments, $R^3$ is of the formula:

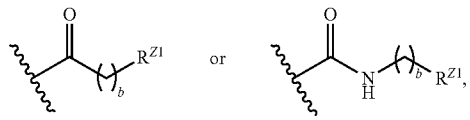

wherein: b is 0, 1, 2, 3, 4, 5, 6, 7, 8, 9, 10, 11, or 12; and $R^{Z1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, —$OR^{w1}$, —$N(R^{w2})_2$, —$SR^{w1}$, —CN, —SCN, —$C(=NR^{w1})R^{w1}$, —$C(=NR^{w1})OR^{w1}$, —$C(=NR^{w1})N(R^{w2})_2$, —$C(=O)R^{w1}$, —$C(=O)OR^{w1}$, —$C(=O)N(R^{w2})_2$, —$NO_2$, —$NR^{w1}C(=O)R^{w1}$, —$NR^{w1}C(=O)OR^{w1}$, —$NR^{w1}C(=O)N(R^{w2})_2$, —$OC(=O)R^{w1}$, —$OC(=O)OR^{w1}$, or —$OC(=O)N(R^{w2})_2$; $R^{w1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, or a sulfur protecting group when attached to a sulfur atom; and $R^{w2}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or nitrogen protecting group when attached to a nitrogen atom; or two instances of $R^{w2}$ are joined to form a substituted or unsubstituted, heterocyclic ring, or substituted or unsubstituted, heteroaryl ring. In certain embodiments, In certain embodiments, b is 0. In certain embodiments, b is 1. In certain embodiments, b is 2. In certain embodiments, b is 3. In certain embodiments, b is 4. In certain embodiments, b is 5. In certain embodiments, b is 6. In certain embodiments, b is 7. In certain embodiments, b is 8. In certain embodiments, b is 9. In certain embodiments, b is 10. In certain embodiments, b is 11. In certain embodiments, b is 12. In certain embodiments, $R^{Z1}$ is substituted or unsubstituted acyl. In certain embodiments, $R^{Z1}$ is substituted or unsubstituted alkyl (e.g., substituted or unsubstituted $C_{1-6}$ alkyl). In certain embodiments, $R^{A3}$ is

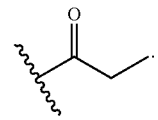

In certain embodiments, $R^{Z1}$ is substituted or unsubstituted alkenyl (e.g., substituted or unsubstituted $C_{2-6}$ alkenyl). In certain embodiments, $R^{A3}$ is

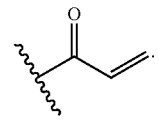

In certain embodiments, $R^{Z1}$ is substituted or unsubstituted alkynyl (e.g., substituted or unsubstituted $C_{2-6}$ alkynyl). In certain embodiments, $R^{Z1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{Z1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{Z1}$ is substituted or unsubstituted aryl (e.g., substituted or unsubstituted, 6- to 10-membered aryl). In certain embodiments, $R^{Z1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{Z1}$ is $-OR^{w1}$ (e.g., $-OH$ or $-O$(substituted or unsubstituted $C_{1-6}$ alkyl) (e.g., $-OMe$)). In certain embodiments, $R^{Z1}$ is $-N(R^{w2})_2$ (e.g., $-NH_2$, $-NH$ (substituted or unsubstituted $C_{1-6}$ alkyl) (e.g., $-NHMe$), or $-NMe_2$). In certain embodiments, $R^{Z1}$ is $-SR^{w1}$ (e.g., $-SH$, $-S$(substituted or unsubstituted $C_{1-6}$ alkyl) (e.g., $-SMe$, $-SEt$, $-SPr$, $-SBu$, or $-SBn$), or $-S$(substituted or unsubstituted phenyl) (e.g., $-SPh$)). In certain embodiments, $R^{Z1}$ is $-CN$. In certain embodiments, $R^{Z1}$ is $-SCN$ or $-NO_2$. In certain embodiments, $R^{Z1}$ is $-C(=NR^{w1})R^{w1}$, $-C(=NR^{w1})OR^{w1}$, or $-C(=NR^{w1})N(R^{w2})_2$. In certain embodiments, $R^{Z1}$ is $-C(=O)R^{w1}$ (e.g., $-C(=O)$(substituted or unsubstituted alkyl) or $-C(=O)$ (substituted or unsubstituted phenyl)). In certain embodiments, $R^{Z1}$ is $-C(=O)OR^{w1}$ (e.g., $-C(=O)OH$, $-C(=O)O$ (substituted or unsubstituted alkyl) (e.g., $-C(=O)OMe$), or $-C(=O)O$ (substituted or unsubstituted phenyl)). In certain embodiments, $R^{Z1}$ is $-C(=O)N(R^{w2})_2$ (e.g., $-C(=O)NH_2$, $-C(=O)NH$ (substituted or unsubstituted alkyl), $-C(=O)NH$ (substituted or unsubstituted phenyl), $-C(=O)N$ (substituted or unsubstituted alkyl)-(substituted or unsubstituted alkyl), or $-C(=O)N$ (substituted or unsubstituted phenyl)-(substituted or unsubstituted alkyl)). In certain embodiments, $R^{Z1}$ is $-NR^{w1}C(=O)R^{w1}$ (e.g., $-NHC(=O)Me$). In certain embodiments, $R^{Z1}$ is $-NR^{w1}C(=O)OR^{w1}$ or $-NR^{w1}C(=O)N(R^{w2})_2$. In certain embodiments, $R^{43}$ is of the formula:

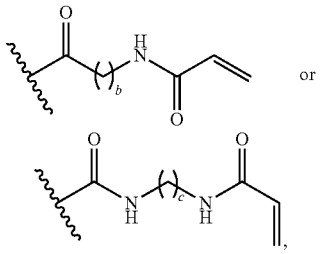

or

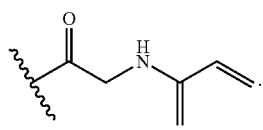

wherein: b is 0, 1, 2, 3, 4, 5, or 6; and c is 1, 2, 3, 4, 5, or 6. In certain embodiments, b is 0. In certain embodiments, b is 1. In certain embodiments, b is 2. In certain embodiments, b is 3. In certain embodiments, b is 4. In certain embodiments, b is 5. In certain embodiments, b is 6. In certain embodiments, c is 1. In certain embodiments, c is 2. In certain embodiments, c is 3. In certain embodiments, c is 4. In certain embodiments, c is 5. In certain embodiments, c is 6. In certain embodiments, $R^{43}$ is of the formula:

In certain embodiments, $R^{43}$ is of the formula:

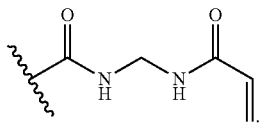 [SMILES: *C(=O)NCNC(=O)C=C]

In certain embodiments, $R^{43}$ is of the formula:

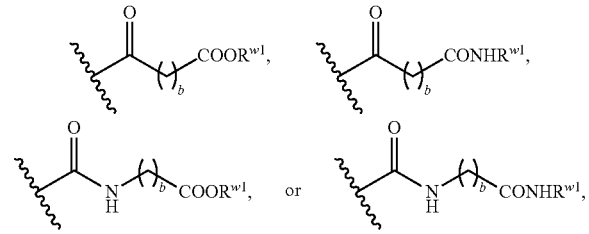

wherein: $R^{w1}$ is $C_{1-12}$ substituted or unsubstituted alkyl; and b is 0, 1, 2, 3, 4, 5, or 6. In certain embodiments, b is 0. In certain embodiments, b is 1. In certain embodiments, b is 2. In certain embodiments, b is 3. In certain embodiments, b is 4. In certain embodiments, b is 5. In certain embodiments, b is 6. In certain embodiments, $R^{w1}$ is $C_{1-12}$ substituted or unsubstituted alkyl (e.g., substituted or unsubstituted Me, Et or Pr). In certain embodiments, $R^{43}$ is of the formula:

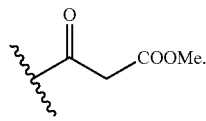

In certain embodiments, $R^{43}$ is of the formula:

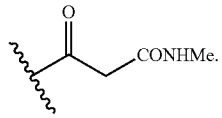

In certain embodiments, $R^{43}$ is of the formula:

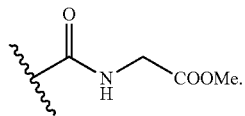

In certain embodiments, $R^{43}$ is of the formula:

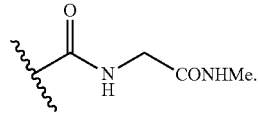

In certain embodiments, $R^{43}$ is substituted or unsubstituted alkyl. In certain embodiments, $R^{43}$ is Me. In certain embodiments, $R^{43}$ is $-CF_3$, Bn, Et, perfluoroethyl, Pr, perfluoropropyl, Bu, or perfluorobutyl. In certain embodiments, $R^{43}$ is of the formula:

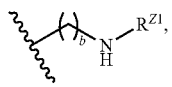

wherein: b is 4, 5, 6, 7, 8, 9, 10, 11, or 12; and $R^{Z1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, $R^{A3}$ is of the formula:

wherein: b is 4, 5, 6, 7, 8, 9, 10, 11, or 12; and $R^{Z1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, $-OR^{w1}$, $-N(R^{w2})_2$, $-SR^{w1}$, $-CN$, $-SCN$, $-C(=NR^{w1})R^{w1}$, $-C(=NR^{w1})OR^{w1}$, $-C(=NR^{w1})N(R^{w2})_2$, $-C(=O)R^{w1}$, $-C(=O)OR^{w1}$, $-C(=O)N(R^{w2})_2$, $-NO_2$, $-NR^{w1}C(=O)R^{w1}$, $-NR^{w1}C(=O)OR^{w1}$, $-NR^{w1}C(=O)N(R^{w2})_2$, $-OC(=O)R^{w1}$, $-OC(=O)OR^{w1}$, or $-OC(=O)N(R^{w2})_2$; $R^{w1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, or a sulfur protecting group when attached to a sulfur atom; and $R^{w2}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or nitrogen protecting group when attached to a nitrogen atom; or two instances of $R^{w2}$ are joined to form a substituted or unsubstituted, heterocyclic ring, or substituted or unsubstituted, heteroaryl ring. In certain embodiments, $R^{Z1}$ is substituted or unsubstituted acyl (e.g., acetyl). In certain embodiments, $R^{Z1}$ is substituted or unsubstituted alkyl (e.g., substituted or unsubstituted $C_{1-6}$ alkyl). In certain embodiments, $R^{Z1}$ is substituted or unsubstituted alkenyl (e.g., substituted or unsubstituted $C_{2-6}$ alkenyl). In certain embodiments, $R^{Z1}$ is substituted or unsubstituted alkynyl (e.g., substituted or unsubstituted $C_{2-6}$ alkynyl). In certain embodiments, $R^{Z1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{Z1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{Z1}$ is substituted or unsubstituted aryl (e.g., substituted or unsubstituted, 6- to 10-membered aryl). In certain embodiments, $R^{Z1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{Z1}$ is $-OR^{w1}$ (e.g., $-OH$ or $-O$(substituted or unsubstituted $C_{1-6}$ alkyl) (e.g., $-OMe$)). In certain embodiments, $R^{Z1}$ is $-N(R^{w2})_2$ (e.g., $-NH_2$, $-NH$ (substituted or unsubstituted $C_{1-6}$ alkyl) (e.g., $-NHMe$), or $-NMe_2$). In certain embodiments, $R^{Z1}$ is $-SR^{w1}$ (e.g., $-SH$, $-S$(substituted or unsubstituted $C_{1-6}$ alkyl) (e.g., $-SMe$, $-SEt$, $-SPr$, $-SBu$, or $-SBn$), or $-S$(substituted or unsubstituted phenyl) (e.g., $-SPh$)). In certain embodiments, $R^{Z1}$ is $-CN$. In certain embodiments, $R^{Z1}$ is $-SCN$ or $-NO_2$. In certain embodiments, $R^{Z1}$ is $-C(=NR^{w1})R^{w1}$, $-C(=NR^{w1})OR^{w1}$, or $-C(=NR^{w1})N(R^{w2})_2$. In certain embodiments, $R^{Z1}$ is $-C(=O)R^{w1}$ (e.g., $-C(=O)$(substituted or unsubstituted alkyl) or $-C(=O)$ (substituted or unsubstituted phenyl)). In certain embodiments, $R^{Z1}$ is $-C(=O)OR^{w1}$ (e.g., $-C(=O)OH$, $-C(=O)O$ (substituted or unsubstituted alkyl) (e.g., $-C(=O)OMe$), or $-C(=O)O$ (substituted or unsubstituted phenyl)). In certain embodiments, $R^{Z1}$ is $-C(=O)N(R^{w2})_2$ (e.g., $-C(=O)NH_2$, $-C(=O)NH$ (substituted or unsubstituted alkyl), $-C(=O)NH$ (substituted or unsubstituted phenyl), $-C(=O)N$ (substituted or unsubstituted alkyl)-(substituted or unsubstituted alkyl), or $-C(=O)N$ (substituted or unsubstituted phenyl)-(substituted or unsubstituted alkyl)). In certain embodiments, $R^{Z1}$ is $-NR^{w1}C(=O)R^{w1}$ (e.g., $-NHC(=O)Me$). In certain embodiments, $R^{Z1}$ is $-NR^{w1}C(=O)OR^{w1}$ or $-NR^{w1}C(=O)N(R^{w2})_2$. In certain embodiments, $R^{A3}$ is of the formula:

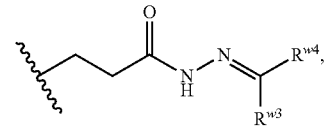

wherein: $R^{w3}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and $R^{w4}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, $R^{w3}$ is H. In certain embodiments, $R^{w3}$ is substituted or unsubstituted acyl (e.g., acetyl). In certain embodiments, $R^{w3}$ is substituted or unsubstituted alkyl (e.g., substituted or unsubstituted $C_{1-6}$ alkyl). In certain embodiments, $R^{w3}$ is substituted or unsubstituted alkenyl (e.g., substituted or unsubstituted $C_{2-6}$ alkenyl). In certain embodiments, $R^{w3}$ is substituted or unsubstituted alkynyl (e.g., substituted or unsubstituted $C_{2-6}$ alkynyl). In certain embodiments, $R^{w3}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{w3}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{w3}$ is substituted or unsubstituted aryl (e.g., substituted or unsubstituted, 6- to 10-membered aryl). In certain embodiments, $R^{w3}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{w4}$ is H. In certain embodiments, $R^{w4}$ is substituted or unsubstituted acyl (e.g., acetyl). In certain embodiments, $R^{w4}$ is substituted or unsubstituted alkyl (e.g., substituted or unsubstituted $C_{1-6}$ alkyl). In certain embodiments, $R^{w4}$ is substituted or unsubstituted alkenyl (e.g., substituted or unsubstituted $C_{2-6}$ alkenyl). In certain embodiments, $R^{w4}$ is substituted or unsubstituted alkynyl (e.g., substituted or unsubstituted $C_{2-6}$ alkynyl). In certain embodiments, $R^{w4}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{w4}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{w4}$ is substituted or unsubstituted aryl (e.g., substituted or unsubstituted, 6- to 10-membered aryl). In certain embodiments, $R^{w4}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, $R^{43}$ is of the formula:

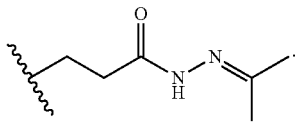 [SMILES: *CCC(=O)NN=C(C)C]

In certain embodiments, $R^{43}$ is of the formula:

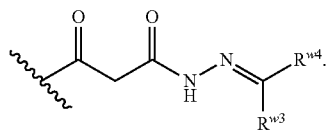

In certain embodiments, $R^{43}$ is of the formula:

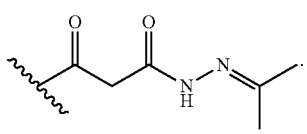 [SMILES: *C(=O)CC(=O)NN=C(C)C]

In certain embodiments, $R^{43}$ is a nitrogen protecting group (e.g., Bn, Boc, Cbz, Fmoc, trifluoroacetyl, triphenylmethyl, acetyl, or Ts). In certain embodiments, $R^{43}$ is Boc.

Formula (I) includes substituent $R^{420}$. In certain embodiments, $R^{420}$ is H. In certain embodiments, $R^{420}$ is halogen (e.g., F, Cl, Br, or I). In certain embodiments, $R^{420}$ is substituted or unsubstituted $C_{1-6}$ alkyl. In certain embodiments, $R^{420}$ is Me. In certain embodiments, $R^{420}$ is —$CF_3$, Bn, Et, perfluoroethyl, Pr, perfluoropropyl, Bu, or perfluorobutyl. In certain embodiments, $R^{420}$ is —$OR^a$, optionally wherein $R^a$ is H, substituted or unsubstituted $C_{1-6}$ alkyl (e.g., Me), substituted or unsubstituted acyl, or an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, $R^{420}$ is —$OC(=O)R^a$, optionally wherein $R^a$ is H, substituted or unsubstituted $C_{1-6}$ alkyl (e.g., Me), or substituted or unsubstituted $C_{2-6}$ alkenyl (e.g., substituted or unsubstituted vinyl). In certain embodiments, $R^{420}$ is —$OC(=O)CH=CH_2$. In certain embodiments, $R^{420}$ is —$N(R^{a1})_2$, optionally wherein each instance of $R^{a1}$ is independently H, substituted or unsubstituted $C_{1-6}$ alkyl (e.g., Me), substituted or unsubstituted acyl, or a nitrogen protecting group (e.g., Bn, Boc, Cbz, Fmoc, trifluoroacetyl, triphenylmethyl, acetyl, or Ts). In certain embodiments, $R^{420}$ is —$N(R^{a1})C(=O)R^{a1}$, optionally wherein each instance of $R^{a1}$ is independently H, substituted or unsubstituted $C_{1-6}$ alkyl (e.g., Me), or substituted or unsubstituted $C_{2-6}$ alkenyl (e.g., substituted or unsubstituted vinyl). In certain embodiments, at least one instance of $R^{a1}$ is H. In certain embodiments, at least one instance of $R^{a1}$ is substituted or unsubstituted $C_{1-6}$ alkyl (e.g., Me). In certain embodiments, at least one instance of $R^{a1}$ is substituted or unsubstituted $C_{2-6}$ alkenyl (e.g., substituted or unsubstituted vinyl). In certain embodiments, $R^{420}$ is of the formula:

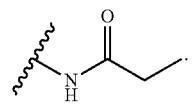

In certain embodiments, $R^{420}$ is of the formula:

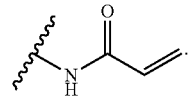

Formula (I) includes substituent $R^{44}$ on a nitrogen atom. In certain embodiments, $R^{44}$ is H. In certain embodiments, $R^{44}$ is substituted or unsubstituted $C_{1-6}$ alkyl. In certain embodiments, $R^{44}$ is Me. In certain embodiments, $R^{44}$ is —$CF_3$, Bn, Et, perfluoroethyl, Pr, perfluoropropyl, Bu, or perfluorobutyl. In certain embodiments, $R^{44}$ is a nitrogen protecting group (e.g., Bn, Boc, Cbz, Fmoc, trifluoroacetyl, triphenylmethyl, acetyl, or Ts).

Formula (I) includes substituent $R^{45}$. In certain embodiments, $R^{45}$ is of the formula:

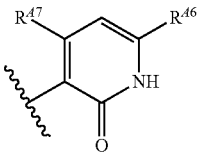

(e.g.,

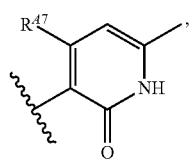

wherein $R^{47}$ is Et, Pr, or Bu). In certain embodiments, $R^{45}$ is of the formula:

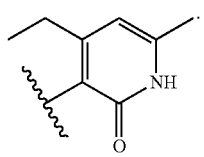 [SMILES: *c1c(CC)cc(C)[nH]c1=O]

In certain embodiments, $R^{45}$ is of the formula:

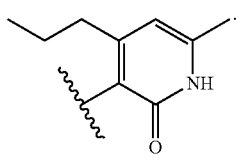 [SMILES: *c1c(CCC)cc(C)[nH]c1=O]

In certain embodiments, $R^{46}$ is H. In certain embodiments, $R^{46}$ is halogen (e.g., F, Cl, Br, or I). In certain embodiments, $R^{46}$ is substituted or unsubstituted $C_{1-6}$ alkyl. In certain embodiments, $R^{46}$ is Me. In certain embodiments, $R^{46}$ is substituted methyl (e.g., —$CF_3$ or Bn). In certain embodiments, $R^{46}$ is Et, substituted ethyl (e.g., perfluoroethyl), Pr, substituted propyl (e.g., perfluoropropyl), Bu, or substituted butyl (e.g., perfluorobutyl). In certain embodiments, $R^{46}$ is —$OR^a$ (e.g., —OH or —O(substituted or unsubstituted $C_{1-6}$ alkyl) (e.g., —OMe)). In certain embodiments, $R^{46}$ is —$N(R^{a1})_2$, optionally wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{46}$ is —$NH_2$, —NHMe, or —$N(Me)_2$. In certain embodiments, $R^{47}$ is H. In certain embodiments, $R^{47}$ is halogen (e.g., F, Cl, Br, or I). In certain embodiments, $R^{47}$ is substituted or unsubstituted $C_{2-6}$ alkyl. In certain embodiments, $R^{47}$ is Et. In certain embodiments, $R^{47}$ is substituted ethyl (e.g., perfluoroethyl). In certain embodiments, $R^{47}$ is n-Pr. In certain embodiments, $R^{47}$ is i-Pr. In certain embodiments, $R^{47}$ is substituted propyl (e.g., perfluoropropyl). In certain embodiments, $R^{47}$ is Bu or unsubstituted pentyl. In certain embodiments, $R^{47}$ is substituted butyl (e.g., perfluorobutyl) or substituted pentyl (e.g., perfluoropentyl). In certain embodiments, $R^{47}$ is substituted or unsubstituted, 3- to 7-membered, monocyclic carbocyclyl comprising 0, 1, or 2 double bonds in the carbocyclic ring system. In certain embodiments, $R^{47}$ is substituted or unsubstituted cyclopropyl, substituted or unsubstituted cyclobutyl, or substituted or unsubstituted cyclopentyl. In certain embodiments, $R^{47}$ is —$OR^a$ (e.g., —OH or —O(substituted or unsubstituted $C_{1-6}$ alkyl) (e.g., —OMe)). In certain embodiments, $R^{47}$ is —$N(R^{a1})_2$, optionally wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{47}$ is —$NH_2$, —NHMe, —NHEt, —$N(Me)_2$, or —$N(Et)_2$. In certain embodiments, $R^{47}$ is substituted or unsubstituted cyclopropyl or —$N(R^{a1})_2$, wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts).

In certain embodiments, $R^{45}$ is of the formula

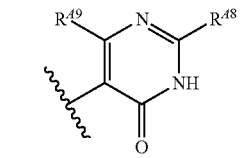

(e.g.,

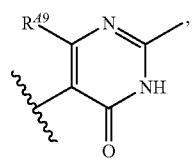

wherein $R^{49}$ is Me, Et, Pr, or Bu). The moiety of the formula:

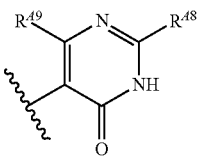

also includes its tautomeric form

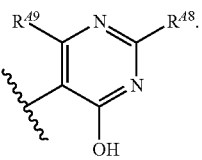

In certain embodiments, $R^{45}$ is of the formula:

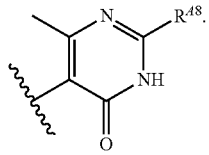

In certain embodiments, $R^{A5}$ is of the formula:

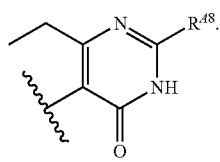

In certain embodiments, $R^{A5}$ is of the formula:

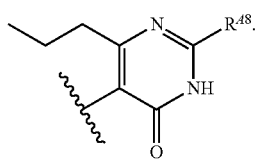

In certain embodiments, $R^{A8}$ is H. In certain embodiments, $R^{A8}$ is halogen (e.g., F, Cl, Br, or I). In certain embodiments, $R^{A8}$ is substituted or unsubstituted $C_{1-6}$ alkyl. In certain embodiments, $R^{A8}$ is Me. In certain embodiments, $R^{A8}$ is substituted methyl (e.g., —CF$_3$ or Bn). In certain embodiments, $R^{A8}$ is Et, substituted ethyl (e.g., perfluoroethyl), Pr, substituted propyl (e.g., perfluoropropyl), Bu, or substituted butyl (e.g., perfluorobutyl). In certain embodiments, $R^{A8}$ is —$OR^a$ (e.g., —OH or —O(substituted or unsubstituted $C_{1-6}$ alkyl) (e.g., —OMe)). In certain embodiments, $R^{A8}$ is —$N(R^{a1})_2$, optionally wherein each instance of $R^{a1}$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{A8}$ is —NH$_2$, —NHMe, or —N(Me)$_2$. In certain embodiments, $R^{A9}$ is H. In certain embodiments, $R^{A9}$ is halogen (e.g., F, Cl, Br, or I). In certain embodiments, $R^{A9}$ is substituted or unsubstituted $C_{1-6}$ alkyl. In certain embodiments, $R^{A9}$ is Me. In certain embodiments, $R^{A9}$ is substituted methyl (e.g., —CF$_3$ or Bn). In certain embodiments, $R^{A9}$ is Et. In certain embodiments, $R^{A9}$ is substituted ethyl (e.g., perfluoroethyl). In certain embodiments, $R^{A9}$ is n-Pr. In certain embodiments, $R^{A9}$ is i-Pr. In certain embodiments, $R^{A9}$ is substituted propyl (e.g., perfluoropropyl). In certain embodiments, $R^{A9}$ is Bu or unsubstituted pentyl. In certain embodiments, $R^{A9}$ is substituted butyl (e.g., perfluorobutyl) or substituted pentyl (e.g., perfluoropentyl). In certain embodiments, $R^{A9}$ is substituted or unsubstituted, 3- to 7-membered, monocyclic carbocyclyl comprising 0, 1, or 2 double bonds in the carbocyclic ring system. In certain embodiments, $R^{A9}$ is substituted or unsubstituted cyclopropyl, substituted or unsubstituted cyclobutyl, or substituted or unsubstituted cyclopentyl. In certain embodiments, $R^{A9}$ is —$OR^a$ (e.g., —OH or —O(substituted or unsubstituted $C_{1-6}$ alkyl) (e.g., —OMe)). In certain embodiments, $R^{A9}$ is —$N(R^{a1})_2$, optionally wherein each instance of $R^{a1}$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{A9}$ is —NH$_2$, —NHMe, —NHEt, —N(Me)$_2$, or —N(Et)$_2$. In certain embodiments, $R^{A9}$ is substituted or unsubstituted cyclopropyl, —$OR^a$, or —$N(R^{a1})_2$, wherein each instance of $R^a$ is independently hydrogen, substituted or unsubstituted $C_{1-6}$ alkyl, or an oxygen protecting group when attached to an oxygen atom, and wherein each instance of $R^{a1}$ is independently hydrogen, substituted or unsubstituted $C_{1-6}$ alkyl, or a nitrogen protecting group when attached to a nitrogen atom.

In certain embodiments, $R^{A5}$ is of the formula:

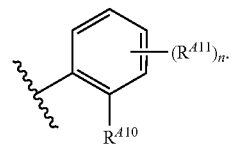

In certain embodiments, $R^{A5}$ is of the formula:

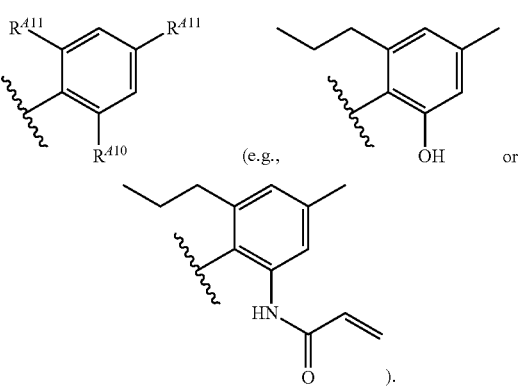

In certain embodiments, $R^{A5}$ is of the formula:

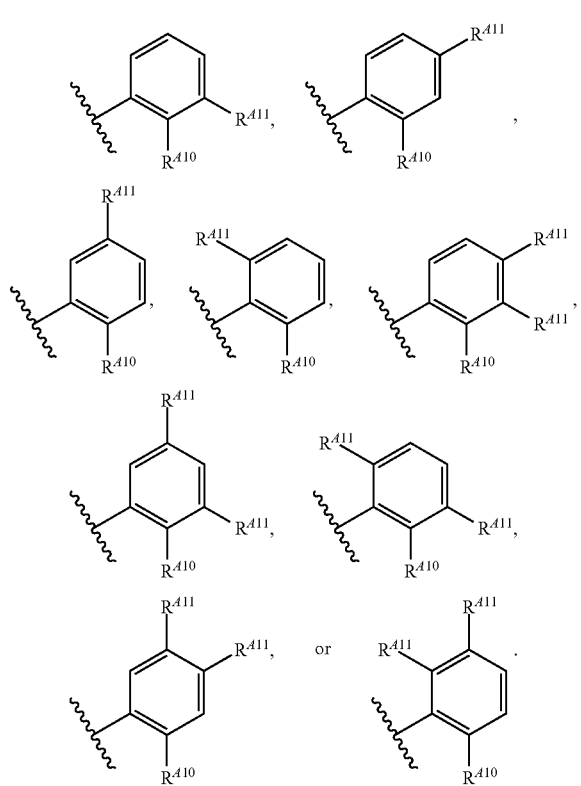

In certain embodiments, $R^{A5}$ is of the formula:

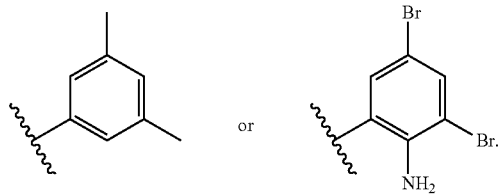

In certain embodiments, $R^{A10}$ is —OR$^a$ (e.g., —OH). In certain embodiments, $R^{A10}$ is —N(R$^{a1}$)$_2$. In certain embodiments, $R^{A10}$ is —NH$_2$. In certain embodiments, $R^{A10}$ is —NHR$^{a1}$, wherein R$^a$ is substituted or unsubstituted C$_{1-6}$ alkyl or a nitrogen protecting group (e.g., Bn, Boc, Cbz, Fmoc, trifluoroacetyl, triphenylmethyl, acetyl, or Ts). In certain embodiments, $R^{A10}$ is —NHC(=O)R$^{a1}$, optionally wherein R$^{a1}$ is substituted or unsubstituted vinyl. In certain embodiments, $R^{A10}$ is —NHC(=O)CH=CH$_2$. In certain embodiments, $R^{A10}$ is a warhead.

Formula (I) may include one or more instances of $R^{A11}$. In certain embodiments, n is 0. In certain embodiments, n is 1. In certain embodiments, n is 2. In certain embodiments, n is 3. In certain embodiments, n is 4. When Formula (I) includes two or more instances of $R^{A11}$, any two instances of $R^{A11}$ may be the same or different from each other. In certain embodiments, at least one instance of $R^{A11}$ is halogen. In certain embodiments, at least one instance of $R^{A11}$ is Br. In certain embodiments, at least one instance of $R^{A11}$ is F, Cl, or I. In certain embodiments, at least one instance of $R^{A11}$ is substituted or unsubstituted C$_{1-6}$ alkyl. In certain embodiments, at least one instance of $R^{A11}$ is Me. In certain embodiments, at least one instance of $R^{A11}$ is substituted methyl (e.g., —CF$_3$ or Bn). In certain embodiments, at least one instance of $R^{A11}$ is Et. In certain embodiments, at least one instance of $R^{A11}$ is substituted ethyl (e.g., perfluoroethyl). In certain embodiments, at least one instance of $R^{A11}$ is n-Pr. In certain embodiments, at least one instance of $R^{A11}$ is i-Pr. In certain embodiments, at least one instance of $R^{A11}$ is substituted propyl (e.g., perfluoropropyl). In certain embodiments, at least one instance of $R^{A11}$ is Me, Et, or n-Pr. In certain embodiments, at least one instance of $R^{A11}$ is Bu or unsubstituted pentyl. In certain embodiments, at least one instance of $R^{A11}$ is substituted butyl (e.g., perfluorobutyl) or substituted pentyl (e.g., perfluoropentyl). In certain embodiments, at least one instance of $R^{A11}$ is substituted or unsubstituted, 3- to 7-membered, monocyclic carbocyclyl comprising 0, 1, or 2 double bonds in the carbocyclic ring system. In certain embodiments, at least one instance of $R^{A11}$ is substituted or unsubstituted cyclopropyl, substituted or unsubstituted cyclobutyl, or substituted or unsubstituted cyclopentyl. In certain embodiments, at least one instance of $R^{A11}$ is —OR$^a$ (e.g., —OH or —O(substituted or unsubstituted C$_{1-6}$ alkyl) (e.g., —OMe)). In certain embodiments, at least one instance of $R^{A11}$ is —N(R$^{a1}$)$_2$, optionally wherein each instance of R$^{a1}$ is independently hydrogen, substituted or unsubstituted C$_{1-6}$ alkyl, or a nitrogen protecting group (e.g., Bn, Boc, Cbz, Fmoc, trifluoroacetyl, triphenylmethyl, acetyl, or Ts). In certain embodiments, at least one instance of $R^{A11}$ is —NH$_2$, —NHMe, —NHEt, —N(Me)$_2$, or —N(Et)$_2$. In certain embodiments, at least one instance of $R^{A11}$ is substituted or unsubstituted C$_{1-6}$ alkyl.

In certain embodiments, $R^{A5}$ is of the formula:

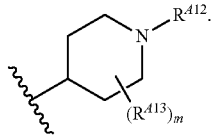

In certain embodiments, $R^{A5}$ is of the formula:

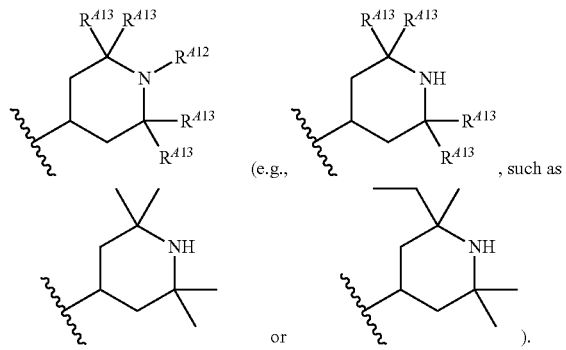

In certain embodiments, $R^{A12}$ is H. In certain embodiments, $R^{A12}$ is substituted or unsubstituted C$_{1-6}$ alkyl. In certain embodiments, $R^{A12}$ is Me. In certain embodiments, $R^{A12}$ is —CF$_3$, Bn, Et, perfluoroethyl, Pr, perfluoropropyl, Bu, or perfluorobutyl. In certain embodiments, $R^{A12}$ is a nitrogen protecting group (e.g., Bn, Boc, Cbz, Fmoc, trifluoroacetyl, triphenylmethyl, acetyl, or Ts). In certain embodiments, $R^{A12}$ is a warhead. Formula (I) may include one or more instances of $R^{A4}$. In certain embodiments, m is 0. In certain embodiments, m is 1. In certain embodiments, m is 2. In certain embodiments, m is 3. In certain embodiments, m is 4. In certain embodiments, m is 5. In certain embodiments, m is 6. In certain embodiments, m is 7. In certain embodiments, m is 8. In certain embodiments, m is 9. When Formula (I) includes two or more instances of $R^{A13}$, any two instances of $R^{A13}$ may be the same or different from each other. In certain embodiments, at least one instance of $R^{A3}$ is halogen (e.g., F, Cl, Br, or I). In certain embodiments, at least one instance of $R^{A3}$ is substituted or unsubstituted C$_{1-6}$ alkyl. In certain embodiments, at least one instance of $R^{A13}$ is Me. In certain embodiments, at least one instance of $R^{A13}$ is substituted methyl (e.g., —CF$_3$ or Bn). In certain embodiments, at least one instance of $R^{A13}$ is Et. In certain embodiments, at least one instance of $R^{A13}$ is substituted ethyl (e.g., perfluoroethyl). In certain embodiments, at least one instance of $R^{A13}$ is n-Pr. In certain embodiments, at least one instance of $R^{A13}$ is i-Pr. In certain embodiments, at least one instance of $R^{A13}$ is substituted propyl (e.g., perfluoropropyl). In certain embodiments, at least one instance of $R^{A13}$ is Me, Et, or n-Pr. In certain embodiments, at least one instance of $R^{A13}$ is Bu or unsubstituted pentyl. In certain embodiments, at least one instance of $R^{A13}$ is substituted butyl (e.g., perfluorobutyl) or substituted pentyl (e.g., perfluoropentyl). In certain embodiments, at least one instance of $R^{A13}$ is substituted or unsubstituted, 3- to 7-membered, monocyclic carbocyclyl comprising 0, 1, or 2 double bonds in the carbocyclic ring system. In certain embodiments, at least one instance of $R^{A13}$ is substituted or unsubstituted cyclopropyl, substituted or unsubstituted cyclobutyl, or substituted or unsubstituted cyclopentyl. In certain embodiments, at least one instance of $R^{A13}$ is —OR$^a$ (e.g., —OH or —O(substituted or unsubstituted $C_{1-6}$ alkyl) (e.g., —OMe)). In certain embodiments, at least one instance of $R^{413}$ is —N($R^{a1}$)$_2$, optionally wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, at least one instance of $R^{413}$ is —NH$_2$, —NHMe, —NHEt, —N(Me)$_2$, or —N(Et)$_2$. In certain embodiments, at least one instance of $R^{413}$ is halogen, substituted or unsubstituted cyclopropyl, —OR$^a$, or —N($R^{a1}$)$_2$, wherein each instance of $R^a$ is independently hydrogen, substituted or unsubstituted $C_{1-6}$ alkyl, or an oxygen protecting group when attached to an oxygen atom, and wherein each instance of $R^{a1}$ is independently hydrogen, substituted or unsubstituted $C_{1-6}$ alkyl, or a nitrogen protecting group when attached to a nitrogen atom.

In certain embodiments, $R^{A5}$ is of the formula:

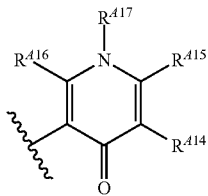

(e.g.,

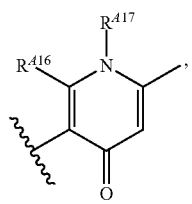

optionally wherein $R^{416}$ is Et, Pr, or Bu). In certain embodiments, $R^{A5}$ is of the formula:

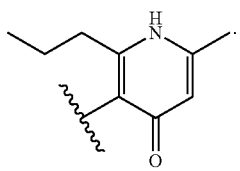 [SMILES: *c1c(CCC)[nH]c(C)cc1=O]

In certain embodiments, $R^{A5}$ is of the formula:

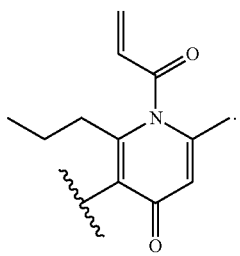 [SMILES: *c1c(CCC)n(C(=O)C=C)c(C)cc1=O]

In certain embodiments, $R^{414}$ is H. In certain embodiments, $R^{414}$ is halogen (e.g., F, Cl, Br, or I). In certain embodiments, $R^{414}$ is substituted or unsubstituted $C_{1-6}$ alkyl. In certain embodiments, $R^{414}$ is Me. In certain embodiments, $R^{414}$ is substituted methyl (e.g., —CF$_3$ or Bn). In certain embodiments, $R^{414}$ is Et, substituted ethyl (e.g., perfluoroethyl), Pr, substituted propyl (e.g., perfluoropropyl), Bu, or substituted butyl (e.g., perfluorobutyl). In certain embodiments, $R^{414}$ is —OR$^a$ (e.g., —OH or —O(substituted or unsubstituted $C_{1-6}$ alkyl) (e.g., —OMe)). In certain embodiments, $R^{414}$ is —N($R^{a1}$)$_2$, optionally wherein each instance of $R^{a1}$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{414}$ is —NH$_2$, —NHMe, or —N(Me)$_2$. In certain embodiments, $R^{415}$ is H. In certain embodiments, $R^{415}$ is halogen (e.g., F, Cl, Br, or I). In certain embodiments, $R^{415}$ is substituted or unsubstituted $C_{1-6}$ alkyl. In certain embodiments, $R^{415}$ is Me. In certain embodiments, $R^{415}$ is substituted methyl (e.g., —CF$_3$ or Bn). In certain embodiments, $R^{415}$ is Et, substituted ethyl (e.g., perfluoroethyl), Pr, substituted propyl (e.g., perfluoropropyl), Bu, or substituted butyl (e.g., perfluorobutyl). In certain embodiments, $R^{415}$ is —OR$^a$ (e.g., —OH or —O(substituted or unsubstituted $C_{1-6}$ alkyl) (e.g., —OMe)). In certain embodiments, $R^{415}$ is —N($R^{a1}$)$_2$, optionally wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{415}$ is —NH$_2$, —NHMe, or —N(Me)$_2$. In certain embodiments, $R^{416}$ is H. In certain embodiments, $R^{416}$ is halogen (e.g., F, Cl, Br, or I). In certain embodiments, $R^{416}$ is substituted or unsubstituted $C_{2-6}$ alkyl. In certain embodiments, $R^{416}$ is Et. In certain embodiments, $R^{416}$ is substituted ethyl (e.g., perfluoroethyl). In certain embodiments, $R^{416}$ is n-Pr. In certain embodiments, $R^{416}$ is i-Pr. In certain embodiments, $R^{416}$ is substituted propyl (e.g., perfluoropropyl). In certain embodiments, $R^{416}$ is Bu or unsubstituted pentyl. In certain embodiments, $R^{416}$ is substituted butyl (e.g., perfluorobutyl) or substituted pentyl (e.g., perfluoropentyl). In certain embodiments, $R^{416}$ is substituted or unsubstituted, 3- to 7-membered, monocyclic carbocyclyl comprising 0, 1, or 2 double bonds in the carbocyclic ring system. In certain embodiments, $R^{416}$ is substituted or unsubstituted cyclopropyl, substituted or unsubstituted cyclobutyl, or substituted or unsubstituted cyclopentyl. In certain embodiments, $R^{416}$ is —OR$^a$ (e.g., —OH or —O(substituted or unsubstituted $C_{1-6}$ alkyl) (e.g., —OMe)). In certain embodiments, $R^{416}$ is —N($R^{a1}$)$_2$, optionally wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{416}$ is —NH$_2$, —NHMe, —NHEt, —N(Me)$_2$, or —N(Et)$_2$. In certain embodiments, $R^{416}$ is substituted or unsubstituted cyclopropyl or —N($R^{a1}$)$_2$, wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{417}$ is H. In certain embodiments, $R^{417}$ is substituted or unsubstituted acyl. In certain embodiments, $R^{417}$ is —C(=O)R$^a$, optionally wherein R$^a$ is substituted or unsubstituted $C_{1-6}$ alkyl (e.g., Me) or substituted or unsubstituted $C_{2-6}$ alkenyl. In certain embodiments, $R^{417}$ is —C(=O)R$^a$, wherein R$^a$ is substituted or unsubstituted vinyl. In certain embodiments, $R^{417}$ is —C(=O)CH=CH$_2$. In certain embodiments, $R^{417}$ is —C(=O)OR$^a$, optionally wherein R$^a$ is H, substituted or unsubstituted $C_{1-6}$ alkyl (e.g., Me), or an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, $R^{A17}$ is —C(=O)N($R^{a1}$)$_2$, optionally wherein each instance of $R^{a1}$ is independently H, substituted or unsubstituted $C_{1-6}$ alkyl (e.g., Me), or a nitrogen protecting group (e.g., Bn, Boc, Cbz, Fmoc, trifluoroacetyl, triphenylmethyl, acetyl, or Ts). In certain embodiments, $R^{A17}$ is substituted or unsubstituted $C_{1-6}$ alkyl. In certain embodiments, $R^{A17}$ is Me. In certain embodiments, $R^{A17}$ is —CF$_3$, Bn, Et, perfluoroethyl, Pr, perfluoropropyl, Bu, or perfluorobutyl. In certain embodiments, $R^{A17}$ is a nitrogen protecting group (e.g., Bn, Boc, Cbz, Fmoc, trifluoroacetyl, triphenylmethyl, acetyl, or Ts). In certain embodiments, $R^{A17}$ is a warhead. In certain embodiments, at least one of $R^{A2}$, $R^{A10}$, $R^{A12}$, and $R^{A17}$ is a warhead; at least one of $R^{A1}$ and $R^{A2}$ is a tag; or, when $R^{A2}$ is of the formula.

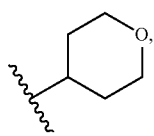 [SMILES: *C1CCOCC1]

$R^{A3}$ is not substituted or unsubstituted $C_{1-3}$ alkyl. In certain embodiments, at least one of $R^{A2}$, $R^{A10}$, $R^{A12}$, and $R^{A17}$ is a warhead. In certain embodiments, at least one of $R^{A1}$ and $R^{A2}$ is a tag (e.g., a biotin moiety

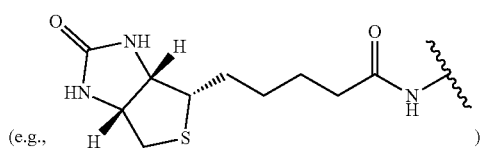 [SMILES: *NC(=O)CCCC[C@@H]1SC[C@@H]2NC(=O)N[C@@H]21]

or a small molecule fluorophore). In certain embodiments, when $R^{A2}$ is of the formula.

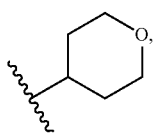 [SMILES: *C1CCOCC1]

$R^{A3}$ is not substituted or unsubstituted $C_{1-3}$ alkyl. In certain embodiments, when $R^{A2}$ is of the formula.

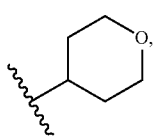 [SMILES: *C1CCOCC1]

$R^{A3}$ is not methyl. In certain embodiments, when $R^{A2}$ is of the formula.

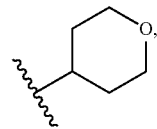

$R^{A3}$ is not ethyl.

In certain embodiments, the compound of Formula (I) is of the formula:

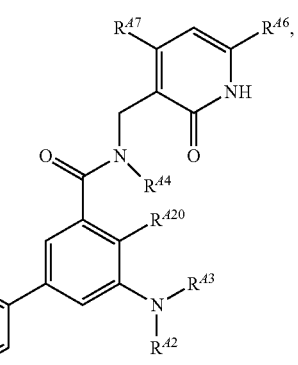

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

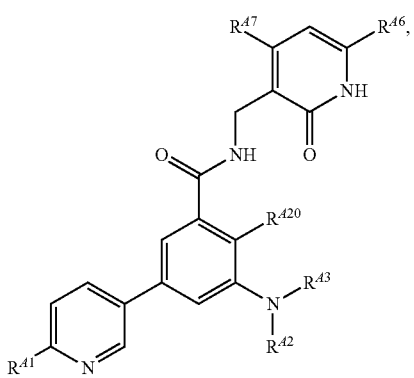

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

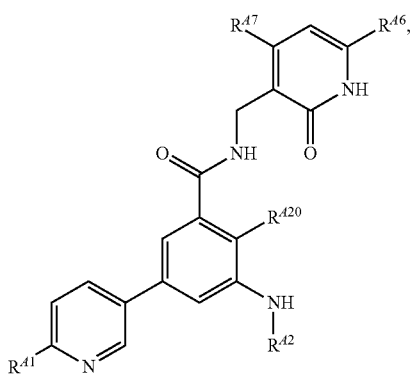

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

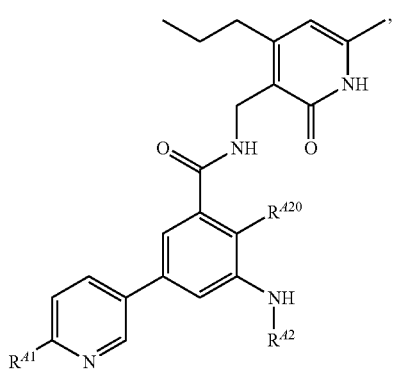

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

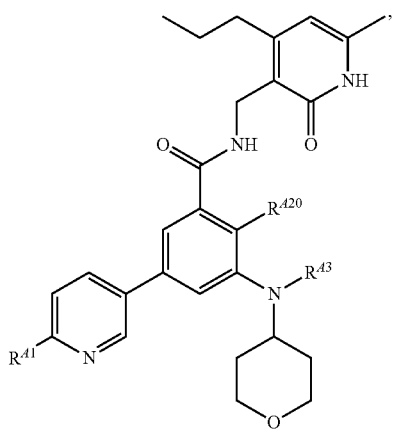

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

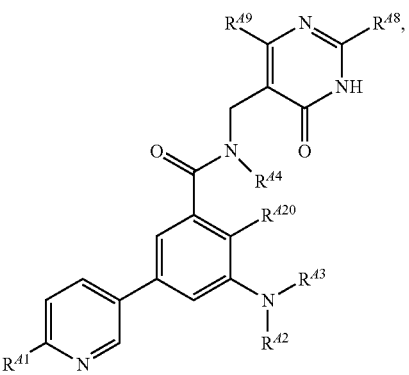

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

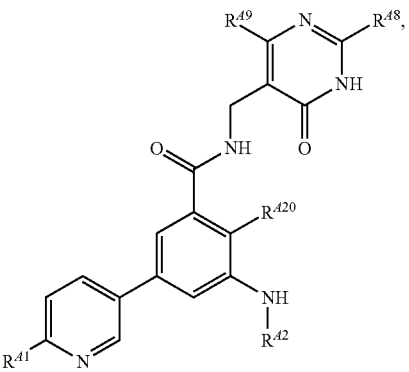

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

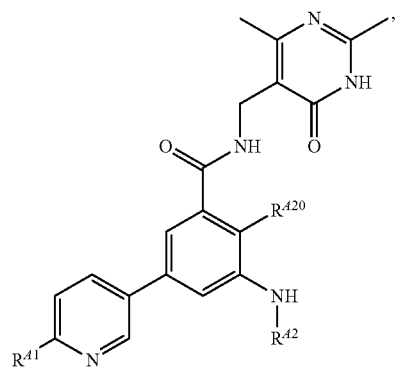

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

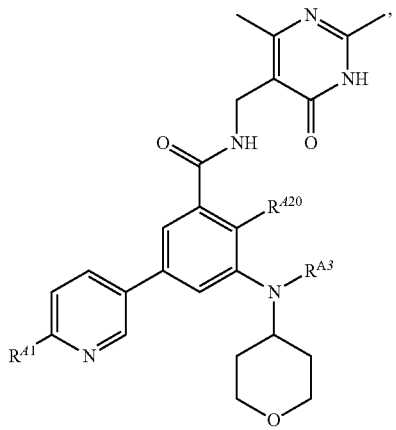

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

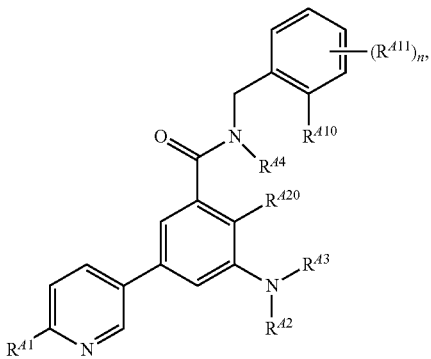

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

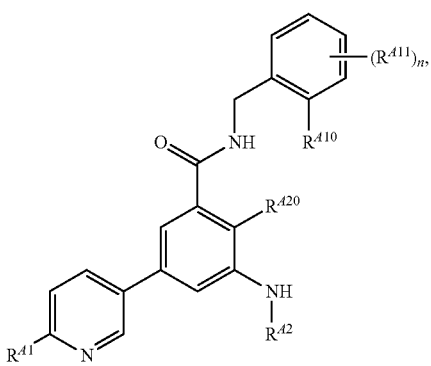

or a pharmaceutically acceptable salt, solvate, hydrate, polymorph, co-crystal, tautomer, stereoisomer, isotopically labeled derivative, or prodrug thereof. In certain embodiments, the compound of Formula (I) is of the formula:

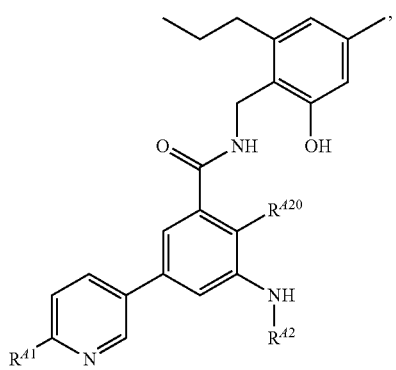

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

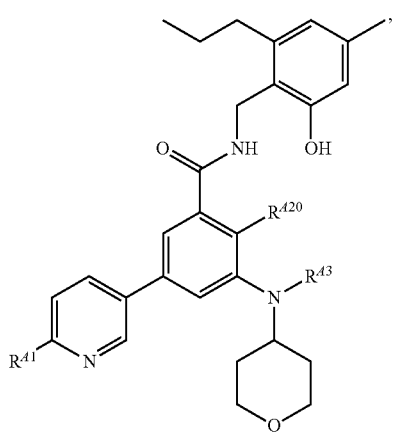

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

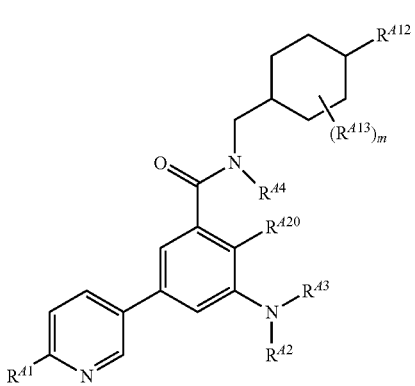

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

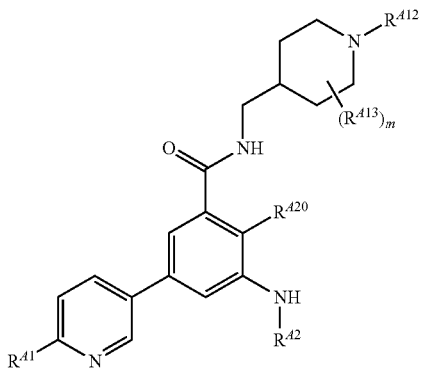

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

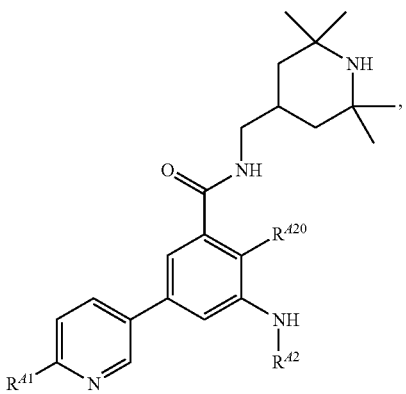

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

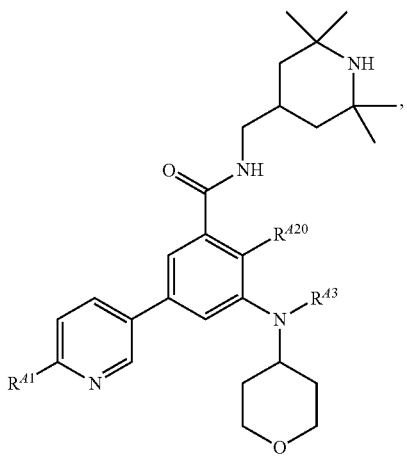

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

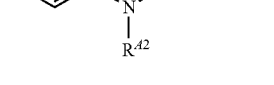

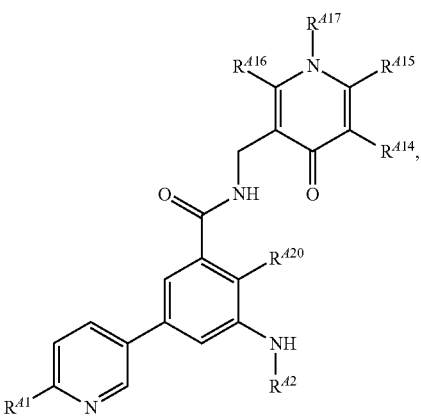

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

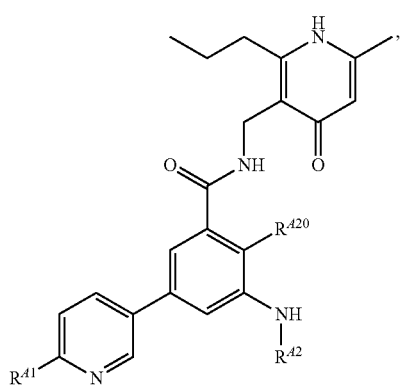

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

or a pharmaceutically acceptable salt, solvate, hydrate, polymorph, co-crystal, tautomer, stereoisomer, isotopically labeled derivative, or prodrug thereof. Exemplary compounds of Formula (I) include, but are not limited to:

and pharmaceutically acceptable salts, solvates, hydrates, polymorphs, co-crystals, tautomers, stereoisomers, isotopically labeled derivatives, and prodrugs thereof.

Exemplary compounds of Formula (I) include, but are not limited to:

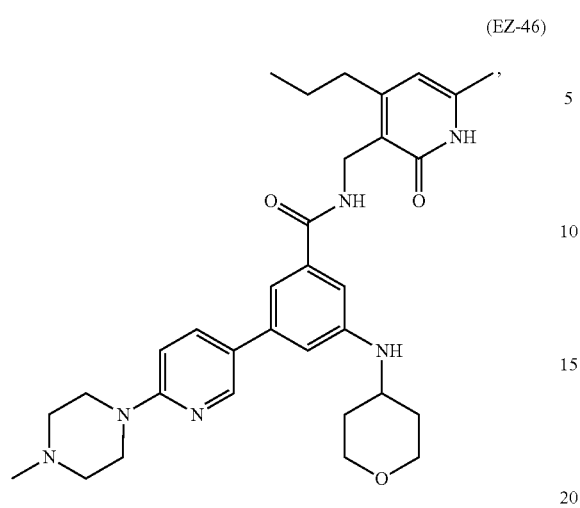
(EZ-46)
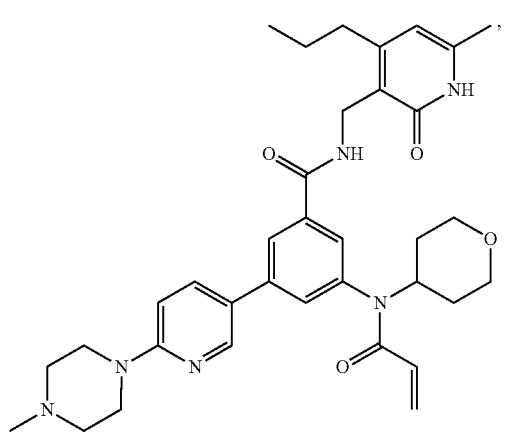
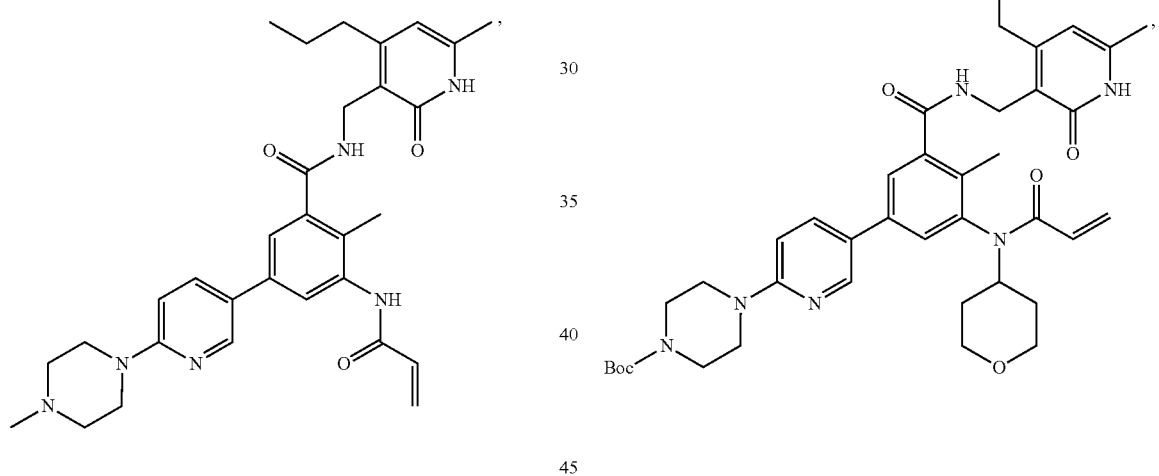
(EZ-40)
(EZ-48)
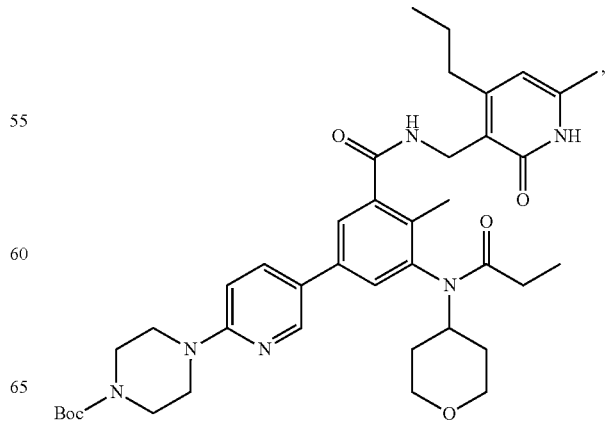
(EZ-49)

(EZ-23)
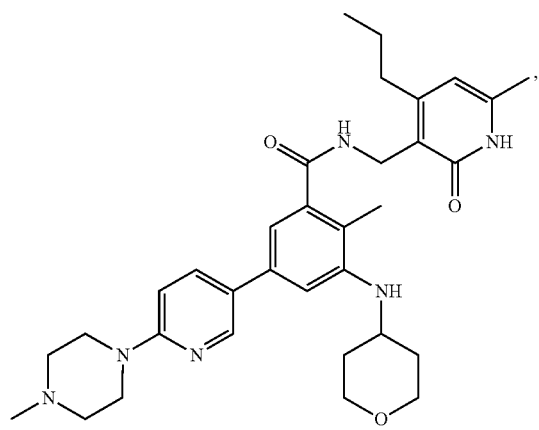
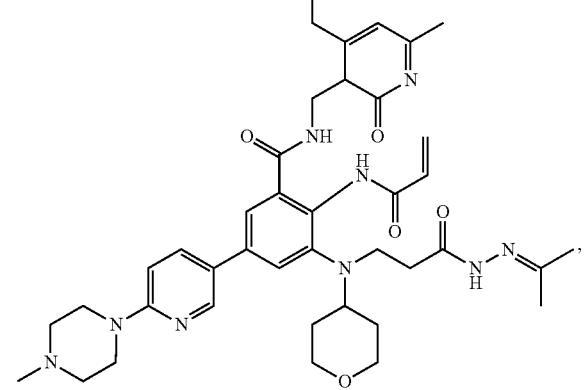
(EZ-53)
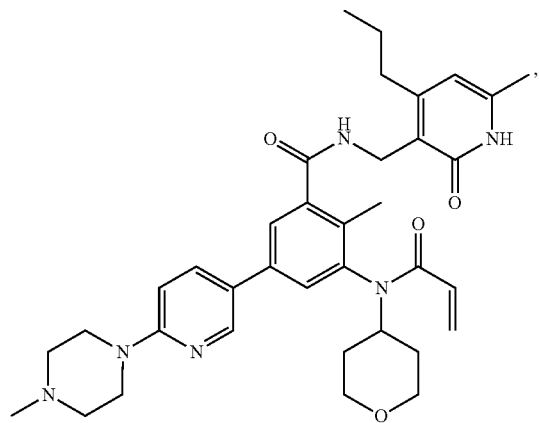
(JQ-80)
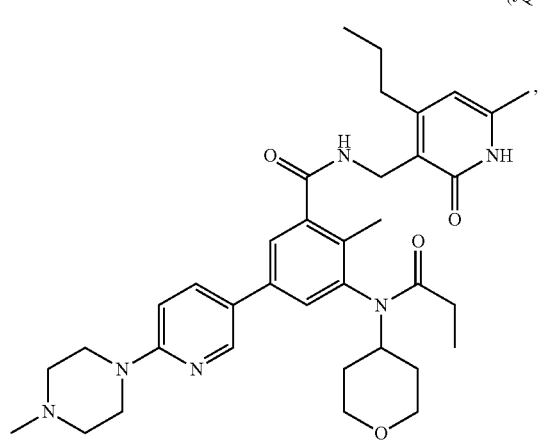
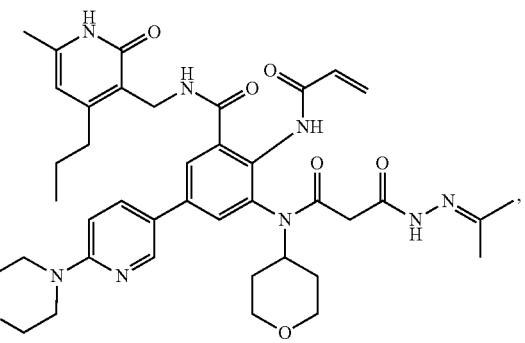
and pharmaceutically acceptable salts, solvates, hydrates, polymorphs, co-crystals, tautomers, stereoisomers, isotopically labeled derivatives, and prodrugs thereof.
Exemplary compounds of Formula (I) include, but are not limited to:

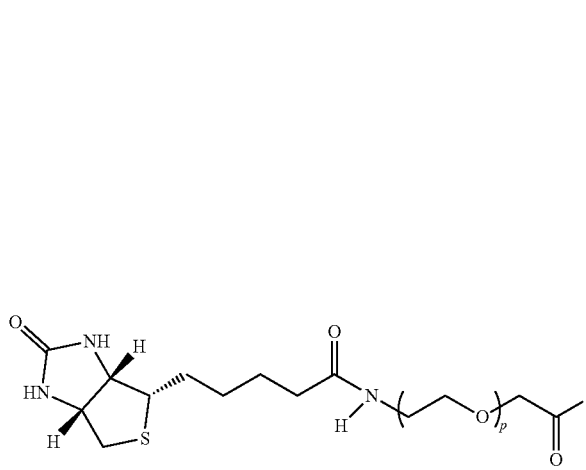
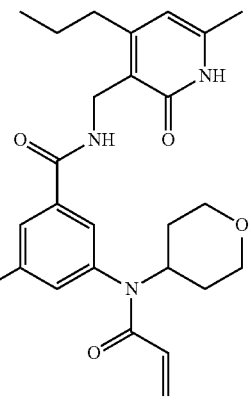

and pharmaceutically acceptable salts, solvates, hydrates, polymorphs, co-crystals, tautomers, stereoisomers, isotopically labeled derivatives, and prodrugs thereof.

In another aspect, the present disclosure provides compounds of Formula (II):

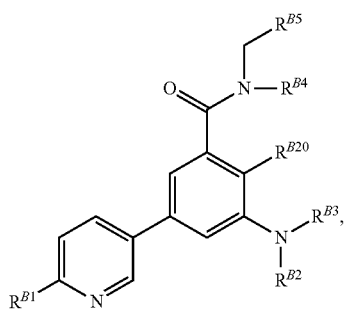

and pharmaceutically acceptable salts, solvates, hydrates, polymorphs, co-crystals, tautomers, stereoisomers, isotopically labeled derivatives, and prodrugs thereof, wherein:

$R^{B1}$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^b$, —$N(R^{b1})_2$, —$SR^b$, —CN, —SCN, —C(=$NR^b$)$R^b$, —C(=$NR^b$)$OR^b$, —C(=$NR^b$)N($R^{b1}$)$_2$, —C(=O)$R^b$, —C(=O)$OR^b$, —C(=O)N($R^{b1}$)$_2$, —NO$_2$, —$NR^b$C(=O)$R^b$, —$NR^b$C(=O)$OR^b$, —$NR^b$C(=O)N($R^{b1}$)$_2$, —OC(=O)$R^b$, —OC(=O)$OR^b$, —OC(=O)N($R^{b1}$)$_2$, a tag, or

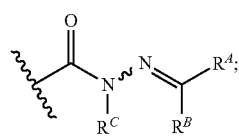

each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom;

each instance of $R^{b1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{b1}$ are joined to form a substituted or unsubstituted, heterocyclic ring, or substituted or unsubstituted, heteroaryl ring;

$R^A$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

or $R^A$ and $R^B$ are joined to form a substituted or unsubstituted, carbocyclic ring, or a substituted or unsubstituted, heterocyclic ring;

$R^C$ is hydrogen, substituted or unsubstituted $C_{1-6}$ alkyl, or a nitrogen protecting group;

$R^{B2}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, a nitrogen protecting group, a tag, or a warhead;

$R^{B3}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or a nitrogen protecting group;

$R^{B20}$ is hydrogen, halogen, substituted or unsubstituted $C_{1-6}$ alkyl, —$OR^b$, or —$N(R^{b1})_2$;

$R^{B4}$ is hydrogen, substituted or unsubstituted acyl, substituted or unsubstituted $C_{1-6}$ alkyl, a nitrogen protecting group;

$R^{B5}$ is of the formula:

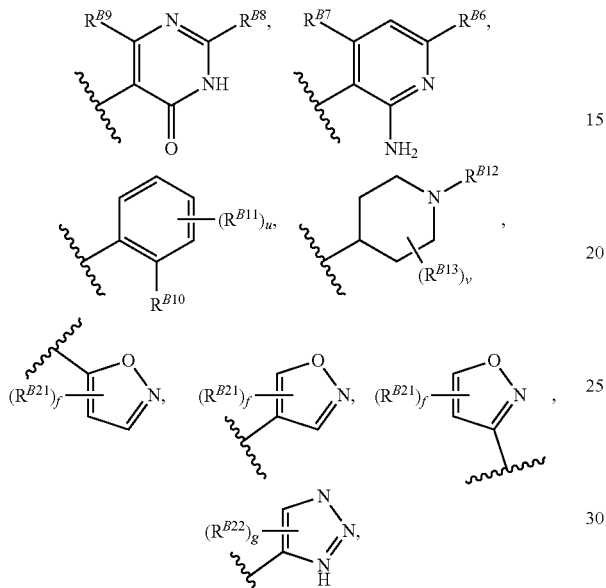

wherein:
$R^{B6}$ is hydrogen, halogen, substituted or unsubstituted $C_{1-6}$ alkyl, —$OR^b$, or —$N(R^{b1})_2$;
$R^{B7}$ is hydrogen, halogen, substituted or unsubstituted $C_{2-6}$ alkyl, substituted or unsubstituted, 3- to 7-membered, monocyclic carbocyclyl comprising 0, 1, or 2 double bonds in the carbocyclic ring system, —$OR^b$, or —$N(R^{b1})_2$;
$R^{B8}$ is hydrogen, halogen, substituted or unsubstituted $C_{1-6}$ alkyl, or —$N(R^{b1})_2$
$R^{B9}$ is hydrogen, halogen, substituted or unsubstituted $C_{1-6}$ alkyl, or substituted or unsubstituted, 3- to 7-membered, monocyclic carbocyclyl comprising 0, 1, or 2 double bonds in the carbocyclic ring system;
$R^{B10}$ is —$OR^b$, —$N(R^{b1})_2$, or a warhead;
each instance of $R^{B11}$ is independently halogen, substituted or unsubstituted $C_{1-6}$ alkyl, substituted or unsubstituted, 3- to 7-membered, monocyclic carbocyclyl comprising 0, 1, or 2 double bonds in the carbocyclic ring system, or —$N(R^{b1})_2$;
u is 0, 1, 2, 3, or 4;
$R^{B12}$ is hydrogen, substituted or unsubstituted $C_{1-6}$ alkyl, a nitrogen protecting group, or a warhead;
each instance of $R^{B13}$ is independently halogen, substituted or unsubstituted $C_{1-6}$ alkyl, substituted or unsubstituted, 3- to 7-membered, monocyclic carbocyclyl comprising 0, 1, or 2 double bonds in the carbocyclic ring system, or —$N(R^{b1})_2$; and
v is 0, 1, 2, 3, 4, 5, 6, 7, 8, or 9;
each instance of $R^{B21}$ is independently hydrogen, halogen, substituted or unsubstituted $C_{1-6}$ alkyl, —$OR^b$, or —$N(R^{b1})_2$;

f is 0, 1, or 2;
each instance of $R^{B22}$ is independently hydrogen, halogen, substituted or unsubstituted $C_{1-6}$ alkyl, —$OR^b$, —$N(R^{b1})_2$, or a nitrogen protecting group when attached to nitrogen;
g is 0, 1, or 2; and
each instance of the warhead is independently:

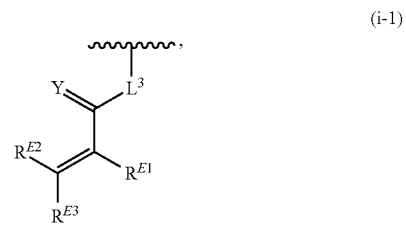

(i-1)

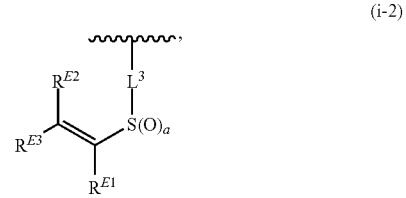

(i-2)

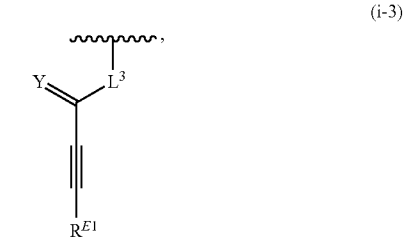

(i-3)

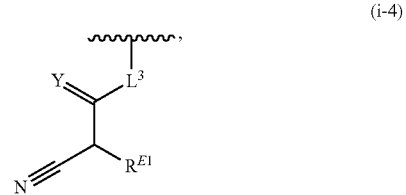

(i-4)

(i-5)

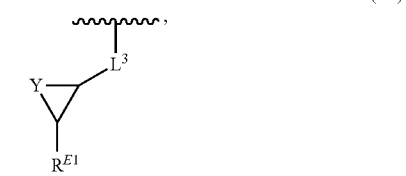

(i-6)

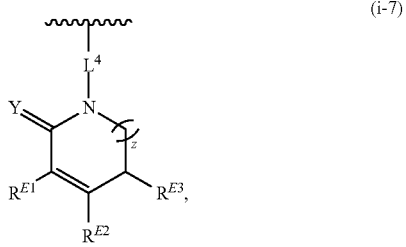

(i-7)

-continued
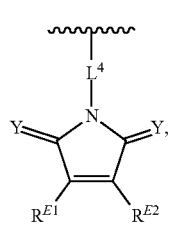 (i-8)
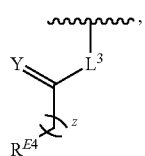 (i-9)
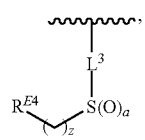 (i-10)
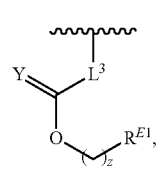 (i-11)
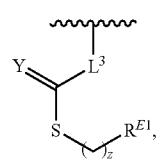 (i-12)
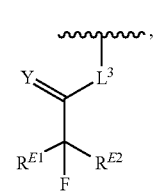 (i-13)
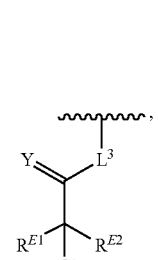 (i-14)
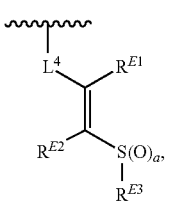 (i-15)
-continued
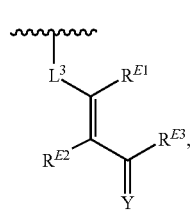 (i-16)
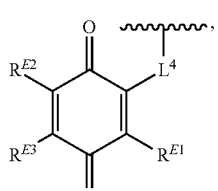 (i-17)
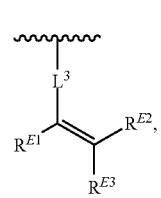 (i-18)
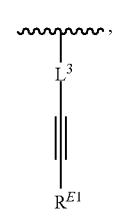 (i-19)
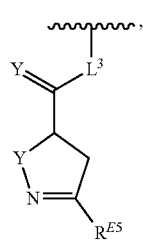 (i-20)
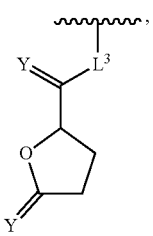 (i-21)
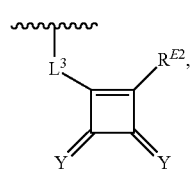 (i-22)

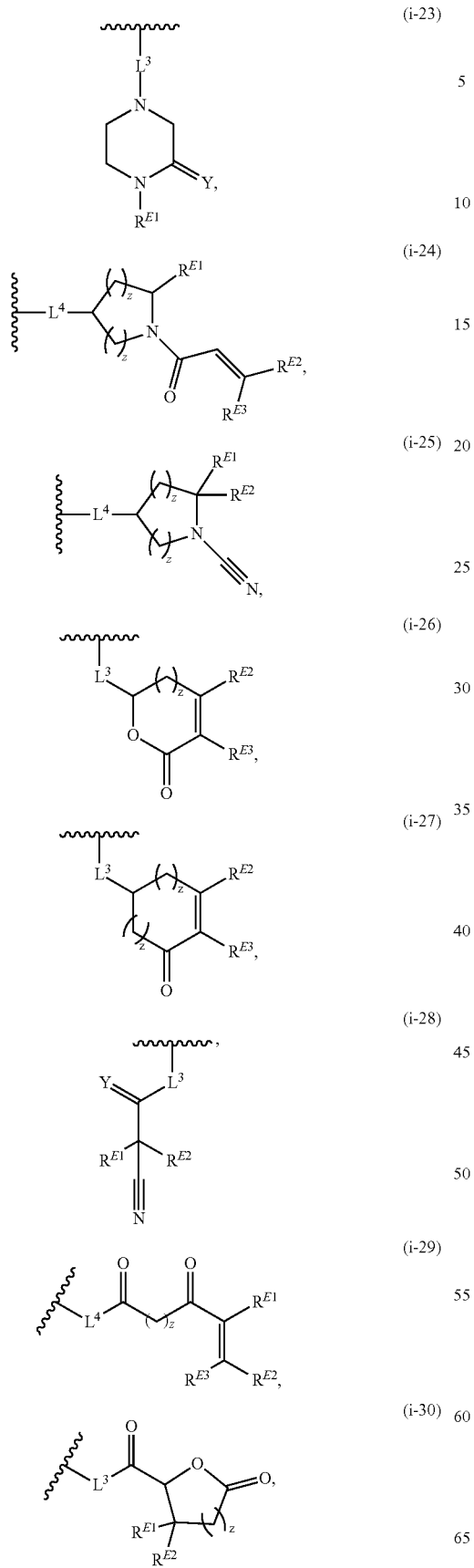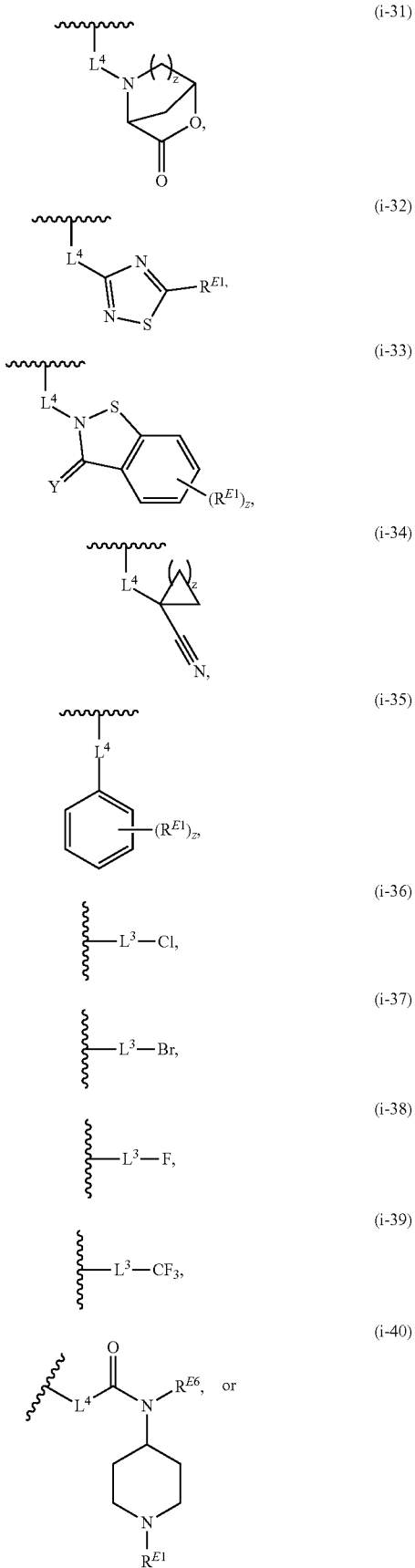

-continued (i-41)

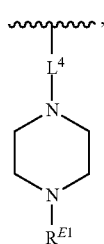

wherein:
L³ is a bond or an optionally substituted $C_{1-4}$ hydrocarbon chain, optionally wherein one or more carbon units of the hydrocarbon chain are independently replaced with —C(=O)—, —O—, —S—, —NR^a—, —NR^{L3a}C(=O)—, —C(=O)NR^{L3a}—, —SC(=O)—, —C(=O)S—, —OC(=O)—, —C(=O)O—, —NR^{L3a}C(=S)—, —C(=S)NR^{L3a}—, trans-CR^{L3b}=CR^{L3b}—, cis-CR^{L3b}=CR^{L3b}—, —C≡C—, —S(=O)—, —S(=O)O—, —OS(=O)—, —S(=O)NR^{L3a}—, —NR^{L3a}S(=O)—, —S(=O)₂—, —S(=O)₂O—, —OS(=O)₂—, —S(=O)₂NR^{L3a}—, or —NR^{L3a}S(=O)₂—, wherein $R^{L3a}$ is hydrogen, substituted or unsubstituted $C_{1-6}$ alkyl, or a nitrogen protecting group, and wherein each occurrence of $R^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{L3b}$ groups are joined to form an optionally substituted carbocyclic or optionally substituted heterocyclic ring;
L⁴ is a bond or an optionally substituted, branched or unbranched $C_{1-6}$ hydrocarbon chain;
each of $R^{E1}$, $R^{E2}$, and $R^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH₂OR^{EE}, —CH₂N(R^{EF})₂, —CH₂SR^{EE}, —OR^{EE}, —N(R^{EF})₂, —Si(R^{EG})₃, or —SR^{EE}, wherein each instance of $R^{EE}$, $R^{EF}$ and $R^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, and optionally wherein two $R^{EF}$ groups are joined to form an optionally substituted heterocyclic ring; or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;
$R^{E4}$ is a leaving group;
$R^{E5}$ is halogen;
$R^{E6}$ is hydrogen, substituted or unsubstituted $C_{1-6}$ alkyl, or a nitrogen protecting group;
each instance of Y is independently O, S, or NR^{E7}, wherein $R^{E7}$ is hydrogen, substituted or unsubstituted $C_{1-6}$ alkyl, or a nitrogen protecting group;
a is 1 or 2; and each instance of z is independently 0, 1, 2, 3, 4, 5, or 6, as valency permits.

Formula (II) includes substituent $R^{B1}$ on the pyridinyl ring. In certain embodiments, $R^{B1}$ is halogen (e.g., F, Cl, Br, or I). In certain embodiments, $R^{B1}$ is substituted or unsubstituted alkyl (e.g., substituted or unsubstituted $C_{1-6}$ alkyl). In certain embodiments, $R^{41}$ is Me. In certain embodiments, $R^{B1}$ is —CF₃, Bn, Et, perfluoroethyl, Pr, perfluoropropyl, Bu, or perfluorobutyl. In certain embodiments, $R^{B1}$ is of the formula:

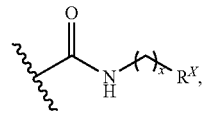

wherein: x is 1, 2, 3, 4, 5, 6, 7, 8, 9, 10, 11, or 12; and $R^X$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, —OR^{y1}, —N(R^{y2})₂, —SR^{y1}, —CN, —SCN, —C(=NR^{y1}) R^{y1}, —C(=NR^{y1})OR^{y1}, —C(=NR^{y1})N(R^{y2})₂, —C(=O)R^{y1}, —C(=O)OR^{y1}, —C(=O)N(R^{y2})₂, —NO₂, —NR^{y1}C(=O)R^{y1}, —NR^{y1}C(=O)OR^{y1}, —NR^{y1}C(=O)N(R^{y2})₂, —OC(=O)R^{y1}, —OC(=O)OR^{y1}, or —OC(=O)N(R^{y2})₂; $R^{y1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, or a sulfur protecting group when attached to a sulfur atom; and $R^{y2}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or nitrogen protecting group when attached to a nitrogen atom; or two instances of $R^{y2}$ are joined to form a substituted or unsubstituted, heterocyclic ring, or substituted or unsubstituted, heteroaryl ring. In certain embodiments, x is 1. In certain embodiments, x is 2. In certain embodiments, x is 3. In certain embodiments, x is 4. In certain embodiments, x is 5. In certain embodiments, x is 6. In certain embodiments, x is 7. In certain embodiments, x is 8. In certain embodiments, x is 9. In certain embodiments, x is 10. In certain embodiments, x is 11. In certain embodiments, x is 12. In certain embodiments, $R^X$ is substituted or unsubstituted acyl. In certain embodiments, $R^X$ is substituted or unsubstituted alkyl (e.g., substituted or unsubstituted $C_{1-6}$ alkyl). In certain embodiments, $R^X$ is substituted or unsubstituted alkenyl (e.g., substituted or unsubstituted $C_{2-6}$ alkenyl). In certain embodiments, $R^X$ is substituted or unsubstituted alkynyl (e.g., substituted or unsubstituted $C_{2-6}$ alkynyl). In certain embodiments, $R^X$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^X$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^X$ is substituted or unsubstituted aryl (e.g., substituted or unsubstituted, 6- to 10-membered aryl). In certain embodiments, $R^X$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^X$ is —$OR^{y1}$ (e.g., —OH or —O(substituted or unsubstituted $C_{1-6}$ alkyl) (e.g., —OMe)). In certain embodiments, $R^{Z1}$ is —$N(R^2)_2$ (e.g., —$NH_2$, —NH (substituted or unsubstituted $C_{1-6}$ alkyl) (e.g., —NHMe), or —$NMe_2$). In certain embodiments, $R^X$ is —$SR^{y1}$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^X$ is —CN. In certain embodiments, $R^X$ is —SCN or —$NO_2$. In certain embodiments, $R^X$ is —$C(=NR^{y1})R^{y1}$, —$C(=NR^{y1})OR^{y1}$, or —$C(=NR^{y1})N(R^2)_2$. In certain embodiments, $R^X$ is —$C(=O)R^{y1}$ (e.g., —C(=O)(substituted or unsubstituted alkyl) or —C(=O)(substituted or unsubstituted phenyl)). In certain embodiments, $R^X$ is —$C(=O)OR^1$ (e.g., —C(=O)OH, —C(=O)O (substituted or unsubstituted alkyl) (e.g., —C(=O)OMe), or —C(=O)O (substituted or unsubstituted phenyl)). In certain embodiments, $R^X$ is —$C(=O)N(R^{y2})_2$ (e.g., —$C(=O)NH_2$, —C(=O)NH (substituted or unsubstituted alkyl), —C(=O) NH (substituted or unsubstituted phenyl), —C(=O)N (substituted or unsubstituted alkyl)-(substituted or unsubstituted alkyl), or —C(=O)N (substituted or unsubstituted phenyl)-(substituted or unsubstituted alkyl)). In certain embodiments, $R^X$ is —$NR^{y1}C(=O)R^{y1}$ (e.g., —NHC(=O)Me). In certain embodiments, $R^X$ is —$NR^{w1}C(=O)OR^{w1}$ or —$NR^{w1}C(=O)N(R^{w2})_2$.

In certain embodiments, $R^{B1}$ is of the formula:

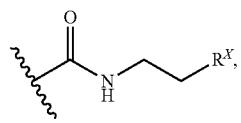

wherein: $R^X$ is substituted or unsubstituted, 5- to 10-membered monocyclic or bicyclic heterocyclic ring, wherein one or two atoms in the heterocyclic ring are independently nitrogen, oxygen, or sulfur. In certain embodiments, $R^X$ is substituted or unsubstituted phenyl. In certain embodiments, $R^X$ is substituted or unsubstituted tetrahydrofuran. In certain embodiments, $R^X$ is substituted or unsubstituted pyrrolidine. In certain embodiments, $R^X$ is substituted or unsubstituted piperazine. In certain embodiments, $R^{B1}$ is of the formula:

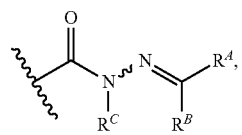

wherein $R^A$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; $R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; or $R^A$ and $R^B$ are joined to form a substituted or unsubstituted, carbocyclic ring, or a substituted or unsubstituted, heterocyclic ring; and $R^C$ is hydrogen, substituted or unsubstituted $C_{1-6}$ alkyl, or a nitrogen protecting group. In certain embodiments, $R^{B1}$ is of the formula:

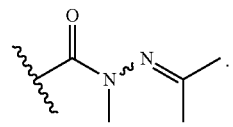

In certain embodiments, $R^{B1}$ is substituted or unsubstituted alkyl (e.g., substituted or unsubstituted $C_{1-6}$ alkyl). In certain embodiments, $R^{B1}$ is Me. In certain embodiments, $R^{B1}$ is —$CF_3$, Bn, Et, perfluoroethyl, Pr, perfluoropropyl, Bu, or perfluorobutyl. In certain embodiments, $R^{B1}$ is substituted or unsubstituted alkenyl (e.g., substituted or unsubstituted $C_{2-6}$ alkenyl). In certain embodiments, $R^{B1}$ is substituted or unsubstituted alkynyl (e.g., substituted or unsubstituted $C_{1-6}$ alkynyl). In certain embodiments, $R^{B1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B1}$ is substituted or unsubstituted, 3- to 7-membered, monocyclic heterocyclyl comprising 0, 1, or 2 double bonds in the heterocyclic ring system, wherein 1, 2, or 3 atoms in the heterocyclic ring system are independently nitrogen, oxygen, or sulfur. In certain embodiments, $R^{B1}$ is substituted or unsubstituted piperazinyl. In certain embodiments, $R^{B1}$ is of the formula:

In certain embodiments, $R^{B1}$ is of the formula:

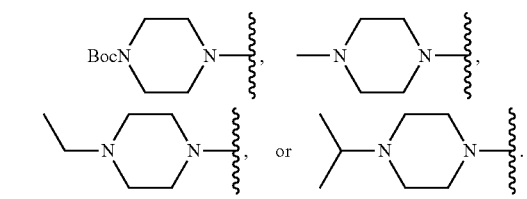

In certain embodiments, $R^{B1}$ is of the formula:

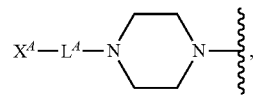

wherein $L^A$ is a bond or substituted or unsubstituted $C_{1-100}$ hydrocarbon chain, optionally wherein one or more chain atoms of the hydrocarbon chain are independently replaced with —O—, —S—, or —$NR^a$—; and $X^A$ is a small molecule, peptide, protein, or polynucleotide. In certain embodiments, $R^{B1}$ is of the formula:

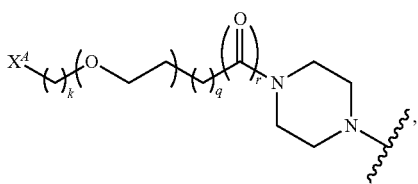

wherein: r is 0 or 1; k is an integer between 0 and 10, inclusive; p is an integer between 2 and 20, inclusive; and q is an integer between 2 and 10, inclusive. In certain embodiments, p is an integer between 3 and 11, inclusive, q is 0, and k is 0, 1, 2, 3, 4, 5, or 6. In certain embodiments, $X^A$ is a small molecule. In certain embodiments, $X^A$ is a small molecule tag (e.g., a biotin moiety

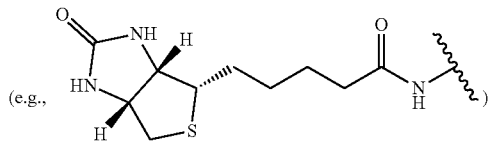 [SMILES: *NC(=O)CCCC[C@@H]1SC[C@@H]2NC(=O)N[C@@H]21]

or a small molecule fluorophore). In certain embodiments, $R^{B1}$ is

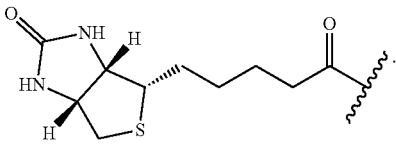 [SMILES: *C(=O)CCCC[C@@H]1SC[C@@H]2NC(=O)N[C@@H]21]

In certain embodiments, $R^{B1}$ is substituted or unsubstituted aryl (e.g., substituted or unsubstituted, 6- to 10-membered aryl). In certain embodiments, $R^{B1}$ is substituted or unsubstituted phenyl. In certain embodiments, $R^{B1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, $R^{B1}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, $R^{B1}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{B1}$ is —$N(R^{a1})_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^{B1}$ is —CN. In certain embodiments, $R^{B1}$ is —SCN or —$NO_2$. In certain embodiments, $R^{B1}$ is C(=$NR^b$)$R^b$, —C(=$NR^b$)$OR^b$, —C(=$NR^b$)N($R^{b1}$)$_2$. In certain embodiments, $R^{B1}$ is —C(=O)$R^b$ (e.g., —C(=O)(substituted or unsubstituted alkyl) or —C(=O)(substituted or unsubstituted phenyl)). In certain embodiments, $R^{B1}$ is —C(=O)$OR^b$ (e.g., —C(=O)OH, —C(=O)O(substituted or unsubstituted alkyl) (e.g., —C(=O)OMe), or —C(=O)O(substituted or unsubstituted phenyl)). In certain embodiments, $R^{B1}$ is —C(=O)N($R^{b1}$)$_2$ (e.g., —C(=O)$NH_2$, —C(=O)NH(substituted or unsubstituted alkyl), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, $R^{B1}$ is —$NR^bC(=O)R^b$ (e.g., —NHC(=O)Me). In certain embodiments, $R^{B1}$ is —$NR^bC(=O)OR^b$ or —$NR^bC(=O)N(R^{b1})_2$. In certain embodiments, $R^{B1}$ is —OC(=O)$R^b$, —OC(=O)$OR^b$, or —OC(=O)N($R^{b1}$)$_2$.

Formula (II) may include one or more instances of substituent $R^b$. When Formula (II) includes two or more instances of $R^b$, any two instances of $R^b$ may be the same or different from each other. In certain embodiments, at least one instance of $R^b$ is H. In certain embodiments, each instance of $R^a$ is H. In certain embodiments, at least one instance of $R^b$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridinesulfenyl, or triphenylmethyl) when attached to a sulfur atom. Formula (II) may include one or more instances of substituent $R^{b1}$. In certain embodiments, $R^b$ is a nitrogen protecting group (e.g., Bn, Boc, Cbz, Fmoc, trifluoroacetyl, triphenylmethyl, acetyl, or Ts) when attached to a nitrogen atom. When Formula (II) includes two or more instances of $R^{b1}$, any two instances of $R^{b1}$ may be the same or different from each other. In certain embodiments, at least one instance of $R^{b1}$ is H. In certain embodiments, each instance of $R^{b1}$ is H. In certain embodiments, at least one instance of $R^{b1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group (e.g., Bn, Boc, Cbz, Fmoc, trifluoroacetyl, triphenylmethyl, acetyl, or Ts) when attached to a nitrogen atom. In certain embodiments, two instances of $R^{b1}$ are joined to form a substituted or unsubstituted, heterocyclic ring, or substituted or unsubstituted, heteroaryl ring. In certain embodiments, $R^{B1}$ is a tag, e.g., a small molecule label (e.g., a biotin moiety

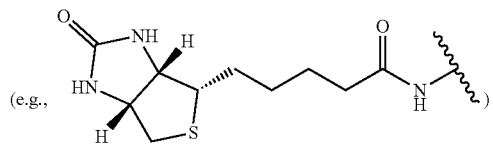 [SMILES: *NC(=O)CCCC[C@@H]1SC[C@@H]2NC(=O)N[C@@H]21]

or a small molecule fluorophore).

Formula (II) includes substituent $R^{B2}$. In certain embodiments, $R^{B2}$ is substituted or unsubstituted acyl. In certain embodiments, $R^{B2}$ is —C(=O)$R^b$, optionally wherein $R^b$ is substituted or unsubstituted $C_{1-6}$ alkyl (e.g., Me) or substituted or unsubstituted $C_{2-6}$ alkenyl. In certain embodiments, $R^{B2}$ is —C(=O)$R^b$, wherein $R^b$ is substituted or unsubstituted vinyl. In certain embodiments, $R^{B2}$ is —C(=O)CH=$CH_2$. In certain embodiments, $R^{B2}$ is —C(=O)$OR^b$, optionally wherein $R^b$ is H, substituted or unsubstituted $C_{1-6}$ alkyl (e.g., Me), or an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, $R^{B2}$ is —C(=O)N($R^{b1}$)$_2$, optionally wherein each instance of $R^{b1}$ is independently H, substituted or unsubstituted C$_{1-6}$ alkyl (e.g., Me), or a nitrogen protecting group (e.g., Bn, Boc, Cbz, Fmoc, trifluoroacetyl, triphenylmethyl, acetyl, or Ts). In certain embodiments, $R^{B2}$ is substituted or unsubstituted alkyl (e.g., substituted or unsubstituted C$_{1-6}$ alkyl). In certain embodiments, $R^{B2}$ is Me. In certain embodiments, $R^{B2}$ is Et. In certain embodiments, $R^{B2}$ is n-Pr. In certain embodiments, $R^{B2}$ is i-Pr. In certain embodiments, $R^{B2}$ is Bu (e.g., n-Bu, i-Bu, sec-Bu, or t-Bu). In certain embodiments, $R^{B2}$ is unsubstituted pentyl (e.g., unsubstituted n-pentyl, unsubstituted t-pentyl, unsubstituted neopentyl, unsubstituted isopentyl, unsubstituted sec-pentyl, or unsubstituted 3-pentyl). In certain embodiments, $R^{B2}$ is sec-Bu, t-Bu, or unsubstituted 3-pentyl. In certain embodiments, $R^{A2}$ is —CF$_3$, Bn, perfluoroethyl, perfluoropropyl, perfluorobutyl, or perfluoropentyl. In certain embodiments, $R^{A2}$ is —CH$_2$C(=O)—NH—N=C($R^{b1}$)$_2$. In certain embodiments, $R^{B2}$ is substituted or unsubstituted alkenyl (e.g., substituted or unsubstituted C$_{2-6}$ alkenyl). In certain embodiments, $R^{B2}$ is substituted or unsubstituted alkynyl (e.g., substituted or unsubstituted C$_{1-6}$ alkynyl). In certain embodiments, $R^{B2}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B2}$ is substituted or unsubstituted cyclopropyl. In certain embodiments, $R^{B2}$ is unsubstituted cyclopropyl. In certain embodiments, $R^{B2}$ is substituted or unsubstituted cyclobutyl. In certain embodiments, $R^{B2}$ is substituted or unsubstituted cyclopentyl. In certain embodiments, $R^{B2}$ is unsubstituted cyclopropyl, unsubstituted cyclobutyl, or unsubstituted cyclopentyl. In certain embodiments, $R^{B2}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{B2}$ is substituted or unsubstituted tetrahydropyranyl. In certain embodiments, $R^{B2}$ is of the formula:

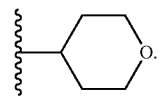

In certain embodiments, $R^{B2}$ is of the formula:

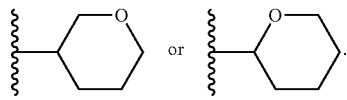

In certain embodiments, $R^{B2}$ is substituted or unsubstituted oxetanyl, substituted or unsubstituted tetrahydrofuranyl, substituted or unsubstituted pyrrolidinyl, substituted or unsubstituted piperidinyl, substituted or unsubstituted morpholinyl, or substituted or unsubstituted piperazinyl. In certain embodiments, $R^{B2}$ is of the formula:

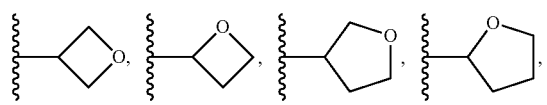

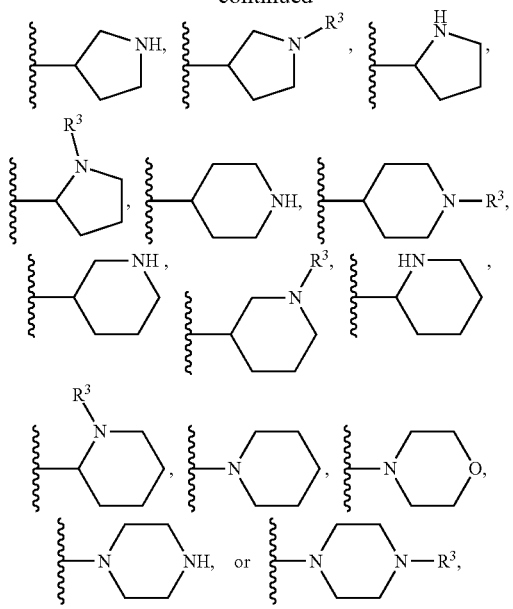

wherein each instance of $R^3$ is independently H or unsubstituted alkyl (e.g., Me)). In certain embodiments, $R^{B2}$ is substituted or unsubstituted aryl (e.g., substituted or unsubstituted, 6- to 10-membered aryl). In certain embodiments, $R^{B2}$ is substituted or unsubstituted phenyl. In certain embodiments, $R^{B2}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, $R^{B2}$ is a nitrogen protecting group (e.g., Bn, Boc, Cbz, Fmoc, trifluoroacetyl, triphenylmethyl, acetyl, or Ts). In certain embodiments, $R^{B2}$ is Boc. In certain embodiments, $R^{B2}$ is a tag, (e.g., a biotin moiety (e.g., 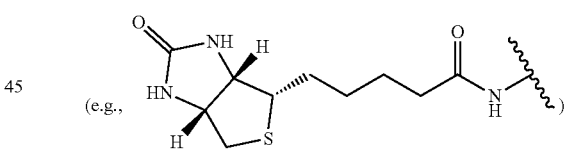)

or a small molecule fluorophore)). In certain embodiments, $R^{B2}$ is a warhead.

Formula (II) includes substituent $R^{B3}$. In certain embodiments, $R^{B3}$ is H. In certain embodiments, $R^{B3}$ is substituted or unsubstituted acyl (e.g., acetyl). In certain embodiments, $R^{B3}$ is of the formula:

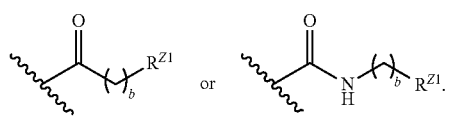

wherein: b is 0, 1, 2, 3, 4, 5, 6, 7, 8, 9, 10, 11, or 12; and $R^{Z1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, —OR$^{w1}$, —N(R$^{w2}$)$_2$, —SR$^{w1}$, —CN, —SCN, —C(=NR$^{w1}$)R$^{w1}$, —C(=NR$^{w1}$)OR$^{w1}$, —C(=NR$^{w1}$)N(R$^{w2}$)$_2$, —C(=O)R$^{w1}$, —C(=O)OR$^{w1}$, —C(=O)N(R$^{w2}$)$_2$, —NO$_2$, —NR$^{w1}$C(=O)R$^{w1}$, —NR$^{w2}$C(=O)OR$^{w2}$, —NR$^{w2}$C(=O)N(R$^{w2}$)$_2$, —OC(=O)R$^{w1}$, —OC(=O)OR$^{w1}$, or —OC(=O)N(R$^{w2}$)$_2$; R$^{w1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, or a sulfur protecting group when attached to a sulfur atom; and R$^{w2}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or nitrogen protecting group when attached to a nitrogen atom; or two instances of R$^{w2}$ are joined to form a substituted or unsubstituted, heterocyclic ring, or substituted or unsubstituted, heteroaryl ring. In certain embodiments, b is 0. In certain embodiments, b is 1. In certain embodiments, b is 2. In certain embodiments, b is 3. In certain embodiments, b is 4. In certain embodiments, b is 5. In certain embodiments, b is 6. In certain embodiments, b is 7. In certain embodiments, b is 8. In certain embodiments, b is 9. In certain embodiments, b is 10. In certain embodiments, b is 11. In certain embodiments, b is 12. In certain embodiments, R$^{Z1}$ is substituted or unsubstituted acyl. In certain embodiments, R$^{Z1}$ is substituted or unsubstituted alkyl (e.g., substituted or unsubstituted C$_{1-6}$ alkyl). In certain embodiments, R$^{B3}$ is

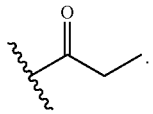 [SMILES: *C(=O)CC]

In certain embodiments, R$^{Z1}$ is substituted or unsubstituted alkenyl (e.g., substituted or unsubstituted C$_{2-6}$ alkenyl). In certain embodiments, R$^{B3}$ is

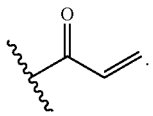 [SMILES: *C(=O)C=C]

In certain embodiments, R$^{Z1}$ is substituted or unsubstituted alkynyl (e.g., substituted or unsubstituted C$_{2-6}$ alkynyl). In certain embodiments, R$^{Z1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, R$^{Z1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R$^{Z1}$ is substituted or unsubstituted aryl (e.g., substituted or unsubstituted, 6- to 10-membered aryl). In certain embodiments, R$^{Z1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, R$^{Z1}$ is —OR$^{w1}$ (e.g., —OH or —O(substituted or unsubstituted C$_{1-6}$ alkyl) (e.g., —OMe)). In certain embodiments, R$^{Z1}$ is —N(R$^{w2}$)$_2$ (e.g., —NH$_2$, —NH (substituted or unsubstituted C$_{1-6}$ alkyl) (e.g., —NHMe), or —NMe$_2$). In certain embodiments, R$^{Z1}$ is —SR$^{w1}$ (e.g., —SH, —S(substituted or unsubstituted C$_{1-6}$ alkyl) (e.g., —SMe, —SEt, —SPr, —SBu, or —SBn), or —S(substituted or unsubstituted phenyl) (e.g., —SPh)). In certain embodiments, R$^{Z1}$ is —CN. In certain embodiments, R$^{Z1}$ is —SCN or —NO$_2$. In certain embodiments, R$^{Z1}$ is —C(=NR$^{w1}$)R$^{w1}$, —C(=NR$^{w1}$)OR$^{w1}$, or —C(=NR$^{w}$)N(R$^{w2}$)$_2$. In certain embodiments, R$^{Z1}$ is —C(=O)R$^{w1}$ (e.g., —C(=O)(substituted or unsubstituted alkyl) or —C(=O) (substituted or unsubstituted phenyl)). In certain embodiments, R$^{Z1}$ is —C(=O)OR$^{w1}$ (e.g., —C(=O)OH, —C(=O)O (substituted or unsubstituted alkyl) (e.g., —C(=O)OMe), or —C(=O)O (substituted or unsubstituted phenyl)). In certain embodiments, R$^{Z1}$ is —C(=O)N(R$^{w2}$)$_2$ (e.g., —C(=O)NH$_2$, —C(=O)NH (substituted or unsubstituted alkyl), —C(=O)NH (substituted or unsubstituted phenyl), —C(=O)N (substituted or unsubstituted alkyl)-(substituted or unsubstituted alkyl), or —C(=O)N (substituted or unsubstituted phenyl)-(substituted or unsubstituted alkyl)). In certain embodiments, R$^{Z1}$ is —NR$^{w}$C(=O)R$^{w1}$ (e.g., —NHC(=O)Me). In certain embodiments, R$^{Z1}$ is —NR$^{w1}$C(=O)OR$^{w1}$ or —NR$^{w1}$C(=O)N(R$^{w2}$)$_2$.

In certain embodiments, R$^{B3}$ is of the formula:

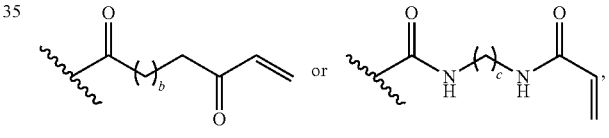

wherein: b is 0, 1, 2, 3, 4, 5, or 6; and c is 1, 2, 3, 4, 5, or 6. In certain embodiments, b is 0. In certain embodiments, b is 1. In certain embodiments, b is 2. In certain embodiments, b is 3. In certain embodiments, b is 4. In certain embodiments, b is 5. In certain embodiments, b is 6. In certain embodiments, c is 1. In certain embodiments, c is 2. In certain embodiments, c is 3. In certain embodiments, c is 4. In certain embodiments, c is 5. In certain embodiments, c is 6. In certain embodiments, R$^{B3}$ is of the formula:

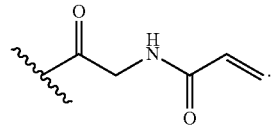 [SMILES: *C(=O)CNC(=O)C=C]

In certain embodiments, R$^{B3}$ is of the formula:

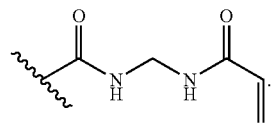 [SMILES: *C(=O)NCNC(=O)C=C]

In certain embodiments, $R^{B3}$ is of the formula:

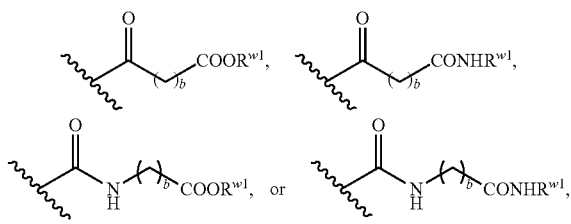

$R^{w1}$ is $C_{1-12}$ substituted or unsubstituted alkyl; and b is 0, 1, 2, 3, 4, 5, or 6. In certain embodiments, b is 0. In certain embodiments, b is 1. In certain embodiments, b is 2. In certain embodiments, b is 3. In certain embodiments, b is 4. In certain embodiments, b is 5. In certain embodiments, b is 6. In certain embodiments, $R^{w1}$ is $C_{1-12}$ substituted or unsubstituted alkyl (e.g., substituted or unsubstituted Me, Et or Pr). In certain embodiments, $R^{A3}$ is of the formula:

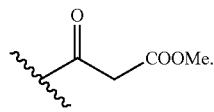

In certain embodiments, $R^{B3}$ is of the formula:

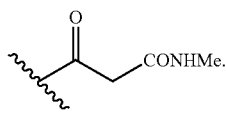

In certain embodiments, $R^{B3}$ is of the formula:

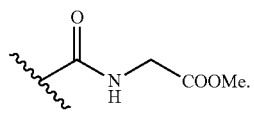 [SMILES: *C(=O)NCC(=O)OC]

In certain embodiments, $R^{B3}$ is of the formula:

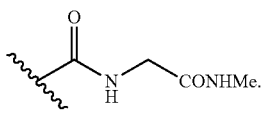

In certain embodiments, $R^{B3}$ is substituted or unsubstituted alkyl. In certain embodiments, $R^{B3}$ is Me. In certain embodiments, $R^{B3}$ is —$CF_3$, Bn, Et, perfluoroethyl, Pr, perfluoropropyl, Bu, or perfluorobutyl. In certain embodiments, $R^{B3}$ is of the formula:

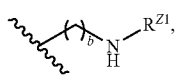

wherein: b is 4, 5, 6, 7, 8, 9, 10, 11, or 12; and $R^{Z1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, In certain embodiments, b is 0. In certain embodiments, b is 1. In certain embodiments, b is 2. In certain embodiments, b is 3. In certain embodiments, b is 4. In certain embodiments, b is 5. In certain embodiments, b is 6. In certain embodiments, b is 7. In certain embodiments, b is 8. In certain embodiments, b is 9. In certain embodiments, b is 10. In certain embodiments, b is 11. In certain embodiments, b is 12. In certain embodiments, $R^{B3}$ is of the formula:

wherein: b is 4, 5, 6, 7, 8, 9, 10, 11, or 12; and $R^{Z1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, —$OR^{w1}$, —$N(R^{w2})_2$, —$SR^{w1}$, —CN, —SCN, —C(=$NR^{w1}$)$R^{w1}$, —C(=$NR^{w1}$)$OR^{w1}$, —C(=$NR^{w1}$)$N(R^{w2})_2$, —C(=O)$R^{w1}$, —C(=O)$OR^{w1}$, —C(=O)$N(R^{w2})_2$, —$NO_2$, —$NR^{w1}$C(=O)$R^{w1}$, —$NR^{w1}$C(=O)$OR^{w1}$, —$NR^{w1}$C(=O)$N(R^{w2})_2$, —OC(=O)$R^{w1}$, —OC(=O)$OR^{w1}$, or —OC(=O)$N(R^{w2})_2$; $R^{w1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, or a sulfur protecting group when attached to a sulfur atom; and $R^{w2}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or nitrogen protecting group when attached to a nitrogen atom; or two instances of $R^{w2}$ are joined to form a substituted or unsubstituted, heterocyclic ring, or substituted or unsubstituted, heteroaryl ring. In certain embodiments, $R^{Z1}$ is substituted or unsubstituted acyl. In certain embodiments, $R^{Z1}$ is substituted or unsubstituted alkyl (e.g., substituted or unsubstituted $C_{1-6}$ alkyl). In certain embodiments, $R^{Z1}$ is substituted or unsubstituted alkenyl (e.g., substituted or unsubstituted $C_{2-6}$ alkenyl). In certain embodiments, $R^{Z1}$ is substituted or unsubstituted alkynyl (e.g., substituted or unsubstituted $C_{2-6}$ alkynyl). In certain embodiments, $R^{Z1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{Z1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{Z1}$ is substituted or unsubstituted aryl (e.g., substituted or unsubstituted, 6- to 10-membered aryl). In certain embodiments, $R^{Z1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{Z1}$ is —$OR^{w1}$ (e.g., —OH or —O(substituted or unsubstituted $C_{1-6}$ alkyl) (e.g., —OMe)). In certain embodiments, $R^{Z1}$ is —$N(R^{w2})_2$ (e.g., —$NH_2$, —NH (substituted or unsubstituted $C_{1-6}$ alkyl) (e.g., —NHMe), or —$NMe_2$). In certain embodiments, $R^{Z1}$ is —$SR^{w1}$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{Z1}$ is —CN. In certain embodiments, $R^{Z1}$ is —SCN or —$NO_2$. In certain embodiments, $R^{Z1}$ is —$C(=NR^{w1})R^{w1}$, —$C(=NR^{w1})OR^{w1}$, or —$C(=NR^{w})N(R^{w2})_2$. In certain embodiments, $R^{Z1}$ is —$C(=O)R^{w1}$ (e.g., —C(=O)(substituted or unsubstituted alkyl) or —C(=O) (substituted or unsubstituted phenyl)). In certain embodiments, $R^{Z1}$ is —$C(=O)OR^{w1}$ (e.g., —C(=O)OH, —C(=O)O (substituted or unsubstituted alkyl) (e.g., —C(=O)OMe), or —C(=O)O (substituted or unsubstituted phenyl)). In certain embodiments, $R^{Z1}$ is —$C(=O)N(R^{w2})_2$ (e.g., —$C(=O)NH_2$, —C(=O)NH (substituted or unsubstituted alkyl), —C(=O)NH (substituted or unsubstituted phenyl), —C(=O)N (substituted or unsubstituted alkyl)-(substituted or unsubstituted alkyl), or —C(=O)N (substituted or unsubstituted phenyl)-(substituted or unsubstituted alkyl)). In certain embodiments, $R^{Z1}$ is —$NR^{w1}C(=O)R^{w1}$ (e.g., —NHC(=O)Me). In certain embodiments, $R^{Z1}$ is —$NR^{w1}C(=O)OR^{w1}$ or —$NR^{w1}C(=O)N(R^{w2})_2$. In certain embodiments, $R^{Z1}$ is a small molecule fluorophore.

In certain embodiments, $R^{B3}$ is of the formula:

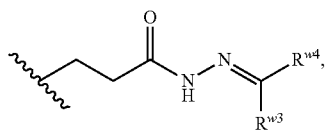

wherein: $R^{w3}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and $R^{w4}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. heteroaryl. In certain embodiments, $R^{w3}$ is H. In certain embodiments, $R^{w3}$ is substituted or unsubstituted acyl (e.g., acetyl). In certain embodiments, $R^{w3}$ is substituted or unsubstituted alkyl (e.g., substituted or unsubstituted $C_{1-6}$ alkyl). In certain embodiments, $R^{w3}$ is substituted or unsubstituted alkenyl (e.g., substituted or unsubstituted $C_{2-6}$ alkenyl). In certain embodiments, $R^{w3}$ is substituted or unsubstituted alkynyl (e.g., substituted or unsubstituted $C_{2-6}$ alkynyl). In certain embodiments, $R^{w3}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{w3}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{w3}$ is substituted or unsubstituted aryl (e.g., substituted or unsubstituted, 6- to 10-membered aryl). In certain embodiments, $R^{w3}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{w4}$ is H. In certain embodiments, $R^{w4}$ is substituted or unsubstituted acyl (e.g., acetyl). In certain embodiments, $R^{w4}$ is substituted or unsubstituted alkyl (e.g., substituted or unsubstituted $C_{1-6}$ alkyl). In certain embodiments, $R^{w4}$ is substituted or unsubstituted alkenyl (e.g., substituted or unsubstituted $C_{2-6}$ alkenyl). In certain embodiments, $R^{w4}$ is substituted or unsubstituted alkynyl (e.g., substituted or unsubstituted $C_{2-6}$ alkynyl). In certain embodiments, $R^{w4}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{w4}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{w4}$ is substituted or unsubstituted aryl (e.g., substituted or unsubstituted, 6- to 10-membered aryl). In certain embodiments, $R^{w4}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{B3}$ is of the formula:

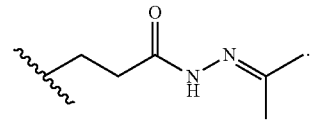 [SMILES: *CCC(=O)NN=C(C)C]

In certain embodiments, $R^{B3}$ is of the formula:

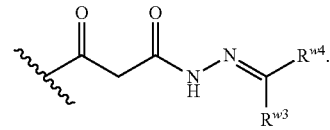

In certain embodiments, $R^{B3}$ is of the formula:

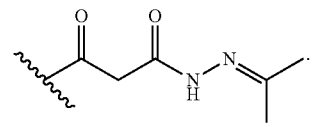 [SMILES: *C(=O)CC(=O)NN=C(C)C]

In certain embodiments, $R^{B3}$ is a nitrogen protecting group (e.g., Bn, Boc, Cbz, Fmoc, trifluoroacetyl, triphenylmethyl, acetyl, or Ts). In certain embodiments, $R^{B3}$ is Boc.

Formula (II) includes substituent $R^{B4}$ on a nitrogen atom. In certain embodiments, $R^{B4}$ is substituted or unsubstituted acyl (e.g., acetyl). In certain embodiments, $R^{B4}$ is —C(=O)$R^Z$, wherein $R^Z$ is substituted or unsubstituted vinyl (e.g., —C(=O)CH=CH$_2$). In certain embodiments, $R^{B4}$ is H. In certain embodiments, $R^{B4}$ is substituted or unsubstituted $C_{1-6}$ alkyl. In certain embodiments, $R^{B4}$ is Me. In certain embodiments, $R^{B4}$ is —CF$_3$, Bn, Et, perfluoroethyl, Pr, perfluoropropyl, Bu, or perfluorobutyl. In certain embodiments, $R^{B4}$ is a nitrogen protecting group (e.g., Bn, Boc, Cbz, Fmoc, trifluoroacetyl, triphenylmethyl, acetyl, or Ts).

Formula (II) includes substituent $R^{B5}$. In certain embodiments, $R^{B5}$ is of the formula:

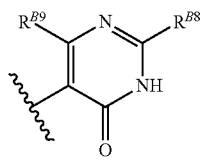

(e.g.,

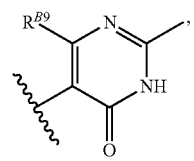

wherein $R^{B9}$ is Me, Et, Pr, or Bu). The moiety of the formula:

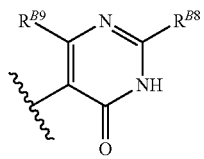

also includes its tautomeric form

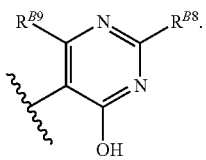

In certain embodiments, $R^{B5}$ is of the formula:

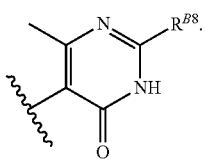

In certain embodiments, $R^{B5}$ is of the formula:

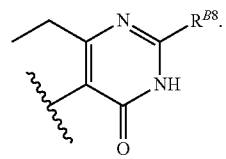

In certain embodiments, $R^{B5}$ is of the formula:

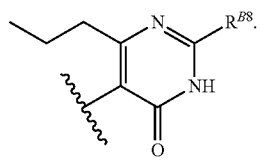

In certain embodiments, $R^{B8}$ is H. In certain embodiments, $R^{B8}$ is halogen (e.g., F, Cl, Br, or I). In certain embodiments, $R^{B8}$ is substituted or unsubstituted $C_{1-6}$ alkyl. In certain embodiments, $R^{B8}$ is Me. In certain embodiments, $R^{B8}$ is substituted methyl (e.g., —CF$_3$ or Bn). In certain embodiments, $R^{B8}$ is Et, substituted ethyl (e.g., perfluoroethyl), Pr, substituted propyl (e.g., perfluoropropyl), Bu, or substituted butyl (e.g., perfluorobutyl). In certain embodiments, $R^{B8}$ is —N($R^{b1}$)$_2$, optionally wherein each instance of $R^{b1}$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{B8}$ is —NH$_2$, —NHMe, or —N(Me)$_2$. In certain embodiments, $R^{B9}$ is H. In certain embodiments, $R^{B9}$ is halogen (e.g., F, Cl, Br, or I). In certain embodiments, $R^{B9}$ is substituted or unsubstituted $C_{1-6}$ alkyl. In certain embodiments, $R^{B9}$ is Me. In certain embodiments, $R^{B9}$ is substituted methyl (e.g., —CF$_3$ or Bn). In certain embodiments, $R^{B9}$ is Et. In certain embodiments, $R^{B9}$ is substituted ethyl (e.g., perfluoroethyl). In certain embodiments, $R^{B9}$ is n-Pr. In certain embodiments, $R^{B9}$ is i-Pr. In certain embodiments, $R^{B9}$ is substituted propyl (e.g., perfluoropropyl). In certain embodiments, $R^{B9}$ is Bu or unsubstituted pentyl. In certain embodiments, $R^{B9}$ is substituted butyl (e.g., perfluorobutyl) or substituted pentyl (e.g., perfluoropentyl). In certain embodiments, $R^{B9}$ is substituted or unsubstituted, 3- to 7-membered, monocyclic carbocyclyl comprising 0, 1, or 2 double bonds in the carbocyclic ring system. In certain embodiments, $R^{B9}$ is substituted or unsubstituted cyclopropyl, substituted or unsubstituted cyclobutyl, or substituted or unsubstituted cyclopentyl.

In certain embodiments, $R^{B5}$ is of the formula:

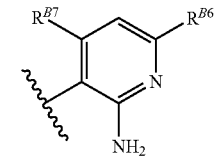

(e.g.,

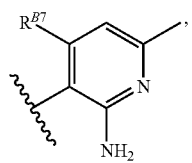

wherein R$^{B7}$ is Me, Et, Pr, or Bu). In certain embodiments, R$^{B5}$ is of the formula:

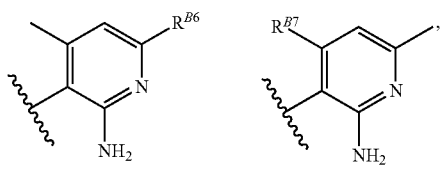

wherein R$^{B7}$ is Me, Et, Pr, or Bu). In certain embodiments, R$^{B5}$ is of the formula:

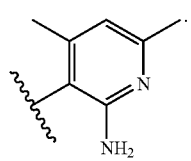

In certain embodiments, R$^{B6}$ is H. In certain embodiments, R$^{B6}$ is halogen (e.g., F, Cl, Br, or I). In certain embodiments, R$^{B6}$ is substituted or unsubstituted C$_{1-6}$ alkyl. In certain embodiments, R$^{B6}$ is Me. In certain embodiments, R$^{B6}$ is substituted methyl (e.g., —CF$_3$ or Bn). In certain embodiments, R$^{B6}$ is Et, substituted ethyl (e.g., perfluoroethyl), Pr, substituted propyl (e.g., perfluoropropyl), Bu, or substituted butyl (e.g., perfluorobutyl). In certain embodiments, R$^{B6}$ is —OR$^b$ (e.g., —OH or —O(substituted or unsubstituted C$_{1-6}$ alkyl) (e.g., —OMe)). In certain embodiments, R$^{B6}$ is —N(R$^{b1}$)$_2$, optionally wherein each instance of R$^{b1}$ is independently hydrogen, substituted or unsubstituted C$_{1-6}$ alkyl, or a nitrogen protecting group (e.g., Bn, Boc, Cbz, Fmoc, trifluoroacetyl, triphenylmethyl, acetyl, or Ts). In certain embodiments, R$^{B6}$ is —NH$_2$, —NHMe, or —N(Me)$_2$. In certain embodiments, R$^{B7}$ is H. In certain embodiments, R$^{B7}$ is halogen (e.g., F, Cl, Br, or I). In certain embodiments, R$^{B7}$ is substituted or unsubstituted C$_{2-6}$ alkyl. In certain embodiments, R$^{B7}$ is Me. In certain embodiments, R$^{B7}$ is substituted methyl (e.g., —CF$_3$ or Bn). In certain embodiments, R$^{B7}$ is Et. In certain embodiments, R$^{B7}$ is substituted ethyl (e.g., perfluoroethyl). In certain embodiments, R$^{B7}$ is n-Pr. In certain embodiments, R$^{B7}$ is i-Pr. In certain embodiments, R$^{B7}$ is substituted propyl (e.g., perfluoropropyl). In certain embodiments, R$^{B7}$ is Bu or unsubstituted pentyl. In certain embodiments, R$^{B7}$ is substituted butyl (e.g., perfluorobutyl) or substituted pentyl (e.g., perfluoropentyl). In certain embodiments, R$^{B7}$ is substituted or unsubstituted, 3- to 7-membered, monocyclic carbocyclyl comprising 0, 1, or 2 double bonds in the carbocyclic ring system. In certain embodiments, R$^{B7}$ is substituted or unsubstituted cyclopropyl, substituted or unsubstituted cyclobutyl, or substituted or unsubstituted cyclopentyl. In certain embodiments, R$^{B7}$ is —OR$^b$ (e.g., —OH or —O(substituted or unsubstituted C$_{1-6}$ alkyl) (e.g., —OMe)). In certain embodiments, R$^{B7}$ is —N(R$^{b1}$)$_2$, optionally wherein each instance of R$^{b1}$ is independently hydrogen, substituted or unsubstituted C$_{1-6}$ alkyl, or a nitrogen protecting group (e.g., Bn, Boc, Cbz, Fmoc, trifluoroacetyl, triphenylmethyl, acetyl, or Ts). In certain embodiments, R$^{B7}$ is —NH$_2$, —NHMe, —NHEt, —N(Me)$_2$, or —N(Et)$_2$. In certain embodiments, R$^{B7}$ is substituted or unsubstituted cyclopropyl, —OR$^b$, or —N(R$^{b1}$)$_2$, wherein each instance of R$^{b1}$ is independently hydrogen, substituted or unsubstituted C$_{1-6}$ alkyl, an oxygen protecting group when attached to an oxygen atom, or a nitrogen protecting group when attached to a nitrogen atom.

In certain embodiments, R$^{B5}$ is of the formula:

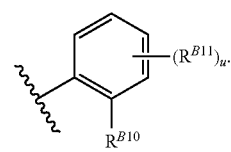

In certain embodiments, R$^{B5}$ is of the formula:

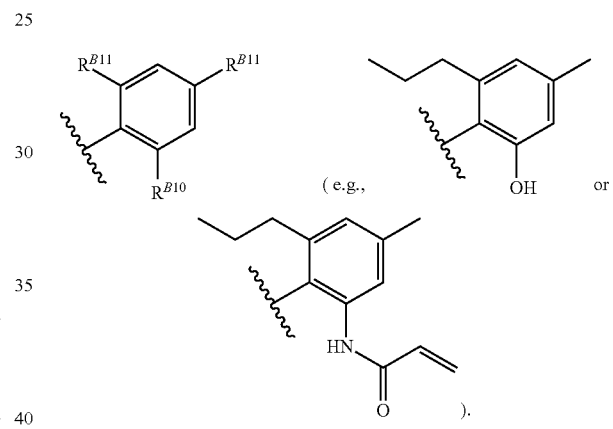

In certain embodiments, R$^{B5}$ is of the formula:

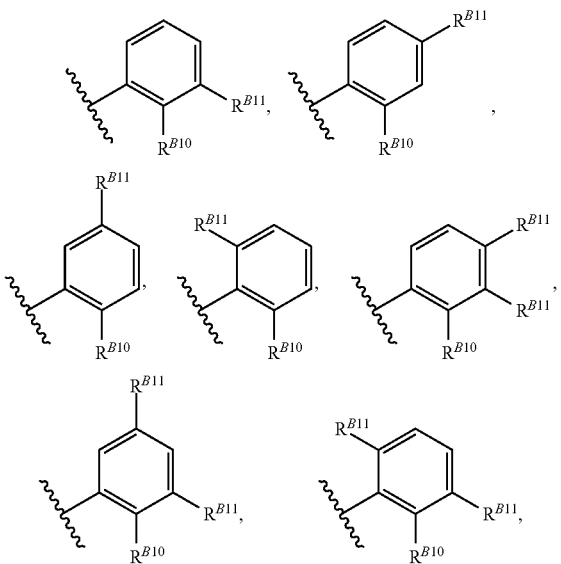

141

-continued

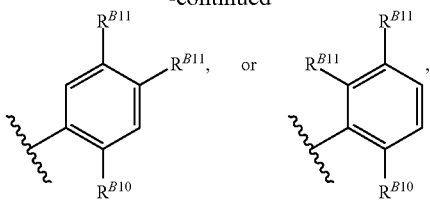

In certain embodiments, $R^{B5}$ is of the formula:

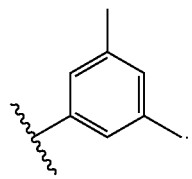 [SMILES: *c1cc(C)cc(C)c1]

In certain embodiments, $R^{B5}$ is of the formula:

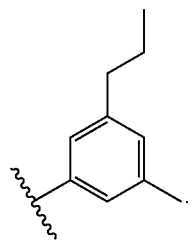 [SMILES: *c1cc(C)cc(CCC)c1]

In certain embodiments, $R^{B10}$ is —$OR^b$ (e.g., —OH). In certain embodiments, $R^{B0}$ is —$N(R^{b1})_2$. In certain embodiments, $R^{B1}$ is —$NH_2$. In certain embodiments, $R^{B10}$ is —$NHR^b1$, wherein $R^{b1}$ is substituted or unsubstituted $C_{1-6}$ alkyl or a nitrogen protecting group (e.g., Bn, Boc, Cbz, Fmoc, trifluoroacetyl, triphenylmethyl, acetyl, or Ts). In certain embodiments, $R^{B10}$ is —$NHC(=O)R^{b1}$, optionally wherein $R^{b1}$ is substituted or unsubstituted vinyl. In certain embodiments, $R^{B10}$ is —$NHC(=O)CH=CH_2$. In certain embodiments, $R^{B10}$ is a warhead. Formula (II) may include one or more instances of $R^{B11}$. When Formula (II) includes two or more instances of $R^{B11}$ any two instances of $R^{B11}$ may be the same or different from each other. In certain embodiments, at least one instance of $R^{B11}$ is halogen. In certain embodiments, at least one instance of $R^{B11}$ is Br. In certain embodiments, at least one instance of $R^{B11}$ is F, Cl, or I. In certain embodiments, at least one instance of $R^{B11}$ is substituted or unsubstituted $C_{1-6}$ alkyl. In certain embodiments, at least one instance of $R^{B11}$ is Me. In certain embodiments, at least one instance of $R^{B11}$ is substituted methyl (e.g., —$CF_3$ or Bn). In certain embodiments, at least one instance of $R^{B11}$ is Et. In certain embodiments, at least one instance of $R^{B1}$ is substituted ethyl (e.g., perfluoroethyl). In certain embodiments, at least one instance of $R^{B11}$ is n-Pr. In certain embodiments, at least one instance of $R^{B11}$ is i-Pr. In certain embodiments, at least one instance of $R^{B11}$ is substituted propyl (e.g., perfluoropropyl). In certain embodiments, at least one instance of $R^{B11}$ is Me, Et, or n-Pr. In certain embodiments, at least one instance of $R^{B11}$ is Bu or unsubstituted pentyl. In certain embodiments, at least one instance of $R^{B11}$ is substituted butyl (e.g., perfluorobutyl) or substituted pentyl (e.g., perfluoropentyl). In certain embodiments,

142 at least one instance of $R^{B11}$ is substituted or unsubstituted, 3- to 7-membered, monocyclic carbocyclyl comprising 0, 1, or 2 double bonds in the carbocyclic ring system. In certain embodiments, at least one instance of $R^{B11}$ is substituted or unsubstituted cyclopropyl, substituted or unsubstituted cyclobutyl, or substituted or unsubstituted cyclopentyl. In certain embodiments, at least one instance of $R^{B11}$ is —$OR^b$ (e.g., —OH or —O(substituted or unsubstituted $C_{1-6}$ alkyl) (e.g., —OMe)). In certain embodiments, at least one instance of $R^{B11}$ is —$N(R^{b1})_2$, optionally wherein each instance of $R^{b1}$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, at least one instance of $R^{B11}$ is —$NH_2$, —NHMe, —NHEt, —$N(Me)_2$, or —$N(Et)_2$. In certain embodiments, at least one instance of $R^{b1}$ is substituted or unsubstituted $C_{1-6}$ alkyl, substituted or unsubstituted cyclopropyl, —$OR^b$, or —$N(R^{b1})_2$, wherein each instance of $R^b$ is independently hydrogen, substituted or unsubstituted $C_{1-6}$ alkyl, an oxygen protecting group when attached to an oxygen atom, or a nitrogen protecting group when attached to a nitrogen atom. In certain embodiments, u is 0. In certain embodiments, u is 1. In certain embodiments, u is 2. In certain embodiments, u is 3. In certain embodiments, u is 4.

In certain embodiments, $R^{B5}$ is of the formula:

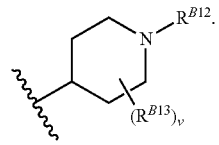

In certain embodiments, $R^{B5}$ is of the formula:

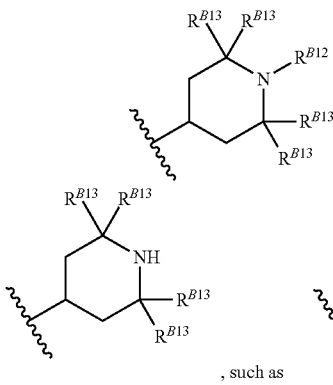

In certain embodiments, $R^{B12}$ is H. In certain embodiments, $R^{B12}$ is substituted or unsubstituted $C_{1-6}$ alkyl. In certain embodiments, $R^{B12}$ is Me. In certain embodiments, $R^{B12}$ is —$CF_3$, Bn, Et, perfluoroethyl, Pr, perfluoropropyl, Bu, or perfluorobutyl. In certain embodiments, $R^{B12}$ is a nitrogen protecting group (e.g., Bn, Boc, Cbz, Fmoc, trifluoroacetyl, triphenylmethyl, acetyl, or Ts). In certain embodiments, $R^{B12}$ is a warhead. Formula (II) may include one or more instances of $R^{B13}$. When Formula (II) includes two or more instances of $R^{B13}$, any two instances of $R^{B13}$ may be the same or different from each other. In certain embodiments, at least one instance of $R^{B13}$ is halogen (e.g., F, Cl, Br, or I). In certain embodiments, at least one instance of $R^{B13}$ is substituted or unsubstituted $C_{1-6}$ alkyl. In certain embodiments, at least one instance of $R^{B13}$ is Me. In certain embodiments, at least one instance of $R^{B13}$ is substituted methyl (e.g., —$CF_3$ or Bn). In certain embodiments, at least one instance of $R^{B13}$ is Et. In certain embodiments, at least one instance of $R^{B13}$ is substituted ethyl (e.g., perfluoroethyl). In certain embodiments, at least one instance of $R^{B13}$ is n-Pr. In certain embodiments, at least one instance of $R^{B13}$ is i-Pr. In certain embodiments, at least one instance of $R^{B13}$ is substituted propyl (e.g., perfluoropropyl). In certain embodiments, at least one instance of $R^{B13}$ is Me, Et, or n-Pr. In certain embodiments, at least one instance of $R^{B13}$ is Bu or unsubstituted pentyl. In certain embodiments, at least one instance of $R^{B13}$ is substituted butyl (e.g., perfluorobutyl) or substituted pentyl (e.g., perfluoropentyl). In certain embodiments, at least one instance of $R^{B13}$ is substituted or unsubstituted, 3- to 7-membered, monocyclic carbocyclyl comprising 0, 1, or 2 double bonds in the carbocyclic ring system. In certain embodiments, at least one instance of $R^{B13}$ is substituted or unsubstituted cyclopropyl, substituted or unsubstituted cyclobutyl, or substituted or unsubstituted cyclopentyl. In certain embodiments, at least one instance of $R^{B13}$ is —$N(R^{b1})_2$, optionally wherein each instance of $R^{b1}$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, at least one instance of $R^{B13}$ is —$NH_2$, —NHMe, —NHEt, —$N(Me)_2$, or —$N(Et)_2$. In certain embodiments, at least one instance of $R^{B13}$ is halogen, substituted or unsubstituted cyclopropyl, or —$N(R^{b1})_2$, wherein each instance of $R^b$ is independently hydrogen, substituted or unsubstituted $C_{1-6}$ alkyl, an oxygen protecting group when attached to an oxygen atom, or a nitrogen protecting group when attached to a nitrogen atom.

In certain embodiments, $R^{B5}$ is of the formula:

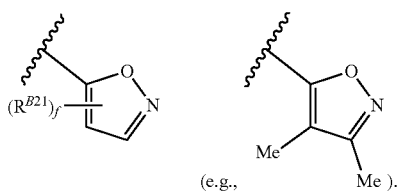

In certain embodiments, $R^{B5}$ is of the formula:

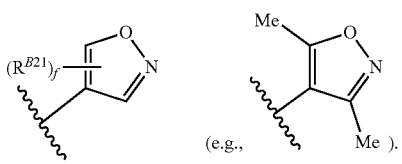

In certain embodiments, $R^{B5}$ is of the formula:

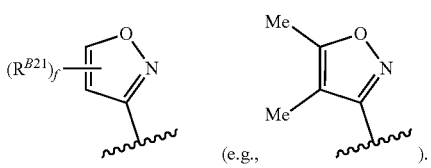

Formula (II) may include one or more instances of $R^{B21}$. When Formula (II) includes two or more instances of $R^{B21}$, any two instances of $R^{B21}$ may be the same or different from each other. In certain embodiments, at least one instance of $R^{B21}$ is H. In certain embodiments, at least one instance of $R^{B21}$ is halogen (e.g., F, Cl, Br, or I). In certain embodiments, at least one instance of $R^{B21}$ is substituted or unsubstituted $C_{1-6}$ alkyl. In certain embodiments, at least one instance of $R^{B21}$ is Me. In certain embodiments, at least one instance of $R^{B21}$ is substituted methyl (e.g., —$CF_3$ or Bn). In certain embodiments, at least one instance of $R^{B21}$ is Et. In certain embodiments, at least one instance of $R^{B21}$ is substituted ethyl (e.g., perfluoroethyl). In certain embodiments, at least one instance of $R^{B21}$ is n-Pr. In certain embodiments, at least one instance of $R^{B21}$ is i-Pr. In certain embodiments, at least one instance of $R^{B21}$ is substituted propyl (e.g., perfluoropropyl). In certain embodiments, at least one instance of $R^{B21}$ is Me, Et, or n-Pr. In certain embodiments, at least one instance of $R^{B21}$ is Bu or unsubstituted pentyl. In certain embodiments, at least one instance of $R^{B21}$ is substituted butyl (e.g., perfluorobutyl) or substituted pentyl (e.g., perfluoropentyl). In certain embodiments, at least one instance of $R^{B21}$ is —$OR^b$ (e.g., —OH or —O(substituted or unsubstituted $C_{1-6}$ alkyl) (e.g., —OMe)). In certain embodiments, at least one instance of $R^{B21}$ is —$N(R^{b1})_2$, optionally wherein each instance of $R^{b1}$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, at least one instance of $R^{B21}$ is —$NH_2$, —NHMe, —NHEt, —$N(Me)_2$, or —$N(Et)_2$. In certain embodiments, f is 0. In certain embodiments, f is 1. In certain embodiments, f is 2.

In certain embodiments, $R^{B5}$ is of the formula:

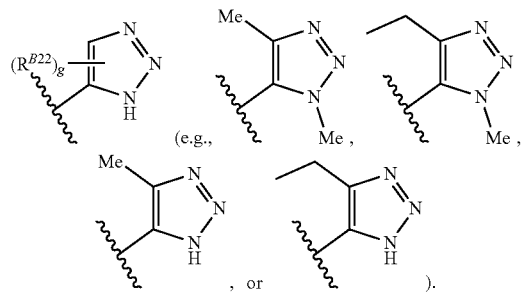

Formula (II) may include one or more instances of $R^{B22}$. When Formula (II) includes two or more instances of $R^{B22}$, any two instances of $R^{B22}$ may be the same or different from each other. In certain embodiments, at least one instance of $R^{B22}$ is H. In certain embodiments, at least one instance of $R^{B22}$ is halogen (e.g., F, Cl, Br, or I). In certain embodiments, at least one instance of $R^{B22}$ is substituted or unsubstituted $C_{1-6}$ alkyl. In certain embodiments, at least one instance of $R^{B22}$ is Me. In certain embodiments, at least one instance of $R^{B22}$ is substituted methyl (e.g., —$CF_3$ or Bn). In certain embodiments, at least one instance of $R^{B22}$ is Et. In certain embodiments, at least one instance of $R^{B22}$ is substituted ethyl (e.g., perfluoroethyl). In certain embodiments, at least one instance of $R^{B21}$ is n-Pr. In certain embodiments, at least one instance of $R^{B22}$ is i-Pr. In certain embodiments, at least one instance of $R^{B22}$ is substituted propyl (e.g., perfluoropropyl). In certain embodiments, at least one instance of $R^{B22}$ is Me, Et, or n-Pr. In certain embodiments, at least one instance of $R^{B22}$ is Bu or unsubstituted pentyl. In certain embodiments, at least one instance of $R^{B22}$ is substituted butyl (e.g., perfluorobutyl) or substituted pentyl (e.g., perfluoropentyl). In certain embodiments, at least one instance of $R^{B22}$ is —$OR^b$ (e.g., —OH or —O(substituted or unsubstituted $C_{1-6}$ alkyl) (e.g., —OMe)). In certain embodiments, at least one instance of $R^{B22}$ is —$N(R^{b1})_2$, optionally wherein each instance of $R^{b1}$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, at least one instance of $R^{B22}$ is —$NH_2$, —NHMe, —NHEt, —$N(Me)_2$, or —$N(Et)_2$. In certain embodiments, at least one instance of $R^{B22}$ is a nitrogen protecting group (e.g., Bn, Boc, Cbz, Fmoc, trifluoroacetyl, triphenylmethyl, acetyl, or Ts) when attached to nitrogen. In certain embodiments, g is 0. In certain embodiments, g is 1. In certain embodiments, g is 2.

Formula (II) includes substituent $R^{B20}$. In certain embodiments, $R^{B20}$ is H. In certain embodiments, $R^{B20}$ is halogen (e.g., F, Cl, Br, or I). In certain embodiments, $R^{B20}$ is substituted or unsubstituted $C_{1-6}$ alkyl. In certain embodiments, $R^{B20}$ is Me. In certain embodiments, $R^{B20}$ is —$CF_3$, Bn, Et, perfluoroethyl, Pr, perfluoropropyl, Bu, or perfluorobutyl. In certain embodiments, $R^{B20}$ is —$OR^b$, optionally wherein $R^b$ is H, substituted or unsubstituted $C_{1-6}$ alkyl (e.g., Me), substituted or unsubstituted acyl, or an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, $R^{B20}$ is —OC(=O)$R^b$, optionally wherein $R^b$ is H, substituted or unsubstituted $C_{1-6}$ alkyl (e.g., Me), or substituted or unsubstituted $C_{2-6}$ alkenyl (e.g., substituted or unsubstituted vinyl). In certain embodiments, $R^{B20}$ is —OC(=O)CH=$CH_2$. In certain embodiments, $R^{B20}$ is —$N(R^{b1})_2$, optionally wherein each instance of $R^{b1}$ is independently H, substituted or unsubstituted $C_{1-6}$ alkyl (e.g., Me), substituted or unsubstituted acyl, or a nitrogen protecting group (e.g., Bn, Boc, Cbz, Fmoc, trifluoroacetyl, triphenylmethyl, acetyl, or Ts). In certain embodiments, $R^{B20}$ is —$N(R^{b1})C(=O)R^{b1}$, optionally wherein each instance of $R^{b1}$ is independently H, substituted or unsubstituted $C_{1-6}$ alkyl (e.g., Me), or substituted or unsubstituted $C_{2-6}$ alkenyl (e.g., substituted or unsubstituted vinyl). In certain embodiments, $R^{B20}$ is of the formula:

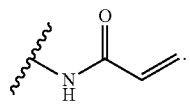 [SMILES: *NC(=O)C=C]

In certain embodiments, $R^{B20}$ is of the formula:

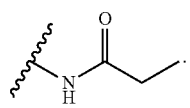

In certain embodiments, the compound of Formula (II) is of the formula:

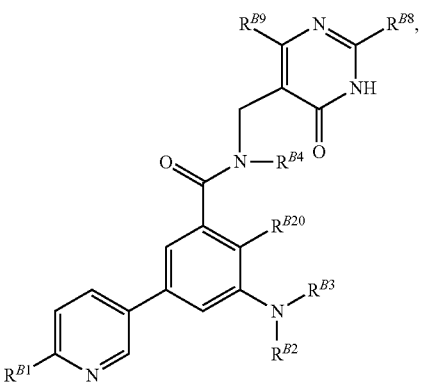

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

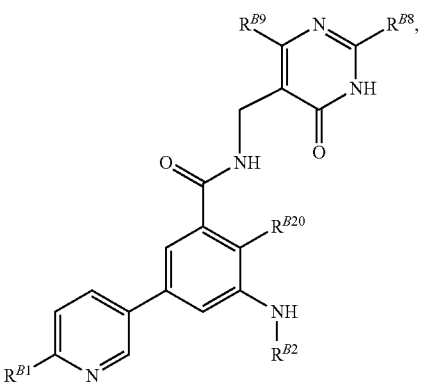

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

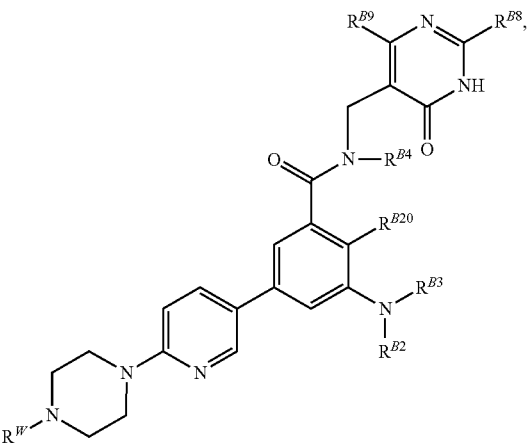

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

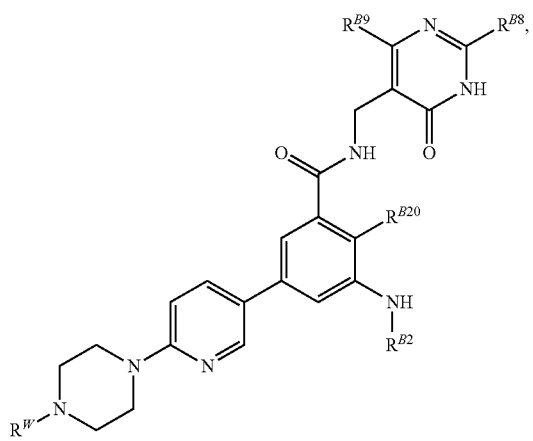

or a pharmaceutically acceptable salt, solvate, hydrate, polymorph, co-crystal, tautomer, stereoisomer, isotopically labeled derivative, or prodrug thereof.
or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

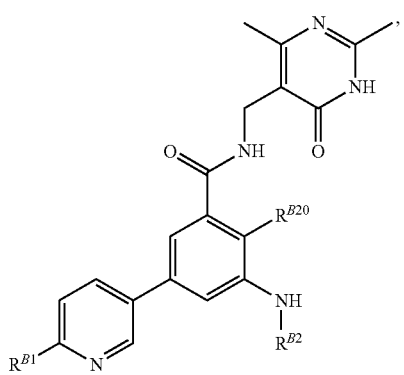

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

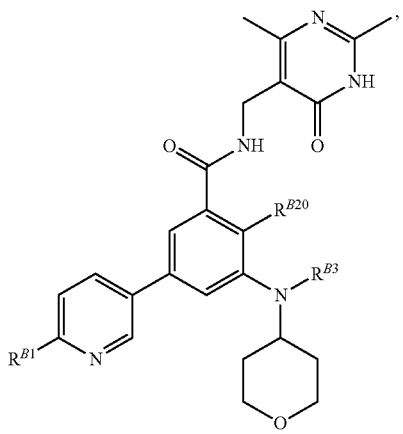

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

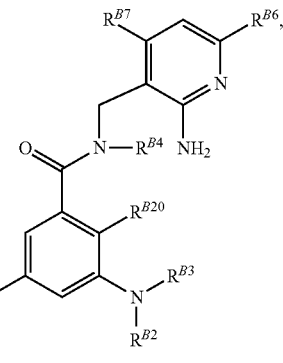

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

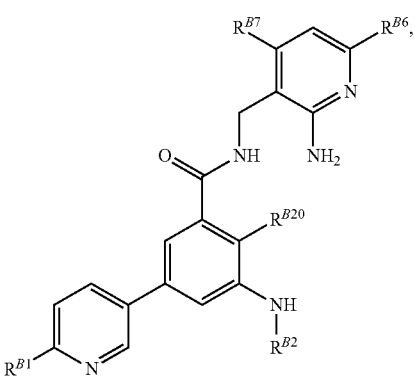

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

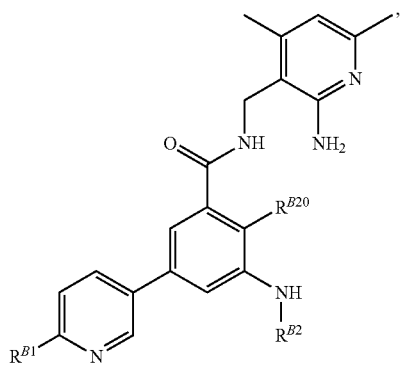

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

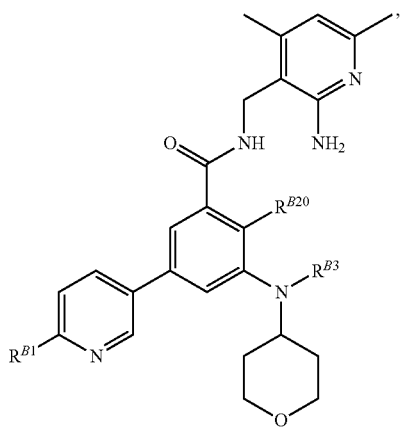

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

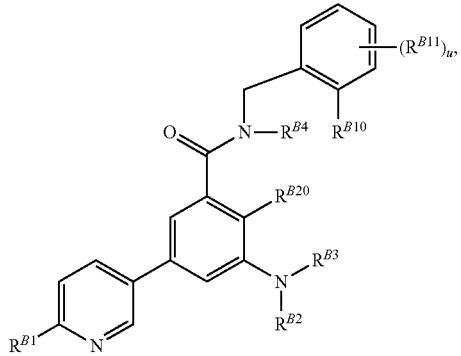

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

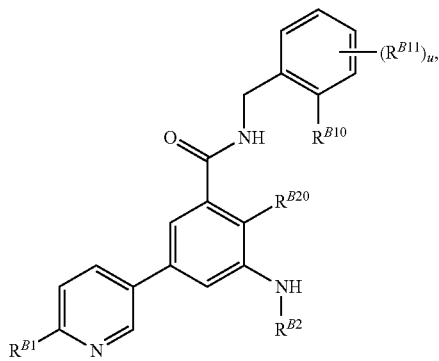

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

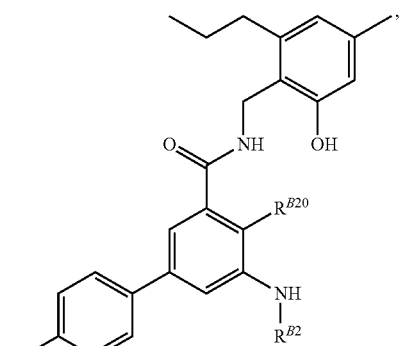

or a pharmaceutically acceptable salt, solvate, hydrate, polymorph, co-crystal, tautomer, stereoisomer, isotopically labeled derivative, or prodrug thereof. In certain embodiments, the compound of Formula (II) is of the formula:

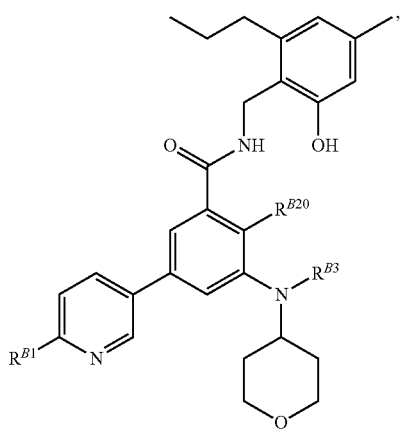

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

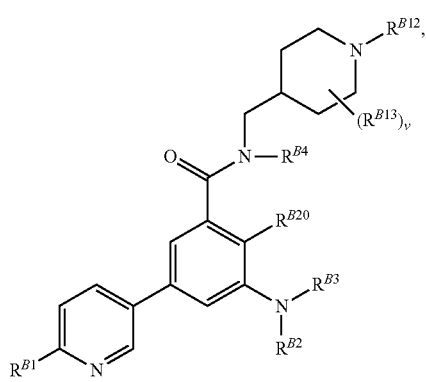

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

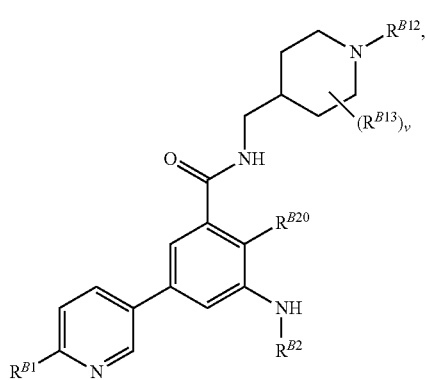

or a pharmaceutically acceptable salt, solvate, hydrate, polymorph, co-crystal, tautomer, stereoisomer, isotopically labeled derivative, or prodrug thereof. In certain embodiments, the compound of Formula (II) is of the formula:

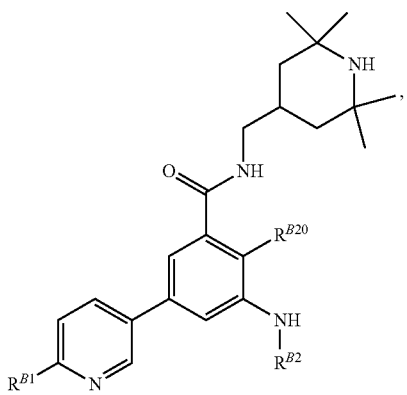

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

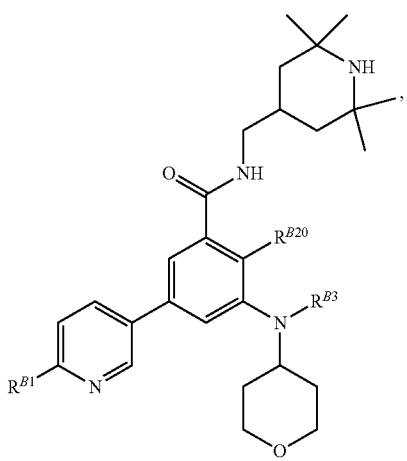

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

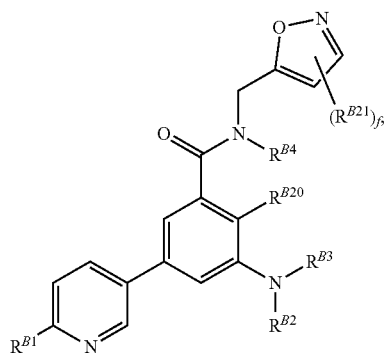

153

-continued

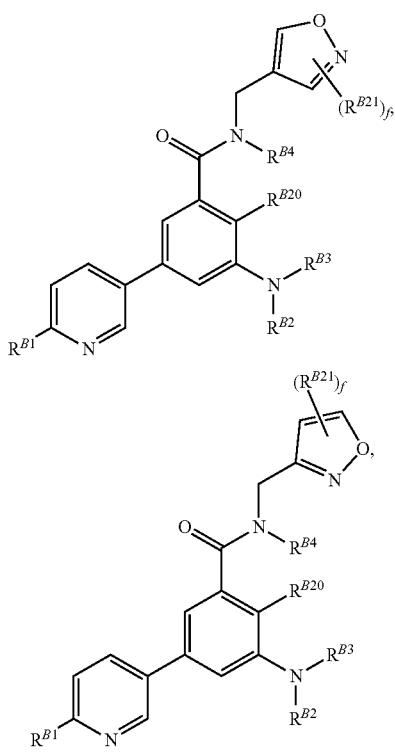

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

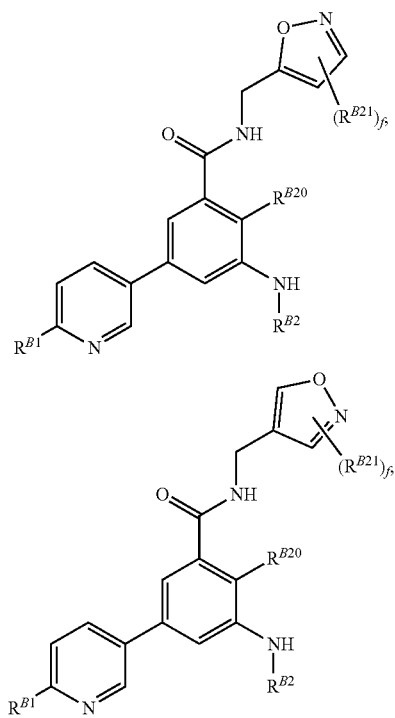

154

-continued

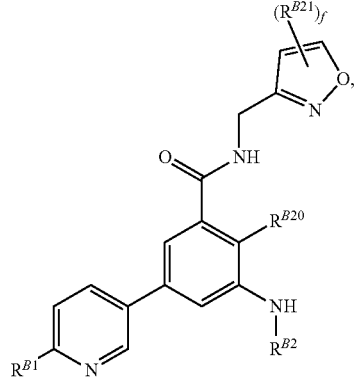

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

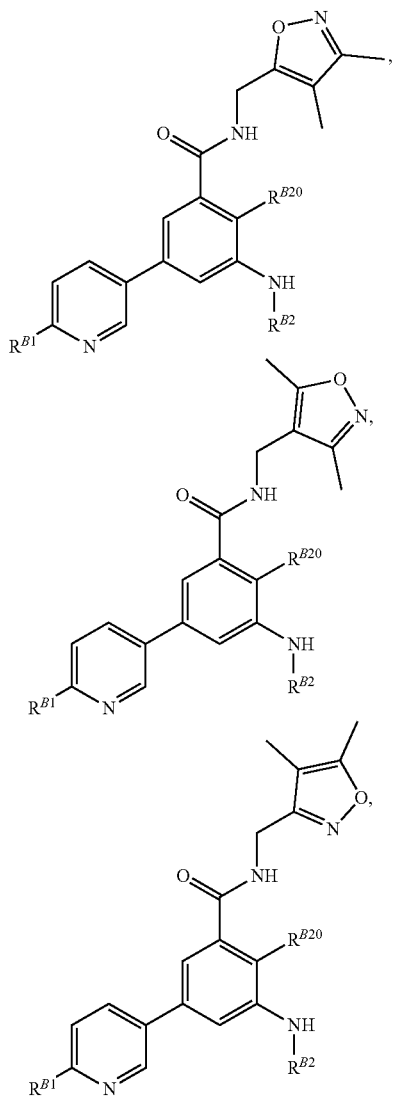

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

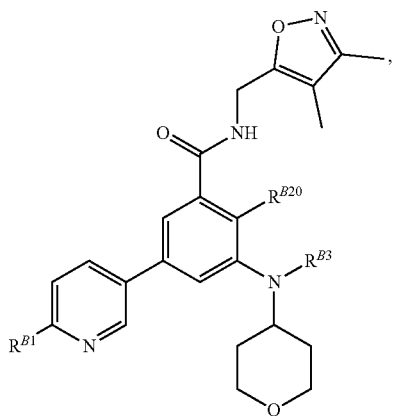

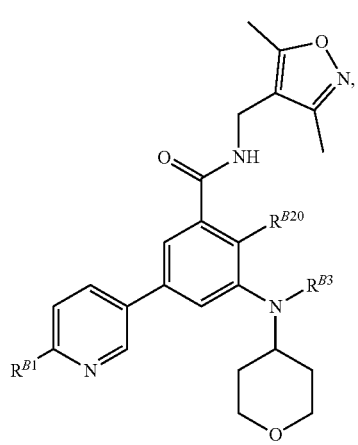

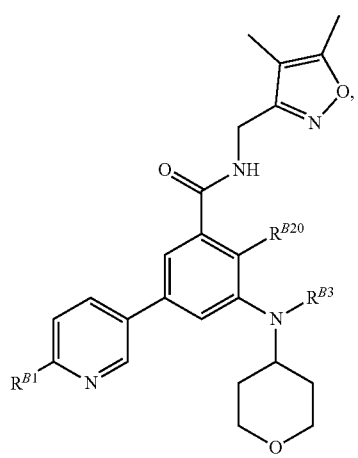

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

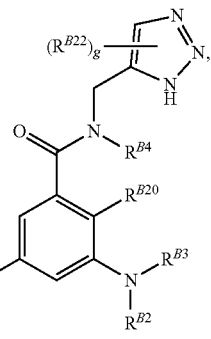

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

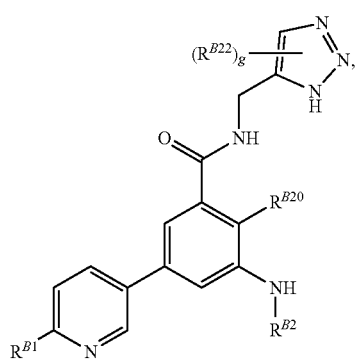

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

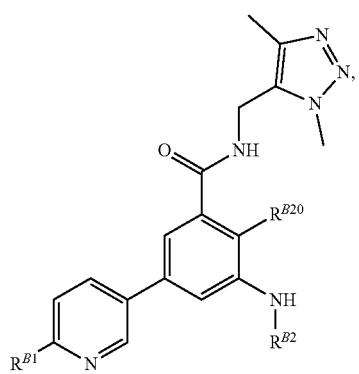

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

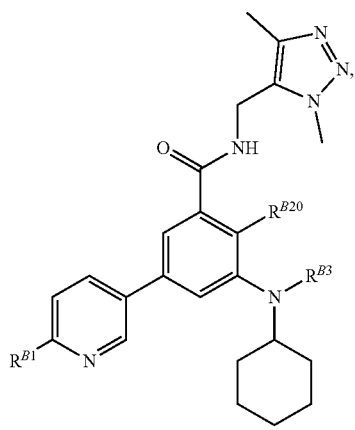

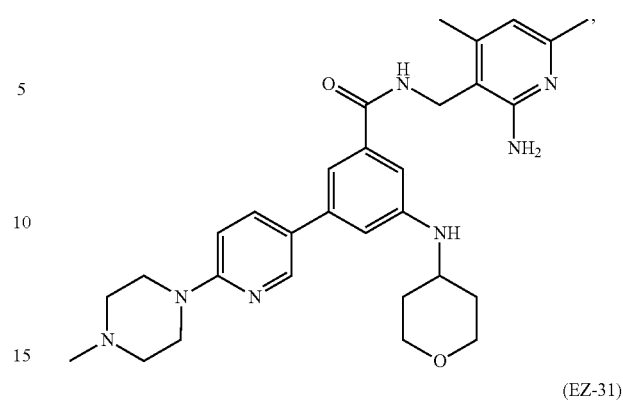

or a pharmaceutically acceptable salt, solvate, hydrate, polymorph, co-crystal, tautomer, stereoisomer, isotopically labeled derivative, or prodrug thereof. Exemplary compounds of Formula (II) include, but are not limited to:

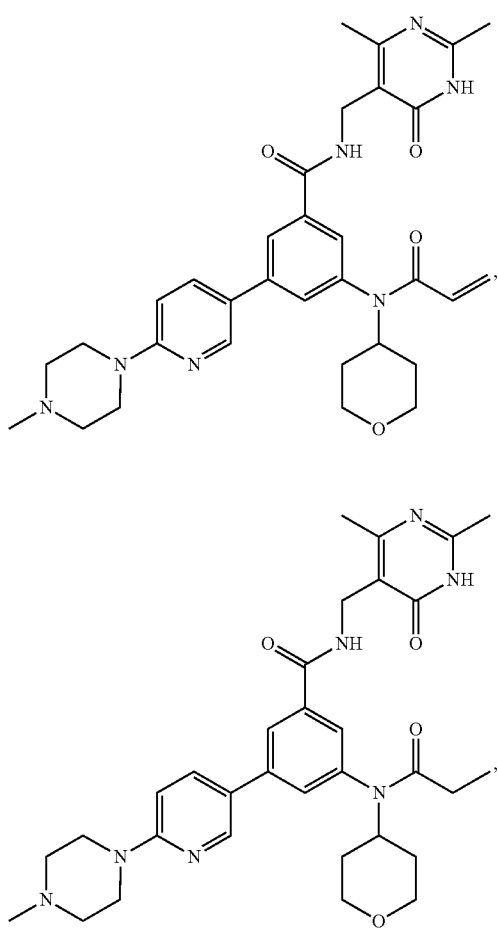

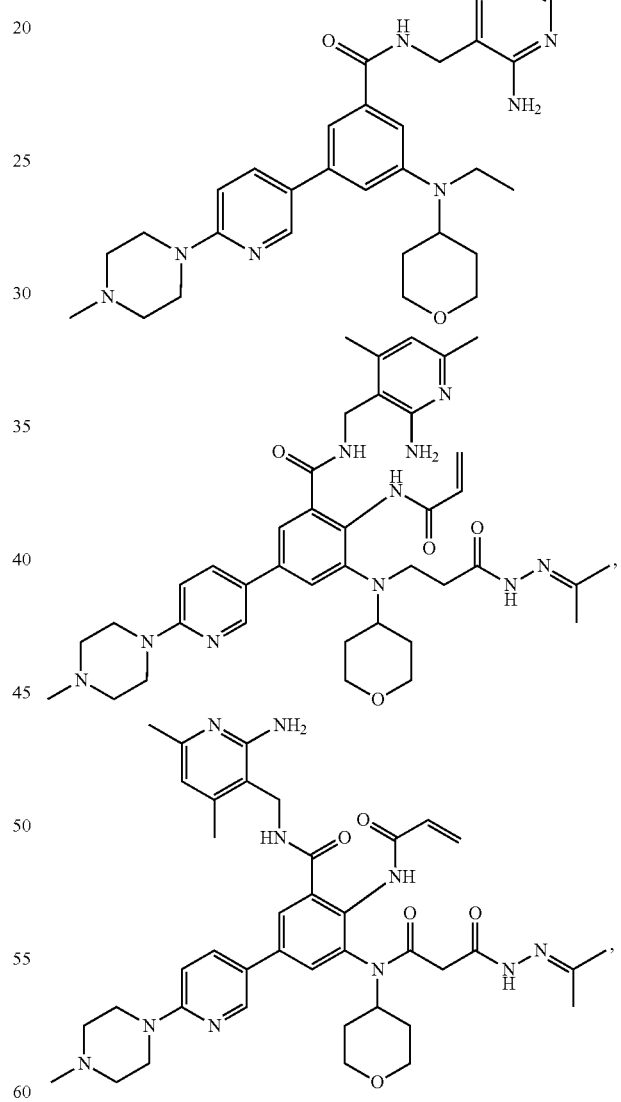

and pharmaceutically acceptable salts, solvates, hydrates, polymorphs, co-crystals, tautomers, stereoisomers, isotopically labeled derivatives, and prodrugs thereof.

Exemplary compounds of Formula (II) include, but are not limited to:

and pharmaceutically acceptable salts, solvates, hydrates, polymorphs, co-crystals, tautomers, stereoisomers, isotopically labeled derivatives, and prodrugs thereof.

Exemplary compounds of Formula (II) include, but are not limited to:

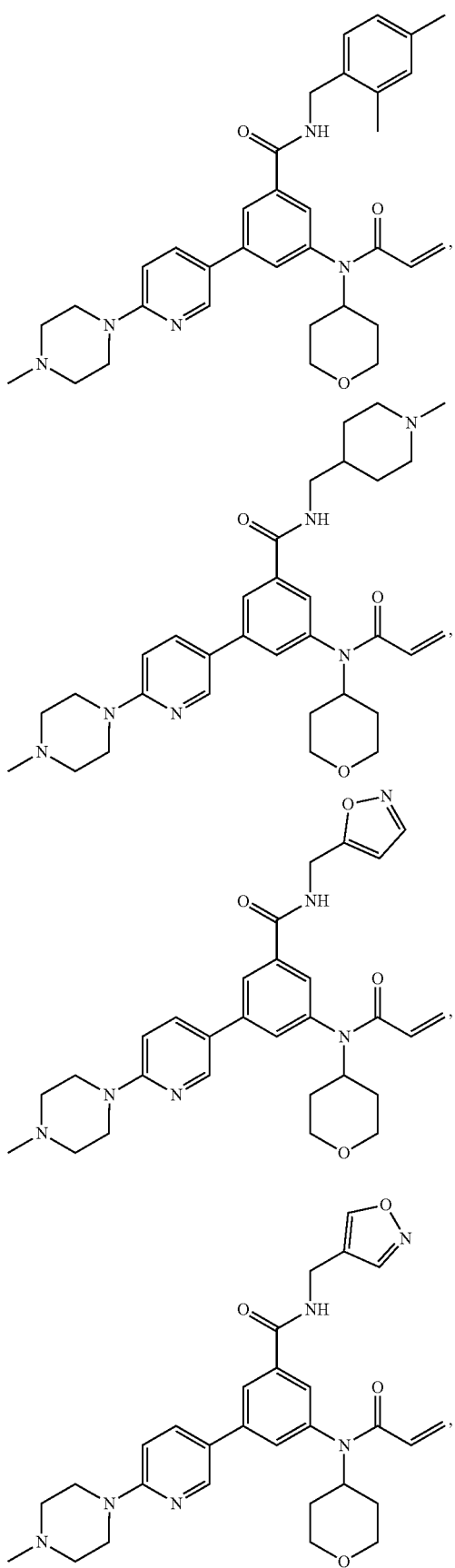

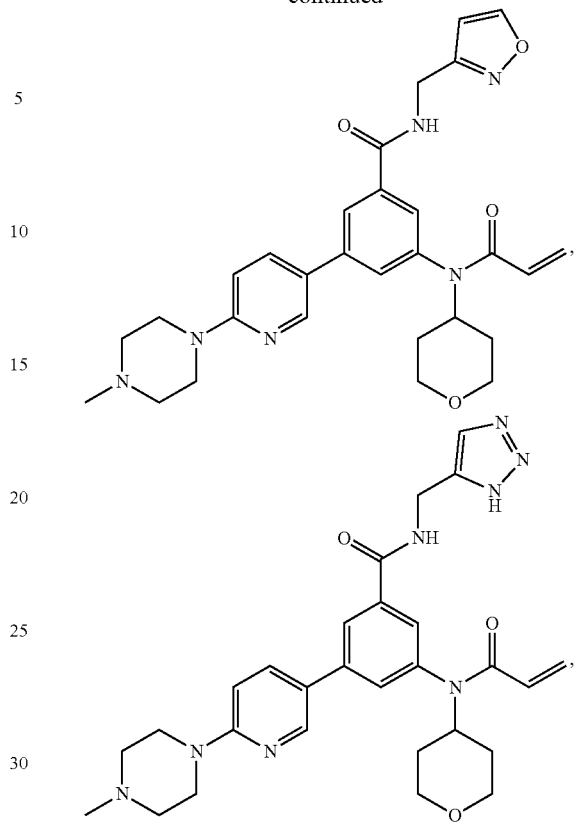

and pharmaceutically acceptable salts, solvates, hydrates, polymorphs, co-crystals, tautomers, stereoisomers, isotopically labeled derivatives, and prodrugs thereof.

In one aspect, the present disclosure provides compounds of Formula (III):

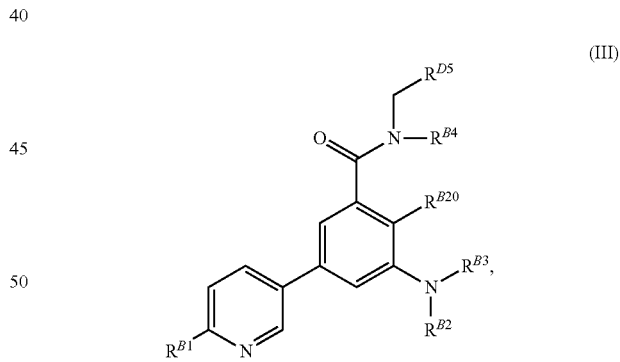

(III)

and pharmaceutically acceptable salts, solvates, hydrates, polymorphs, co-crystals, tautomers, stereoisomers, isotopically labeled derivatives, and prodrugs thereof, wherein:

$R^{B1}$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^b$, —N(R$^{b1}$)$_2$, —SR$^b$, —CN, —SCN, —C(=NR$^b$)R$^b$, —C(=NR$^b$)OR$^b$, —C(=NR$^b$)N(R$^{b1}$)$_2$, —C(=O)R$^b$, —C(=O)OR$^b$, —C(=O)N(R$^{b1}$)$_2$, —NO$_2$, —NR$^b$C(=O) R$^b$, —NR$^b$C(=O)OR$^b$, —NR$^b$C(=O)N(R$^{b1}$)$_2$, —OC(=O) R$^b$, —OC(=O)OR$^b$, —OC(=O)N(R$^{b1}$)$_2$, a tag, or

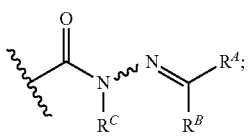

each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom;

each instance of $R^{b1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or two instances of $R^{b1}$ are joined to form a substituted or unsubstituted, heterocyclic ring, or substituted or unsubstituted, heteroaryl ring;

$R^A$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

or $R^A$ and $R^B$ are joined to form a substituted or unsubstituted, carbocyclic ring, or a substituted or unsubstituted, heterocyclic ring;

$R^C$ is hydrogen, substituted or unsubstituted $C_{1-6}$ alkyl, or a nitrogen protecting group;

$R^{B2}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, a nitrogen protecting group, a tag, or a warhead;

$R^{B3}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or a nitrogen protecting group;

$R^{B20}$ is hydrogen, halogen, substituted or unsubstituted $C_{1-6}$ alkyl, —$OR^b$, or —$N(R^{b1})_2$;

$R^{B4}$ is hydrogen, substituted or unsubstituted acyl, substituted or unsubstituted $C_{1-6}$ alkyl, a nitrogen protecting group;

$R^{D5}$ is of the formula:

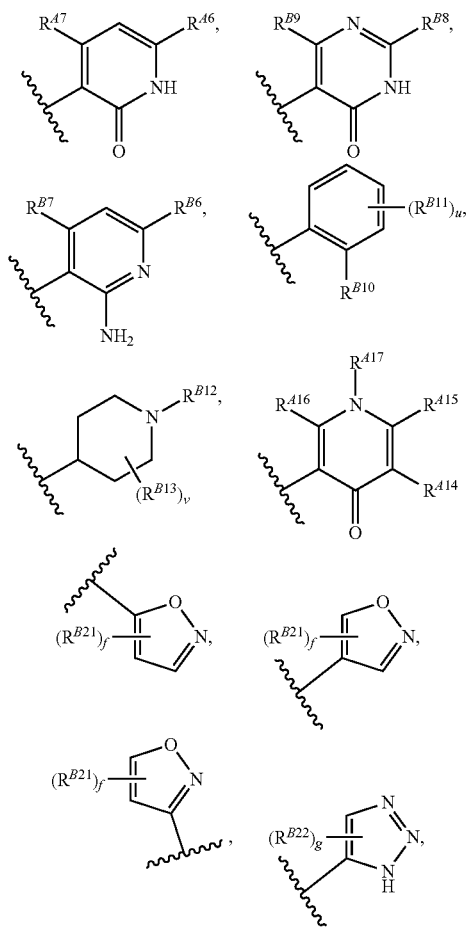

wherein:

$R^{A6}$ is hydrogen, halogen, substituted or unsubstituted $C_{1-6}$ alkyl, —$OR^a$, or —$N(R^{a1})_2$;

$R^{A7}$ is hydrogen, halogen, substituted or unsubstituted $C_{2-6}$ alkyl, substituted or unsubstituted, 3- to 7-membered, monocyclic carbocyclyl comprising 0, 1, or 2 double bonds in the carbocyclic ring system, —$OR^a$, or —$N(R^{a1})_2$;

$R^{A14}$ is hydrogen, halogen, substituted or unsubstituted $C_{1-6}$ alkyl, —$OR^a$, or —$N(R^{a1})_2$;

$R^{A15}$ is hydrogen, halogen, substituted or unsubstituted $C_{1-6}$ alkyl, —$OR^a$, or —$N(R^{a1})_2$;

$R^{A16}$ is hydrogen, halogen, substituted or unsubstituted $C_{2-6}$ alkyl, substituted or unsubstituted, 3- to 7-membered, monocyclic carbocyclyl comprising 0, 1, or 2 double bonds in the carbocyclic ring system, —$OR^a$, or —$N(R^{a1})_2$; and $R^{A17}$ is hydrogen, substituted or unsubstituted acyl, substituted or unsubstituted $C_{1-6}$ alkyl, a nitrogen protecting group, or a warhead;

$R^{B6}$ is hydrogen, halogen, substituted or unsubstituted $C_{1-6}$ alkyl, —$OR^b$, or —$N(R^{b1})_2$;

$R^{B7}$ is hydrogen, halogen, substituted or unsubstituted $C_{2-6}$ alkyl, substituted or unsubstituted, 3- to 7-membered, monocyclic carbocyclyl comprising 0, 1, or 2 double bonds in the carbocyclic ring system, —$OR^b$, or —$N(R^{b1})_2$;

$R^{B8}$ is hydrogen, halogen, substituted or unsubstituted $C_{1-6}$ alkyl, or —$N(R^{b1})_2$ $R^{B9}$ is hydrogen, halogen, substituted or unsubstituted $C_{1-6}$ alkyl, or substituted or unsubstituted, 3- to 7-membered, monocyclic carbocyclyl comprising 0, 1, or 2 double bonds in the carbocyclic ring system;

$R^{B10}$ is —$OR^b$, —$N(R^{b1})_2$, or a warhead;

each instance of $R^{B1}$ is independently halogen, substituted or unsubstituted $C_{1-6}$ alkyl, substituted or unsubstituted, 3- to 7-membered, monocyclic carbocyclyl comprising 0, 1, or 2 double bonds in the carbocyclic ring system, or —$N(R^{b1})_2$; u is 0, 1, 2, 3, or 4;

$R^{B12}$ is hydrogen, substituted or unsubstituted $C_{1-6}$ alkyl, a nitrogen protecting group, or a warhead;

each instance of $R^{B3}$ is independently halogen, substituted or unsubstituted $C_{1-6}$ alkyl, substituted or unsubstituted, 3- to 7-membered, monocyclic carbocyclyl comprising 0, 1, or 2 double bonds in the carbocyclic ring system, or —$N(R^{b1})_2$; and v is 0, 1, 2, 3, 4, 5, 6, 7, 8, or 9;

each instance of $R^{B21}$ is independently hydrogen, halogen, substituted or unsubstituted $C_{1-6}$ alkyl, —$OR^b$, or —$N(R^{b1})_2$;

f is 0, 1, or 2;

each instance of $R^{B22}$ is independently hydrogen, halogen, substituted or unsubstituted $C_{1-6}$ alkyl, —$OR^b$, —$N(R^{b1})_2$, or a nitrogen protecting group when attached to nitrogen;

g is 0, 1, or 2; and each instance of the warhead is independently:

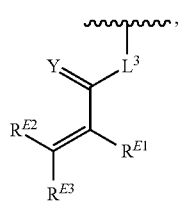 (i-1)

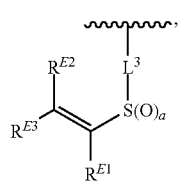 (i-2)

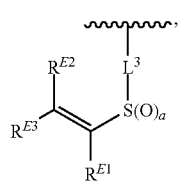 (i-3)

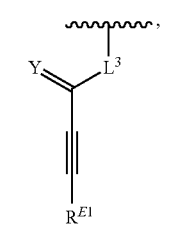 (i-4)

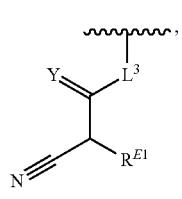 (i-5)

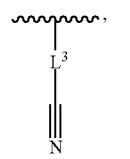 (i-5)

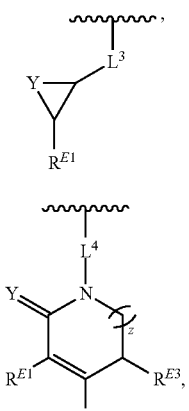 (i-6), (i-7), (i-8)

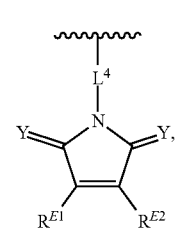 (i-9)

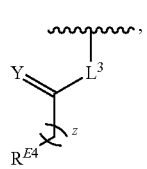 (i-10)

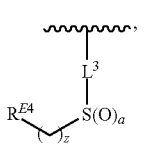 (i-11)

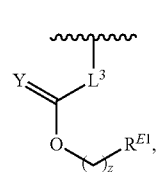 (i-11)

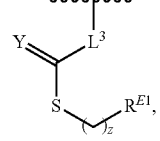 (i-12)

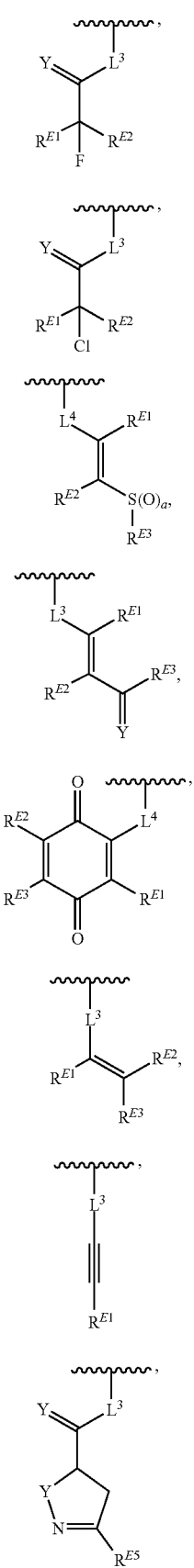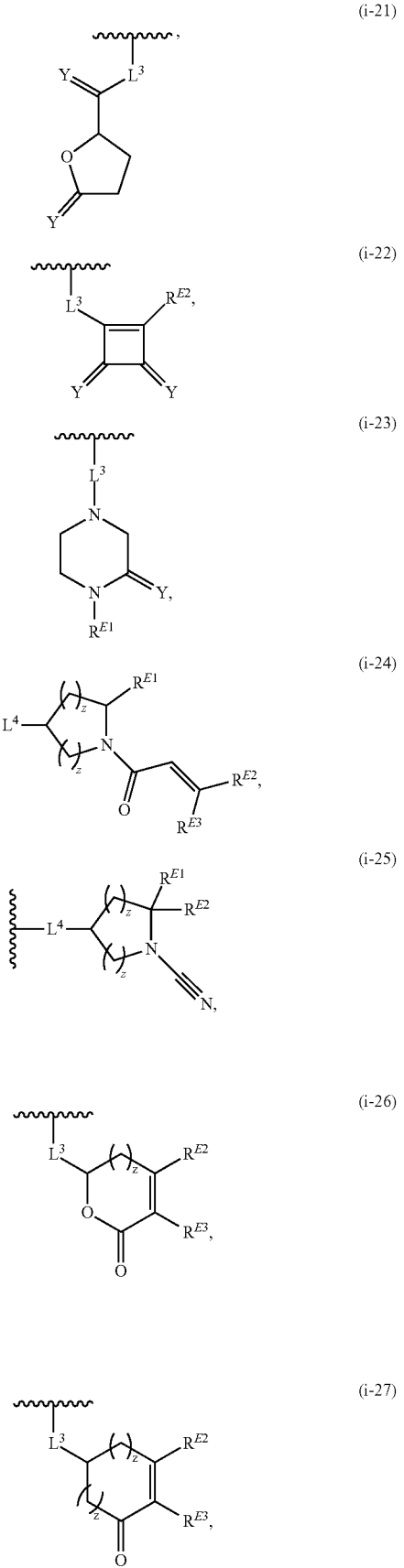

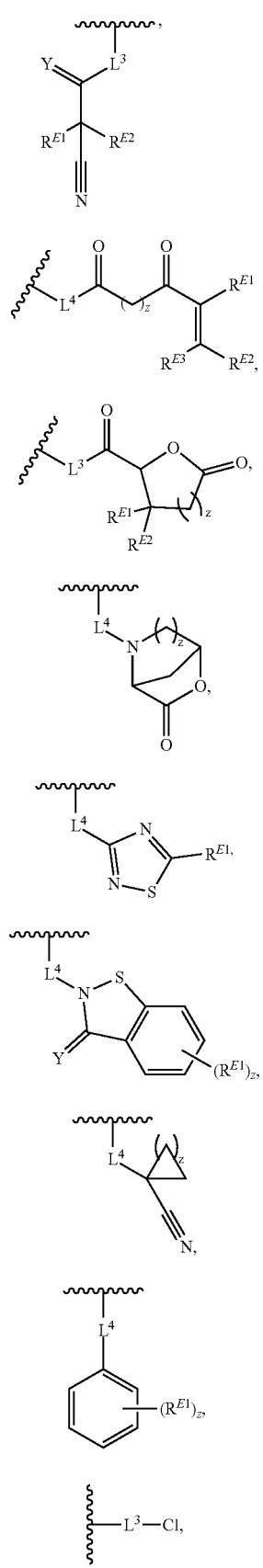

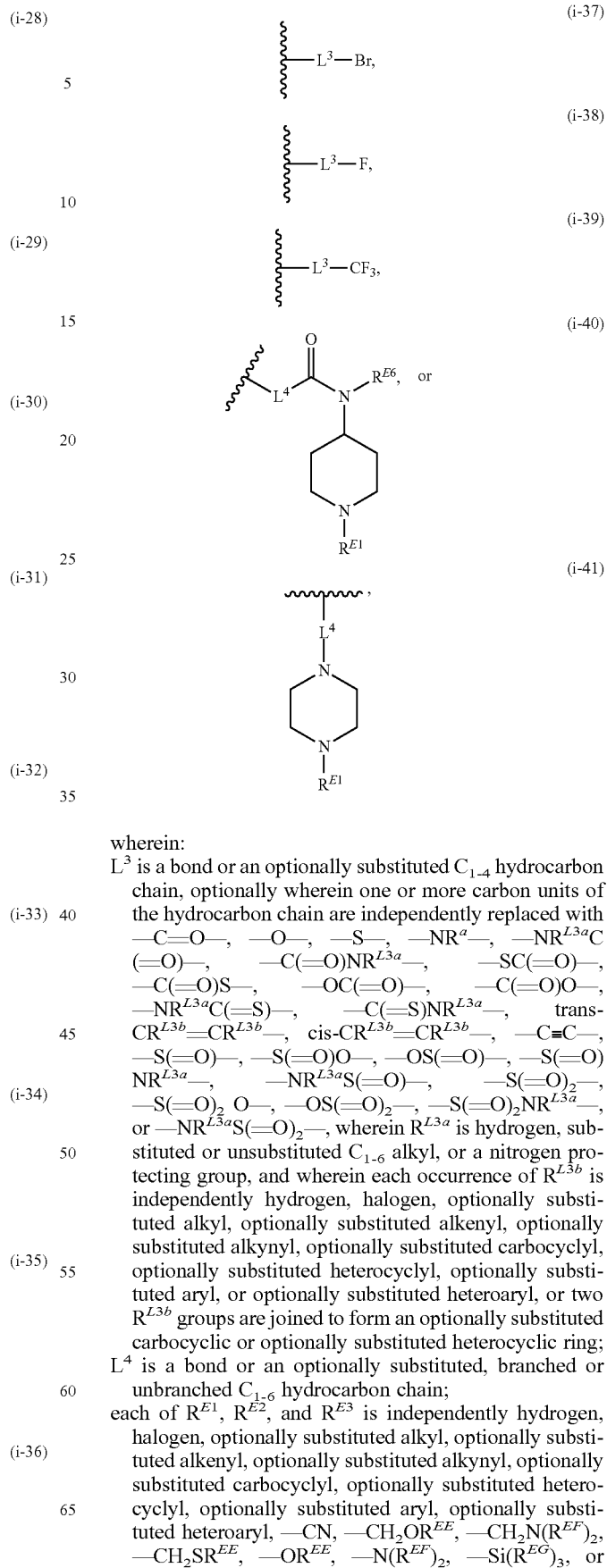

wherein:

L³ is a bond or an optionally substituted $C_{1-4}$ hydrocarbon chain, optionally wherein one or more carbon units of the hydrocarbon chain are independently replaced with —C=O—, —O—, —S—, —NR$^a$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

L⁴ is a bond or an optionally substituted, branched or unbranched $C_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EF}$)$_2$, —CH$_2$SR$^{EE}$, —OR$^{EE}$, —N(R$^{EF}$)$_2$, —Si(R$^{EG}$)$_3$, or —SR$^{EE}$, wherein each instance of R$^{EE}$, R$^{EF}$ and R$^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, and optionally wherein two R$^{EF}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, substituted or unsubstituted C$_{1-6}$ alkyl, or a nitrogen protecting group;

each instance of Y is independently O, S, or NR$^{E7}$, wherein R$^{E7}$ is hydrogen, substituted or unsubstituted C$_{1-6}$ alkyl, or a nitrogen protecting group;

a is 1 or 2; and each instance of z is independently 0, 1, 2, 3, 4, 5, or 6, as valency permits.

Formula (III) includes substituent R$^{B1}$. In certain embodiments, R$^{B1}$ is halogen (e.g., F, Cl, Br, or I). In certain embodiments, R$^{B1}$ is substituted or unsubstituted alkyl (e.g., substituted or unsubstituted C$_{1-6}$ alkyl). In certain embodiments, R$^{A1}$ is Me. In certain embodiments, R$^{B1}$ is —CF$_3$, Bn, Et, perfluoroethyl, Pr, perfluoropropyl, Bu, or perfluorobutyl. In certain embodiments, R$^{B1}$ is of the formula:

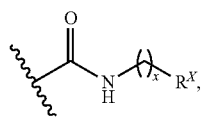

wherein: x is 1, 2, 3, 4, 5, 6, 7, 8, 9, 10, 11, or 12; and R$^X$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, —OR$^{y1}$, —N(R$^{y2}$)$_2$, —SR$^{y1}$, —CN, —SCN, —C(=NR$^{y1}$)R$^{y1}$, —C(=NR$^{y1}$)OR$^{y1}$, —C(=NR$^{y1}$)N(R$^{y2}$)$_2$, —C(=O)R$^{y1}$, —C(=O)OR$^{y1}$, —C(=O)N(R$^{y2}$)$_2$, —NO$_2$, —NR$^{y1}$C(=O)R$^{y1}$, —NR$^{y1}$C(=O)OR$^{y1}$, —NR$^{y1}$C(=O)N(R$^{y2}$)$_2$, —OC(=O)R$^{y1}$, —OC(=O)OR$^{y1}$, or —OC(=O)N(R$^{y2}$)$_2$; R$^{y1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, or a sulfur protecting group when attached to a sulfur atom; and R$^{y2}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or nitrogen protecting group when attached to a nitrogen atom; or two instances of R$^{y2}$ are joined to form a substituted or unsubstituted, heterocyclic ring, or substituted or unsubstituted, heteroaryl ring. In certain embodiments, x is 1. In certain embodiments, x is 2. In certain embodiments, x is 3. In certain embodiments, x is 4. In certain embodiments, x is 5. In certain embodiments, x is 6. In certain embodiments, x is 7. In certain embodiments, x is 8. In certain embodiments, x is 9. In certain embodiments, x is 10. In certain embodiments, x is 11. In certain embodiments, x is 12. In certain embodiments, R$^X$ is substituted or unsubstituted acyl. In certain embodiments, R$^X$ is substituted or unsubstituted alkyl (e.g., substituted or unsubstituted C$_{1-6}$ alkyl). In certain embodiments, R$^X$ is substituted or unsubstituted alkenyl (e.g., substituted or unsubstituted C$_{2-6}$ alkenyl). In certain embodiments, R$^X$ is substituted or unsubstituted alkynyl (e.g., substituted or unsubstituted C$_{2-6}$ alkynyl). In certain embodiments, R$^X$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, R$^X$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R$^X$ is substituted or unsubstituted aryl (e.g., substituted or unsubstituted, 6- to 10-membered aryl). In certain embodiments, R$^X$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, R$^X$ is —OR$^{y1}$ (e.g., —OH or —O(substituted or unsubstituted C$_{1-6}$ alkyl) (e.g., —OMe)). In certain embodiments, R$^{Z1}$ is —N(R$^{y2}$)$_2$ (e.g., —NH$_2$, —NH (substituted or unsubstituted C$_{1-6}$ alkyl) (e.g., —NHMe), or —NMe$_2$). In certain embodiments, R$^X$ is —SR$^{y1}$ (e.g., —SH, —S(substituted or unsubstituted C$_{1-6}$ alkyl) (e.g., —SMe, —SEt, —SPr, —SBu, or —SBn), or —S(substituted or unsubstituted phenyl) (e.g., —SPh)). In certain embodiments, R$^X$ is —CN. In certain embodiments, R$^X$ is —SCN or —NO$_2$. In certain embodiments, R$^X$ is —C(=NR$^{y1}$)R$^{y1}$, —C(=NR$^{y1}$)OR$^{y1}$, or —C(=NR$^{y1}$)N(R$^2$)$_2$. In certain embodiments, R$^X$ is —C(=O)R$^{y1}$ (e.g., —C(=O)(substituted or unsubstituted alkyl) or —C(=O)(substituted or unsubstituted phenyl)). In certain embodiments, R$^X$ is —C(=O)OR$^{y1}$ (e.g., —C(=O)OH, —C(=O)O (substituted or unsubstituted alkyl) (e.g., —C(=O)OMe), or —C(=O)O (substituted or unsubstituted phenyl)). In certain embodiments, R$^X$ is —C(=O)N(R$^{y2}$)$_2$ (e.g., —C(=O)NH$_2$, —C(=O)NH (substituted or unsubstituted alkyl), —C(=O)NH (substituted or unsubstituted phenyl), —C(=O)N (substituted or unsubstituted alkyl)-(substituted or unsubstituted alkyl), or —C(=O)N (substituted or unsubstituted phenyl)-(substituted or unsubstituted alkyl)). In certain embodiments, R$^X$ is —NR$^{y1}$C(=O)R$^{y1}$ (e.g., —NHC(=O)Me). In certain embodiments, R$^X$ is —NR$^{w1}$C(=O)OR$^{w1}$ or —NR$^{w1}$C(=O)N(R$^{w2}$)$_2$.

In certain embodiments, R$^{B1}$ is of the formula:

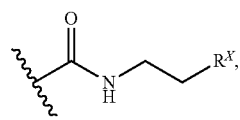

wherein: R$^X$ is substituted or unsubstituted, 5- to 10-membered monocyclic or bicyclic heterocyclic ring, wherein one or two atoms in the heterocyclic ring are independently nitrogen, oxygen, or sulfur. In certain embodiments, R$^X$ is substituted or unsubstituted phenyl. In certain embodiments, $R^X$ is substituted or unsubstituted tetrahydrofuran. In certain embodiments, $R^X$ is substituted or unsubstituted pyrrolidine. In certain embodiments, $R^X$ is substituted or unsubstituted piperazine. In certain embodiments, $R^{B1}$ is of the formula:

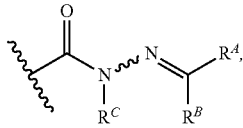

wherein $R^A$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; $R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; or $R^A$ and $R^B$ are joined to form a substituted or unsubstituted, carbocyclic ring, or a substituted or unsubstituted, heterocyclic ring; and $R^C$ is hydrogen, substituted or unsubstituted $C_{1-6}$ alkyl, or a nitrogen protecting group. In certain embodiments, $R^{B1}$ is of the formula:

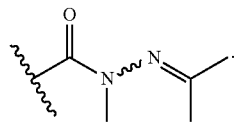 [SMILES: *C(=O)N(C)N=C(C)C]

In certain embodiments, $R^{B1}$ is substituted or unsubstituted alkyl (e.g., substituted or unsubstituted $C_{1-6}$ alkyl). In certain embodiments, $R^{B1}$ is Me. In certain embodiments, $R^{B1}$ is —$CF_3$, Bn, Et, perfluoroethyl, Pr, perfluoropropyl, Bu, or perfluorobutyl. In certain embodiments, $R^{B1}$ is substituted or unsubstituted alkenyl (e.g., substituted or unsubstituted $C_{2-6}$ alkenyl). In certain embodiments, $R^{B1}$ is substituted or unsubstituted alkynyl (e.g., substituted or unsubstituted $C_{1-6}$ alkynyl). In certain embodiments, $R^{B1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B1}$ is substituted or unsubstituted, 3- to 7-membered, monocyclic heterocyclyl comprising 0, 1, or 2 double bonds in the heterocyclic ring system, wherein 1, 2, or 3 atoms in the heterocyclic ring system are independently nitrogen, oxygen, or sulfur. In certain embodiments, $R^{B1}$ is substituted or unsubstituted piperazinyl. In certain embodiments, $R^{B1}$ is of the formula:

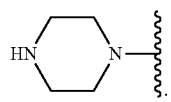

In certain embodiments, $R^{B1}$ is of the formula:

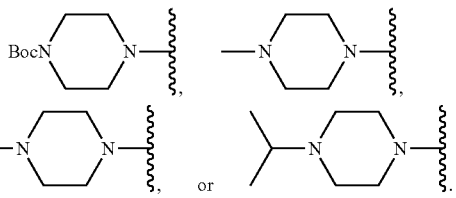

In certain embodiments, $R^{B1}$ is of the formula:

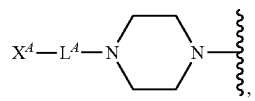

wherein $L^A$ is a bond or substituted or unsubstituted $C_{1-100}$ hydrocarbon chain, optionally wherein one or more chain atoms of the hydrocarbon chain are independently replaced with —O—, —S—, or —$NR^a$—; and $X^A$ is a small molecule, peptide, protein, or polynucleotide. In certain embodiments, $R^{B1}$ is of the formula:

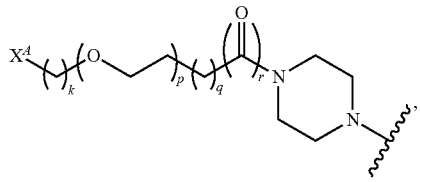

wherein: r is 0 or 1; k is an integer between 0 and 10, inclusive; p is an integer between 2 and 20, inclusive; and q is an integer between 2 and 10, inclusive. In certain embodiments, p is an integer between 3 and 11, inclusive, q is 0, and k is 0, 1, 2, 3, 4, 5, or 6. In certain embodiments, $X^A$ is a small molecule. In certain embodiments, $X^A$ is a small molecule tag (e.g., a biotin moiety (e.g., 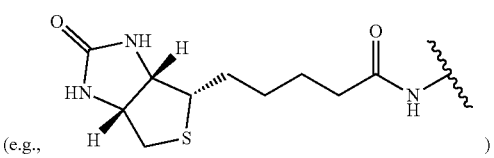 [SMILES: *NC(=O)CCCC[C@@H]1SC[C@@H]2NC(=O)N[C@@H]21] )

or a small molecule fluorophore). In certain embodiments, $R^{B1}$ is

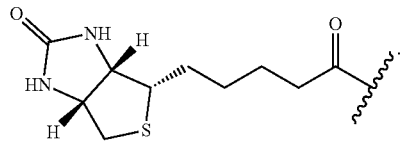 [SMILES: *C(=O)CCCC[C@@H]1SC[C@@H]2NC(=O)N[C@@H]21]

In certain embodiments, $R^{B1}$ substituted or unsubstituted aryl (e.g., substituted or unsubstituted, 6- to 10-membered aryl). In certain embodiments, $R^{B1}$ is substituted or unsubstituted phenyl. In certain embodiments, $R^{B1}$ is substituted or unsubstituted heteroaryl (e.g., substituted or unsubsti tuted, 5- to 6-membered, monocyclic heteroaryl, wherein one, two, three, or four atoms in the heteroaryl ring system are independently nitrogen, oxygen, or sulfur). In certain embodiments, $R^{B1}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, $R^{B1}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{B1}$ is —$N(R^{a1})_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^{B1}$ is —CN. In certain embodiments, $R^{B1}$ is —SCN or —$NO_2$. In certain embodiments, $R^{B1}$ is $C(=NR^b)R^b$, —$C(=NR^b)OR^b$, —$C(=NR^b)N(R^{b1})_2$. In certain embodiments, $R^{B1}$ is —$C(=O)R^b$ (e.g., —C(=O)(substituted or unsubstituted alkyl) or —C(=O)(substituted or unsubstituted phenyl)). In certain embodiments, $R^{B1}$ is —$C(=O)OR^b$ (e.g., —C(=O)OH, —C(=O)O (substituted or unsubstituted alkyl) (e.g., —C(=O)OMe), or —C(=O)O (substituted or unsubstituted phenyl)). In certain embodiments, $R^{B1}$ is —C(=O)OH. In certain embodiments, $R^{B1}$ is —$C(=O)N(R^{b1})_2$ (e.g., —$C(=O)NH_2$, —C(=O)NH (substituted or unsubstituted alkyl), —C(=O)NH (substituted or unsubstituted phenyl), —C(=O)N (substituted or unsubstituted alkyl)-(substituted or unsubstituted alkyl), or —C(=O)N (substituted or unsubstituted phenyl)-(substituted or unsubstituted alkyl)). In certain embodiments, $R^{B1}$ is

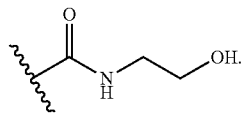 [SMILES: *C(=O)NCCO]

In certain embodiments, $R^{B1}$ is —$NR^bC(=O)R^b$ (e.g., —NHC(=O)Me). In certain embodiments, $R^{B1}$ is —$NR^bC(=O)OR^b$ or —$NR^bC(=O)N(R^{b1})_2$. In certain embodiments, $R^{B1}$ is —$OC(=O)R^b$, —$OC(=O)OR^b$, or —$OC(=O)N(R^{b1})_2$.

Formula (III) may include one or more instances of substituent $R^b$. When Formula (III) includes two or more instances of $R^b$, any two instances of $R^b$ may be the same or different from each other. In certain embodiments, at least one instance of $R^b$ is H. In certain embodiments, each instance of $R^a$ is H. In certain embodiments, at least one instance of $R^b$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridinesulfenyl, or triphenylmethyl) when attached to a sulfur atom. Formula (III) may include one or more instances of substituent $R^{b1}$. In certain embodiments, $R^b$ is a nitrogen protecting group (e.g., Bn, Boc, Cbz, Fmoc, trifluoroacetyl, triphenylmethyl, acetyl, or Ts) when attached to a nitrogen atom. When Formula (III) includes two or more instances of $R^{b1}$, any two instances of $R^{b1}$ may be the same or different from each other. In certain embodiments, at least one instance of $R^{b1}$ is H. In certain embodiments, each instance of $R^{b1}$ is H. In certain embodiments, at least one instance of $R^{b1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group (e.g., Bn, Boc, Cbz, Fmoc, trifluoroacetyl, triphenylmethyl, acetyl, or Ts) when attached to a nitrogen atom. In certain embodiments, two instances of $R^{b1}$ are joined to form a substituted or unsubstituted, heterocyclic ring, or substituted or unsubstituted, heteroaryl ring. In certain embodiments, $R^{b1}$ is a tag, (e.g., a biotin moiety (e.g., 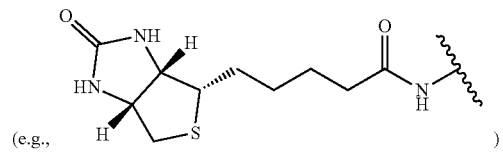 [SMILES: *NC(=O)CCCC[C@@H]1SC[C@@H]2NC(=O)N[C@@H]21] )

or a small molecule fluorophore)).

Formula (III) includes substituent $R^{B2}$. In certain embodiments, $R^{B2}$ is substituted or unsubstituted acyl. In certain embodiments, $R^{B2}$ is —$C(=O)R^b$, optionally wherein $R^b$ is substituted or unsubstituted $C_{1-6}$ alkyl (e.g., Me) or substituted or unsubstituted $C_{2-6}$ alkenyl. In certain embodiments, $R^{B2}$ is —$C(=O)R^b$, wherein $R^b$ is substituted or unsubstituted vinyl. In certain embodiments, $R^{B2}$ is —C(=O)CH=$CH_2$. In certain embodiments, $R^{B2}$ is —$C(=O)OR^b$, optionally wherein $R^b$ is H, substituted or unsubstituted $C_{1-6}$ alkyl (e.g., Me), or an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, $R^{B2}$ is —$C(=O)N(R^{b1})_2$, optionally wherein each instance of $R^{b1}$ is independently H, substituted or unsubstituted $C_{1-6}$ alkyl (e.g., Me), or a nitrogen protecting group (e.g., Bn, Boc, Cbz, Fmoc, trifluoroacetyl, triphenylmethyl, acetyl, or Ts). In certain embodiments, $R^{B2}$ is substituted or unsubstituted alkyl (e.g., substituted or unsubstituted $C_{1-6}$ alkyl). In certain embodiments, $R^{B2}$ is Me. In certain embodiments, $R^{B2}$ is Et. In certain embodiments, $R^{B2}$ is n-Pr. In certain embodiments, $R^{B2}$ is i-Pr. In certain embodiments, $R^{B2}$ is Bu (e.g., n-Bu, i-Bu, sec-Bu, or t-Bu). In certain embodiments, $R^{B2}$ is unsubstituted pentyl (e.g., unsubstituted n-pentyl, unsubstituted t-pentyl, unsubstituted neopentyl, unsubstituted isopentyl, unsubstituted sec-pentyl, or unsubstituted 3-pentyl). In certain embodiments, $R^{B2}$ is sec-Bu, t-Bu, or unsubstituted 3-pentyl. In certain embodiments, $R^{A2}$ is —$CF_3$, Bn, perfluoroethyl, perfluoropropyl, perfluorobutyl, or perfluoropentyl. In certain embodiments, $R^{A2}$ is —$CH_2C(=O)$—NH—N=$C(R^{b1})_2$. In certain embodiments, $R^{B2}$ is substituted or unsubstituted alkenyl (e.g., substituted or unsubstituted $C_{2-6}$ alkenyl). In certain embodiments, $R^{B2}$ is substituted or unsubstituted alkynyl (e.g., substituted or unsubstituted $C_{1-6}$ alkynyl). In certain embodiments, $R^{B2}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B2}$ is substituted or unsubstituted cyclopropyl. In certain embodiments, $R^{B2}$ is unsubstituted cyclopropyl. In certain embodiments, $R^{B2}$ is substituted or unsubstituted cyclobutyl. In certain embodiments, $R^{B2}$ is substituted or unsubstituted cyclopentyl. In certain embodiments, $R^{B2}$ is unsubstituted cyclopropyl, unsubstituted cyclobutyl, or unsubstituted cyclopentyl. In certain embodiments, $R^{B2}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{B2}$ is substituted or unsubstituted tetrahydropyranyl. In certain embodiments, $R^{B2}$ is of the formula:

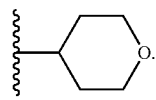

In certain embodiments, $R^{B2}$ is of the formula:

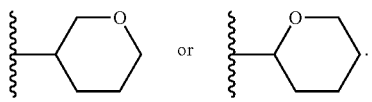 [SMILES: *C1CCCOC1 ; *C1CCCCO1]

In certain embodiments, $R^{B2}$ is substituted or unsubstituted oxetanyl, substituted or unsubstituted tetrahydrofuranyl, substituted or unsubstituted pyrrolidinyl, substituted or unsubstituted piperidinyl, substituted or unsubstituted morpholinyl, or substituted or unsubstituted piperazinyl. In certain embodiments, $R^{B2}$ is of the formula:

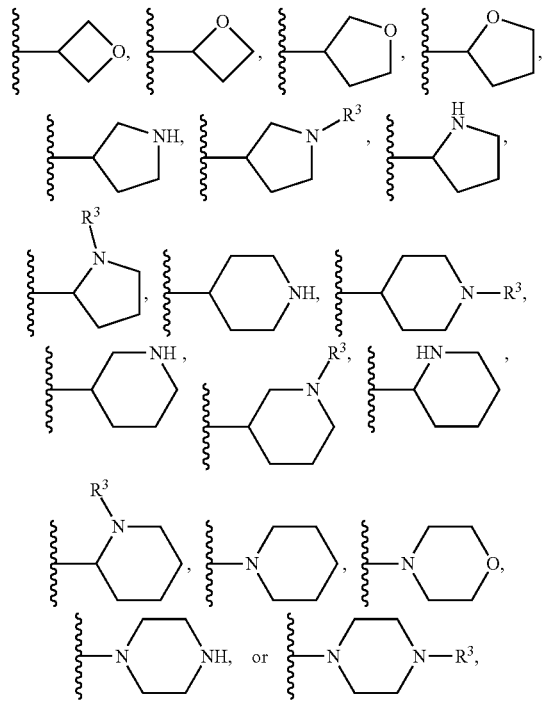

wherein each instance of $R^3$ is independently H or unsubstituted alkyl (e.g., Me)). In certain embodiments, $R^{B2}$ is substituted or unsubstituted aryl (e.g., substituted or unsubstituted, 6- to 10-membered aryl). In certain embodiments, $R^{B2}$ is substituted or unsubstituted phenyl. In certain embodiments, $R^{B2}$ is substituted or unsubstituted heteroaryl (e.g., substituted or unsubstituted, 5- to 6-membered, mono-cyclic heteroaryl, wherein one, two, three, or four atoms in the heteroaryl ring system are independently nitrogen, oxygen, or sulfur). In certain embodiments, $R^{B2}$ is a nitrogen protecting group (e.g., Bn, Boc, Cbz, Fmoc, trifluoroacetyl, triphenylmethyl, acetyl, or Ts). In certain embodiments, $R^{B2}$ is Boc. In certain embodiments, $R^{B2}$ is a tag, (e.g., a biotin moiety

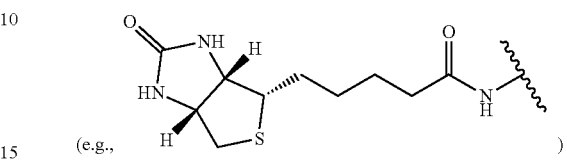

(e.g., )

or a small molecule fluorophore)). In certain embodiments, $R^{B2}$ is a warhead.

Formula (III) includes substituent $R^{B3}$. In certain embodiments, $R^{B3}$ is H. In certain embodiments, $R^{B3}$ is substituted or unsubstituted acyl (e.g., acetyl). In certain embodiments, $R^{B3}$ is of the formula:

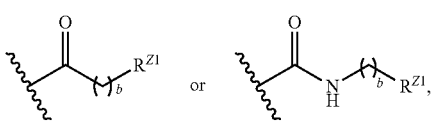

wherein: b is 0, 1, 2, 3, 4, 5, 6, 7, 8, 9, 10, 11, or 12; and $R^{Z1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, —$OR^{w1}$, —$N(R^{w2})_2$, —$SR^{w1}$, —CN, —SCN, —C(=$NR^{w1}$)$R^{w1}$, —C(=$NR^{w1}$)$OR^{w1}$, —C(=$NR^{w1}$)N($R^{w2}$)$_2$, —C(=O)$R^{w1}$, —C(=O)$OR^{w1}$, —C(=O)N($R^{w2}$)$_2$, —NO$_2$, —$NR^{w1}$C(=O)$R^{w1}$, —$NR^{w1}$C(=O)$OR^{w1}$, —$NR^{w1}$C(=O)N($R^{w2}$)$_2$, —OC(=O)$R^{w1}$, —OC(=O)$OR^{w1}$, or —OC(=O)N($R^{w2}$)$_2$; $R^{w1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, or a sulfur protecting group when attached to a sulfur atom; and $R^{w2}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or nitrogen protecting group when attached to a nitrogen atom; or two instances of $R^{w2}$ are joined to form a substituted or unsubstituted, heterocyclic ring, or substituted or unsubstituted, heteroaryl ring. In certain embodiments, b is 0. In certain embodiments, b is 1. In certain embodiments, b is 2. In certain embodiments, b is 3. In certain embodiments, b is 4. In certain embodiments, b is 5. In certain embodiments, b is 6. In certain embodiments, b is 7. In certain embodiments, b is 8. In certain embodiments, b is 9. In certain embodiments, b is 10. In certain embodiments, b is 11. In certain embodiments, b is 12. In certain embodiments, $R^{Z1}$ is substituted or unsubstituted acyl. In certain embodiments, $R^{Z1}$ is substituted or unsubstituted alkyl (e.g., substituted or unsubstituted $C_{1-6}$ alkyl). In certain embodiments, $R^{B3}$ is

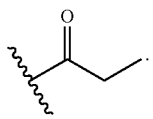

In certain embodiments, $R^{Z1}$ is substituted or unsubstituted alkenyl (e.g., substituted or unsubstituted $C_{2-6}$ alkenyl). In certain embodiments, $R^{B3}$ is

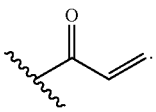 [SMILES: *C(=O)C=C]

In certain embodiments, $R^{Z1}$ is substituted or unsubstituted alkynyl (e.g., substituted or unsubstituted $C_{2-6}$ alkynyl). In certain embodiments, $R^{Z1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{Z1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{Z1}$ is substituted or unsubstituted aryl (e.g., substituted or unsubstituted, 6- to 10-membered aryl). In certain embodiments, $R^{Z1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{Z1}$ is —$OR^{w1}$ (e.g., —OH or —O(substituted or unsubstituted $C_{1-6}$ alkyl) (e.g., —OMe)). In certain embodiments, $R^{Z1}$ is —$N(R^{w2})_2$ (e.g., —$NH_2$, —NH (substituted or unsubstituted $C_{1-6}$ alkyl) (e.g., —NHMe), or —$NMe_2$). In certain embodiments, $R^{Z1}$ is —$SR^{w1}$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{Z1}$ is —CN. In certain embodiments, $R^{Z1}$ is —SCN or —$NO_2$. In certain embodiments, $R^{Z1}$ is —$C(=NR^{w1})R^{w1}$, —$C(=NR^{w1})OR^{w1}$, or —$C(=NR^{w1})N(R^{w2})_2$. In certain embodiments, $R^{Z1}$ is —$C(=O)R^{w1}$ (e.g., —C(=O)(substituted or unsubstituted alkyl) or —C(=O)(substituted or unsubstituted phenyl)). In certain embodiments, $R^{Z1}$ is —$C(=O)OR^{w1}$ (e.g., —C(=O)OH, —C(=O)O (substituted or unsubstituted alkyl) (e.g., —C(=O)OMe), or —C(=O)O (substituted or unsubstituted phenyl)). In certain embodiments, $R^Z$ is —$C(=O)N(R^w)_2$ (e.g., —$C(=O)NH_2$, —C(=O)NH (substituted or unsubstituted alkyl), —C(=O)NH (substituted or unsubstituted phenyl), —C(=O)N (substituted or unsubstituted alkyl)-(substituted or unsubstituted alkyl), or —C(=O)N (substituted or unsubstituted phenyl)-(substituted or unsubstituted alkyl)). In certain embodiments, $R^{Z1}$ is —$NR^{w1}C(=O)R^{w1}$ (e.g., —NHC(=O)Me). In certain embodiments, $R^{Z1}$ is —$NR^{w1}C(=O)OR^{w1}$ or —$NR^{w1}C(=O)N(R^{w2})_2$. In certain embodiments, $R^{B3}$ is of the formula:

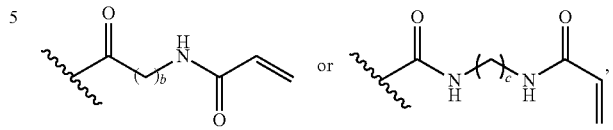

wherein: b is 0, 1, 2, 3, 4, 5, or 6; and c is 1, 2, 3, 4, 5, or 6. In certain embodiments, b is 0. In certain embodiments, b is 1. In certain embodiments, b is 2. In certain embodiments, b is 3. In certain embodiments, b is 4. In certain embodiments, b is 5. In certain embodiments, b is 6. In certain embodiments, c is 1. In certain embodiments, c is 2. In certain embodiments, c is 3. In certain embodiments, c is 4. In certain embodiments, c is 5. In certain embodiments, c is 6. In certain embodiments, $R^{B3}$ is of the formula:

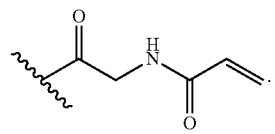 [SMILES: *C(=O)CNC(=O)C=C]

In certain embodiments, $R^{B3}$ is of the formula:

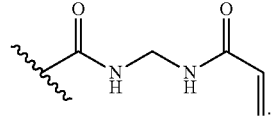 [SMILES: *C(=O)NCNC(=O)C=C]

In certain embodiments, $R^{B3}$ is of the formula:

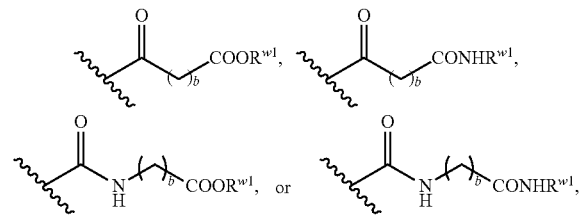

wherein: $R^{w1}$ is $C_{1-12}$ substituted or unsubstituted alkyl; and b is 0, 1, 2, 3, 4, 5, or 6. In certain embodiments, b is 0. In certain embodiments, b is 1. In certain embodiments, b is 2. In certain embodiments, b is 3. In certain embodiments, b is 4. In certain embodiments, b is 5. In certain embodiments, b is 6. In certain embodiments, $R^{w1}$ is $C_{1-12}$ substituted or unsubstituted alkyl (e.g., substituted or unsubstituted Me, Et or Pr). In certain embodiments, $R^{A3}$ is of the formula:

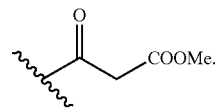 [SMILES: *C(=O)CC(=O)OC]

In certain embodiments, $R^{B3}$ is of the formula:

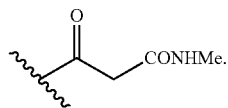

In certain embodiments, $R^{B3}$ is of the formula:

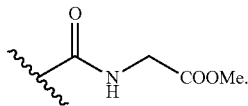

In certain embodiments, $R^{B3}$ is of the formula:

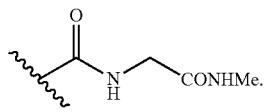

In certain embodiments, $R^{B3}$ is substituted or unsubstituted alkyl. In certain embodiments, $R^{B3}$ is Me. In certain embodiments, $R^{B3}$ is Et. In certain embodiments, $R^{B3}$ is —CF$_3$, Bn, Et, perfluoroethyl, Pr, perfluoropropyl, Bu, or perfluorobutyl. In certain embodiments, $R^{B3}$ is of the formula:

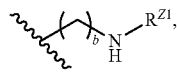

wherein: b is 4, 5, 6, 7, 8, 9, 10, 11, or 12; and $R^{Z1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, b is 4. In certain embodiments, b is 5. In certain embodiments, b is 6. In certain embodiments, b is 7. In certain embodiments, b is 8. In certain embodiments, b is 9. In certain embodiments, b is 10. In certain embodiments, b is 11. In certain embodiments, b is 12. In certain embodiments, $R^{B3}$ is of the formula:

wherein: b is 4, 5, 6, 7, 8, 9, 10, 11, or 12; and $R^{Z1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, —OR$^{w1}$, —N(R$^{w2}$)$_2$, —SR$^{w1}$, —CN, —SCN, —C(=NR$^{w1}$)R$^{w1}$, —C(=NR$^{w1}$)OR$^{w1}$, —C(=NR$^{w1}$)N(R$^{w2}$)$_2$, —C(=O)R$^{w1}$, —C(=O)OR$^{w1}$, —C(=O)N(R$^{w2}$)$_2$, —NO$_2$, —NR$^{w1}$C(=O)R$^{w1}$, —NR$^{w1}$C(=O)OR$^{w1}$, —NR$^{w1}$C(=O)N(R$^{w2}$)$_2$, —OC(=O)R$^{w1}$, —OC(=O)OR$^{w1}$, or —OC(=O)N(R$^{w2}$)$_2$; R$^{w1}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, or a sulfur protecting group when attached to a sulfur atom; and R$^{w2}$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or nitrogen protecting group when attached to a nitrogen atom; or two instances of R$^{w2}$ are joined to form a substituted or unsubstituted, heterocyclic ring, or substituted or unsubstituted, heteroaryl ring. In certain embodiments, b is 4. In certain embodiments, b is 5. In certain embodiments, b is 6. In certain embodiments, b is 7. In certain embodiments, b is 8. In certain embodiments, b is 9. In certain embodiments, b is 10. In certain embodiments, b is 11. In certain embodiments, b is 12. In certain embodiments, $R^{Z1}$ is a small molecule fluorophore. In certain embodiments, $R^{B3}$ is of the formula:

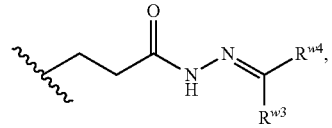

wherein: R$^{w3}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and R$^{w4}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, $R^{B3}$ is of the formula:

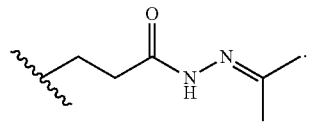 [SMILES: *CCC(=O)NN=C(C)C]

In certain embodiments, $R^{B3}$ is of the formula:

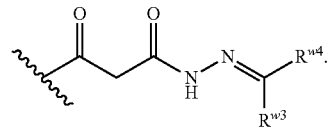

In certain embodiments, $R^{B3}$ is of the formula:

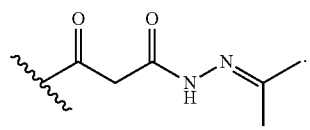 [SMILES: *C(=O)CC(=O)NN=C(C)C]

In certain embodiments, $R^{B3}$ is a nitrogen protecting group (e.g., Bn, Boc, Cbz, Fmoc, trifluoroacetyl, triphenylmethyl, acetyl, or Ts). In certain embodiments, $R^{B3}$ is Boc.

Formula (III) includes substituent $R^{B4}$ on a nitrogen atom. In certain embodiments, $R^{B4}$ is H. In certain embodiments, $R^{B4}$ is substituted or unsubstituted acyl (e.g., acetyl). In certain embodiments, $R^{B4}$ is —C(=O)$R^Z$, wherein $R^Z$ is substituted or unsubstituted vinyl (e.g., —C(=O)CH=CH$_2$). In certain embodiments, $R^{B4}$ is substituted or unsubstituted $C_{1-6}$ alkyl. In certain embodiments, $R^{B4}$ is Me. In certain embodiments, $R^{B4}$ is —CF$_3$, Bn, Et, perfluoroethyl, Pr, perfluoropropyl, Bu, or perfluorobutyl. In certain embodiments, $R^{B4}$ is a nitrogen protecting group (e.g., Bn, Boc, Cbz, Fmoc, trifluoroacetyl, triphenylmethyl, acetyl, or Ts).

Formula (III) includes substituent $R^{D5}$. In certain embodiments, $R^{D5}$ is of the formula:

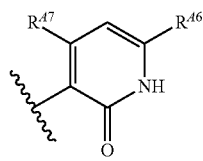

(e.g.,

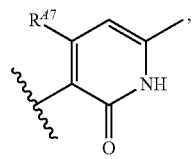

wherein $R^{A7}$ is Et, Pr, or Bu). In certain embodiments, $R^{D5}$ is of the formula:

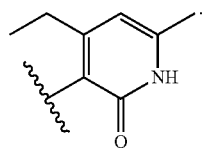

O. In certain embodiments, $R^{D5}$ is of the formula:

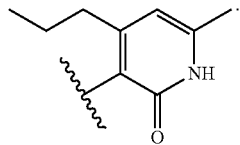

In certain embodiments, $R^{A6}$ is H. In certain embodiments, $R^{A6}$ is halogen (e.g., F, Cl, Br, or I). In certain embodiments, $R^{A6}$ is substituted or unsubstituted $C_{1-6}$ alkyl. In certain embodiments, $R^{A6}$ is Me. In certain embodiments, $R^{A6}$ is substituted methyl (e.g., —CF$_3$ or Bn). In certain embodiments, $R^{A6}$ is Et, substituted ethyl (e.g., perfluoroethyl), Pr, substituted propyl (e.g., perfluoropropyl), Bu, or substituted butyl (e.g., perfluorobutyl). In certain embodiments, $R^{A6}$ is —OR$^a$ (e.g., —OH or —O(substituted or unsubstituted $C_{1-6}$ alkyl) (e.g., —OMe)). In certain embodiments, $R^{A6}$ is —N(R$^{a1}$)$_2$, optionally wherein each instance of R$^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{A6}$ is —NH$_2$, —NHMe, or —N(Me)$_2$. In certain embodiments, $R^{A7}$ is H. In certain embodiments, $R^{A7}$ is halogen (e.g., F, Cl, Br, or I). In certain embodiments, $R^{A7}$ is substituted or unsubstituted $C_{2-6}$ alkyl. In certain embodiments, $R^{A7}$ is Et. In certain embodiments, $R^{A7}$ is substituted ethyl (e.g., perfluoroethyl). In certain embodiments, $R^{A7}$ is n-Pr. In certain embodiments, $R^{A7}$ is i-Pr. In certain embodiments, $R^{A7}$ is substituted propyl (e.g., perfluoropropyl). In certain embodiments, $R^{A7}$ is Bu or unsubstituted pentyl. In certain embodiments, $R^{A7}$ is substituted butyl (e.g., perfluorobutyl) or substituted pentyl (e.g., perfluoropentyl). In certain embodiments, $R^{A7}$ is substituted or unsubstituted, 3- to 7-membered, monocyclic carbocyclyl comprising 0, 1, or 2 double bonds in the carbocyclic ring system. In certain embodiments, $R^{A7}$ is substituted or unsubstituted cyclopropyl, substituted or unsubstituted cyclobutyl, or substituted or unsubstituted cyclopentyl. In certain embodiments, $R^{A7}$ is —OR$^a$ (e.g., —OH or —O(substituted or unsubstituted $C_{1-6}$ alkyl) (e.g., —OMe)). In certain embodiments, $R^{A7}$ is —N(R$^{a1}$)$_2$, optionally wherein each instance of R$^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{A7}$ is —NH$_2$, —NHMe, —NHEt, —N(Me)$_2$, or —N(Et)$_2$. In certain embodiments, $R^{A7}$ is substituted or unsubstituted cyclopropyl or —N(R$^{a1}$)$_2$, wherein each instance of R$^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts).

Formula (III) includes substituent $R^{D5}$. In certain embodiments, $R^{D5}$ is of the formula:

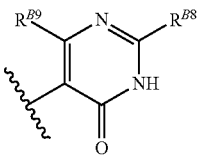

(e.g.,

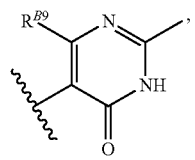

wherein $R^{B9}$ is Me, Et, Pr, or Bu). The moiety of the formula:

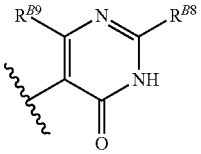

also includes its tautomeric form

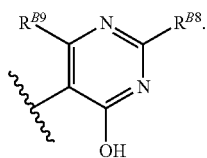

In certain embodiments, $R^{D5}$ is of the formula:

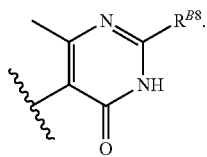

In certain embodiments, $R^{D5}$ is of the formula:

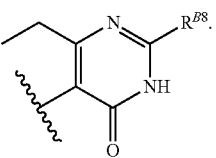

In certain embodiments, $R^{D5}$ is of the formula:

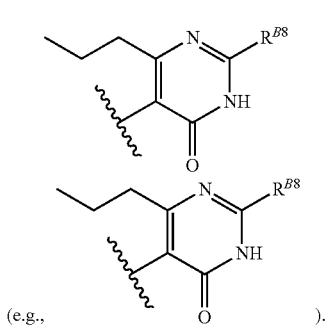

(e.g., ).

In certain embodiments, $R^{D5}$ is of the formula:

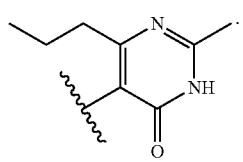 [SMILES: *c1c(CCC)nc(C)[nH]c1=O]

In certain embodiments, $R^{B8}$ is H. In certain embodiments, $R^{B8}$ is halogen (e.g., F, Cl, Br, or I). In certain embodiments, $R^{B8}$ is substituted or unsubstituted $C_{1-6}$ alkyl. In certain embodiments, $R^{B8}$ is Me. In certain embodiments, $R^{B8}$ is substituted methyl (e.g., —CF$_3$ or Bn). In certain embodiments, $R^{B8}$ is Et, substituted ethyl (e.g., perfluoroethyl), Pr, substituted propyl (e.g., perfluoropropyl), Bu, or substituted butyl (e.g., perfluorobutyl). In certain embodiments, $R^{B8}$ is —N($R^{b1}$)$_2$, optionally wherein each instance of $R^{b1}$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{B8}$ is —NH$_2$, —NHMe, or —N(Me)$_2$. In certain embodiments, $R^{B9}$ is H. In certain embodiments, $R^{B9}$ is halogen (e.g., F, Cl, Br, or I). In certain embodiments, $R^{B9}$ is substituted or unsubstituted $C_{1-6}$ alkyl. In certain embodiments, $R^{B9}$ is Me. In certain embodiments, $R^{B9}$ is substituted methyl (e.g., —CF$_3$ or Bn). In certain embodiments, $R^{B9}$ is Et. In certain embodiments, $R^{B9}$ is substituted ethyl (e.g., perfluoroethyl). In certain embodiments, $R^{B9}$ is n-Pr. In certain embodiments, $R^{B9}$ is i-Pr. In certain embodiments, $R^{B9}$ is substituted propyl (e.g., perfluoropropyl). In certain embodiments, $R^{B9}$ is Bu or unsubstituted pentyl. In certain embodiments, $R^{B9}$ is substituted butyl (e.g., perfluorobutyl) or substituted pentyl (e.g., perfluoropentyl). In certain embodiments, $R^{B9}$ is substituted or unsubstituted, 3- to 7-membered, monocyclic carbocyclyl comprising 0, 1, or 2 double bonds in the carbocyclic ring system. In certain embodiments, $R^{B9}$ is substituted or unsubstituted cyclopropyl, substituted or unsubstituted cyclobutyl, or substituted or unsubstituted cyclopentyl.

In certain embodiments, $R^{D5}$ is of the formula:

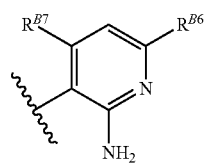

(e.g.,

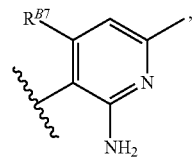

wherein $R^{B7}$ is Me, Et, Pr, or Bu). In certain embodiments, $R^{D5}$ is of the formula:

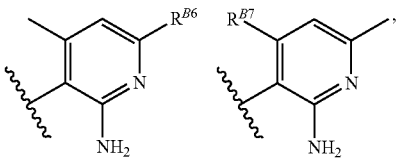

wherein $R^{B7}$ is Me, Et, Pr, or Bu). In certain embodiments, $R^{D5}$ is of the formula:

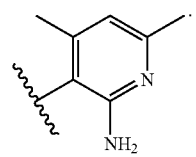

In certain embodiments, $R^{B6}$ is H. In certain embodiments, $R^{B6}$ is halogen (e.g., F, Cl, Br, or I). In certain embodiments, $R^{B6}$ is substituted or unsubstituted $C_{1-6}$ alkyl. In certain embodiments, $R^{B6}$ is Me. In certain embodiments, $R^{B6}$ is substituted methyl (e.g., —$CF_3$ or Bn). In certain embodiments, $R^{B6}$ is Et, substituted ethyl (e.g., perfluoroethyl), Pr, substituted propyl (e.g., perfluoropropyl), Bu, or substituted butyl (e.g., perfluorobutyl). In certain embodiments, $R^{B6}$ is —$OR^b$ (e.g., —OH or —O(substituted or unsubstituted $C_{1-6}$ alkyl) (e.g., —OMe)). In certain embodiments, $R^{B6}$ is —$N(R^{b1})_2$, optionally wherein each instance of $R^{b1}$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{B6}$ is —$NH_2$, —NHMe, or —$N(Me)_2$. In certain embodiments, $R^{B7}$ is H. In certain embodiments, $R^{B7}$ is halogen (e.g., F, Cl, Br, or I). In certain embodiments, $R^{B7}$ is substituted or unsubstituted $C_{2-6}$ alkyl. In certain embodiments, $R^{B7}$ is Me. In certain embodiments, $R^{B7}$ is substituted methyl (e.g., —$CF_3$ or Bn). In certain embodiments, $R^{B7}$ is Et. In certain embodiments, $R^{B7}$ is substituted ethyl (e.g., perfluoroethyl). In certain embodiments, $R^{B7}$ is n-Pr. In certain embodiments, $R^{B7}$ is i-Pr. In certain embodiments, $R^{B7}$ is substituted propyl (e.g., perfluoropropyl). In certain embodiments, $R^{B7}$ is Bu or unsubstituted pentyl. In certain embodiments, $R^{B7}$ is substituted butyl (e.g., perfluorobutyl) or substituted pentyl (e.g., perfluoropentyl). In certain embodiments, $R^{B7}$ is substituted or unsubstituted, 3- to 7-membered, monocyclic carbocyclyl comprising 0, 1, or 2 double bonds in the carbocyclic ring system. In certain embodiments, $R^{B7}$ is substituted or unsubstituted cyclopropyl, substituted or unsubstituted cyclobutyl, or substituted or unsubstituted cyclopentyl. In certain embodiments, $R^{B7}$ is —$OR^b$ (e.g., —OH or —O(substituted or unsubstituted $C_{1-6}$ alkyl) (e.g., —OMe)). In certain embodiments, $R^{B7}$ is —$N(R^{b1})_2$, optionally wherein each instance of $R^{b1}$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{B7}$ is —$NH_2$, —NHMe, —NHEt, —$N(Me)_2$, or —$N(Et)_2$. In certain embodiments, $R^{B7}$ is substituted or unsubstituted cyclopropyl, —$OR^b$, or —$N(R^{b1})_2$, wherein each instance of $R^{b1}$ is independently hydrogen, substituted or unsubstituted $C_{1-6}$ alkyl, an oxygen protecting group when attached to an oxygen atom, or a nitrogen protecting group when attached to a nitrogen atom.

In certain embodiments, $R^{D5}$ is of the formula:

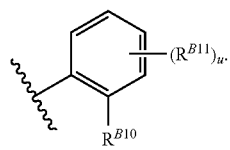

In certain embodiments, $R^{D5}$ is of the formula:

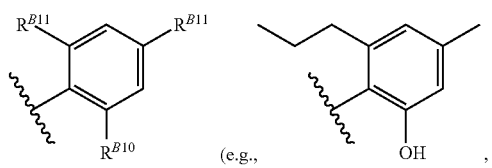

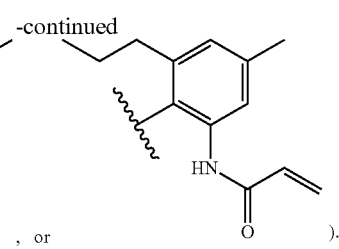

, or

In certain embodiments, $R^{D5}$ is of the formula:

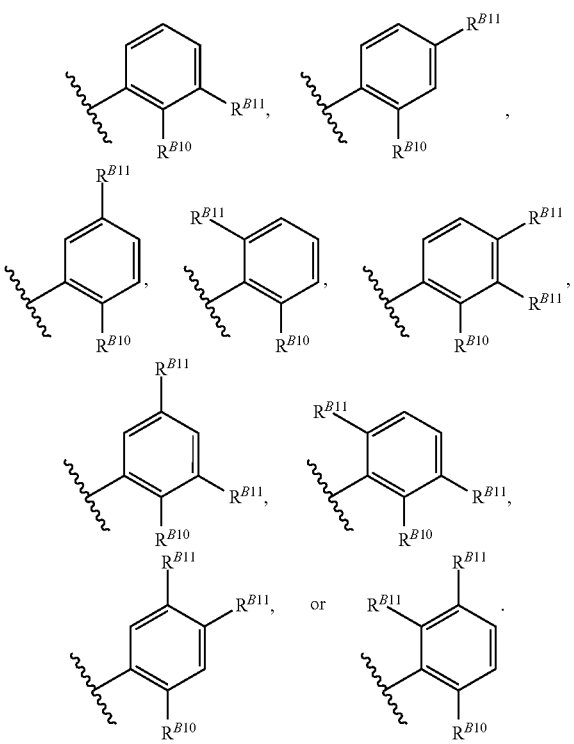

In certain embodiments, $R^{D5}$ is of the formula:

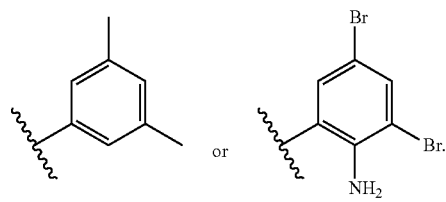

In certain embodiments, $R^{B10}$ is —$OR^b$ (e.g., —OH). In certain embodiments, $R^{B10}$ is —$N(R^{b1})_2$. In certain embodiments, $R^{B10}$ is —$NH_2$. In certain embodiments, $R^{B10}$ is —$NHR^{b1}$, wherein $R^{b1}$ is substituted or unsubstituted $C_{1-6}$ alkyl or a nitrogen protecting group (e.g., Bn, Boc, Cbz, Fmoc, trifluoroacetyl, triphenylmethyl, acetyl, or Ts). In certain embodiments, $R^{B10}$ is —$NHC(=O)R^{b1}$, optionally wherein $R^{b1}$ is substituted or unsubstituted vinyl. In certain embodiments, $R^{B10}$ is —$NHC(=O)CH=CH_2$. In certain embodiments, $R^{B10}$ is a warhead. In certain embodiments, Formula (III) includes one or more instances of $R^{B11}$. When Formula (III) includes two or more instances of $R^{B11}$, any two instances of $R^{B11}$ may be the same or different from each other. In certain embodiments, at least one instance of $R^{B11}$ is halogen. In certain embodiments, at least one instance of $R^{B11}$ is Br. In certain embodiments, at least one instance of $R^{B11}$ is F, Cl, or I. In certain embodiments, at least one instance of $R^{B11}$ is substituted or unsubstituted $C_{1-6}$ alkyl. In certain embodiments, at least one instance of $R^{B11}$ is Me. In certain embodiments, at least one instance of $R^{B11}$ is substituted methyl (e.g., —$CF_3$ or Bn). In certain embodiments, at least one instance of $R^{B11}$ is Et. In certain embodiments, at least one instance of $R^{B11}$ is substituted ethyl (e.g., perfluoroethyl). In certain embodiments, at least one instance of $R^{B1}$ is n-Pr. In certain embodiments, at least one instance of $R^{B1}$ is i-Pr. In certain embodiments, at least one instance of $R^{B1}$ is substituted propyl (e.g., perfluoropropyl). In certain embodiments, at least one instance of $R^{B1}$ is Me, Et, or n-Pr. In certain embodiments, at least one instance of $R^{B11}$ is Bu or unsubstituted pentyl. In certain embodiments, at least one instance of $R^{B11}$ is substituted butyl (e.g., perfluorobutyl) or substituted pentyl (e.g., perfluoropentyl). In certain embodiments, at least one instance of $R^{B11}$ is substituted or unsubstituted, 3- to 7-membered, monocyclic carbocyclyl comprising 0, 1, or 2 double bonds in the carbocyclic ring system. In certain embodiments, at least one instance of $R^{B1}$ is substituted or unsubstituted cyclopropyl, substituted or unsubstituted cyclobutyl, or substituted or unsubstituted cyclopentyl. In certain embodiments, at least one instance of $R^{B11}$ is —$OR^b$ (e.g., —OH or —O(substituted or unsubstituted $C_{1-6}$ alkyl) (e.g., —OMe)). In certain embodiments, at least one instance of $R^{B11}$ is —$N(R^{b1})_2$, optionally wherein each instance of $R^{b1}$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, at least one instance of $R^{B11}$ is —$NH_2$, —NHMe, —NHEt, —$N(Me)_2$, or —$N(Et)_2$. In certain embodiments, at least one instance of $R^{B1}$ is substituted or unsubstituted $C_{1-6}$ alkyl, substituted or unsubstituted cyclopropyl, —$OR^b$, or —$N(R^{b1})_2$, wherein each instance of $R^b$ is independently hydrogen, substituted or unsubstituted $C_{1-6}$ alkyl, an oxygen protecting group when attached to an oxygen atom, or a nitrogen protecting group when attached to a nitrogen atom. In certain embodiments, u is 0. In certain embodiments, u is 1. In certain embodiments, u is 2. In certain embodiments, u is 3. In certain embodiments, u is 4.

In certain embodiments, $R^{D5}$ is of the formula:

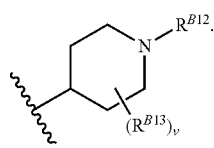

In certain embodiments, $R^{D5}$ is of the formula:

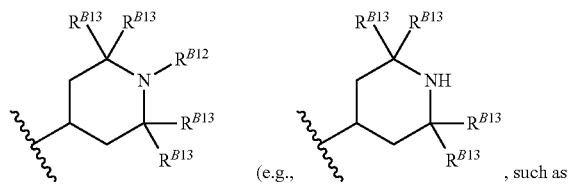

(e.g., 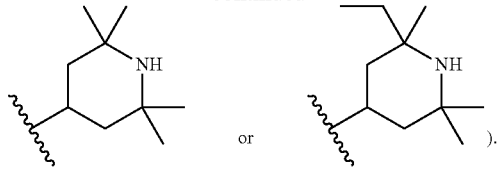, such as

-continued

[two structures shown: or ].

In certain embodiments, $R^{B12}$ is H. In certain embodiments, $R^{B12}$ is substituted or unsubstituted $C_{1-6}$ alkyl. In certain embodiments, $R^{B12}$ is Me. In certain embodiments, $R^{B12}$ is —$CF_3$, Bn, Et, perfluoroethyl, Pr, perfluoropropyl, Bu, or perfluorobutyl. In certain embodiments, $R^{B12}$ is a nitrogen protecting group (e.g., Bn, Boc, Cbz, Fmoc, trifluoroacetyl, triphenylmethyl, acetyl, or Ts). In certain embodiments, $R^{B12}$ is a warhead. In certain embodiments, Formula (III) includes one or more instances of $R^{B13}$ When Formula (III) includes two or more instances of $R^{B13}$, any two instances of $R^{B13}$ may be the same or different from each other. In certain embodiments, at least one instance of $R^{B13}$ is halogen (e.g., F, Cl, Br, or I). In certain embodiments, at least one instance of $R^{B13}$ is substituted or unsubstituted $C_{1-6}$ alkyl. In certain embodiments, at least one instance of $R^{B13}$ is Me. In certain embodiments, at least one instance of $R^{B13}$ is substituted methyl (e.g., —$CF_3$ or Bn). In certain embodiments, at least one instance of $R^{B13}$ is Et. In certain embodiments, at least one instance of $R^{B13}$ is substituted ethyl (e.g., perfluoroethyl). In certain embodiments, at least one instance of $R^{B13}$ is n-Pr. In certain embodiments, at least one instance of $R^{B13}$ is i-Pr. In certain embodiments, at least one instance of $R^{B13}$ is substituted propyl (e.g., perfluoropropyl). In certain embodiments, at least one instance of $R^{B13}$ is Me, Et, or n-Pr. In certain embodiments, at least one instance of $R^{B13}$ is Bu or unsubstituted pentyl. In certain embodiments, at least one instance of $R^{B13}$ is substituted butyl (e.g., perfluorobutyl) or substituted pentyl (e.g., perfluoropentyl). In certain embodiments, at least one instance of $R^{B13}$ is substituted or unsubstituted, 3- to 7-membered, monocyclic carbocyclyl comprising 0, 1, or 2 double bonds in the carbocyclic ring system. In certain embodiments, at least one instance of $R^{B13}$ is substituted or unsubstituted cyclopropyl, substituted or unsubstituted cyclobutyl, or substituted or unsubstituted cyclopentyl. In certain embodiments, at least one instance of $R^{B13}$ is —$N(R^{b1})_2$, optionally wherein each instance of $R^{b1}$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, at least one instance of $R^{B3}$ is —$NH_2$, —NHMe, —NHEt, —$N(Me)_2$, or —$N(Et)_2$. In certain embodiments, at least one instance of $R^{B3}$ is halogen, substituted or unsubstituted cyclopropyl, or —$N(R^{b1})_2$, wherein each instance of $R^b$ is independently hydrogen, substituted or unsubstituted $C_{1-6}$ alkyl, an oxygen protecting group when attached to an oxygen atom, or a nitrogen protecting group when attached to a nitrogen atom. In certain embodiments, v is 0. In certain embodiments, v is 1. In certain embodiments, v is 2. In certain embodiments, v is 3, 4, 5, 6, 7, or 8. In certain embodiments, v is 9.

In certain embodiments, $R^{D5}$ is of the formula:

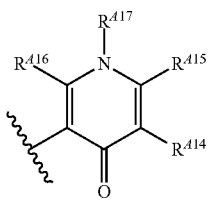

(e.g.,

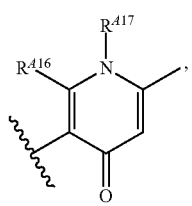

optionally wherein $R^{A16}$ is Et, Pr, or Bu). In certain embodiments, $R^{D5}$ is of the formula:

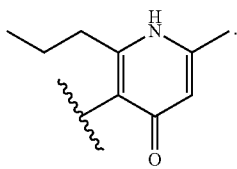

In certain embodiments, $R^{D5}$ is of the formula:

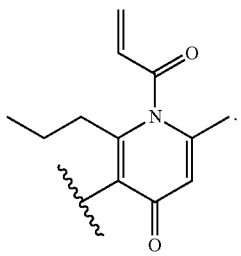

In certain embodiments, $R^{A14}$ is H. In certain embodiments, $R^{A14}$ is halogen (e.g., F, Cl, Br, or I). In certain embodiments, $R^{A14}$ is substituted or unsubstituted $C_{1-6}$ alkyl. In certain embodiments, $R^{A14}$ is Me. In certain embodiments, $R^{A14}$ is substituted methyl (e.g., —CF$_3$ or Bn). In certain embodiments, $R^{A14}$ is Et, substituted ethyl (e.g., perfluoroethyl), Pr, substituted propyl (e.g., perfluoropropyl), Bu, or substituted butyl (e.g., perfluorobutyl). In certain embodiments, $R^{A14}$ is —OR$^a$ (e.g., —OH or —O(substituted or unsubstituted $C_{1-6}$ alkyl) (e.g., —OMe)). In certain embodiments, $R^{A14}$ is —N(R$^{a1}$)$_2$, optionally wherein each instance of R$^{a1}$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{A14}$ is —NH$_2$, —NHMe, or —N(Me)$_2$. In certain embodiments, $R^{A15}$ is H. In certain embodiments, $R^{A15}$ is halogen (e.g., F, Cl, Br, or I). In certain embodiments, $R^{A15}$ is substituted or unsubstituted $C_{1-6}$ alkyl. In certain embodiments, $R^{A15}$ is Me. In certain embodiments, $R^{A15}$ is substituted methyl (e.g., —CF$_3$ or Bn). In certain embodiments, $R^{A15}$ is Et, substituted ethyl (e.g., perfluoroethyl), Pr, substituted propyl (e.g., perfluoropropyl), Bu, or substituted butyl (e.g., perfluorobutyl). In certain embodiments, $R^{A15}$ is —OR$^a$ (e.g., —OH or —O(substituted or unsubstituted $C_{1-6}$ alkyl) (e.g., —OMe)). In certain embodiments, $R^{A15}$ is —N(R$^{a1}$)$_2$, optionally wherein each instance of R$^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{A15}$ is —NH$_2$, —NHMe, or —N(Me)$_2$. In certain embodiments, $R^{A16}$ is H. In certain embodiments, $R^{A16}$ is halogen (e.g., F, Cl, Br, or I). In certain embodiments, $R^{A16}$ is substituted or unsubstituted $C_{2-6}$ alkyl. In certain embodiments, $R^{A16}$ is Et. In certain embodiments, $R^{A16}$ is substituted ethyl (e.g., perfluoroethyl). In certain embodiments, $R^{A16}$ is n-Pr. In certain embodiments, $R^{A16}$ is i-Pr. In certain embodiments, $R^{A16}$ is substituted propyl (e.g., perfluoropropyl). In certain embodiments, $R^{A16}$ is Bu or unsubstituted pentyl. In certain embodiments, $R^{A16}$ is substituted butyl (e.g., perfluorobutyl) or substituted pentyl (e.g., perfluoropentyl). In certain embodiments, $R^{A16}$ is substituted or unsubstituted, 3- to 7-membered, monocyclic carbocyclyl comprising 0, 1, or 2 double bonds in the carbocyclic ring system. In certain embodiments, $R^{A16}$ is substituted or unsubstituted cyclopropyl, substituted or unsubstituted cyclobutyl, or substituted or unsubstituted cyclopentyl. In certain embodiments, $R^{A16}$ is —OR$^a$ (e.g., —OH or —O(substituted or unsubstituted $C_{1-6}$ alkyl) (e.g., —OMe)). In certain embodiments, $R^{A16}$ is —N(R$^{a1}$)$_2$, optionally wherein each instance of R$^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{A16}$ is —NH$_2$, —NHMe, —NHEt, —N(Me)$_2$, or —N(Et)$_2$. In certain embodiments, $R^{A16}$ is substituted or unsubstituted cyclopropyl or —N(R$^{a1}$)$_2$, wherein each instance of R$^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{A17}$ is H. In certain embodiments, $R^{A17}$ is substituted or unsubstituted acyl. In certain embodiments, $R^{A17}$ is —C(=O)R$^a$, optionally wherein R$^a$ is substituted or unsubstituted $C_{1-6}$ alkyl (e.g., Me) or substituted or unsubstituted $C_{2-6}$ alkenyl. In certain embodiments, $R^{A17}$ is —C(=O)R$^a$, wherein R$^a$ is substituted or unsubstituted vinyl. In certain embodiments, $R^{A17}$ is —C(=O)CH=CH$_2$. In certain embodiments, $R^{A17}$ is —C(=O)OR$^a$, optionally wherein R$^a$ is H, substituted or unsubstituted $C_{1-6}$ alkyl (e.g., Me), or an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, $R^{A17}$ is —C(=O)N(R$^{a1}$)$_2$, optionally wherein each instance of R$^{a1}$ is independently H, substituted or unsubstituted $C_{1-6}$ alkyl (e.g., Me), or a nitrogen protecting group (e.g., Bn, Boc, Cbz, Fmoc, trifluoroacetyl, triphenylmethyl, acetyl, or Ts). In certain embodiments, $R^{A17}$ is substituted or unsubstituted $C_{1-6}$ alkyl. In certain embodiments, $R^{A17}$ is Me. In certain embodiments, $R^{A17}$ is —CF$_3$, Bn, Et, perfluoroethyl, Pr, perfluoropropyl, Bu, or perfluorobutyl. In certain embodiments, $R^{A17}$ is a nitrogen protecting group (e.g., Bn, Boc, Cbz, Fmoc, trifluoroacetyl, triphenylmethyl, acetyl, or Ts). In certain embodiments, $R^{A17}$ is a warhead.

In certain embodiments, $R^{D5}$ is of the formula:

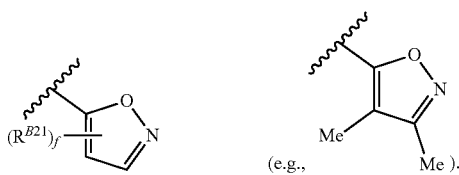

In certain embodiments, $R^{D5}$ is of the formula:

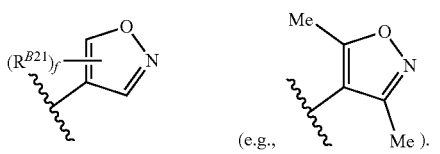

In certain embodiments, $R^{D5}$ is of the formula:

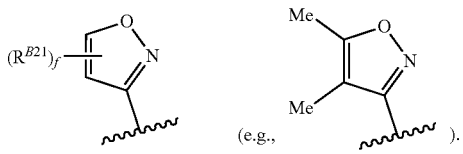

In certain embodiments, Formula (III) includes one or more instances of $R^{B21}$. When Formula (III) includes two or more instances of $R^{B21}$, any two instances of $R^{B21}$ may be the same or different from each other. In certain embodiments, at least one instance of $R^{B21}$ is H. In certain embodiments, at least one instance of $R^{B21}$ is halogen (e.g., F, Cl, Br, or I). In certain embodiments, at least one instance of $R^{B21}$ is substituted or unsubstituted $C_{1-6}$ alkyl. In certain embodiments, at least one instance of $R^{B21}$ is Me. In certain embodiments, at least one instance of $R^{B21}$ is substituted methyl (e.g., —CF$_3$ or Bn). In certain embodiments, at least one instance of $R^{B21}$ is Et. In certain embodiments, at least one instance of $R^{B21}$ is substituted ethyl (e.g., perfluoroethyl). In certain embodiments, at least one instance of $R^{B21}$ is n-Pr. In certain embodiments, at least one instance of $R^{B21}$ is i-Pr. In certain embodiments, at least one instance of $R^{B21}$ is substituted propyl (e.g., perfluoropropyl). In certain embodiments, at least one instance of $R^{B21}$ is Me, Et, or n-Pr. In certain embodiments, at least one instance of $R^{B21}$ is Bu or unsubstituted pentyl. In certain embodiments, at least one instance of $R^{B21}$ is substituted butyl (e.g., perfluorobutyl) or substituted pentyl (e.g., perfluoropentyl). In certain embodiments, at least one instance of $R^{B21}$ is —OR$^b$ (e.g., —OH or —O(substituted or unsubstituted $C_{1-6}$ alkyl) (e.g., —OMe)). In certain embodiments, at least one instance of $R^{B21}$ is —N(R$^{b1}$)$_2$, optionally wherein each instance of R$^{b1}$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, at least one instance of $R^{B21}$ is —NH$_2$, —NHMe, —NHEt, —N(Me)$_2$, or —N(Et)$_2$. In certain embodiments, f is 0. In certain embodiments, f is 1. In certain embodiments, f is 2.

In certain embodiments, $R^{D5}$ is of the formula:

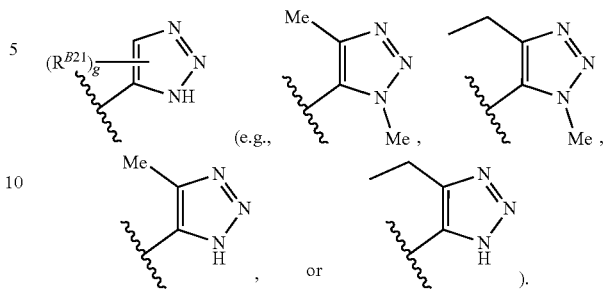

In certain embodiments, Formula (III) includes one or more instances of $R^{B22}$. When Formula (III) includes two or more instances of $R^{B22}$, any two instances of $R^{B22}$ may be the same or different from each other. In certain embodiments, at least one instance of $R^{B22}$ is H. In certain embodiments, at least one instance of $R^{B22}$ is halogen (e.g., F, Cl, Br, or I). In certain embodiments, at least one instance of $R^{B22}$ is substituted or unsubstituted $C_{1-6}$ alkyl. In certain embodiments, at least one instance of $R^{B22}$ is Me. In certain embodiments, at least one instance of $R^{B22}$ is substituted methyl (e.g., —CF$_3$ or Bn). In certain embodiments, at least one instance of $R^{B22}$ is Et. In certain embodiments, at least one instance of $R^{B22}$ is substituted ethyl (e.g., perfluoroethyl). In certain embodiments, at least one instance of $R^{B21}1$ is n-Pr. In certain embodiments, at least one instance of $R^{B22}$ is i-Pr. In certain embodiments, at least one instance of $R^{B22}$ is substituted propyl (e.g., perfluoropropyl). In certain embodiments, at least one instance of $R^{B22}$ is Me, Et, or n-Pr. In certain embodiments, at least one instance of $R^{B22}$ is Bu or unsubstituted pentyl. In certain embodiments, at least one instance of $R^{B22}$ is substituted butyl (e.g., perfluorobutyl) or substituted pentyl (e.g., perfluoropentyl). In certain embodiments, at least one instance of $R^{B22}$ is —OR$^b$ (e.g., —OH or —O(substituted or unsubstituted $C_{1-6}$ alkyl) (e.g., —OMe)). In certain embodiments, at least one instance of $R^{B22}$ is —N(R$^{b1}$)$_2$, optionally wherein each instance of R$^{b1}$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, at least one instance of $R^{B22}$ is —NH$_2$, —NHMe, —NHEt, —N(Me)$_2$, or —N(Et)$_2$. In certain embodiments, at least one instance of $R^{B22}$ is a nitrogen protecting group (e.g., Bn, Boc, Cbz, Fmoc, trifluoroacetyl, triphenylmethyl, acetyl, or Ts) when attached to nitrogen. In certain embodiments, g is 0. In certain embodiments, g is 1. In certain embodiments, g is 2.

Formula (III) includes substituent $R^{B20}$. In certain embodiments, $R^{B20}$ is H. In certain embodiments, $R^{B20}$ is halogen (e.g., F, Cl, Br, or I). In certain embodiments, $R^{B20}$ is substituted or unsubstituted $C_{1-6}$ alkyl. In certain embodiments, $R^{B20}$ is Me. In certain embodiments, $R^{B20}$ is —CF$_3$, Bn, Et, perfluoroethyl, Pr, perfluoropropyl, Bu, or perfluorobutyl. In certain embodiments, $R^{B20}$ is —OR$^b$, optionally wherein R$^b$ is H, substituted or unsubstituted $C_{1-6}$ alkyl (e.g., Me), substituted or unsubstituted acyl, or an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, $R^{B20}$ is —OC(═O)R$^b$, optionally wherein R$^b$ is H, substituted or unsubstituted $C_{1-6}$ alkyl (e.g., Me), or substituted or unsubstituted $C_{2-6}$ alkenyl (e.g., substituted or unsubstituted vinyl). In certain embodiments, $R^{B20}$ is —OC(═O)CH═CH$_2$. In certain embodiments, $R^{B20}$ is —N(R$^{b1}$)$_2$, optionally wherein each instance of $R^{b1}$ is independently H, substituted or unsubstituted $C_{1-6}$ alkyl (e.g., Me), substituted or unsubstituted acyl, or a nitrogen protecting group (e.g., Bn, Boc, Cbz, Fmoc, trifluoroacetyl, triphenylmethyl, acetyl, or Ts). In certain embodiments, $R^{B20}$ is $-N(R^{b1})C(=O)R^{b1}$, optionally wherein each instance of $R^{b1}$ is independently H, substituted or unsubstituted $C_{1-6}$ alkyl (e.g., Me), or substituted or unsubstituted $C_{2-6}$ alkenyl (e.g., substituted or unsubstituted vinyl). In certain embodiments, $R^{B20}$ is of the formula:

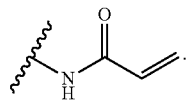 [SMILES: *NC(=O)C=C]

In certain embodiments, $R^{B20}$ is of the formula:

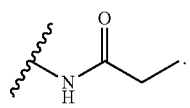 [SMILES: *NC(=O)CC]

In certain embodiments, the compound of Formula (III) is of the formula:

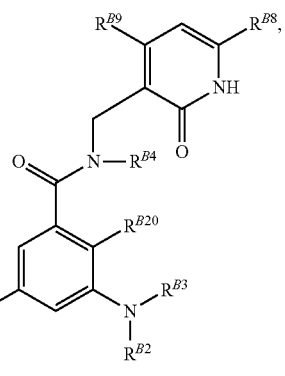

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

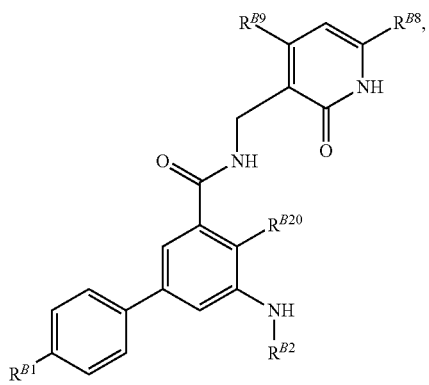

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

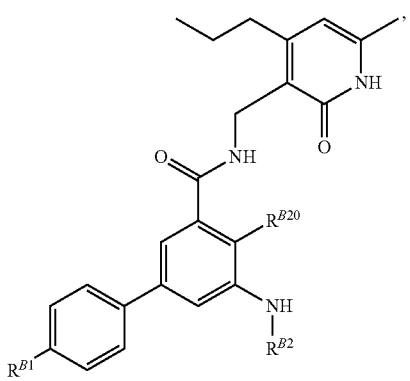

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

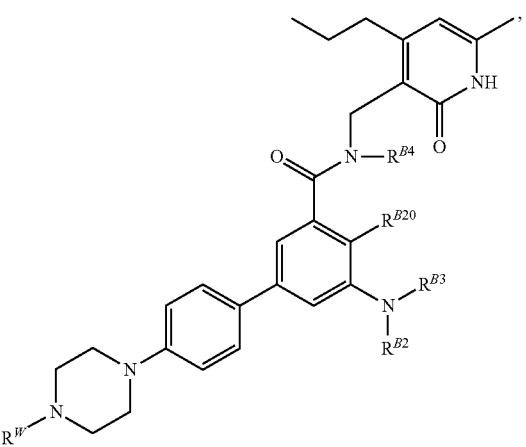

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

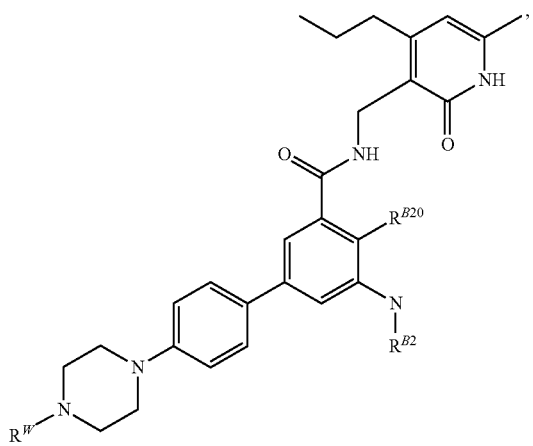

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

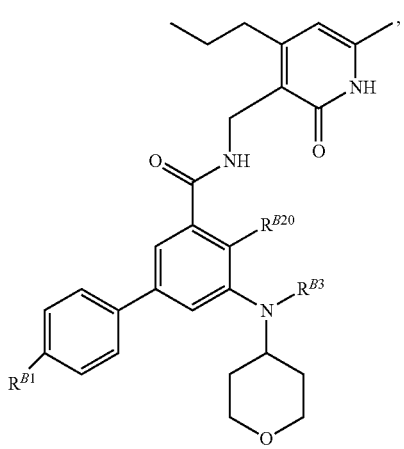

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

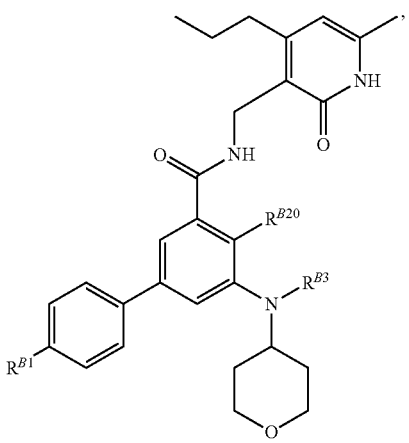

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

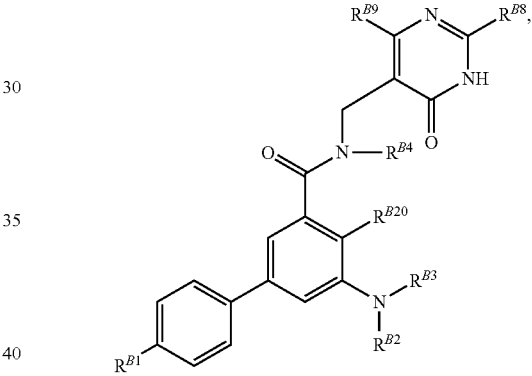

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

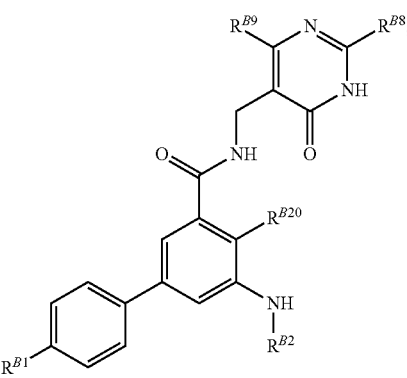

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

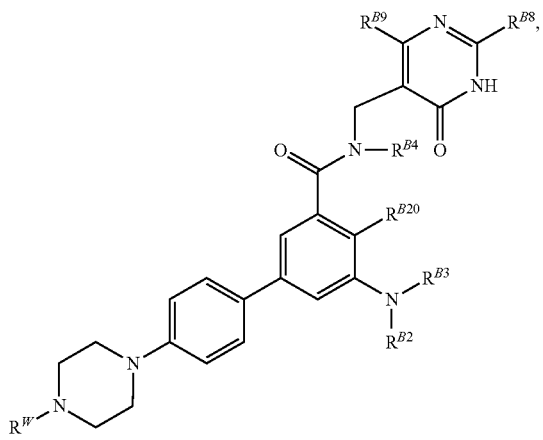

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

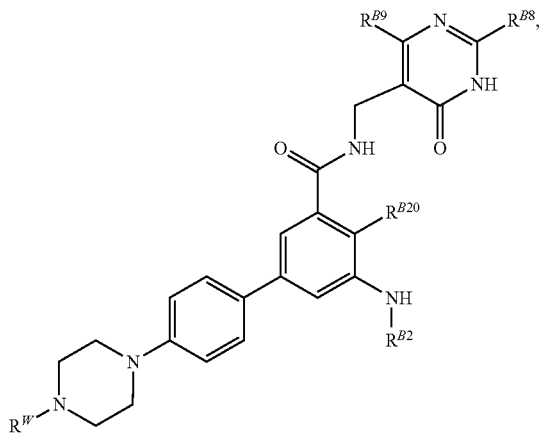

or a pharmaceutically acceptable salt, solvate, hydrate, polymorph, co-crystal, tautomer, stereoisomer, isotopically labeled derivative, or prodrug thereof.

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

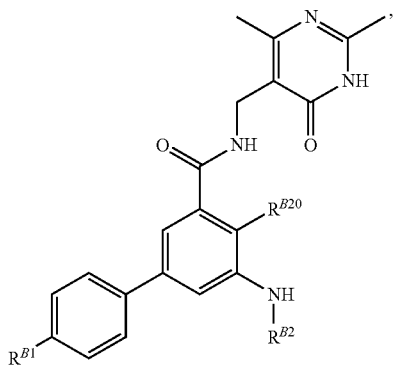

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

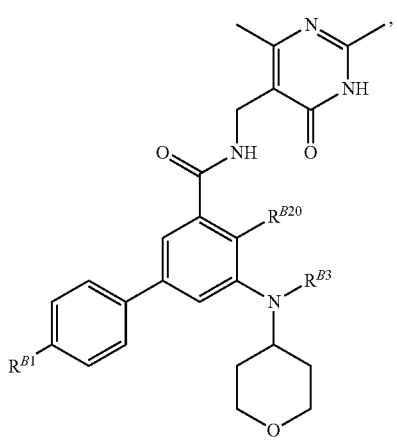

or a pharmaceutically acceptable salt, solvate, hydrate, polymorph, co-crystal, tautomer, stereoisomer, isotopically labeled derivative, or prodrug thereof. In certain embodiments, the compound of Formula (III) is of the formula:

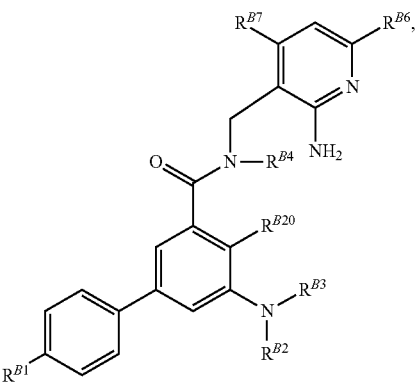

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

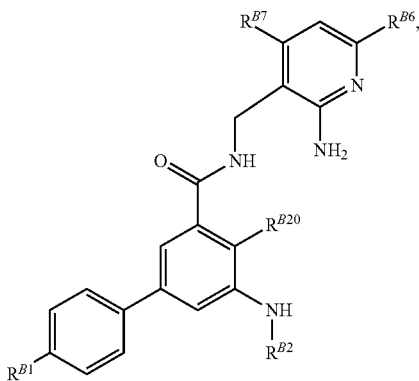

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

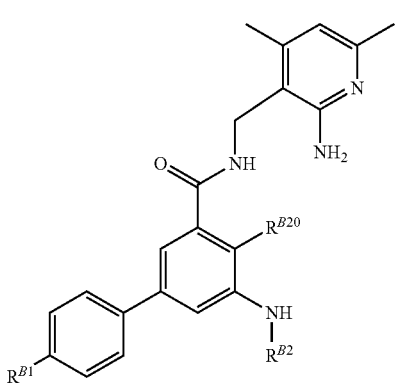

or a pharmaceutically acceptable salt, solvate, hydrate, polymorph, co-crystal, tautomer, stereoisomer, isotopically labeled derivative, or prodrug thereof. In certain embodiments, the compound of Formula (III) is of the formula:

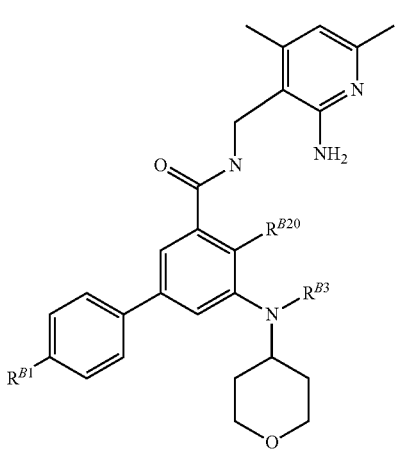

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

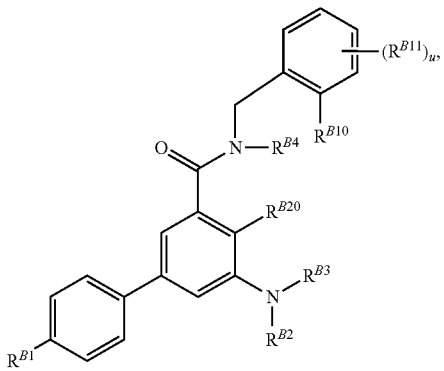

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

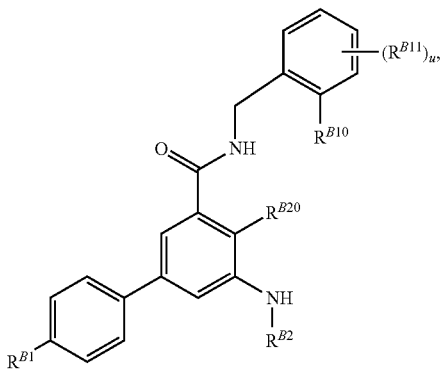

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

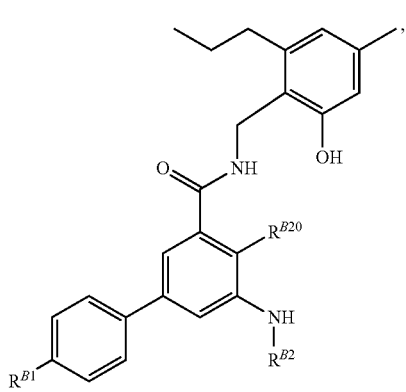

201 or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

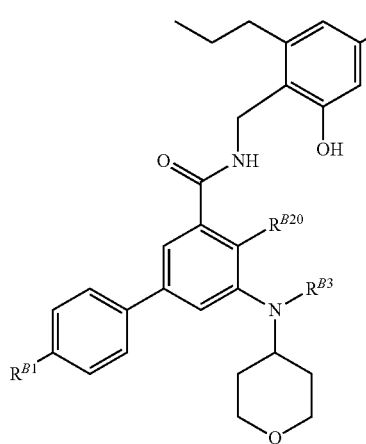

or a pharmaceutically acceptable salt, solvate, hydrate, polymorph, co-crystal, tautomer, stereoisomer, isotopically labeled derivative, or prodrug thereof. In certain embodiments, the compound of Formula (III) is of the formula:

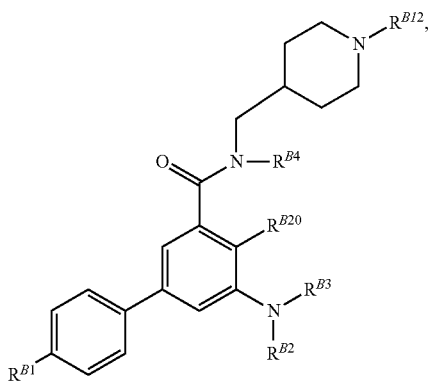

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

202

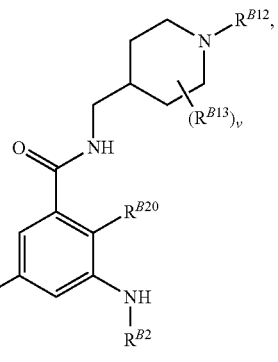

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

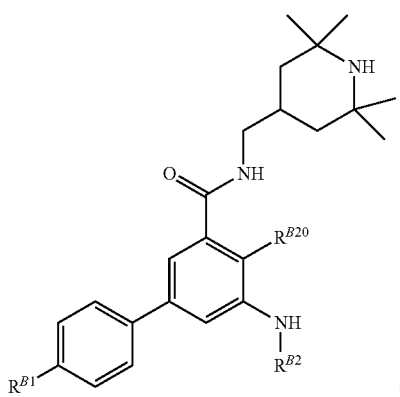

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

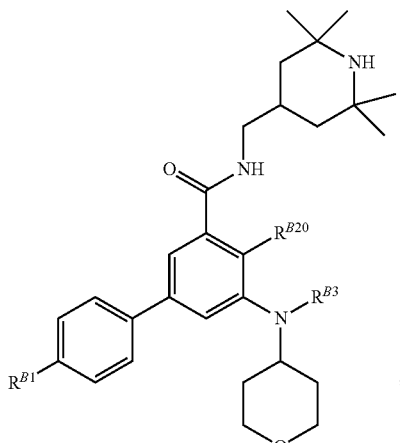

or a pharmaceutically acceptable salt, solvate, hydrate, polymorph, co-crystal, tautomer, stereoisomer, isotopically labeled derivative, or prodrug thereof. In certain embodiments, the compound of Formula (III) is of the formula:

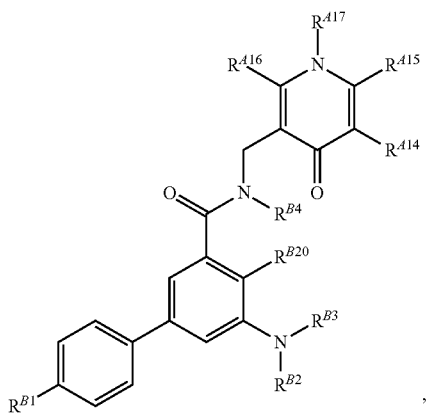

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

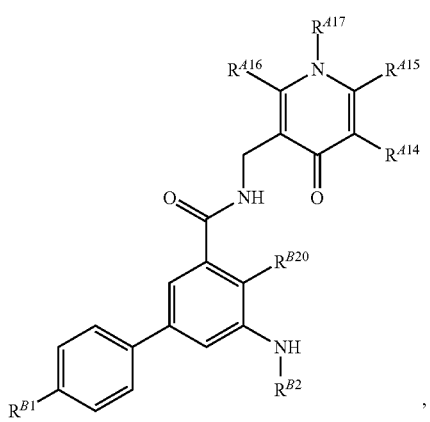

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

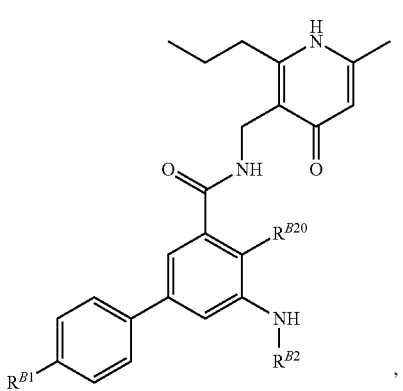

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

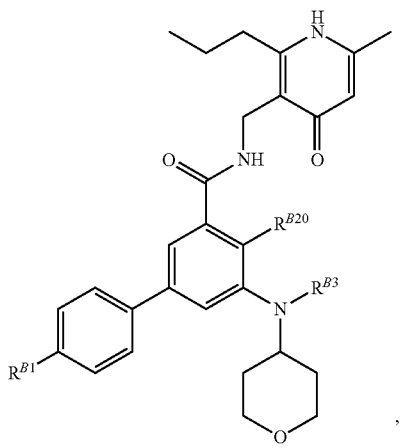

or a pharmaceutically acceptable salt, solvate, hydrate, polymorph, co-crystal, tautomer, stereoisomer, isotopically labeled derivative, or prodrug thereof. In certain embodiments, the compound of Formula (III) is of the formula:

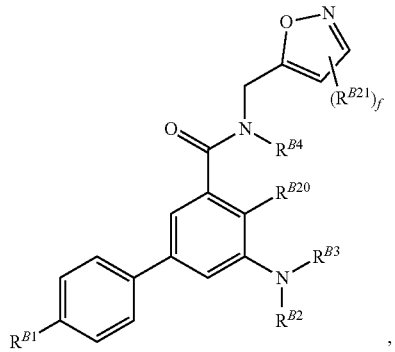

or a pharmaceutically acceptable salt, solvate, hydrate, polymorph, co-crystal, tautomer, stereoisomer, isotopically labeled derivative, or prodrug thereof. In certain embodiments, the compound of Formula (III) is of the formula:

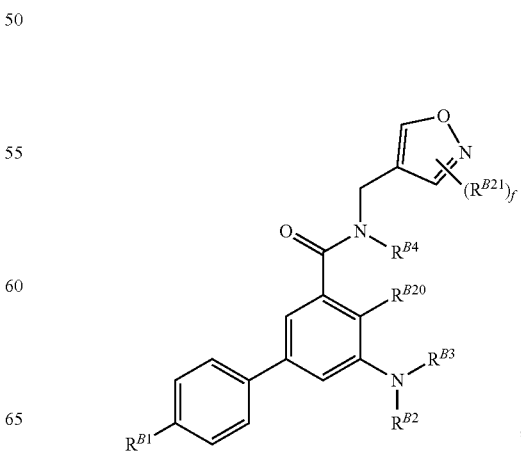

-continued

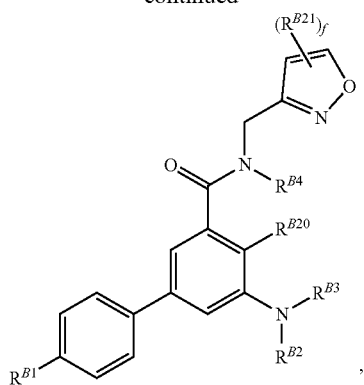

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

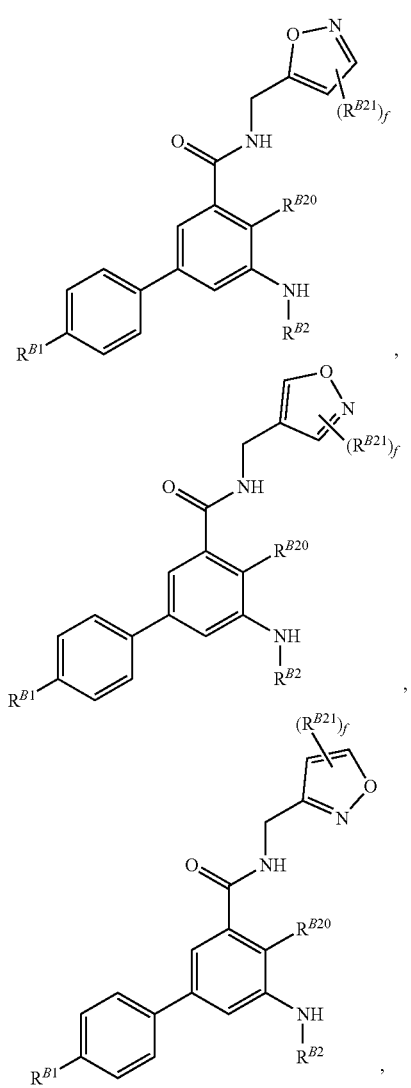

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

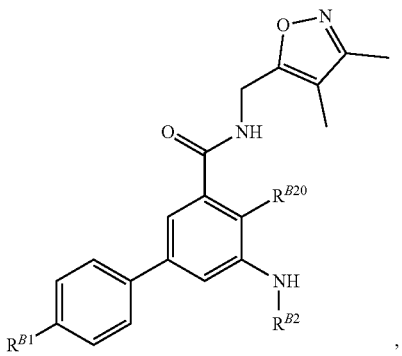

or a pharmaceutically acceptable salt, solvate, hydrate, polymorph, co-crystal, tautomer, stereoisomer, isotopically labeled derivative, or prodrug thereof. In certain embodiments, the compound of Formula (III) is of the formula:

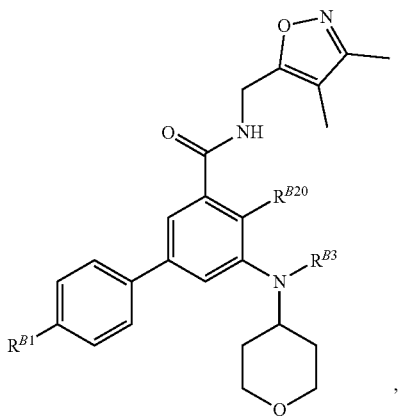

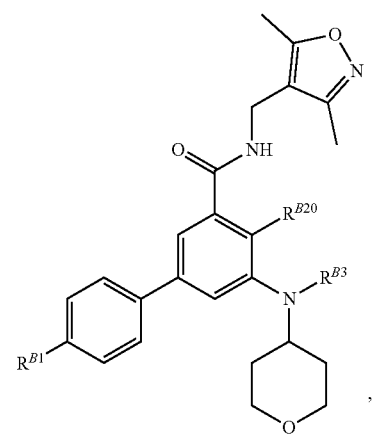

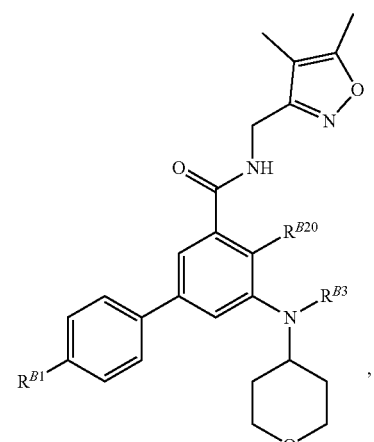

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

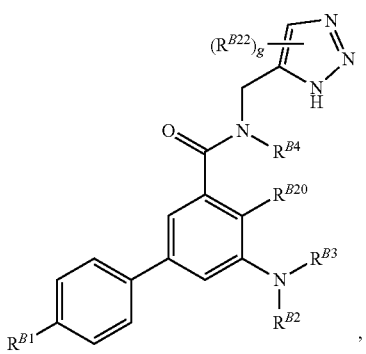

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

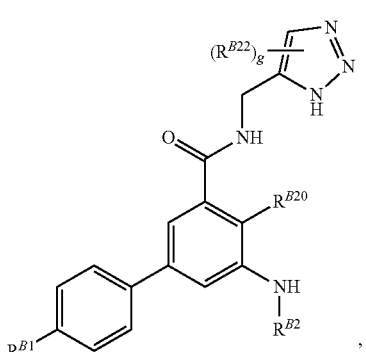

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

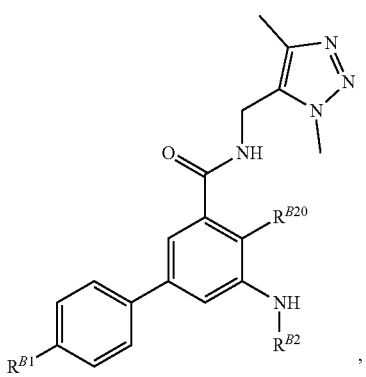

or a pharmaceutically acceptable salt, solvate, hydrate, polymorph, co-crystal, tautomer, stereoisomer, isotopically labeled derivative, or prodrug thereof. In certain embodiments, the compound of Formula (III) is of the formula:

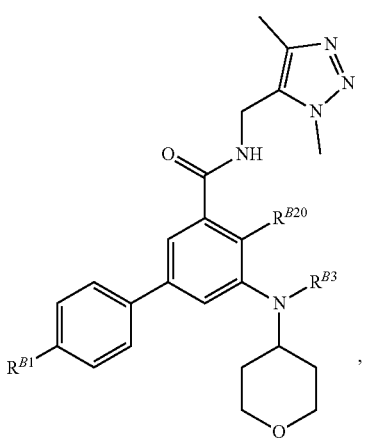

or a pharmaceutically acceptable salt, solvate, hydrate, polymorph, co-crystal, tautomer, stereoisomer, isotopically labeled derivative, or prodrug thereof.

Exemplary compounds of Formula (III) include, but are not limited to:

(EZ-50)

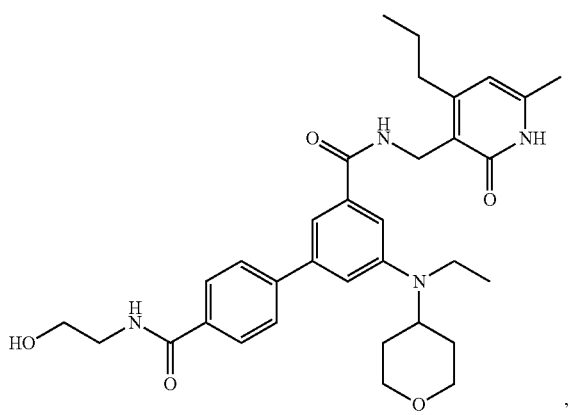

(EZ-52)

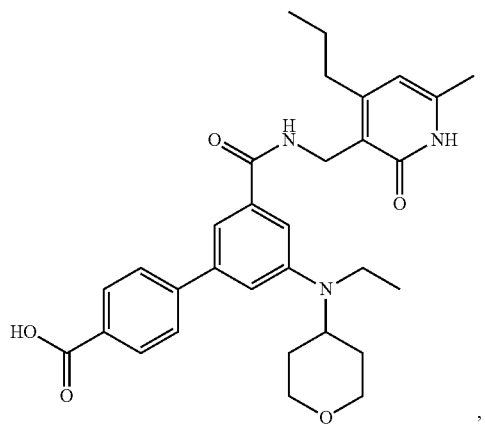

and pharmaceutically acceptable salts, solvates, hydrates, polymorphs, co-crystals, tautomers, stereoisomers, isotopically labeled derivatives, and prodrugs thereof.

Pharmaceutical Compositions, Kits, and Administration

The present disclosure also provides pharmaceutical compositions comprising a compound described herein and optionally a pharmaceutically acceptable excipient. In certain embodiments, a compound described herein is of Formula (I). In certain embodiments, a compound described herein is of Formula (II). In certain embodiments, a compound described herein is of Formula (III).

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, a therapeutically effective amount is an amount effective for inhibiting the aberrant activity of an HMT (e.g., EZH1, EZH2, DOT1). In certain embodiments, a therapeutically effective amount is an amount effective for treating a disease (e.g., a disease associated with aberrant activity of an HMT (e.g., proliferative disease)). In certain embodiments, a therapeutically effective amount is an amount effective for inhibiting the aberrant activity of an HMT (e.g., EZH1, EZH2, DOT1) and treating a disease (e.g., a disease associated with aberrant activity of an HMT (e.g., proliferative disease)). In certain embodiments, a therapeutically effective amount is an amount effective for inducing apoptosis in a cell. In certain embodiments, a prophylactically effective amount is an amount effective for inhibiting the aberrant activity of an HMT (e.g., EZH1, EZH2, DOT1). In certain embodiments, a prophylactically effective amount is an amount effective for preventing or keeping a subject in need thereof in remission of a disease (e.g., a disease associated with aberrant activity of an HMT (e.g., proliferative disease)). In certain embodiments, a prophylactically effective amount is an amount effective for inhibiting the aberrant activity of an HMT (e.g., EZH1, EZH2, DOT1), and preventing or keeping a subject in need thereof in remission of a disease (e.g., a disease associated with aberrant activity of an HMT (e.g., proliferative disease)). In certain embodiments, a prophylactically effective amount is an amount effective for inducing apoptosis in a cell.

In certain embodiments, the effective amount is an amount effective for inhibiting the activity of an HMT (e.g., EZH1, EZH2, DOT1) by at least 10%, at least 20%, at least 30%, at least 40%, at least 50%, at least 60%, at least 70%, at least 80%, at least 90%, at least 95%, or at least 98%. In certain embodiments, the effective amount is an amount effective for inhibiting the activity of an HMT (e.g., EZH1, EZH2, DOT1) by not more than 10%, not more than 20%, not more than 30%, not more than 40%, not more than 50%, not more than 60%, not more than 70%, not more than 80%, not more than 90%, not more than 95%, or not more than 98%.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal.

In certain embodiments, the animal is a transgenic animal (e.g., transgenic mice and transgenic pigs). In certain embodiments, the subject is a fish or reptile.

In certain embodiments, the cell is present in vitro. In certain embodiments, the cell is present in vivo.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner.

Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in inhibiting the activity of an HMT (e.g., EZH1 or EZH2) in a subject, biological sample, tissue, or cell), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, inflammatory disease, autoimmune disease, genetic disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase *Erwinia Chrysanthemi*), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In certain embodiments, the additional pharmaceutical agent is a binder or inhibitor of an HMT (e.g., EZH1, EZH2, DOT1). In certain embodiments, the additional pharmaceutical agent is a protein kinase inhibitor (e.g., tyrosine protein kinase inhibitor). In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and *vinca* alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits are useful for preventing a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits are useful for inhibiting the activity (e.g., aberrant activity, such as increased activity) of an HMT in a subject, biological sample, tissue, or cell. In certain embodiments, the kits are useful for inducing apoptosis in a cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits and instructions provide for preventing a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits and instructions provide for modulating (e.g., inhibiting) the activity (e.g., aberrant activity, such as increased activity) of an HMT in a subject, biological sample, tissue, or cell. In certain embodiments, the kits and instructions provide for inducing apoptosis in a cell. A kit described herein may include one or more additional pharmaceutical agents described herein as a separate composition.

Methods of Treatment and Uses

The compounds described herein are capable of binding (e.g., reversibly binding or irreversibly binding) HMTs and modulating (e.g., reversibly modulating or irreversibly modulating) the activity of the HMTs. The present disclosure thus also provides methods of modulating (e.g., inhibiting or increasing) the activity (e.g., aberrant activity, such as increased or decreased activity) of an HMT in a subject, biological sample, tissue, or cell. The present disclosure further provides methods for the treatment of a wide range of diseases, such as diseases associated with aberrant or increased activity) of an HMT, proliferative diseases, inflammatory diseases, autoimmune diseases, genetic diseases, hematological diseases, neurological diseases, painful conditions, psychiatric disorders, and metabolic disorders in a subject in need thereof.

In another aspect, the present disclosure provides methods of modulating (e.g., inhibiting) the activity of an HMT in a subject in need thereof, the methods comprising administering to the subject an effective amount of a compound or pharmaceutical composition described herein.

In another aspect, the present disclosure provides methods of modulating (e.g., inhibiting) the activity of an HMT in a biological sample, tissue, or cell, the methods comprising contacting the biological sample, tissue, or cell with an effective amount of a compound or pharmaceutical composition described herein.

In certain embodiments, the activity of an HMT in a subject, biological sample, tissue, or cell is inhibited by a compound, pharmaceutical composition, kit, use, or method described herein by at least 1%, at least 3%, at least 10%, at least 20%, at least 30%, at least 40%, at least 50%, at least 60%, at least 70%, at least 80%, or at least 90%. In certain embodiments, the activity of an HMT in a subject, biological sample, tissue, or cell is inhibited by a compound, pharmaceutical composition, kit, use, or method described herein by not more than 1%, not more than 3%, not more than 10%, not more than 20%, not more than 30%, not more than 40%, not more than 50%, not more than 60%, not more than 70%, not more than 80%, or not more than 90%. In some embodiments, the activity of an HMT in a subject, biological sample, tissue, or cell is selectively inhibited by the compound, pharmaceutical composition, kit, use, or method. In some embodiments, the activity of EZH2 in a subject, biological sample, tissue, or cell is selectively inhibited by the compound, pharmaceutical composition, kit, use, or method, compared to a different HMT (e.g., EZH1). In some embodiments, the activity of EZH1 in a subject, biological sample, tissue, or cell is selectively inhibited by the compound, pharmaceutical composition, kit, use, or method, compared to a different HMT (e.g., EZH2). In some embodiments, the activity of an HMT described herein in a subject, biological sample, tissue, or cell is reversibly inhibited by the compound, pharmaceutical composition, kit, use, or method. In some embodiments, the activity of an HMT described herein in a subject, biological sample, tissue, or cell is irreversibly inhibited by the compound, pharmaceutical composition, kit, use, or method. In certain embodiments, the compound, pharmaceutical composition, kit, use, or method inhibits the activity of a mutant form of an HMT (e.g., mutant form of EZH1, or mutant form of EZH2). In certain embodiments, the compound, pharmaceutical composition, kit, use, or method decreases the methylation of a histone.

Another aspect of the present disclosure relates to methods of decreasing the methylation of a histone in a subject in need thereof, the methods comprising administering to the subject an effective amount of a compound or pharmaceutical composition described herein.

Another aspect of the present disclosure relates to methods of decreasing the methylation of a histone in a biological sample, tissue, or cell, the methods comprising contacting the biological sample, tissue, or cell with an effective amount of a compound or pharmaceutical composition described herein (e.g., contacting the biological sample, tissue, or cell in vivo or in vitro). In certain embodiments, the contacting of the biological sample, tissue, or cell with an effective amount of a compound or pharmaceutical composition described herein is in vitro.

Another aspect of the present disclosure relates to methods of modulating (e.g., down-regulating or up-regulating) the expression of a gene in a subject in need thereof, the methods comprising administering to the subject an effective amount of a compound or pharmaceutical composition described herein.

Another aspect of the present disclosure relates to methods of modulating (e.g., down-regulating or up-regulating) the expression of a gene in a biological sample, tissue, or cell, the methods comprising contacting the biological sample, tissue, or cell with an effective amount of a compound or pharmaceutical composition described herein.

In certain embodiments, a gene described herein is a gene that encodes an HMT described herein (e.g., a gene that encodes EZH1, EZH2, or DOT1).

Another aspect of the present disclosure relates to methods of treating a disease in a subject in need thereof, the methods comprising administering to the subject a therapeutically effective amount of a compound or pharmaceutical composition described herein.

HMTs are implicated in a wide range of diseases. For example, changes in the EZH2 gene have been associated with various types of cancers. Mutations of this gene have been identified in hematological malignancies (e.g., lymphoma, leukemia). These mutations may be described as "gain-of-function" because they appear to enhance the activity of the EZH2 enzyme and/or give the enzyme a new, atypical function. In addition, increased activity (overexpression) of the EZH2 gene has been identified in cancerous tumors of the prostate, breast, and other organs. Changes involving the EZH2 gene likely impair normal control of cell division (proliferation), allowing cells to grow and divide too fast or in an uncontrolled way and leading to the development of cancer. Moreover, at least 20 EZH2 gene mutations have been identified in people with Weaver syndrome. Signs and symptoms of this condition include bone overgrowth, a distinctive facial appearance, and joint problems. People with Weaver syndrome have an increased risk of developing cancer. EZH2 gene mutations may disrupt methylation and impair regulation of certain genes in many of the subject's organs and tissues, resulting in the abnormalities characteristic of Weaver syndrome. Weaver syndrome is also associated with aberrant activity of EZH1. It has also been reported that DOT1 was implicated in leukemia (e.g., AML, ALL). In a subject with leukemia, DOT1 may be mis-localized on the chromatin, affecting local H3K79 methylation status. The global levels of H3K79 methylation were not affected, but the local levels of H3K79 methylation at specific regions were aberrantly altered, resulting in the dysregulated transcription of what is likely to be the important players in leukemia.

In certain embodiments, a disease to be treated with a compound or pharmaceutical composition described herein is a disease associated with an HMT. In certain embodiments, a disease described herein is a disease associated with aberrant activity (e.g., increased activity) of an HMT. In certain embodiments, a disease described herein is a proliferative disease. In certain embodiments, a disease described herein is cancer. In certain embodiments, a disease described herein is hyperplasia (e.g., germinal center (GC) hyperplasia). In certain embodiments, a disease described herein is brain cancer, breast cancer, or prostate cancer. In certain embodiments, a disease described herein is a benign neoplasm. In certain embodiments, a disease described herein is or is associated with pathological angiogenesis. In certain embodiments, a disease described herein is an inflammatory disease. In certain embodiments, a disease described herein is an autoimmune disease. In certain embodiments, a disease described herein is a genetic disease. In certain embodiments, a disease described herein is Weaver syndrome. In certain embodiments, a disease described herein is a hematological disease. In certain embodiments, a disease described herein is lymphoma (e.g., follicular large B-cell lymphoma, diffuse large B-cell lymphoma). In certain embodiments, a disease described herein is leukemia (e.g., CML). In certain embodiments, a disease described herein is a neurological disease. In certain embodiments, a disease described herein is a painful condition. In certain embodiments, a disease described herein is a psychiatric disorder. In certain embodiments, a disease described herein is a metabolic disorder.

In still another aspect, the present disclosure provides methods of preventing a a disease to be treated with a compound or pharmaceutical composition described herein in a subject in need thereof, the methods comprising administering to the subject a prophylactically effective amount of a compound or pharmaceutical composition described herein.

In another aspect, the present disclosure provides the compounds described herein for use in a method described herein (e.g., a method of inhibiting the activity of an HMT, a method of treating a disease (e.g., a proliferative disease), a method of preventing a disease (e.g., a proliferative disease), a method of inducing apoptosis, or a method of screening a library of compounds).

In another aspect, the present disclosure provides the compounds described herein for use in treating or preventing a proliferative disease in a subject. In certain embodiments, the disease relates to increased activity of an HMT.

In still another aspect, the present disclosure provides the pharmaceutical compositions described herein for use in a method described herein (e.g., a method of inhibiting the activity of an HMT, a method of treating a disease (e.g., a proliferative disease), a method of preventing a disease (e.g., a proliferative disease), a method of inducing apoptosis, or a method of screening a library of compounds).

Methods of Screening a Library of Compounds

Another aspect of the disclosure relates to methods of screening a library of compounds, and pharmaceutical acceptable salts thereof, to identify a compound, or a pharmaceutical acceptable salt thereof, that is useful in a method described herein. In certain embodiments, the methods of screening a library include obtaining at least two different compounds described herein; and performing at least one assay using the different compounds described herein. In certain embodiments, at least one assay is useful in identifying a compound that is useful in a method described herein.

Typically, the methods of screening a library of compounds involve at least one assay. In certain embodiments, the assay is performed to detect one or more characteristics associated with the treatment and/or prevention of a disease described herein or with the modulation (e.g., inhibition) of the activity of an HMT (e.g., EZH1 or EZH2). The characteristics may be desired characteristics (e.g., a disease having been treated, a disease having been prevented, the activity of an HMT having been modulated, and/or apoptosis having been induced). The characteristics may be undesired characteristics (e.g., a disease having not been treated, a disease having not been prevented, the activity of an HMT having not been modulated, and/or apoptosis having not been induced). The assay may be an immunoassay, such as a sandwich-type assay, competitive binding assay, one-step direct test, two-step test, or blot assay. The step of performing at least one assay may be performed robotically or manually. In certain embodiments, the assay comprises (a) contacting a library of compounds with an HMT; and (b) detecting the binding of the library of compounds to the HMT. In certain embodiments, the assay comprises detecting the specific binding of the library of compounds to the HMT. In certain embodiments, the detected binding of the library of compounds to the HMT is useful in identifying the compound that is useful in a method described herein. In certain embodiments, the step of detecting the binding comprises using differential scanning fluorimetry (DSF), isothermal titration calorimetry (ITC), and/or an amplified luminescence proximity homogeneous assay (ALPHA). The step of performing at least one assay may be performed in a cell in vitro or in vivo.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Preparation of the Compounds Described Herein

The compounds provided herein can be prepared from readily available starting materials using the following general methods and procedures. For example, compounds of Formula (I) can be prepared according to any one of Schemes 1-3, compounds of Formula (II) can be prepared according to methods similar to the methods shown in any one of Schemes 1 to 3, and compounds of Formula (III) can be prepared according to methods similar to the methods shown in any one of Schemes 1 to 3. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Scheme 1. Exemplary Preparation of Compounds of Formula (I)

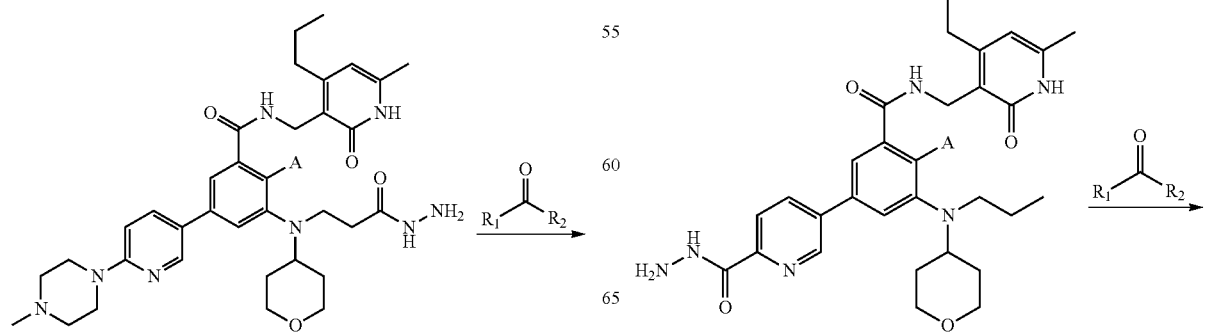

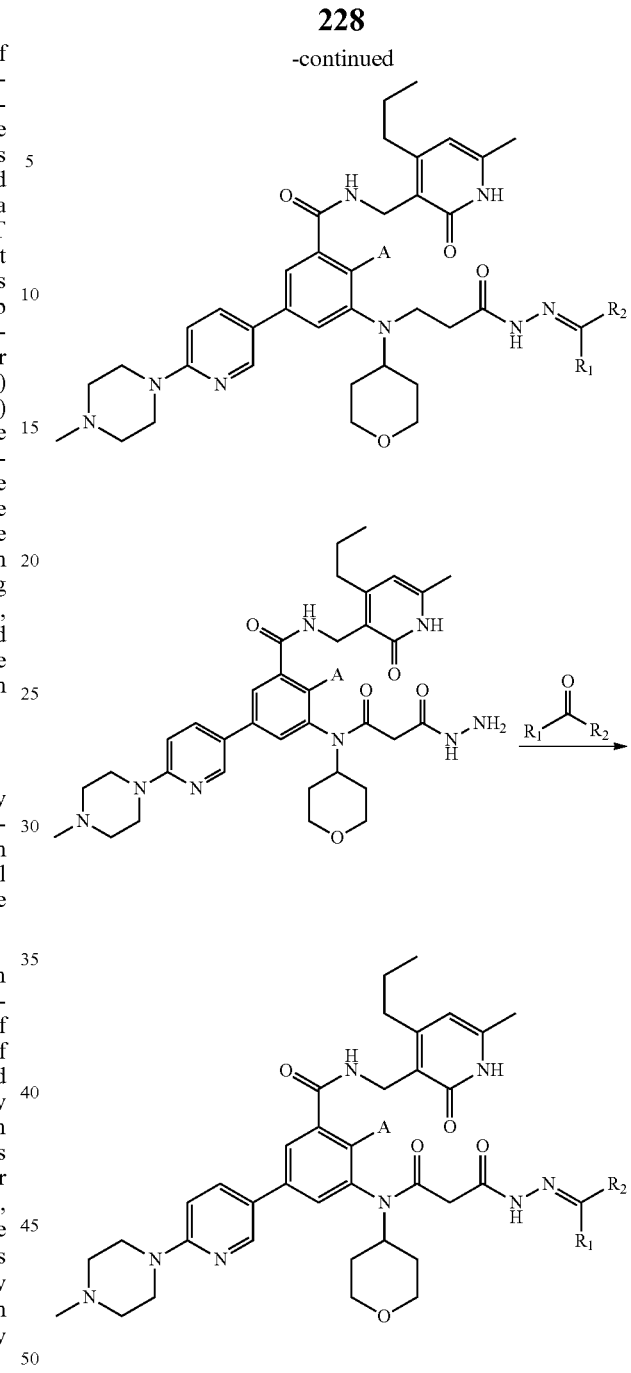

229
-continued
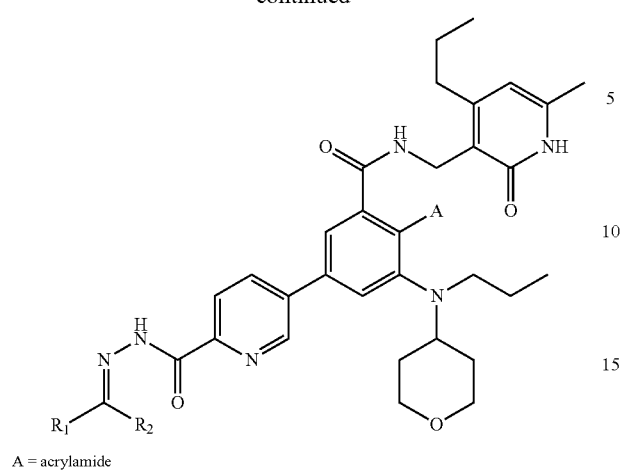
A = acrylamide
Scheme 2. Exemplary Preparation of compound EZ-31
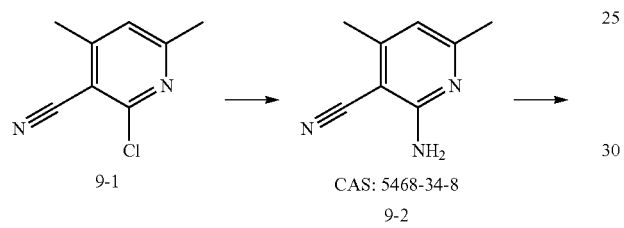
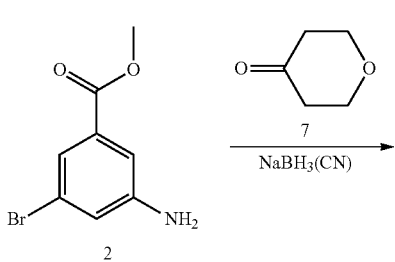
230
-continued
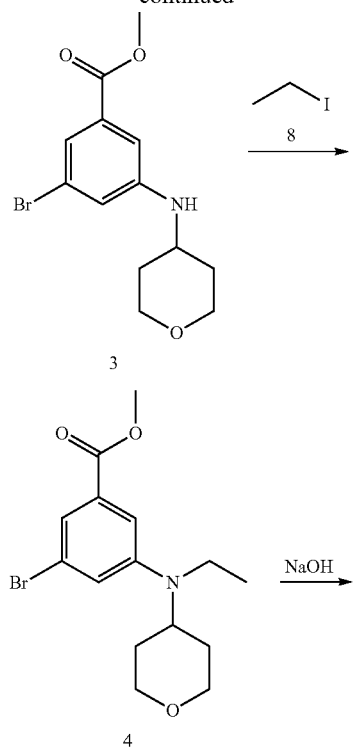
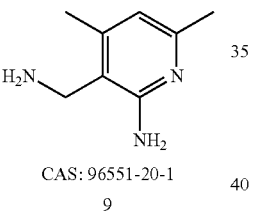
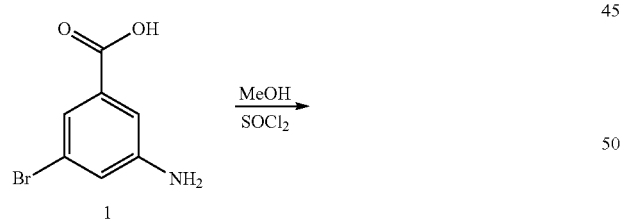
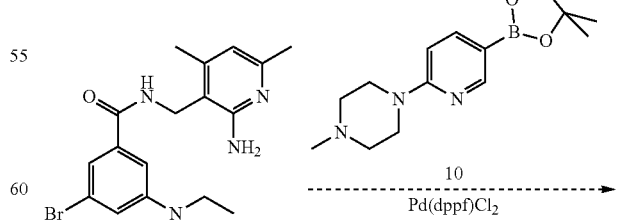

231
-continued

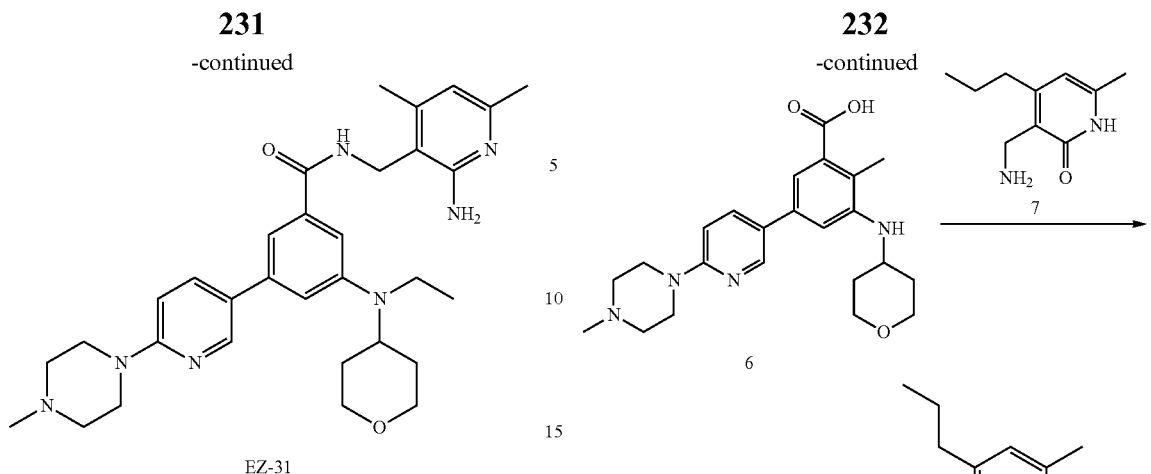

Scheme 3. Exemplary Preparation of compound EZ-53

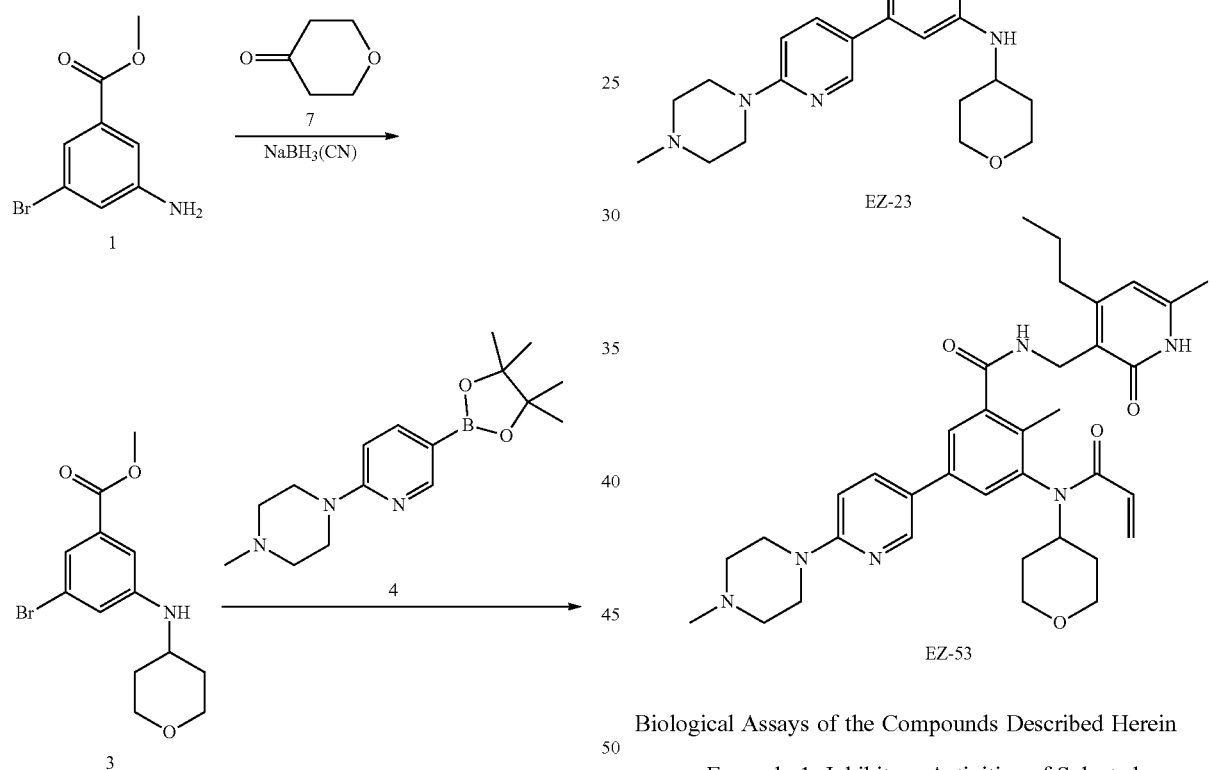

232
-continued

Biological Assays of the Compounds Described Herein

Example 1. Inhibitory Activities of Selected Compounds

As depicted in FIG. 2A, Compounds EZ-40, EZ-49, EZ-51, EZ-52, EZ-53, and JQ-80 were profiled for inhibitory activity and time dependence against EZH1 and EZH2. Compound EZ-53 displays time dependency and high potency, and compound EZ-53 is an irreversible inhibitor.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula (I):

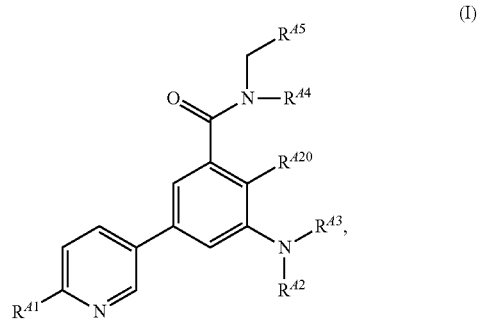

or a pharmaceutically acceptable salt thereof, wherein:
$R^{A1}$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^{a1})_2$, —$SR^a$, —CN, —SCN, —C(=$NR^a$)$R^a$, —C(=$NR^a$)$OR^a$, —C(=$NR^a$)N($R^{a1}$)$_2$, —C(=O)$R^a$, —C(=O)$OR^a$, —C(=O)N($R^{a1}$)$_2$, —$NO_2$, —$NR^a$C(=O)$R^a$, —$NR^a$C(=O)$OR^a$, —$NR^a$C(=O)N($R^{a1}$)$_2$, —OC(=O)$R^a$, —OC(=O)$OR^a$, —OC(=O)N($R^{a1}$)$_2$, a tag, or

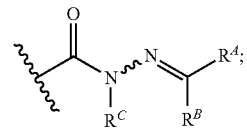

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom;

each instance of $R^{a1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or two instances of $R^{a1}$ are joined to form a substituted or unsubstituted, heterocyclic ring, or substituted or unsubstituted, heteroaryl ring;

$R^A$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

or $R^A$ and $R^B$ are joined to form a substituted or unsubstituted, carbocyclic ring, or a substituted or unsubstituted, heterocyclic ring;

$R^C$ is hydrogen, substituted or unsubstituted $C_{1-6}$ alkyl, or a nitrogen protecting group;

$R^{A2}$ is substituted or unsubstituted acyl, substituted or unsubstituted $C_{4-10}$ alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group, a tag, or a warhead;

$R^{A3}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{A20}$ is hydrogen, halogen, substituted or unsubstituted $C_{1-6}$ alkyl, —$OR^a$, or —$N(R^{a1})_2$;

$R^{A4}$ is hydrogen, substituted or unsubstituted $C_{1-6}$ alkyl, or a nitrogen protecting group;

$R^{A5}$ is of the formula:

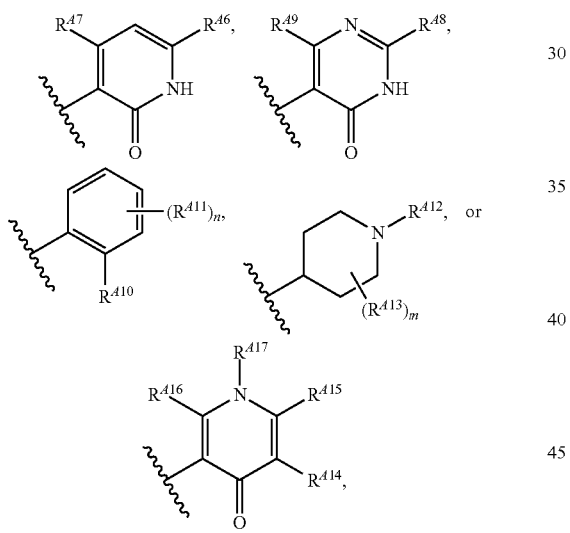

wherein:

$R^{A6}$ is hydrogen, halogen, substituted or unsubstituted $C_{1-6}$ alkyl, —$OR^a$, or —$N(R^{a1})_2$;

$R^{A7}$ is hydrogen, halogen, substituted or unsubstituted $C_{2-6}$ alkyl, substituted or unsubstituted, 3- to 7-membered, monocyclic carbocyclyl comprising 0, 1, or 2 double bonds in the carbocyclic ring system, —$OR^a$, or —$N(R^{a1})_2$;

$R^{A8}$ is hydrogen, halogen, substituted or unsubstituted $C_{1-6}$ alkyl, —$OR^a$, or —$N(R^{a1})_2$;

$R^{A9}$ is hydrogen, halogen, substituted or unsubstituted $C_{1-6}$ alkyl, substituted or unsubstituted, 3- to 7-membered, monocyclic carbocyclyl comprising 0, 1, or 2 double bonds in the carbocyclic ring system, —$OR^a$, or —$N(R^{a1})_2$;

$R^{A10}$ is —$OR^a$, —$N(R^{a1})_2$, or a warhead;

each instance of $R^{A11}$ is independently halogen, substituted or unsubstituted $C_{1-6}$ alkyl, substituted or unsubstituted, 3- to 7-membered, monocyclic carbocyclyl comprising 0, 1, or 2 double bonds in the carbocyclic ring system, —$OR^a$, or —$N(R^{a1})_2$;

n is 0, 1, 2, 3, or 4;

$R^{A12}$ is hydrogen, substituted or unsubstituted $C_{1-6}$ alkyl, a nitrogen protecting group, or a warhead;

each instance of $R^{A13}$ is independently halogen, substituted or unsubstituted $C_{1-6}$ alkyl, substituted or unsubstituted, 3- to 7-membered, monocyclic carbocyclyl comprising 0, 1, or 2 double bonds in the carbocyclic ring system, —$OR^a$, or —$N(R^{a1})_2$;

m is 0, 1, 2, 3, 4, 5, 6, 7, 8, or 9;

$R^{A14}$ is hydrogen, halogen, substituted or unsubstituted $C_{1-6}$ alkyl, —$OR^a$, or —$N(R^{a1})_2$;

$R^{A15}$ is hydrogen, halogen, substituted or unsubstituted $C_{1-6}$ alkyl, —$OR^a$, or —$N(R^{a1})_2$;

$R^{A16}$ is hydrogen, halogen, substituted or unsubstituted $C_{2-6}$ alkyl, substituted or unsubstituted, 3- to 7-membered, monocyclic carbocyclyl comprising 0, 1, or 2 double bonds in the carbocyclic ring system, —$OR^a$, or —$N(R^{a1})_2$; and $R^{A17}$ is hydrogen, substituted or unsubstituted acyl, substituted or unsubstituted $C_{1-6}$ alkyl, a nitrogen protecting group, or a warhead; and each instance of the warhead is independently:

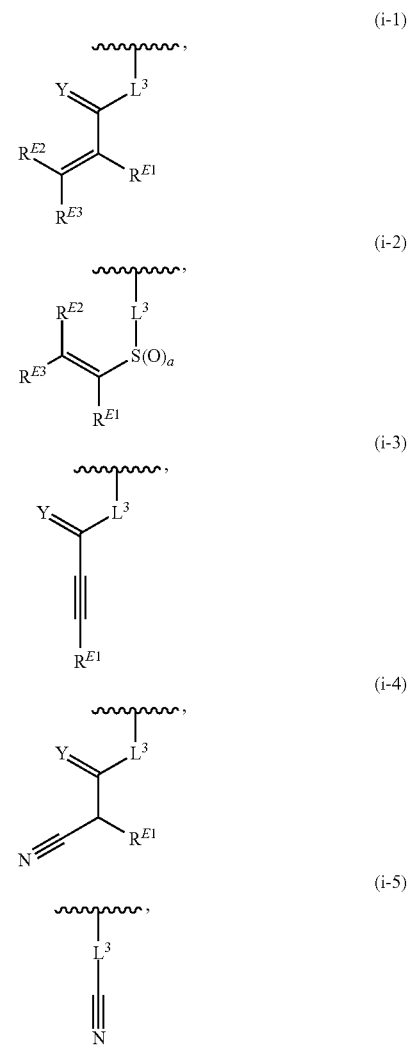

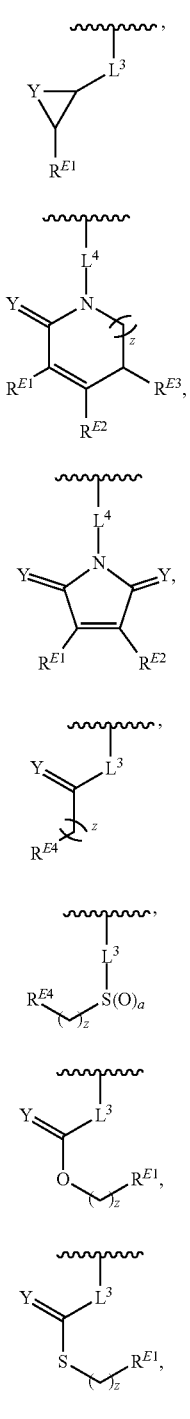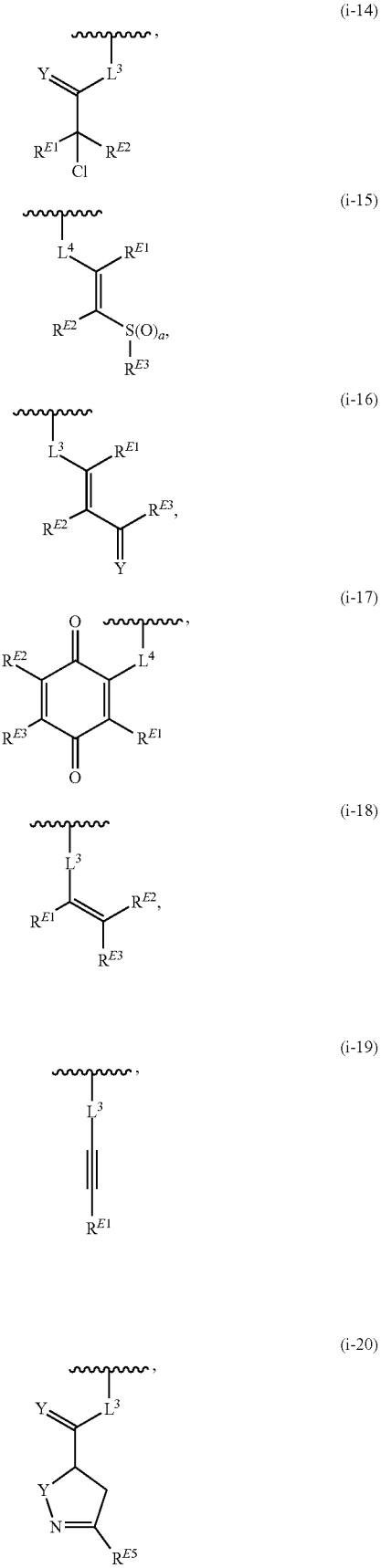

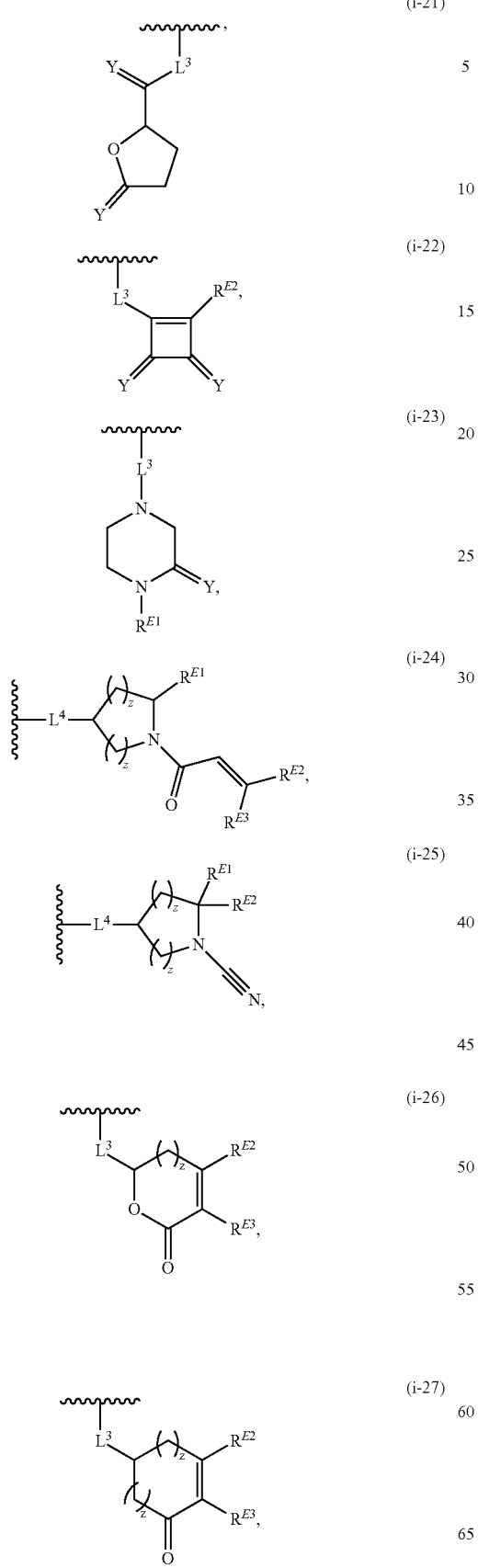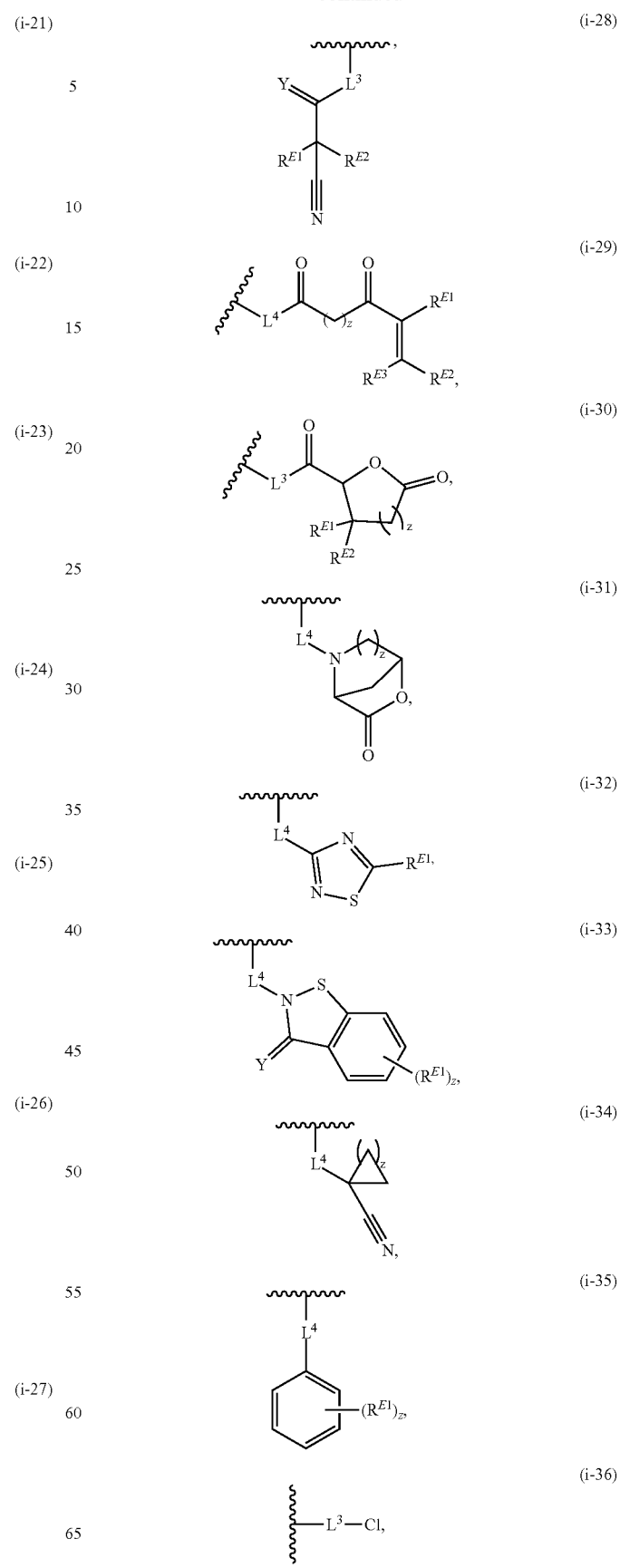

-continued

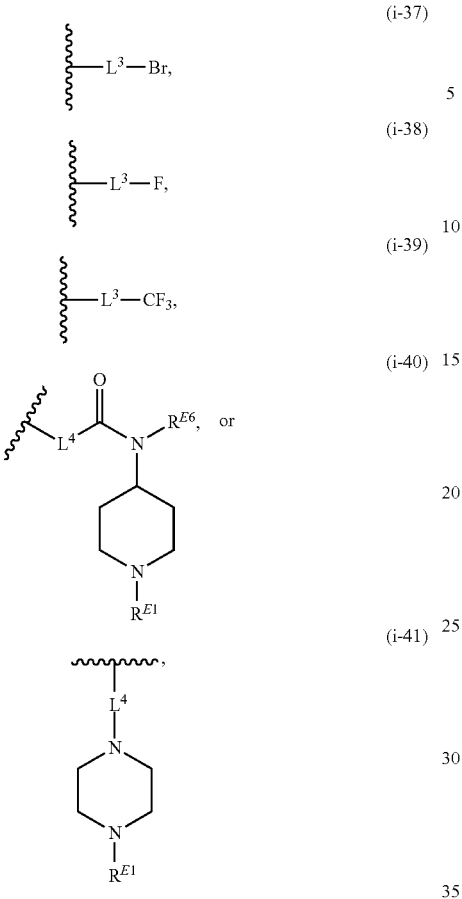

wherein:
L³ is a bond or an optionally substituted C₁₋₄ hydrocarbon chain, optionally wherein one or more carbon units of the hydrocarbon chain are independently replaced with —C(=O)—, —O—, —S—, —NR^{L3a}—, —NR^{L3a}C(=O)—, —C(=O)NR^{L3a}—, —SC(=O)—, —C(=O)S—, —OC(=O)—, —C(=O)O—, —NR^{L3a}C(=S)—, —C(=S)NR^{L3a}—, trans-CR^{L3b}=CR^{L3b}—, cis-CR^{L3b}=CR^{L3b}—, —C≡C—, —S(=O)—, —S(=O)O—, —OS(=O)—, —S(=O)NR^{L3a}—, —NR^{L3a}S(=O)—, —S(=O)₂—, —S(=O)₂P—, —OS(=O)₂—, —S(=O)₂NR^{L3a}—, or —NR^{L3a}S(=O)₂—, wherein R^{L3a} is hydrogen, substituted or unsubstituted C₁₋₆ alkyl, or a nitrogen protecting group, and wherein each occurrence of R^{L3b} is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R^{L3b} groups are joined to form an optionally substituted carbocyclic or optionally substituted heterocyclic ring;
L⁴ is a bond or an optionally substituted, branched or unbranched C₁₋₆ hydrocarbon chain;
each of R^{E1}, R^{E2}, and R^{E3} is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH₂OR^{EE}, —CH₂N(R^{EF})₂, —CH₂SR^{EE}, —OR^{EE}, —N(R^{EF})₂, —Si(R^{EG})₃, or —SR^{EE}, wherein each instance of R^{EE}, R^{EF}, and R^{EG} is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, and optionally wherein two R^{EF} groups are joined to form an optionally substituted heterocyclic ring; or R^{E1} and R^{E3}, or R^{E2} and R^{E3}, or R^{E1} and R^{E2} are joined to form an optionally substituted carbocyclic or optionally substituted heterocyclic ring;

R^{E4} is a leaving group;
R^{E5} is halogen;
R^{E6} is hydrogen, substituted or unsubstituted C₁₋₆ alkyl, or a nitrogen protecting group;
each instance of Y is independently O, S, or NR^{E7}, wherein R^{E7} is hydrogen, substituted or unsubstituted C₁-alkyl, or a nitrogen protecting group;
a is 1 or 2; and
each instance of z is independently 0, 1, 2, 3, 4, 5, or 6, as valency permits;
provided that:
at least one of R^{A2}, R^{A10}, R^{A12}, and R^{A17} is a warhead; and/or
at least one of R^{A1} and R^{A2} is a tag; and/or
when R^{A2} is of the formula:

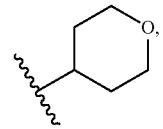 [SMILES: *C1CCOCC1]

R^{A3} is not substituted or unsubstituted C₁₋₃ alkyl.

2. The compound of claim 1, wherein the compound is of the formula:

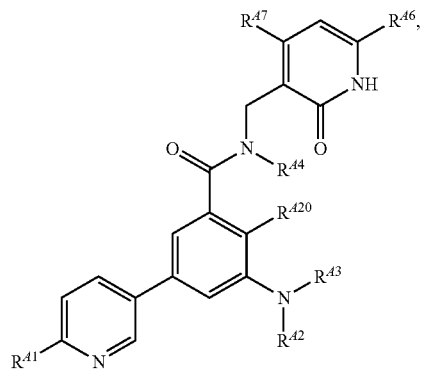

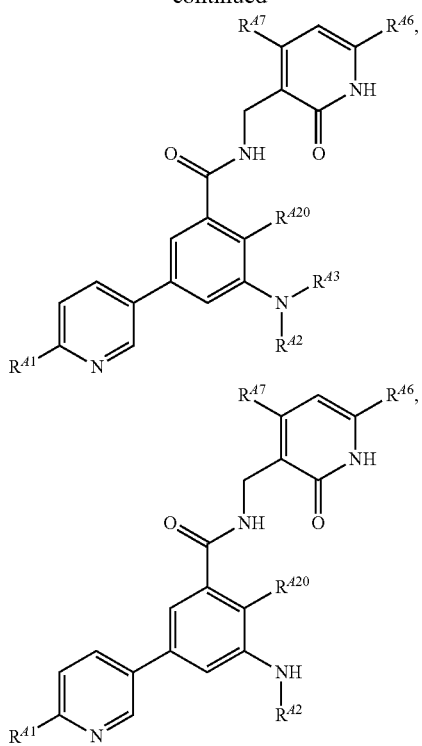
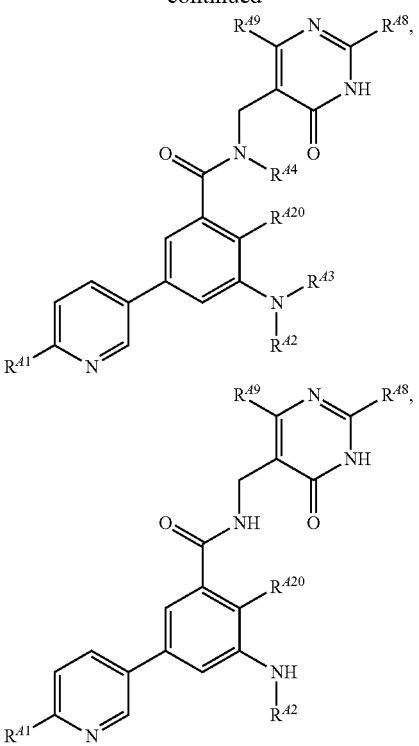
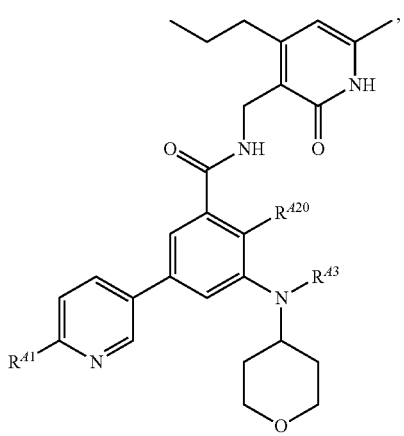

-continued
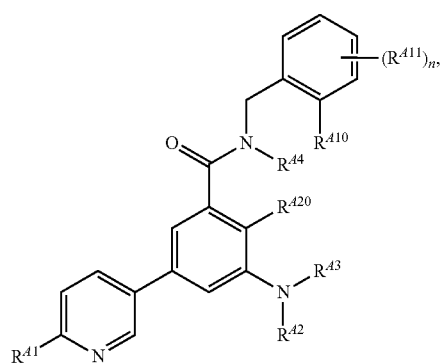
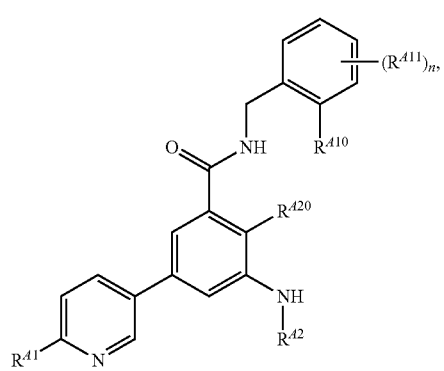
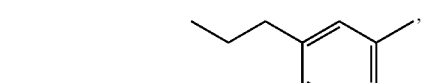
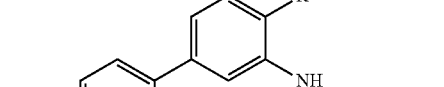
-continued
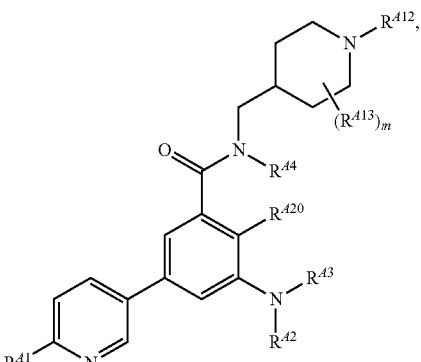
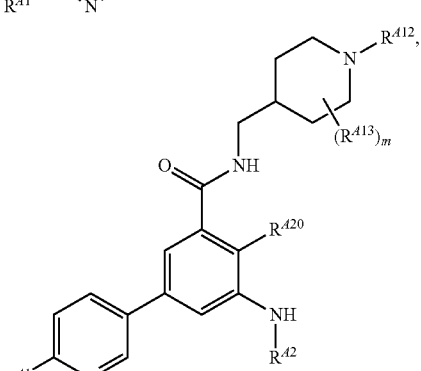
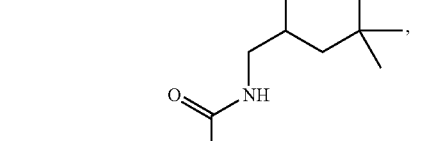
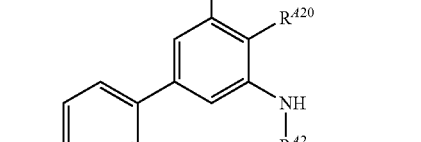

247
-continued

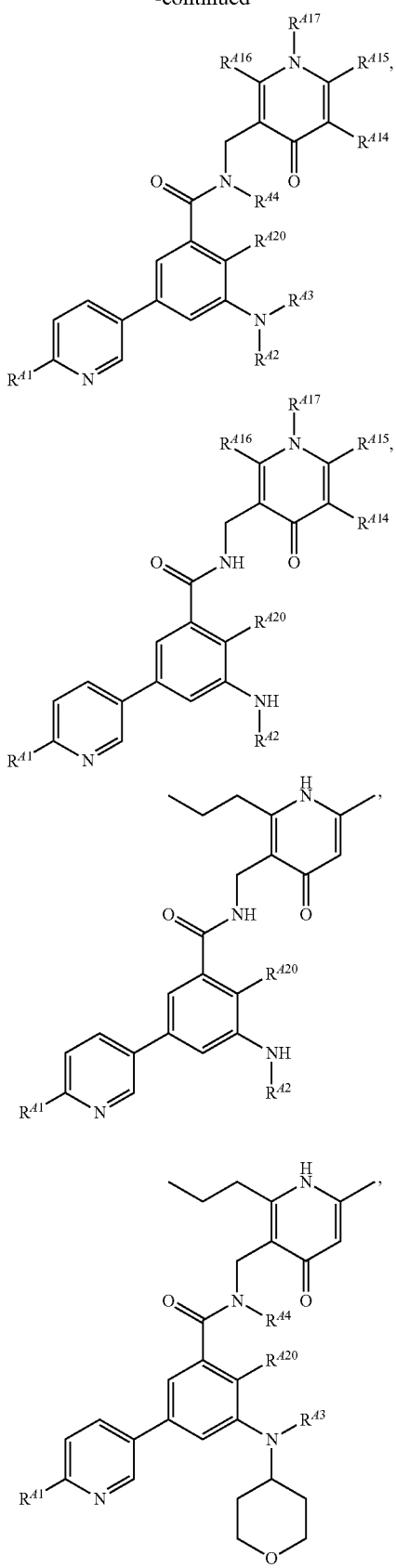

or a pharmaceutically acceptable salt thereof.

248

3. The compound of claim 1, wherein $R^{A1}$ is of the formula:

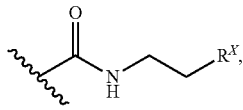

wherein:
$R^X$ is substituted or unsubstituted, 5- to 10-membered, monocyclic or bicyclic heterocyclic ring, wherein one or two atoms in the heterocyclic ring are independently nitrogen, oxygen, or sulfur.

4. The compound of claim 1, wherein $R^{A1}$ is substituted or unsubstituted, 3- to 7-membered, monocyclic heterocyclyl comprising 0, 1, or 2 double bonds in the heterocyclic ring system, wherein 1, 2, or 3 atoms in the heterocyclic ring system are independently nitrogen, oxygen, or sulfur.

5. The compound of claim 1, wherein $R^{A1}$ is substituted or unsubstituted alkyl.

6. The compound of claim 1, wherein $R^{A2}$ is substituted or unsubstituted acyl.

7. The compound of claim 1, wherein $R^{A2}$ is substituted or unsubstituted heterocyclyl.

8. The compound of claim 1, wherein $R^{A3}$ is hydrogen, substituted or unsubstituted alkyl, or is substituted or unsubstituted acyl.

9. The compound of claim 1, wherein $R^{A4}$ is hydrogen.

10. The compound of claim 1, wherein $R^{A5}$ is of the formula:

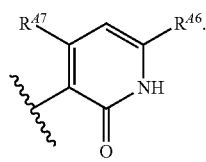

11. The compound of claim 1, wherein $R^{A6}$ is substituted or unsubstituted $C_{1-6}$ alkyl.

12. The compound of claim 1, wherein at least one of $R^{A2}$, $R^{A10}$, $R^{A12}$, and $R^{A17}$ is a warhead.

13. The compound of claim 1, wherein $R^{A20}$ is hydrogen, methyl, or of the formula:

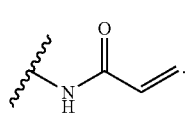

14. The compound of claim 1, wherein the compound is of the formula:

249            250
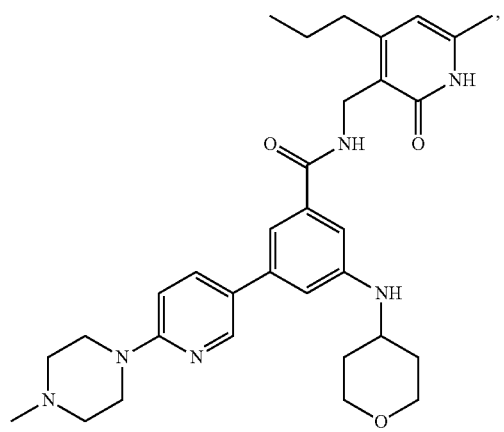      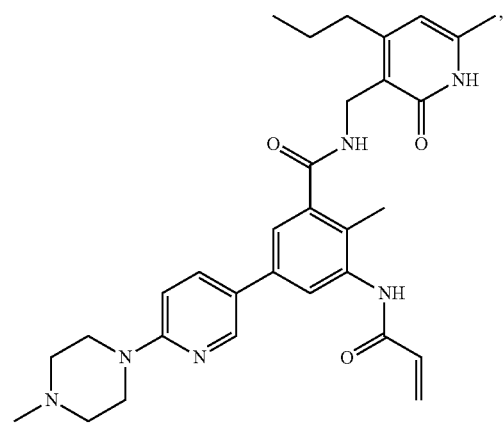
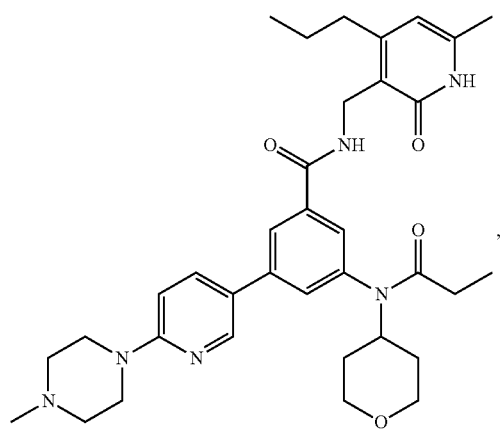      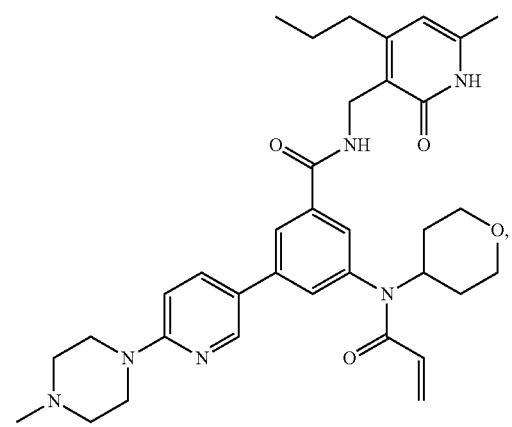
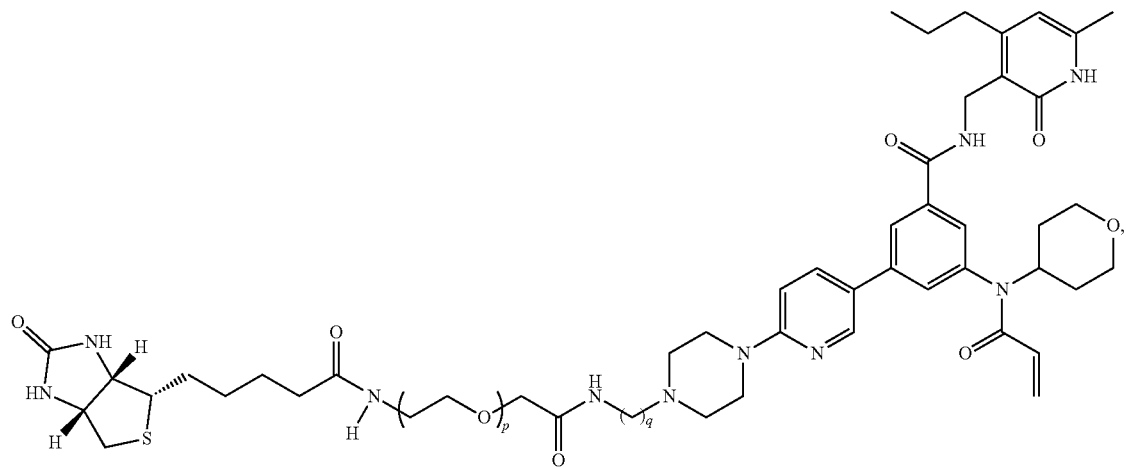

wherein:
p is an integer between 2 and 20, inclusive; and
q is an integer between 2 and 10, inclusive;
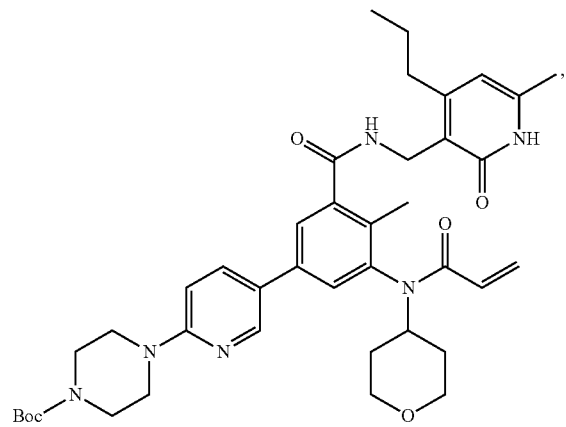
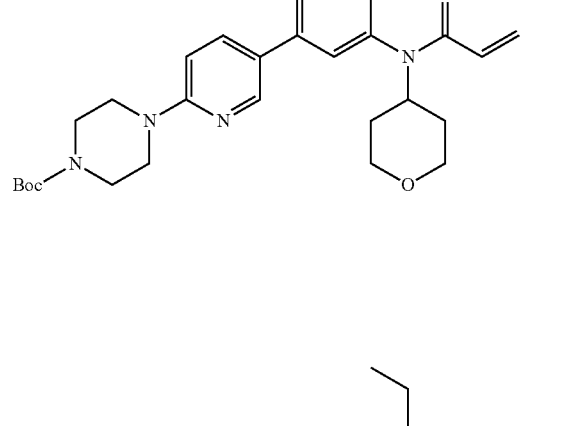
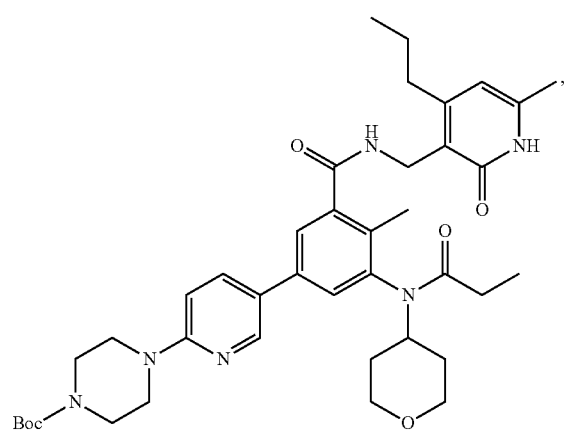
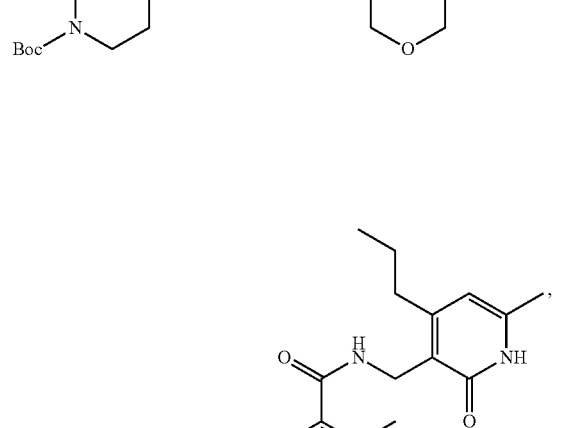
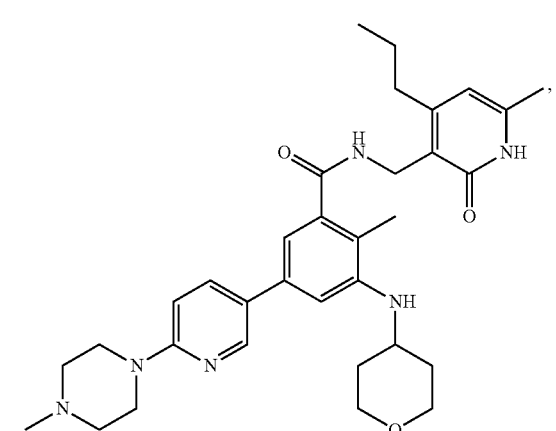
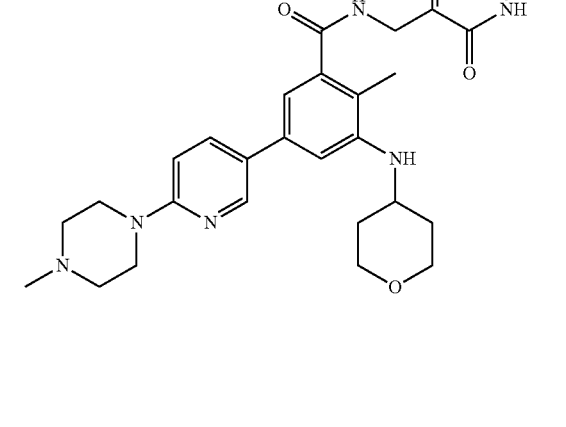
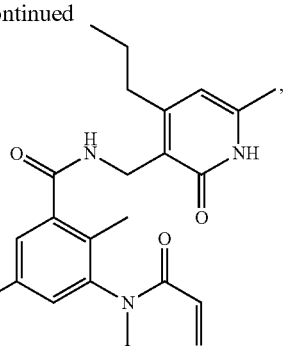
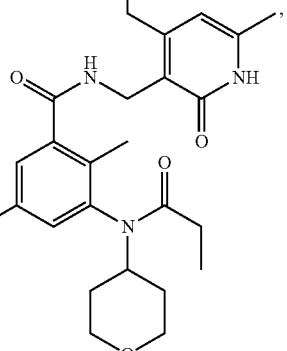
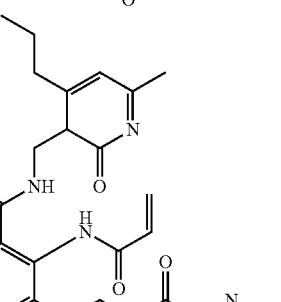
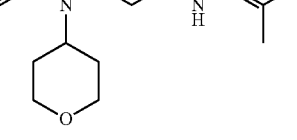
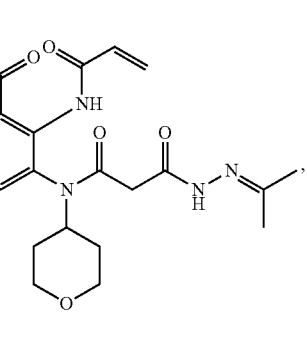
or a pharmaceutically acceptable salt thereof.
15. A pharmaceutical composition comprising a compound of claim 1 and a pharmaceutically acceptable excipient.

16. A method of inhibiting the activity of an histone methyltransferase in a subject in need thereof, the method comprising administering to the subject an effective amount of claim 1.

17. A method of inhibiting the activity of an histone methyltransferase in a cell, the method comprising contacting the cell with an effective amount of a compound of claim 1.

* * * * *